US010398787B2

(12) United States Patent
Vandendriessche et al.

(10) Patent No.: US 10,398,787 B2
(45) Date of Patent: Sep. 3, 2019

(54) VECTORS FOR LIVER-DIRECTED GENE THERAPY OF HEMOPHILIA AND METHODS AND USE THEREOF

(71) Applicant: Vrije Universiteit Brussel, Brussels (BE)

(72) Inventors: Thierry Vandendriessche, Bierbeek (BE); Marinee Chuah, Bierbeek (BE)

(73) Assignee: Vrije Universiteit Brussel, Brussels (BE)

( * ) Notice: Subject to any disclaimer, the term of this patent is extended or adjusted under 35 U.S.C. 154(b) by 0 days.

(21) Appl. No.: 14/438,571

(22) PCT Filed: Oct. 25, 2013

(86) PCT No.: PCT/EP2013/072450
§ 371 (c)(1),
(2) Date: Apr. 24, 2015

(87) PCT Pub. No.: WO2014/064277
PCT Pub. Date: May 1, 2014

(65) Prior Publication Data
US 2015/0283267 A1    Oct. 8, 2015

(30) Foreign Application Priority Data

Oct. 26, 2012 (WO) ............... PCT/EP2012/071297
Jul. 3, 2013 (WO) ............... PCT/EP2013/064054

(51) Int. Cl.
*C12N 15/864* (2006.01)
*C12N 15/12* (2006.01)
*C12N 15/52* (2006.01)
*C12N 15/113* (2010.01)
*A61K 48/00* (2006.01)
*A61K 38/36* (2006.01)
*C12N 15/86* (2006.01)
*A61K 38/16* (2006.01)
*A61K 38/37* (2006.01)
*A61K 38/48* (2006.01)
*A61K 38/00* (2006.01)

(52) U.S. Cl.
CPC ......... *A61K 48/0058* (2013.01); *A61K 38/16* (2013.01); *A61K 38/36* (2013.01); *A61K 38/37* (2013.01); *A61K 38/4846* (2013.01); *A61K 48/005* (2013.01); *C12N 15/86* (2013.01); *A61K 38/00* (2013.01); *C12N 2750/14343* (2013.01); *C12N 2799/025* (2013.01); *C12N 2830/008* (2013.01); *C12N 2830/42* (2013.01)

(58) Field of Classification Search
None
See application file for complete search history.

(56) References Cited

U.S. PATENT DOCUMENTS

| 2010/0284971 | A1* | 11/2010 | Samulski | ............... | C12N 9/644 |
| | | | | | 424/93.2 |
| 2011/0184049 | A1* | 7/2011 | Chuah | ................ | A61K 38/4846 |
| | | | | | 514/44 R |
| 2012/0308540 | A1* | 12/2012 | Madison | .......... | C12Y 304/2102 |
| | | | | | 424/93.72 |
| 2013/0024960 | A1* | 1/2013 | Nathwani | ............ | C07K 14/755 |
| | | | | | 800/16 |

FOREIGN PATENT DOCUMENTS

| WO | WO2001027303 A1 | 4/2001 |
| WO | 2009130208 A1 | 10/2009 |
| WO | WO2010151736 A1 | 12/2010 |
| WO | 2011005968 A1 | 1/2011 |

OTHER PUBLICATIONS

Wu et al, Optimization of Self-complementary AAV Vectors for Liver-directed Expression Results in Sustained Correction of Hemophilia B at Low Vector Dose, Molecular Therapy, 2008, pp. 280-289.*
Mikkelson et al, Helper-Independent Sleeping Beauty Transposon-Transposase Vectors for Efficient Nonviral Gene Delivery and Persistent Gene Expression in Vivo, Molecular Therapy vol. 8(4), 2003, pp. 654-665.*
Sabatino et al, Animal Models of Hemophilia, Prog Mol Biol Transl Sci. 2012 ; 105: 1-49.*
Arruda and Samelson-Jones, Obstacles and future of gene therapy for hemophilia, Expert Opin Orphan Drugs. 2015 ; 3(9): 997-1010.*
Cancio et al, Developments in the treatment of hemophilia B: focus on emerging gene therapy, The Application of Clinical Genetics 2013:6 91-101.*
Nathwani et al, Our Journey to Successful Gene Therapy for Hemophilia B, Human Gene Therapy 25:923-926 (Nov. 2014).*
Rogers and Herzog, Gene therapy for hemophilia, 2015, Front Biosci (Landmark Ed). ; 20: 556-603.*
French et al, Complete correction of hemophilia B phenotype by FIX-Padua skeletal muscle gene therapy in an inhibitor-prone dog model, Blood Advances, Mar. 13, 2018, pp. 505-508.*
Matsui et al., "A microRNA-regulated and GP64-pseudotyped lentiviral vector mediates stable expression of FVIII in a murine model of Hemophilia A," 2011, Mol Ther., 19:723-30.
McCarty et al., "Self-complementary recombinant adeno-associated virus (scAAV) vectors promote efficient transduction independently of DNA synthesis," 2001, Gene Ther., 8:1248-54.

(Continued)

*Primary Examiner* — Maria Marvich
(74) *Attorney, Agent, or Firm* — McDonnell Boehnen Hulbert & Berghoff LLP

(57) ABSTRACT

The present invention relates to vectors containing liver-specific regulatory sequences and codon-optimized factor IX or factor VIII genes, methods employing these vectors and uses of these vectors. Expression cassettes and vectors containing these liver-specific regulatory elements and codon-optimized factor IX or factor VIII genes are also disclosed. The present invention is particularly useful for applications using gene therapy, in particular for the treatment of hemophilia A and B.

4 Claims, 75 Drawing Sheets

Specification includes a Sequence Listing.

(56) References Cited

OTHER PUBLICATIONS

McCarty et al., "Adeno-associated virus terminal repeat (TR) mutant generates self-complementary vectors to overcome the rate-limiting step to transduction in vivo," 2003, Gene Ther., 10:2112-8.

McIntosh et al., "Therapeutic levels of FVIII following a single peripheral vein administration of rAA V vector ancoding a novel human factor VIII variant," 2013, Blood, 121:3335-44.

Meir et al. "Genome-wide target profiling of piggyBac and Tol2 in HEK 293: pros and cons for gene discovery and jene therapy," 2011, BMC Biotechnol. 11:28.

Miao et al., "Inclusion of the hepatic locus control region, an intron, and untranslated region increases and stabilizes hepatic factor IX gene expression in vivo but not in vitro," 2000, Mol Ther, 1:522-32.

Miao et al., "Bioengineering of coagulation factor VIII for improved secretion," 2004, Blood, 103:3412-3419.

Milanov et al., "Engineered factor IX variants bypass FVIII and correct hemophilia A phenotype in mice," 2012, Blood 119:602-611.

Miller, "Retrovirus packaging cells," 1990, Hum Gene Ther.,1:5-14.

Mingozzi et al., "Induction of immune tolerance to coagulation factor IX antigen by in vivo hepatic gene transfer," 2003, J Clin Invest., 111:1347-56.

Mingozzi et al., "CD8(+) T-cell responses to adeno-associated virus capsid in humans," 2007, Nat Med, 13:419-22.

Mount et al., "Sustained phenotypic correction of hemophilia B dogs with a factor IX null mutation by liver-directed gene therapy," 2002, Blood 99:2670-6.

Naldini et al., "In vivo gene delivery and stable transduction of nondividing cells by a lentiviral vector," 1996, Science, 272:263-7.

Nathwani et al., "Sustained high-level expression of human factor IX (hFIX) after liver-targeted delivery of recombinant adeno-associated virus encoding the hFIX gene in rhesus macaques," 2002, Blood 100:1662-1669.

Nathwani et al., "Self-complementary adeno-associated virus vectors containing a novel liver-specific human factor IX expression cassette enable highly efficient transduction of murine and nonhuman primate liver," 2006, Blood 107:2653-61.

Nathwani et al., "Adenovirus-associated virus vector-mediated gene transfer in hemophilia B," 2011, N Engl J Med. 365:2357-2365.

Ohlfest et al., "Phenotypic correction and long-term expression of factor VIII in hemophilic mice by immunotolerization and nonviral gene transfer using the Sleeping Beauty transposon system," 2004, Blood, 105:2691-8.

Petrus et al., "Gene therapy strategies for hemophilia: benefits versus risks," 2010, J Gene Med 12:797-809.

Sandberg et al., "Structural and functional characteristics of the B domain-deleted recombinant factor VIII protein, r-VIII SQ," 2001, Thromb Haemost., 85:93-100.

Schuettrumpf et al., "Factor IX variants improve gene therapy efficacy for hemophilia B," 2005, Blood 105:2316-2323.

Simioni et al., "X-linked thrombophilia with a mutant factor IX (factor IX Padua)," 2009, N Engl J Med 361:1671-1675.

Snyder et al., "Persistent and therapeutic concentrations of human factor IX in mice after hepatic gene transfer of recombinant AA V vectors," 1997, Nat Genet., 16:270-276.

Snyder et al., "Correction of hemophilia B in canine and murine models using recombinant adeno-associated viral vectors," 1999, Nature Med., 5:64-70.

Trapnell BC., "Adenoviral vectors for gene transfer," 1993, Adv. Drug Del. Rev. 12:185-199.

Vandenberghe et al., "Heparin binding directs activation of T cells against adeno-associated virus serotype 2 capsid," 2006, Nat Med. 12:967-71.

Vandendriessche et al., "Long-term expression of human coagulation factor VIII and correction of hemophilia A after in vivo retroviral gene transfer in factor VIII-deficient mice," 1999, Proc Natl Acad Sci USA, 96:10379-84.

Vandendriessche et al., "Lentiviral vectors containing the human immunodeficiency virus type-1 central polypurine tract can efficiently transduce nondividing hepatocytes and antigen-presenting cells in vivo," 2002, Blood 100:813-22.

Vandendriessche et al., "Efficacy and safety of adeno-associated viral vectors based on serotype 8 and 9 vs. lentiviral vectors for hemophilia B gene therapy," 2007, J Thromb Haemost, 5:16-24.

Vandendriessche et al., "Emerging potential of transposons for gene therapy and generation of induced pluripotent stem cells," 2009, Blood 114:1461-8.

Vandendriessche et al., "Clinical progress in gene therapy: sustained partial correction of the bleeding disorder in patients suffering from severe hemophilia B," 2012, Hum Gene Ther., 23:4-6.

Wang et al., "Sustained correction of bleeding disorder in hemophilia B mice by gene therapy," 1999, Proc Natl Acad Sci USA, 96:3906-3910.

Wang et al., "Sustained expression of therapeutic level of factor IX in hemophilia B dogs by AAV-mediated gene therapy in liver," 2000, Mol Ther, 1:154-158.

Wang et al., "Major role of local immune responses in antibody formation to factor IX in AAV-mediated gene transfer," 2005, Gene Ther., 12:1453-464.

Ward et al., "Codon optimization of human factor VIII cDNAs leads to high-level expression," 2010, Blood 117:798-807.

Wu et al., "Optimization of self-complementary AAV vectors for liver-directed expression results in sustained correction of hemophilia B at low vector dose," 2008,Mol Ther. 16:280-9.

Xu et al., "Neonatal or hepatocyte growth factor-potentiated adult gene therapy with a retroviral vector results in therapeutic levels of canine factor IX for hemophilia B," 2003, Blood 101:3924-3932.

Xu et al., "Absence of a desmopressin response after therapeutic expression of factor VIII in hemophilia A dogs with liver-directed neonatal gene therapy," 2005, Proc Natl Acad Sci USA, 102:6080-6085.

Yamada et al., "Nanoparticles for the delivery of genes and drugs to human hepatocytes," Nat Biotechnol., 21:885-90.

Yant et al., "Somatic integration and long-term transgene expression in normal and haemophilic mice using a DNA transposon system," 2000, Nat Genet., 25:35-41.

Yusa et al. "A hyperactive piggyBac transposase for mammalian applications," 2011, Proc Natl Acad Sci USA., 108:1531-6.

Zhang et al., "High levels of foreign gene expression in hepatocytes after tail vein injections of naked plasmid DNA," 1999, Hum Gene Ther, 10:1735-7.

Zhijian Wu et al., "Optimization of Self-complementary AAV Vectors for Liver-directed Expression Results in SustainedCorrection of Hemophilia B at Low Vector Dose," 2008, Mol. Ther., 16:280-289.

Zhong et al., Next generation of adeno-associated virus 2 vectors: point mutations in tyrosines lead to high-efficiency transduction at lower doses, 2008, Proc Natl Acad Sci USA 105:7827-32.

Annoni et al., "In vivo delivery of a microRNA-regulated transgene induces antigen-specific regulatory T cells and promotes immunologic tolerance," 2009, Blood 114:5152-5161.

Arruda et al., "Peripheral transvenular delivery of adeno-associated viral vectors to skeletal muscle as a novel therapy for hemophilia B," 2010, Blood 115:4578-88.

Axelrod et al., "Phenotypic correction of factor IX deficiency in skin fibroblasts of hemophilic dogs," 1990, Proc. Natl Acad. Sci. USA, 87:5173-7.

Brown et al., "Helper-dependent adenoviral vectors mediate therapeutic factor VIII expression for several months with minimal accompanying toxicity in a canine model of severe hemophilia A," 2004, Blood, 103:804-10.

Brown et al., "A microRNA-regulated lentiviral vector mediates stable correction of hemophilia B mice," 2007, Blood, 110:4144-52.

Brunetti-Pierri et al., "Bioengineered factor IX molecules with increased catalytic activity improve the therapeutic index of gene therapy vectors for hemophilia B," 2009, Hum Gene Ther., 20:479-85.

Buchlis et al., "Factor IX expression in skeletal muscle of a severe hemophilia B patient 10 years after AAV-mediated gene transfer," 2012, Blood 119:3038-41.

(56) References Cited

OTHER PUBLICATIONS

Budker et al., "Naked DNA delivered intraportally expresses efficiently in hepatocytes," 1996, Gene Ther., 3:593-8.
Cantore et al., "Hyper-functional coagulation factor IX improves the efficacy of gene therapy in hemophilic mice," 2012, Blood, 4:4517-4520.
Chang et al., "Changing residue 338 in human factor IX from arginine to alanine causes an increase in catalytic activity," 1998, J Bioi Chem 273:12089-12094.
Chowdhury et al., "Long-term improvement of hypercholesterolemia after ex vivo gene therapy in LDLR-deficient rabbits," 1991, Science, 254:1802-5.
Chuah et al., "Therapeutic factor VIII levels and negligible toxicity in mouse and dog models of hemophilia A following gene therapy with high-capacity adenoviral vectors," 2003, Blood, 101:1734-43.
Chuah et al., "Recent progress in gene therapy for hemophilia," 2012, Hum Gene Ther., 23:557-65.
Chuah et al., "Platelet-directed gene therapy overcomes inhibitory antibodies to factor VIII," 2012, J Thromb Haemost., 10:1566-9.
Donsante et al., "AAV vector integration sites in mouse hepatocellular carcinoma," 2007, Science 317:477.
Dobrzynski et al., "Prevention of cytotoxic T lymphocyte responses to factor IX-expressing hepatocytes by gene transfer-induced regulatory T cells," 2006, Proc Natl Acad Sci USA, 103:4592-4597.
Ehrhardt et al., "A new adenoviral helper-dependent vector results in long-term therapeutic levels of human coagulation factor IX at low doses in vivo," 2002, Blood 99:3923-30.
Fields et al., "Risk and prevention of anti-factor IX formation in AAV-mediated gene transfer in the context of a large deletion of F9," 2001, Mol. Ther. 4:201-210.
Follenzi et al., "Targeting lentiviral vector expression to hepatocytes limits transgene-specific immune response and establishes long-term expression to hepatocytes limits transgene-specific immune response and establishes long-term expression of human antihemophilic factor IX in mice," 2004, Bllod, 103:3700-9
Gao et al., "Novel adeno-associated viruses from rhesus monkeys as vectors for human gene therapy," 2002, Proc Natl Acad Sci USA, 99:11854-9.
Gao et al., "Clades of Adeno-associated viruses are widely disseminated in human tissues," 2004, J. Viro, 178:6381-6388.
Herzog et al., "Long-term correction of canine hemophilia B by gene transfer of blood coagulation factor IX mediated by adeno-associated viral vector," 1999, Nat Med., 5:56-63.
Herzog et al., "Muscle-directed gene transfer and transient immune suppression result in sustained partial correction of canine hemophilia B caused by a null mutation," 2001, Mol Ther., 4:192-200.
Herzog et al., "Stable gene transfer and expression of human blood coagulation factor IX after intramuscular injection of recombinant adeno-associated virus," 1997, Proc Natl Acad Sci USA, 94:5804-5809.
Herzog et al., "Influence of vector dose on factor IX-specific T and B cell responses in muscle-directed gene therapy," 2002, Hum Gene Ther., 13:1281-1291.
High, "Gene Transfer as an approach to treating Hemophilia," 2001, Circ Res., 88:137-144.
High, "Gene therapy for hemophilia: a long and winding road," 2011, J Thromb Haemost., 9 Suppl. 1:2-11.
Bainbridge et al., "Effect of Gene Therapy on Visual Function in Leber's Congenital Amaurosis," 2008, N Engl J Med., 358: 2231-2239.
Jiang et al., "Multiyear therapeutic benefit of AAV serotypes 2, 6, and 8 delivering factor VIII to hemophilia A mice and dogs," 2006, Blood, 108:107-15.
Kao et al., "FIX-Triple, a gain-of-function factor IX variant, improves haemostasis in mouse models without increased risk of thrombosis," 2010, Thromb Haemost 104:355-365.
Kay et al., "Expression of human alpha 1-antitrpsin in dogs after autologous transplantation of retroviral transduced hepatocytes," 1992, Proc. Natl. Acad. Sci. USA, 89:89-93.
Kay et al., "Evidence for gene transfer and expression of factor IX in hemophilia B patients treated with an AAV vector," 2000, Nat Genet. 24:257-61.
Kistner et al., Doxycycline—mediated quantitative and tissue-specific control of gene expression in transgenic mice, 1996, Proc Natl Acad Sci USA, 93:10933-8.
Kren et al., "Nanocapsule-delivered Sleeping Beauty mediates therapeutic Factor VIII expression in liver sinusoidal endothelial cells of hemophilia A mice," 2009, J Clin Invest., 19:2086-99.
Kuriyama et al., "A potential approach for gene therapy targeting hepatoma using a liver-specific promoter on a retroviral vector," 1991, Cell Struct Funct., 16:503-10.
Li et al., "Assessing the potential for AA V vector genotoxicity in a murine model," 2011, Blood, 117:3311-9.
Lin et al., "Generation of a novel factor IX with augmented clotting activities in vitro an in vivo," 2010, J Thromb Haemost, 8:1773-1783.
Liu et al., "Hydrodynamics-based transfection in animals by systemic administration of plasmid DNA," 1999, Gene Ther., 6:1258-66.
Manno et al., "Successful transduction of liver in hemophilia by AA V-Factor IX and limitations imposed by the host immune response," 2006, Nat Med., 12:342-7.
Mates et al., "Molecular evolution of a novel hyperactive Sleeping Beauty transposase enable robust stable gene transfer in vertebrates," 2009, Nat Genet., 41:753-61.
Matrai et al., "Pre-clinical and clinical progress in hemophilia gene therapy," 2010, Curr Opin Hematol., 17:387-92.
Matrai et al., "Recent advances in lentiviral vectro development and applications" 2010, Mol Ther., 18:477-90.
Matrai et al., "Hepatocyte-targeted expression by integrase-defective lentiviral vectors induces antigen-specific tolerance in mice with low genotoxic risk," 2011, Hepatology, 53:1696-707.
Matsui et al., "A murine model for induction of long-term immunologic tolerance to factor VIII does not require persistent detectable levels of plasma factor VIII and involves contributions from Foxp3+ T regulatory cells," 2009, Blood. 114:677-85.
Buchlis et al., "Factor IX expression in skeletal muscle of a severe hemophilia B patient 10 years after AAV-mediated gene transfer," 2012, Blood 119:3038-41 [ERRATA, 2014, Blood 123:1768].
Genbank: Accession No. NM_000133 "*Homo sapiens* coagulation factor IX (F9), transcript variant 1, mRNA," published on Oct. 8, 2016 [retrieved on Nov. 30, 2016][retrieved from the internet https://www.ncbi.nlm.nih.gov/nuccore/NM_000133][6 pages].
UniProtKB Accession No. P00451 "Coagulation factor VIII" published on Jul. 21, 1986 [retrieved on Nov. 30, 2016 from the internet http://www.uniprot.org/uniprot/p00451][55 pages].

\* cited by examiner

FIG. 1B

SEQ ID 1

```
         10        20        30        40        50
CAGCAGCTGGCGTAATAGCGAAGAGGCCCGCACCGATCGCCCTTCCCAAC
GTCGTCGACCGCATTATCGCTTCTCCGGGCGTGGCTAGCGGGAAGGGTTG 60        70        80        90       100
AGTTGCGCAGCCTGAATGGCGAATGGAATTCCAGACGATTGAGCGTCAAA
TCAACGCGTCGGACTTACCGCTTACCTTAAGGTCTGCTAACTCGCAGTTT 110       120       130       140       150
ATGTAGGTATTTCCATGAGCGTTTTTCCTGTTGCAATGGCTGGCGGTAAT
TACATCCATAAAGGTACTCGCAAAAAGGACAACGTTACCGACCGCCATTA 160       170       180       190       200
ATTGTTCTGGATATTACCAGCAAGGCCGATAGTTTGAGTTCTTCTACTCA
TAACAAGACCTATAATGGTCGTTCCGGCTATCAAACTCAAGAAGATGAGT 210       220       230       240       250
GGCAAGTGATGTTATTACTAATCAAAGAAGTATTGCGACAACGGTTAATT
CCGTTCACTACAATAATGATTAGTTTCTTCATAACGCTGTTGCCAATTAA 260       270       280       290       300
TGCGTGATGGACAGACTCTTTTACTCGGTGGCCTCACTGATTATAAAAAC
ACGCACTACCTGTCTGAGAAAATGAGCCACCGGAGTGACTAATATTTTTG 310       320       330       340       350
ACTTCTCAGGATTCTGGCGTACCGTTCCTGTCTAAAATCCCTTTAATCGG
TGAAGAGTCCTAAGACCGCATGGCAAGGACAGATTTTAGGGAAATTAGCC 360       370       380       390       400
CCTCCTGTTTAGCTCCCGCTCTGATTCTAACGAGGAAAGCACGTTATACG
GGAGGACAAATCGAGGGCGAGACTAAGATTGCTCCTTTCGTGCAATATGC 410       420       430       440       450
TGCTCGTCAAAGCAACCATAGTACGCGCCCTGTAGCGGCGCATTAAGCGC
ACGAGCAGTTTCGTTGGTATCATGCGCGGGACATCGCCGCGTAATTCGCG
                                                      >

460       470       480       490       500
GGCGGGTGTGGTGGTTACGCGCAGCGTGACCGCTACACTTGCCAGCGCCC
CCGCCCACACCACCAATGCGCGTCGCACTGGCGATGTGAACGGTCGCGGG
            F1 ORIGIN                                 >

510       520       530       540       550
TAGCGCCCGCTCCTTTCGCTTTCTTCCCTTCCTTTCTCGCCACGTTCGCC
ATCGCGGGCGAGGAAAGCGAAAGAAGGGAAGGAAAGAGCGGTGCAAGCGG
            F1 ORIGIN                                 >

560       570       580       590       600
GGCTTTCCCCGTCAAGCTCTAAATCGGGGGCTCCCTTTAGGGTTCCGATT
CCGAAAGGGGCAGTTCGAGATTTAGCCCCCGAGGGAAATCCCAAGGCTAA
            F1 ORIGIN                                 >

```
TAGTGCTTTACGGCACCTCGACCCCAAAAAACTTGATTAGGGTGATGGTT
ATCACGAAATGCCGTGGAGCTGGGGTTTTTTGAACTAATCCCACTACCAA
                       F1 ORIGIN                  >

660       670       680       690       700
CACGTAGTGGGCCATCGCCCTGATAGACGGTTTTTCGCCCTTTGACGTTG
GTGCATCACCCGGTAGCGGGACTATCTGCCAAAAAGCGGGAAACTGCAAC
                       F1 ORIGIN                  >

710       720       730       740       750
GAGTCCACGTTCTTTAATAGTGGACTCTTGTTCCAAACTGGAACAACACT
CTCAGGTGCAAGAAATTATCACCTGAGAACAAGGTTTGACCTTGTTGTGA
                       F1 ORIGIN          >

760       770       780       790       800
CAACCCTATCTCGGTCTATTCTTTTGATTTATAAGGGATTTTGCCGATTT
GTTGGGATAGAGCCAGATAAGAAAACTAAATATTCCCTAAAACGGCTAAA 810       820       830       840       850
CGGCCTATTGGTTAAAAAATGAGCTGATTTAACAAAAATTTAACGCGAAT
GCCGGATAACCAATTTTTTACTCGACTAAATTGTTTTTAAATTGCGCTTA 860       870       880       890       900
TTTAACAAAATATTAACGTTTACAATTTAAATATTTGCTTATACAATCTT
AAATTGTTTTATAATTGCAAATGTTAAATTTATAAACGAATATGTTAGAA 910       920       930       940       950
CCTGTTTTTGGGGCTTTTCTGATTATCAACCGGGGTACATATGATTGACA
GGACAAAAACCCCGAAAAGACTAATAGTTGGCCCCATGTATACTAACTGT 960       970       980       990      1000
TGCTAGTTTTACGATTACCGTTCATCGCCTGCACTGCGCGCTCGCTCGCT
ACGATCAAAATGCTAATGGCAAGTAGCGGACGTGACGCGCGAGCGAGCGA
                                        MUTATEDITR >

1010      1020      1030      1040      1050
CACTGAGGCCGCCCGGGCAAAGCCCGGGCGTCGGGCGACCTTTGGTCGCC
GTGACTCCGGCGGGCCCGTTTCGGGCCCGCAGCCCGCTGGAAACCAGCGG
                      MUTATEDITR                  >

1060      1070      1080      1090      1100
CGGCCTCAGTGAGCGAGCGAGCGCGCAGAGAGGGAGTGGAATTCACGCGT
GCCGGAGTCACTCGCTCGCTCGCGCGTCTCTCCCTCACCTTAAGTGCGCA
             MUTATEDITR           >

1110      1120      1130      1140      1150
GGTACGATCTGAATTCGGTACAATTCACGCGTGGTACGGCCGCGGTACCG
CCATGCTAGACTTAAGCCATGTTAAGTGCGCACCATGCCGGCGCCATGGC 1160      1170      1180      1190      1200
GCGCGCCGGGGGAGGCTGCTGGTGAATATTAACCAAGGTCACCCCAGTTA
CGCGCGGCCCCCTCCGACGACCACTTATAATTGGTTCCAGTGGGGTCAAT

>Serp_enh   >mTTR/promoter
                             |            |
```

FIG. 1B (continued)

```
         1210      1220      1230     |1240 |    1250
    TCGGAGGAGCAAACAGGGGCTAAGTCCACACGCGTGGTACCGTCTGTCTG
    AGCCTCCTCGTTTGTCCCCGATTCAGGTGTGCGCACCATGGCAGACAGAC 1260      1270      1280      1290      1300
    CACATTTCGTAGAGCGAGTGTTCCGATACTCTAATCTCCCTAGGCAAGGT
    GTGTAAAGCATCTCGCTCACAAGGCTATGAGATTAGAGGGATCCGTTCCA 1310      1320      1330      1340      1350
    TCATATTTGTGTAGGTTACTTATTCTCCTTTTGTTGACTAAGTCAATAAT
    AGTATAAACACATCCAATGAATAAGAGGAAAACAACTGATTCAGTTATTA 1360      1370      1380      1390      1400
    CAGAATCAGCAGGTTTGGAGTCAGCTTGGCAGGGATCAGCAGCCTGGGTT
    GTCTTAGTCGTCCAAACCTCAGTCGAACCGTCCCTAGTCGTCGGACCCAA

>mTTR/5'/ut
                                            |
         1410      1420      1430      1440 |    1450
    GGAAGGAGGGGGTATAAAAGCCCCTTCACCAGGAGAAGCCGTCACACAGA
    CCTTCCTCCCCATATTTTCGGGGAAGTGGTCCTCTTCGGCAGTGTGTCT

>MVMint
              |
         1460 |    1470      1480      1490      1500
    TCCACAAGCTCCTGAAGAGGTAAGGGTTTAAGGGATGGTTGGTTGGTGGG
    AGGTGTTCGAGGACTTCTCCATTCCCAAATTCCCTACCAACCAACCACCC 1510      1520      1530      1540      1550
    GTATTAATGTTTAATTACCTGGAGCACCTGCCTGAAATCACTTTTTTTCA
    CATAATTACAAATTAATGGACCTCGTGGACGGACTTTAGTGAAAAAAGT 1560      1570      1580      1590      1600
    GGTTGGCTAGCATGCAGCGCGTGAACATGATCATGGCCGAGAGCCCCGGC
    CCAACCGATCGTACGTCGCGCACTTGTACTAGTACCGGCTCTCGGGGCCG
                       ---------------HUFIXCOPTMT--------------------->

1610      1620      1630      1640      1650
    CTGATCACCATCTGCCTGCTGGGCTACCTGCTGAGCGCCGAGTGCACCGT
    GACTAGTGGTAGACGGACGACCCGATGGACGACTCGCGGCTCACGTGGCA
                       ---------------HUFIXCOPTMT--------------------->

1660      1670      1680      1690      1700
    GTTCCTGGACCACGAGAACGCCAACAAGATCCTGAACCGCCCCAAGCGCT
    CAAGGACCTGGTGCTCTTGCGGTTGTTCTAGGACTTGGCGGGGTTCGCGA
                       ---------------HUFIXCOPTMT--------------------->

1710      1720      1730      1740      1750
    ACAACAGCGGCAAGCTGGAGGAGTTCGTGCAGGGCAACCTGGAGCGCGAG
    TGTTGTCGCCGTTCGACCTCCTCAAGCACGTCCCGTTGGACCTCGCGCTC
                       ---------------HUFIXCOPTMT--------------------->

1760      1770      1780      1790      1800
    TGCATGGAGGAGAAGTGCAGCTTCGAGGAGGCCCGCGAGGTGTTCGAGAA
    ACGTACCTCCTCTTCACGTCGAAGCTCCTCCGGGCGCTCCACAAGCTCTT
```

FIG. 1B (continued)

```
                          HUFIXCOPTMT                           >
          1810      1820      1830      1840      1850
       CACCGAGCGCACCACCGAGTTCTGGAAGCAGTACGTGGACGGCGACCAGT
       GTGGCTCGCGTGGTGGCTCAAGACCTTCGTCATGCACCTGCCGCTGGTCA
                          HUFIXCOPTMT                           >
          1860      1870      1880      1890      1900
       GCGAGAGCAACCCCTGCCTGAACGGCGGCAGCTGCAAGGACGACATCAAC
       CGCTCTCGTTGGGGACGGACTTGCCGCCGTCGACGTTCCTGCTGTAGTTG
                          HUFIXCOPTMT                           >
          1910      1920      1930      1940      1950
       AGCTACGAGTGCTGGTGCCCCTTCGGCTTCGAGGGCAAGAACTGCGAGCT
       TCGATGCTCACGACCACGGGGAAGCCGAAGCTCCCGTTCTTGACGCTCGA
                          HUFIXCOPTMT                           >
          1960      1970      1980      1990      2000
       GGACGTGACCTGCAACATCAAGAACGGCCGCTGCGAGCAGTTCTGCAAGA
       CCTGCACTGGACGTTGTAGTTCTTGCCGGCGACGCTCGTCAAGACGTTCT
                          HUFIXCOPTMT                           >
          2010      2020      2030      2040      2050
       ACAGCGCCGACAACAAGGTGGTGTGCAGCTGCACCGAGGGCTACCGCCTG
       TGTCGCGGCTGTTGTTCCACCACACGTCGACGTGGCTCCCGATGGCGGAC
                          HUFIXCOPTMT                           >
          2060      2070      2080      2090      2100
       GCCGAGAACCAGAAGAGCTGCGAGCCCGCCGTGCCCTTCCCCTGCGGCCG
       CGGCTCTTGGTCTTCTCGACGCTCGGGCGGCACGGGAAGGGGACGCCGGC
                          HUFIXCOPTMT                           >
          2110      2120      2130      2140      2150
       CGTGAGCGTGAGCCAGACCAGCAAGCTGACCCGCGCCGAGGCCGTGTTCC
       GCACTCGCACTCGGTCTGGTCGTTCGACTGGGCGCGGCTCCGGCACAAGG
                          HUFIXCOPTMT                           >
          2160      2170      2180      2190      2200
       CCGACGTGGACTACGTGAACAGCACCGAGGCCGAGACCATCCTGGACAAC
       GGCTGCACCTGATGCACTTGTCGTGGCTCCGGCTCTGGTAGGACCTGTTG
                          HUFIXCOPTMT                           >
          2210      2220      2230      2240      2250
       ATCACCCAGAGCACCCAGAGCTTCAACGACTTCACCCGCGTGGTGGGCGG
       TAGTGGGTCTCGTGGGTCTCGAAGTTGCTGAAGTGGGCGCACCACCCGCC
                          HUFIXCOPTMT                           >
          2260      2270      2280      2290      2300
       CGAGGACGCCAAGCCCGGCCAGTTCCCCTGGCAGGTGGTGCTGAACGGCA
       GCTCCTGCGGTTCGGGCCGGTCAAGGGGACCGTCCACCACGACTTGCCGT
                          HUFIXCOPTMT                           >
          2310      2320      2330      2340      2350
       AGGTGGACGCCTTCTGCGGCGGCAGCATCGTGAACGAGAAGTGGATCGTG
       TCCACCTGCGGAAGACGCCGCCGTCGTAGCACTTGCTCTTCACCTAGCAC
```

FIG. 1B (continued)

```
                          HUFIXCOPTMT                    >
         2360      2370      2380      2390      2400
   ACCGCCGCCCACTGCGTGGAGACCGGCGTGAAGATCACCGTGGTGGCCGG
   TGGCGGCGGGTGACGCACCTCTGGCCGCACTTCTAGTGGCACCACCGGCC
                          HUFIXCOPTMT                    >
         2410      2420      2430      2440      2450
   CGAGCACAACATCGAGGAGACCGAGCACACCGAGCAGAAGCGCAACGTGA
   GCTCGTGTTGTAGCTCCTCTGGCTCGTGTGGCTCGTCTTCGCGTTGCACT
                          HUFIXCOPTMT                    >
         2460      2470      2480      2490      2500
   TCCGCATCATCCCCCACCACAACTACAACGCCGCCATCAACAAGTACAAC
   AGGCGTAGTAGGGGGTGGTGTTGATGTTGCGGCGGTAGTTGTTCATGTTG
                          HUFIXCOPTMT                    >
         2510      2520      2530      2540      2550
   CACGACATCGCCCTGCTGGAGCTGGACGAGCCCCTGGTGCTGAACAGCTA
   GTGCTGTAGCGGGACGACCTCGACCTGCTCGGGGACCACGACTTGTCGAT
                          HUFIXCOPTMT                    >
         2560      2570      2580      2590      2600
   CGTGACCCCCATCTGCATCGCCGACAAGGAGTACACCAACATCTTCCTGA
   GCACTGGGGGTAGACGTAGCGGCTGTTCCTCATGTGGTTGTAGAAGGACT
                          HUFIXCOPTMT                    >
         2610      2620      2630      2640      2650
   AGTTCGGCAGCGGCTACGTGAGCGGCTGGGGCCGCGTGTTCCACAAGGGC
   TCAAGCCGTCGCCGATGCACTCGCCGACCCCGGCGCACAAGGTGTTCCCG
                          HUFIXCOPTMT                    >
         2660      2670      2680      2690      2700
   CGCAGCGCCCTGGTGCTGCAGTACCTGCGCGTGCCCCTGGTGGACCGCGC
   GCGTCGCGGGACCACGACGTCATGGACGCGCACGGGGACCACCTGGCGCG
                          HUFIXCOPTMT                    >
         2710      2720      2730      2740      2750
   CACCTGCCTGCGCAGCACCAAGTTCACCATCTACAACAACATGTTCTGCG
   GTGGACGGACGCGTCGTGGTTCAAGTGGTAGATGTTGTTGTACAAGACGC
                          HUFIXCOPTMT                    >
         2760      2770      2780      2790      2800
   CCGGCTTCCACGAGGGCGGCCGCGACAGCTGCCAGGGCGACAGCGGCGGC
   GGCCGAAGGTGCTCCCGCCGGCGCTGTCGACGGTCCCGCTGTCGCCGCCG
                          HUFIXCOPTMT                    >
         2810      2820      2830      2840      2850
   CCCCACGTGACCGAGGTGGAGGGCACCAGCTTCCTGACCGGCATCATCAG
   GGGGTGCACTGGCTCCACCTCCCGTGGTCGAAGGACTGGCCGTAGTAGTC
                          HUFIXCOPTMT                    >
         2860      2870      2880      2890      2900
   CTGGGGCGAGGAGTGCGCCATGAAGGGCAAGTACGGCATCTACACCAAGG
   GACCCCGCTCCTCACGCGGTACTTCCCGTTCATGCCGTAGATGTGGTTCC
```

FIG. 1B (continued)

```
                        HUFIXCOPTMT                          >
         2910      2920      2930      2940      2950
     TGAGCCGCTACGTGAACTGGATCAAGGAGAAGACCAAGCTGACCTGGAGA
     ACTCGGCGATGCACTTGACCTAGTTCCTCTTCTGGTTCGACTGGACCTCT
                             HUFIXCOPTMT                     >
         2960      2970      2980      2990      3000
     TCTGATCAGCCTCGACTGTGCCTTCTAGTTGCCAGCCATCTGTTGTTTGC
     AGACTAGTCGGAGCTGACACGGAAGATCAACGGTCGGTAGACAACAAACG
                                BGHPA                        >
         3010      3020      3030      3040      3050
     CCCTCCCCCGTGCCTTCCTTGACCCTGGAAGGTGCCACTCCCACTGTCCT
     GGGAGGGGGCACGGAAGGAACTGGGACCTTCCACGGTGAGGGTGACAGGA
                                BGHPA                        >
         3060      3070      3080      3090      3100
     TTCCTAATAAAATGAGGAAATTGCATCGCATTGTCTGAGTAGGTGTCATT
     AAGGATTATTTTACTCCTTTAACGTAGCGTAACAGACTCATCCACAGTAA
                                BGHPA                        >
         3110      3120      3130      3140      3150
     CTATTCTGGGGGGTGGGGTGGGGCAGGACAGCAAGGGGGAGGATTGGGAA
     GATAAGACCCCCCACCCCACCCCGTCCTGTCGTTCCCCCTCCTAACCCTT
                                BGHPA                        >
         3160      3170      3180      3190      3200
     GACAATAGCAGGCATGCTGGGGATCTGATAGCAGGCATGCTGGGGAGAGA
     CTGTTATCGTCCGTACGACCCCTAGACTATCGTCCGTACGACCCCTCTCT
              BGHPA             >
         3210      3220      3230      3240      3250
     TCGATCTAGGAACCCCTAGTGATGGAGTTGGCCACTCCCTCTCTGCGCGC
     AGCTAGATCCTTGGGGATCACTACCTCAACCGGTGAGGGAGAGACGCGCG
                                 ITR                         >
         3260      3270      3280      3290      3300
     TCGCTCGCTCACTGAGGCCGCCCGGGCAAAGCCCGGGCGTCGGGCGACCT
     AGCGAGCGAGTGACTCCGGCGGGCCCGTTTCGGGCCCGCAGCCCGCTGGA
                                 ITR                         >
         3310      3320      3330      3340      3350
     TTGGTCGCCCGGCCTCAGTGAGCGAGCGAGCGCGCAGAGAGGGAGTGGCC
     AACCAGCGGGCCGGAGTCACTCGCTCGCTCGCGCGTCTCTCCCTCACCGG
                                 ITR                         >
         3360      3370      3380      3390      3400
     AACCCCCCCCCCCCCCCCCTGCATGCAGGCGATTCTCTTGTTTGCTCCA
     TTGGGGGGGGGGGGGGGGGACGTACGTCCGCTAAGAGAACAAACGAGGT
     ----->
         3410      3420      3430      3440      3450
     GACTCTCAGGCAATGACCTGATAGCCTTTGTAGAGACCTCTCAAAAATAG
     CTGAGAGTCCGTTACTGGACTATCGGAAACATCTCTGGAGAGTTTTTATC
```

FIG. 1B (continued)

```
       3460       3470       3480       3490       3500
CTACCCTCTCCGGCATGAATTTATCAGCTAGAACGGTTGAATATCATATT
GATGGGAGAGGCCGTACTTAAATAGTCGATCTTGCCAACTTATAGTATAA
       3510       3520       3530       3540       3550
GATGGTGATTTGACTGTCTCCGGCCTTTCTCACCCGTTTGAATCTTTACC
CTACCACTAAACTGACAGAGGCCGGAAAGAGTGGGCAAACTTAGAAATGG
       3560       3570       3580       3590       3600
TACACATTACTCAGGCATTGCATTTAAAATATATGAGGGTTCTAAAAATT
ATGTGTAATGAGTCCGTAACGTAAATTTTATATACTCCCAAGATTTTTAA
       3610       3620       3630       3640       3650
TTTATCCTTGCGTTGAAATAAAGGCTTCTCCCGCAAAAGTATTACAGGGT
AAATAGGAACGCAACTTTATTTCCGAAGAGGGCGTTTTCATAATGTCCCA
       3660       3670       3680       3690       3700
CATAATGTTTTTGGTACAACCGATTTAGCTTTATGCTCTGAGGCTTTATT
GTATTACAAAAACCATGTTGGCTAAATCGAAATACGAGACTCCGAAATAA
       3710       3720       3730       3740       3750
GCTTAATTTTGCTAATTCTTTGCCTTGCCTGTATGATTTATTGGATGTTG
CGAATTAAAACGATTAAGAAACGGAACGGACATACTAAATAACCTACAAC
       3760       3770       3780       3790       3800
GAATTCCTGATGCGGTATTTTCTCCTTACGCATCTGTGCGGTATTTCACA
CTTAAGGACTACGCCATAAAGAGGAATGCGTAGACACGCCATAAAGTGT
       3810       3820       3830       3840       3850
CCGCATATGGTGCACTCTCAGTACAATCTGCTCTGATGCCGCATAGTTAA
GGCGTATACCACGTGAGAGTCATGTTAGACGAGACTACGGCGTATCAATT
       3860       3870       3880       3890       3900
GCCAGCCCCGACACCCGCCAACACCCGCTGACGCGCCCTGACGGGCTTGT
CGGTCGGGGCTGTGGGCGGTTGTGGGCGACTGCGCGGGACTGCCCGAACA
       3910       3920       3930       3940       3950
CTGCTCCCGGCATCCGCTTACAGACAAGCTGTGACCGTCTCCGGGAGCTG
GACGAGGGCCGTAGGCGAATGTCTGTTCGACACTGGCAGAGGCCCTCGAC
       3960       3970       3980       3990       4000
CATGTGTCAGAGGTTTTCACCGTCATCACCGAAACGCGCGAGACGAAAGG
GTACACAGTCTCCAAAAGTGGCAGTAGTGGCTTTGCGCGCTCTGCTTTCC
       4010       4020       4030       4040       4050
GCCTCGTGATACGCCTATTTTTATAGGTTAATGTCATGATAATAATGGTT
CGGAGCACTATGCGGATAAAAATATCCAATTACAGTACTATTATTACCAA
       4060       4070       4080       4090       4100
TCTTAGACGTCAGGTGGCACTTTTCGGGGAAATGTGCGCGGAACCCCTAT
AGAATCTGCAGTCCACCGTGAAAAGCCCCTTTACACGCGCCTTGGGGATA
       4110       4120       4130       4140       4150
TTGTTTATTTTTCTAAATACATTCAAATATGTATCCGCTCATGAGACAAT
```

FIG. 1B (continued)

```
AACAAATAAAAAGATTTATGTAAGTTTATACATAGGCGAGTACTCTGTTA 4160      4170      4180      4190      4200
AACCCTGATAAATGCTTCAATAATATTGAAAAAGGAAGAGTATGAGTATT
TTGGGACTATTTACGAAGTTATTATAACTTTTTCCTTCTCATACTCATAA
                                          ....................>
        4210      4220      4230      4240      4250
CAACATTTCCGTGTCGCCCTTATTCCCTTTTTTGCGGCATTTTGCCTTCC
GTTGTAAAGGCACAGCGGGAATAAGGGAAAAAACGCCGTAAAACGGAAGG
................................AMPR................................>
        4260      4270      4280      4290      4300
TGTTTTTGCTCACCCAGAAACGCTGGTGAAAGTAAAAGATGCTGAAGATC
ACAAAAACGAGTGGGTCTTTGCGACCACTTTCATTTTCTACGACTTCTAG
................................AMPR................................>
        4310      4320      4330      4340      4350
AGTTGGGTGCACGAGTGGGTTACATCGAACTGGATCTCAACAGCGGTAAG
TCAACCCACGTGCTCACCCAATGTAGCTTGACCTAGAGTTGTCGCCATTC
................................AMPR................................>
        4360      4370      4380      4390      4400
ATCCTTGAGAGTTTTCGCCCCGAAGAACGTTTTCCAATGATGAGCACTTT
TAGGAACTCTCAAAAGCGGGGCTTCTTGCAAAAGGTTACTACTCGTGAAA
................................AMPR................................>
        4410      4420      4430      4440      4450
TAAAGTTCTGCTATGTGGCGCGGTATTATCCCGTATTGACGCCGGGCAAG
ATTTCAAGACGATACACCGCGCCATAATAGGGCATAACTGCGGCCCGTTC
................................AMPR................................>
        4460      4470      4480      4490      4500
AGCAACTCGGTCGCCGCATACACTATTCTCAGAATGACTTGGTTGAGTAC
TCGTTGAGCCAGCGGCGTATGTGATAAGAGTCTTACTGAACCAACTCATG
................................AMPR................................>
        4510      4520      4530      4540      4550
TCACCAGTCACAGAAAAGCATCTTACGGATGGCATGACAGTAAGAGAATT
AGTGGTCAGTGTCTTTTCGTAGAATGCCTACCGTACTGTCATTCTCTTAA
................................AMPR................................>
        4560      4570      4580      4590      4600
ATGCAGTGCTGCCATAACCATGAGTGATAACACTGCGGCCAACTTACTTC
TACGTCACGACGGTATTGGTACTCACTATTGTGACGCCGGTTGAATGAAG
................................AMPR................................>
        4610      4620      4630      4640      4650
TGACAACGATCGGAGGACCGAAGGAGCTAACCGCTTTTTTGCACAACATG
ACTGTTGCTAGCCTCCTGGCTTCCTCGATTGGCGAAAAAACGTGTTGTAC
................................AMPR................................>
        4660      4670      4680      4690      4700
GGGGATCATGTAACTCGCCTTGATCGTTGGGAACCGGAGCTGAATGAAGC
CCCCTAGTACATTGAGCGGAACTAGCAACCCTTGGCCTCGACTTACTTCG
```

FIG. 1B (continued)

```
                             AMPR                               >
        4710      4720      4730      4740      4750
CATACCAAACGACGAGCGTGACACCACGATGCCTGTAGCAATGGCAACAA
GTATGGTTTGCTGCTCGCACTGTGGTGCTACGGACATCGTTACCGTTGTT
                              AMPR                              >
        4760      4770      4780      4790      4800
CGTTGCGCAAACTATTAACTGGCGAACTACTTACTCTAGCTTCCCGGCAA
GCAACGCGTTTGATAATTGACCGCTTGATGAATGAGATCGAAGGGCCGTT
                              AMPR                              >
        4810      4820      4830      4840      4850
CAATTAATAGACTGGATGGAGGCGGATAAAGTTGCAGGACCACTTCTGCG
GTTAATTATCTGACCTACCTCCGCCTATTTCAACGTCCTGGTGAAGACGC
                              AMPR                              >
        4860      4870      4880      4890      4900
CTCGGCCCTTCCGGCTGGCTGGTTTATTGCTGATAAATCTGGAGCCGGTG
GAGCCGGGAAGGCCGACCGACCAAATAACGACTATTTAGACCTCGGCCAC
                              AMPR                              >
        4910      4920      4930      4940      4950
AGCGTGGGTCTCGCGGTATCATTGCAGCACTGGGGCCAGATGGTAAGCCC
TCGCACCCAGAGCGCCATAGTAACGTCGTGACCCCGGTCTACCATTCGGG
                              AMPR                              >
        4960      4970      4980      4990      5000
TCCCGTATCGTAGTTATCTACACGACGGGGAGTCAGGCAACTATGGATGA
AGGGCATAGCATCAATAGATGTGCTGCCCCTCAGTCCGTTGATACCTACT
                              AMPR                              >
        5010      5020      5030      5040      5050
ACGAAATAGACAGATCGCTGAGATAGGTGCCTCACTGATTAAGCATTGGT
TGCTTTATCTGTCTAGCGACTCTATCCACGGAGTGACTAATTCGTAACCA
                              AMPR                              >
        5060      5070      5080      5090      5100
AACTGTCAGACCAAGTTTACTCATATATACTTTAGATTGATTTAAAACTT
TTGACAGTCTGGTTCAAATGAGTATATATGAAATCTAACTAAATTTTGAA
....>
        5110      5120      5130      5140      5150
CATTTTAATTTAAAAGGATCTAGGTGAAGATCCTTTTTGATAATCTCAT
GTAAAAATTAAATTTTCCTAGATCCACTTCTAGGAAAAACTATTAGAGTA
        5160      5170      5180      5190      5200
GACCAAAATCCCTTAACGTGAGTTTTCGTTCCACTGAGCGTCAGACCCCG
CTGGTTTTAGGGAATTGCACTCAAAAGCAAGGTGACTCGCAGTCTGGGGC
        5210      5220      5230      5240      5250
TAGAAAAGATCAAAGGATCTTCTTGAGATCCTTTTTTTCTGCGCGTAATC
ATCTTTTCTAGTTTCCTAGAAGAACTCTAGGAAAAAAAGACGCGCATTAG
                         PBR322 ORIGIN                          >
```

FIG. 1B (continued)

```
         5260      5270      5280      5290      5300
TGCTGCTTGCAAACAAAAAAACCACCGCTACCAGCGGTGGTTTGTTTGCC
ACGACGAACGTTTGTTTTTTTGGTGGCGATGGTCGCCACCAAACAAACGG
                    PBR322 ORIGIN                   >

5310      5320      5330      5340      5350
GGATCAAGAGCTACCAACTCTTTTTCCGAAGGTAACTGGCTTCAGCAGAG
CCTAGTTCTCGATGGTTGAGAAAAAGGCTTCCATTGACCGAAGTCGTCTC
                    PBR322 ORIGIN                   >

5360      5370      5380      5390      5400
CGCAGATACCAAATACTGTCCTTCTAGTGTAGCCGTAGTTAGGCCACCAC
GCGTCTATGGTTTATGACAGGAAGATCACATCGGCATCAATCCGGTGGTG
                    PBR322 ORIGIN                   >

5410      5420      5430      5440      5450
TTCAAGAACTCTGTAGCACCGCCTACATACCTCGCTCTGCTAATCCTGTT
AAGTTCTTGAGACATCGTGGCGGATGTATGGAGCGAGACGATTAGGACAA
                    PBR322 ORIGIN                   >

5460      5470      5480      5490      5500
ACCAGTGGCTGCTGCCAGTGGCGATAAGTCGTGTCTTACCGGGTTGGACT
TGGTCACCGACGACGGTCACCGCTATTCAGCACAGAATGGCCCAACCTGA
                    PBR322 ORIGIN                   >

5510      5520      5530      5540      5550
CAAGACGATAGTTACCGGATAAGGCGCAGCGGTCGGGCTGAACGGGGGGT
GTTCTGCTATCAATGGCCTATTCCGCGTCGCCAGCCCGACTTGCCCCCCA
                    PBR322 ORIGIN                   >

5560      5570      5580      5590      5600
TCGTGCACACAGCCCAGCTTGGAGCGAACGACCTACACCGAACTGAGATA
AGCACGTGTGTCGGGTCGAACCTCGCTTGCTGGATGTGGCTTGACTCTAT
                    PBR322 ORIGIN                   >

5610      5620      5630      5640      5650
CCTACAGCGTGAGCTATGAGAAAGCGCCACGCTTCCCGAAGGGAGAAAGG
GGATGTCGCACTCGATACTCTTTCGCGGTGCGAAGGGCTTCCCTCTTTCC
                    PBR322 ORIGIN                   >

5660      5670      5680      5690      5700
CGGACAGGTATCCGGTAAGCGGCAGGGTCGGAACAGGAGAGCGCACGAGG
GCCTGTCCATAGGCCATTCGCCGTCCCAGCCTTGTCCTCTCGCGTGCTCC
                    PBR322 ORIGIN                   >

5710      5720      5730      5740      5750
GAGCTTCCAGGGGGAAACGCCTGGTATCTTTATAGTCCTGTCGGGTTTCG
CTCGAAGGTCCCCCTTTGCGGACCATAGAAATATCAGGACAGCCCAAAGC
                    PBR322 ORIGIN                   >

5760      5770      5780      5790      5800
CCACCTCTGACTTGAGCGTCGATTTTTGTGATGCTCGTCAGGGGGCGGA
GGTGGAGACTGAACTCGCAGCTAAAAACACTACGAGCAGTCCCCCCGCCT
                    PBR322 ORIGIN                   >
```

FIG. 1B (continued)

```
         5810      5820      5830      5840      5850
GCCTATGGAAAAACGCCAGCAACGCGGCCTTTTTACGGTTCCTGGCCTTT
CGGATACCTTTTTGCGGTCGTTGCGCCGGAAAAATGCCAAGGACCGGAAA
         PBR322 ORIGIN         >

5860      5870      5880      5890      5900
TGCTGGCCTTTTGCTCACATGTTCTTTCCTGCGTTATCCCCTGATTCTGT
ACGACCGGAAAACGAGTGTACAAGAAAGGACGCAATAGGGGACTAAGACA 5910      5920      5930      5940      5950
GGATAACCGTATTACCGCCTTTGAGTGAGCTGATACCGCTCGCCGCAGCC
CCTATTGGCATAATGGCGGAAACTCACTCGACTATGGCGAGCGGCGTCGG 5960      5970      5980      5990      6000
GAACGACCGAGCGCAGCGAGTCAGTGAGCGAGGAAGCGGAAGAGCGCCCA
CTTGCTGGCTCGCGTCGCTCAGTCACTCGCTCCTTCGCCTTCTCGCGGGT 6010      6020      6030      6040
ATACGCAAACCGCCTCTCCCCGCGCGTTGGCCGATTCATTAATG
TATGCGTTTGGCGGAGAGGGGCGCGCAACCGGCTAAGTAATTAC
```

FIG. 1C

SEQ ID 2

```
          10        20        30        40        50
CAGCAGCTGGCGTAATAGCGAAGAGGCCCGCACCGATCGCCCTTCCCAAC
GTCGTCGACCGCATTATCGCTTCTCCGGGCGTGGCTAGCGGGAAGGGTTG 60        70        80        90       100
AGTTGCGCAGCCTGAATGGCGAATGGAATTCCAGACGATTGAGCGTCAAA
TCAACGCGTCGGACTTACCGCTTACCTTAAGGTCTGCTAACTCGCAGTTT 110       120       130       140       150
ATGTAGGTATTTCCATGAGCGTTTTTCCTGTTGCAATGGCTGGCGGTAAT
TACATCCATAAAGGTACTCGCAAAAAGGACAACGTTACCGACCGCCATTA 160       170       180       190       200
ATTGTTCTGGATATTACCAGCAAGGCCGATAGTTTGAGTTCTTCTACTCA
TAACAAGACCTATAATGGTCGTTCCGGCTATCAAACTCAAGAAGATGAGT 210       220       230       240       250
GGCAAGTGATGTTATTACTAATCAAAGAAGTATTGCGACAACGGTTAATT
CCGTTCACTACAATAATGATTAGTTTCTTCATAACGCTGTTGCCAATTAA 260       270       280       290       300
TGCGTGATGGACAGACTCTTTTACTCGGTGGCCTCACTGATTATAAAAAC
ACGCACTACCTGTCTGAGAAAATGAGCCACCGGAGTGACTAATATTTTTG 310       320       330       340       350
ACTTCTCAGGATTCTGGCGTACCGTTCCTGTCTAAAATCCCTTTAATCGG
TGAAGAGTCCTAAGACCGCATGGCAAGGACAGATTTTAGGGAAATTAGCC 360       370       380       390       400
CCTCCTGTTTAGCTCCCGCTCTGATTCTAACGAGGAAAGCACGTTATACG
GGAGGACAAATCGAGGGCGAGACTAAGATTGCTCCTTTCGTGCAATATGC 410       420       430       440       450
TGCTCGTCAAAGCAACCATAGTACGCGCCCTGTAGCGGCGCATTAAGCGC
ACGAGCAGTTTCGTTGGTATCATGCGCGGGACATCGCCGCGTAATTCGCG
                                               ─────────>
         460       470       480       490       500
GGCGGGTGTGGTGGTTACGCGCAGCGTGACCGCTACACTTGCCAGCGCCC
CCGCCCACACCACCAATGCGCGTCGCACTGGCGATGTGAACGGTCGCGGG
─────────────────────F1 ORIGIN─────────────────────>
         510       520       530       540       550
TAGCGCCCGCTCCTTTCGCTTTCTTCCCTTCCTTTCTCGCCACGTTCGCC
ATCGCGGGCGAGGAAAGCGAAAGAAGGGAAGGAAAGAGCGGTGCAAGCGG
─────────────────────F1 ORIGIN─────────────────────>
         560       570       580       590       600
GGCTTTCCCCGTCAAGCTCTAAATCGGGGGCTCCCTTTAGGGTTCCGATT
CCGAAAGGGGCAGTTCGAGATTTAGCCCCCGAGGGAAATCCCAAGGCTAA
─────────────────────F1 ORIGIN─────────────────────>
```

FIG. 1C (continued)

```
           610        620        630        640        650
    TAGTGCTTTACGGCACCTCGACCCCAAAAAACTTGATTAGGGTGATGGTT
    ATCACGAAATGCCGTGGAGCTGGGGTTTTTTGAACTAATCCCACTACCAA
    ................................F1 ORIGIN........................................>

660        670        680        690        700
    CACGTAGTGGGCCATCGCCCTGATAGACGGTTTTTCGCCCTTTGACGTTG
    GTGCATCACCCGGTAGCGGGACTATCTGCCAAAAAGCGGGAAACTGCAAC
    ................................F1 ORIGIN........................................>

710        720        730        740        750
    GAGTCCACGTTCTTTAATAGTGGACTCTTGTTCCAAACTGGAACAACACT
    CTCAGGTGCAAGAAATTATCACCTGAGAACAAGGTTTGACCTTGTTGTGA
    ................................F1 ORIGIN........................................>

760        770        780        790        800
    CAACCCTATCTCGGTCTATTCTTTTGATTTATAAGGGATTTTGCCGATTT
    GTTGGGATAGAGCCAGATAAGAAAACTAAATATTCCCTAAAACGGCTAAA 810        820        830        840        850
    CGGCCTATTGGTTAAAAAATGAGCTGATTTAACAAAAATTTAACGCGAAT
    GCCGGATAACCAATTTTTTACTCGACTAAATTGTTTTTAAATTGCGCTTA 860        870        880        890        900
    TTTAACAAAATATTAACGTTTACAATTTAAATATTTGCTTATACAATCTT
    AAATTGTTTTATAATTGCAAATGTTAAATTTATAAACGAATATGTTAGAA 910        920        930        940        950
    CCTGTTTTTGGGGCTTTTCTGATTATCAACCGGGGTACATATGATTGACA
    GGACAAAAACCCCGAAAAGACTAATAGTTGGCCCCATGTATACTAACTGT 960        970        980        990       1000
    TGCTAGTTTTACGATTACCGTTCATCGCCTGCACTGCGCGCTCGCTCGCT
    ACGATCAAAATGCTAATGGCAAGTAGCGGACGTGACGCGCGAGCGAGCGA
                                              .....MUTATEDITR......>

1010       1020       1030       1040       1050
    CACTGAGGCCGCCCGGGCAAAGCCCGGGCGTCGGGCGACCTTTGGTCGCC
    GTGACTCCGGCGGGCCCGTTTCGGGCCCGCAGCCCGCTGGAAACCAGCGG
    ................................MUTATEDITR........................................>

1060       1070       1080       1090       1100
    CGGCCTCAGTGAGCGAGCGAGCGCGCAGAGAGGGAGTGGAATTCACGCGT
    GCCGGAGTCACTCGCTCGCTCGCGCGTCTCTCCCTCACCTTAAGTGCGCA
    ................MUTATEDITR.................>

1110       1120       1130       1140       1150
    GGTACGATCTGAATTCGGTACAATTCACGCGTGGTACGGCCGCGGTACCG
    CCATGCTAGACTTAAGCCATGTTAAGTGCGCACCATGCCGGCGCCATGGC 1160       1170       1180       1190       1200
    GCGCGCCGGGGGAGGCTGCTGGTGAATATTAACCAAGGTCACCCCAGTTA
    CGCGCGGCCCCCTCCGACGACCACTTATAATTGGTTCCAGTGGGGTCAAT

>Serp_enh    >mTTR/promoter
```

FIG. 1C (continued)

```
              1210      1220      1230     |1240 |    1250
       TCGGAGGAGCAAACAGGGGCTAAGTCCACACGCGTGGTACCGTCTGTCTG
       AGCCTCCTCGTTTGTCCCCGATTCAGGTGTGCGCACCATGGCAGACAGAC 1260      1270      1280      1290      1300
       CACATTTCGTAGAGCGAGTGTTCCGATACTCTAATCTCCCTAGGCAAGGT
       GTGTAAAGCATCTCGCTCACAAGGCTATGAGATTAGAGGGATCCGTTCCA 1310      1320      1330      1340      1350
       TCATATTTGTGTAGGTTACTTATTCTCCTTTTGTTGACTAAGTCAATAAT
       AGTATAAACACATCCAATGAATAAGAGGAAAACAACTGATTCAGTTATTA 1360      1370      1380      1390      1400
       CAGAATCAGCAGGTTTGGAGTCAGCTTGGCAGGGATCAGCAGCCTGGGTT
       GTCTTAGTCGTCCAAACCTCAGTCGAACCGTCCCTAGTCGTCGGACCCAA

>mTTR/5'/ut
                                                      |
              1410      1420      1430      1440    | 1450
       GGAAGGAGGGGGTATAAAAGCCCCTTCACCAGGAGAAGCCGTCACACAGA
       CCTTCCTCCCCCATATTTTCGGGGAAGTGGTCCTCTTCGGCAGTGTGTCT

>MVMint
                         |
              1460    | 1470      1480      1490      1500
       TCCACAAGCTCCTGAAGAGGTAAGGGTTTAAGGGATGGTTGGTTGGTGGG
       AGGTGTTCGAGGACTTCTCCATTCCCAAATTCCCTACCAACCAACCACCC 1510      1520      1530      1540      1550
       GTATTAATGTTTAATTACCTGGAGCACCTGCCTGAAATCACTTTTTTTCA
       CATAATTACAAATTAATGGACCTCGTGGACGGACTTTAGTGAAAAAAGT 1560      1570      1580      1590      1600
       GGTTGGCTAGCATGCAGCGCGTGAACATGATCATGGCCGAGAGCCCCGGC
       CCAACCGATCGTACGTCGCGCACTTGTACTAGTACCGGCTCTCGGGGCCG
                              HUFIXCOPTMT                  >

1610      1620      1630      1640      1650
       CTGATCACCATCTGCCTGCTGGGCTACCTGCTGAGCGCCGAGTGCACCGT
       GACTAGTGGTAGACGGACGACCCGATGGACGACTCGCGGCTCACGTGGCA
                              HUFIXCOPTMT                  >

1660      1670      1680      1690      1700
       GTTCCTGGACCACGAGAACGCCAACAAGATCCTGAACCGCCCCAAGCGCT
       CAAGGACCTGGTGCTCTTGCGGTTGTTCTAGGACTTGGCGGGGTTCGCGA
                              HUFIXCOPTMT                  >

1710      1720      1730      1740      1750
       ACAACAGCGGCAAGCTGGAGGAGTTCGTGCAGGGCAACCTGGAGCGCGAG
       TGTTGTCGCCGTTCGACCTCCTCAAGCACGTCCCGTTGGACCTCGCGCTC
                              HUFIXCOPTMT                  >

1760      1770      1780      1790      1800
       TGCATGGAGGAGAAGTGCAGCTTCGAGGAGGCCCGCGAGGTGTTCGAGAA
```

FIG. 1C (continued)

```
ACGTACCTCCTCTTCACGTCGAAGCTCCTCCGGGCGCTCCACAAGCTCTT
                       HUFIXCOPTMT                >

1810      1820      1830      1840      1850
CACCGAGCGCACCACCGAGTTCTGGAAGCAGTACGTGGACGGCGACCAGT
GTGGCTCGCGTGGTGGCTCAAGACCTTCGTCATGCACCTGCCGCTGGTCA
                       HUFIXCOPTMT                >

1860      1870      1880      1890      1900
GCGAGAGCAACCCCTGCCTGAACGGCGGCAGCTGCAAGGACGACATCAAC
CGCTCTCGTTGGGGACGGACTTGCCGCCGTCGACGTTCCTGCTGTAGTTG
                       HUFIXCOPTMT                >

1910      1920      1930      1940      1950
AGCTACGAGTGCTGGTGCCCCTTCGGCTTCGAGGGCAAGAACTGCGAGCT
TCGATGCTCACGACCACGGGGAAGCCGAAGCTCCCGTTCTTGACGCTCGA
                       HUFIXCOPTMT                >

1960      1970      1980      1990      2000
GGACGTGACCTGCAACATCAAGAACGGCCGCTGCGAGCAGTTCTGCAAGA
CCTGCACTGGACGTTGTAGTTCTTGCCGGCGACGCTCGTCAAGACGTTCT
                       HUFIXCOPTMT                >

2010      2020      2030      2040      2050
ACAGCGCCGACAACAAGGTGGTGTGCAGCTGCACCGAGGGCTACCGCCTG
TGTCGCGGCTGTTGTTCCACCACACGTCGACGTGGCTCCCGATGGCGGAC
                       HUFIXCOPTMT                >

2060      2070      2080      2090      2100
GCCGAGAACCAGAAGAGCTGCGAGCCCGCCGTGCCCTTCCCCTGCGGCCG
CGGCTCTTGGTCTTCTCGACGCTCGGGCGGCACGGGAAGGGGACGCCGGC
                       HUFIXCOPTMT                >

2110      2120      2130      2140      2150
CGTGAGCGTGAGCCAGACCAGCAAGCTGACCCGCGCCGAGGCCGTGTTCC
GCACTCGCACTCGGTCTGGTCGTTCGACTGGGCGCGGCTCCGGCACAAGG
                       HUFIXCOPTMT                >

2160      2170      2180      2190      2200
CCGACGTGGACTACGTGAACAGCACCGAGGCCGAGACCATCCTGGACAAC
GGCTGCACCTGATGCACTTGTCGTGGCTCCGGCTCTGGTAGGACCTGTTG
                       HUFIXCOPTMT                >

2210      2220      2230      2240      2250
ATCACCCAGAGCACCCAGAGCTTCAACGACTTCACCCGCGTGGTGGGCGG
TAGTGGGTCTCGTGGGTCTCGAAGTTGCTGAAGTGGGCGCACCACCCGCC
                       HUFIXCOPTMT                >

2260      2270      2280      2290      2300
CGAGGACGCCAAGCCCGGCCAGTTCCCCTGGCAGGTGGTGCTGAACGGCA
GCTCCTGCGGTTCGGGCCGGTCAAGGGGACCGTCCACCACGACTTGCCGT
                       HUFIXCOPTMT                >

2310      2320      2330      2340      2350
AGGTGGACGCCTTCTGCGGCGGCAGCATCGTGAACGAGAAGTGGATCGTG
```

FIG. 1C (continued)

```
TCCACCTGCGGAAGACGCCGCCGTCGTAGCACTTGCTCTTCACCTAGCAC
                        HUFIXCOPTMT                >
       2360      2370      2380      2390      2400
ACCGCCGCCCACTGCGTGGAGACCGGCGTGAAGATCACCGTGGTGGCCGG
TGGCGGCGGGTGACGCACCTCTGGCCGCACTTCTAGTGGCACCACCGGCC
                        HUFIXCOPTMT                >
       2410      2420      2430      2440      2450
CGAGCACAACATCGAGGAGACCGAGCACACCGAGCAGAAGCGCAACGTGA
GCTCGTGTTGTAGCTCCTCTGGCTCGTGTGGCTCGTCTTCGCGTTGCACT
                        HUFIXCOPTMT                >
       2460      2470      2480      2490      2500
TCCGCATCATCCCCCACCACAACTACAACGCCGCCATCAACAAGTACAAC
AGGCGTAGTAGGGGGTGGTGTTGATGTTGCGGCGGTAGTTGTTCATGTTG
                        HUFIXCOPTMT                >
       2510      2520      2530      2540      2550
CACGACATCGCCCTGCTGGAGCTGGACGAGCCCCTGGTGCTGAACAGCTA
GTGCTGTAGCGGGACGACCTCGACCTGCTCGGGGACCACGACTTGTCGAT
                        HUFIXCOPTMT                >
       2560      2570      2580      2590      2600
CGTGACCCCCATCTGCATCGCCGACAAGGAGTACACCAACATCTTCCTGA
GCACTGGGGGTAGACGTAGCGGCTGTTCCTCATGTGGTTGTAGAAGGACT
                        HUFIXCOPTMT                >
       2610      2620      2630      2640      2650
AGTTCGGCAGCGGCTACGTGAGCGGCTGGGGCCGCGTGTTCCACAAGGGC
TCAAGCCGTCGCCGATGCACTCGCCGACCCCGGCGCACAAGGTGTTCCCG
                        HUFIXCOPTMT                >
       2660      2670      2680      2690      2700
CGCAGCGCCCTGGTGCTGCAGTACCTGCGCGTGCCCCTGGTGGACCGCGC
GCGTCGCGGGACCACGACGTCATGGACGCGCACGGGGACCACCTGGCGCG
                        HUFIXCOPTMT                >
       2710      2720      2730      2740      2750
CACCTGCCTGCGCAGCACCAAGTTCACCATCTACAACAACATGTTCTGCG
GTGGACGGACGCGTCGTGGTTCAAGTGGTAGATGTTGTTGTACAAGACGC
                        HUFIXCOPTMT                >
       2760      2770      2780      2790      2800
CCGGCTTCCACGAGGGCGGCCGCGACAGCTGCCAGGGCGACAGCGGCGGC
GGCCGAAGGTGCTCCCGCCGGCGCTGTCGACGGTCCCGCTGTCGCCGCCG
                        HUFIXCOPTMT                >
       2810      2820      2830      2840      2850
CCCCACGTGACCGAGGTGGAGGGCACCAGCTTCCTGACCGGCATCATCAG
GGGGTGCACTGGCTCCACCTCCCGTGGTCGAAGGACTGGCCGTAGTAGTC
                        HUFIXCOPTMT                >
       2860      2870      2880      2890      2900
CTGGGGCGAGGAGTGCGCCATGAAGGGCAAGTACGGCATCTACACCAAGG
```

FIG. 1C (continued)

```
GACCCCGCTCCTCACGCGGTACTTCCCGTTCATGCCGTAGATGTGGTTCC
                      HUFIXCOPTMT                              >

2910      2920      2930      2940      2950
TGAGCCGCTACGTGAACTGGATCAAGGAGAAGACCAAGCTGACCTGGAGA
ACTCGGCGATGCACTTGACCTAGTTCCTCTTCTGGTTCGACTGGACCTCT
                      HUFIXCOPTMT                              >

2960      2970      2980      2990      3000
TCTGATCAGCCTCGACTGTGCCTTCTAGTTGCCAGCCATCTGTTGTTTGC
AGACTAGTCGGAGCTGACACGGAAGATCAACGGTCGGTAGACAACAAACG
                           BGHPA                              >

3010      3020      3030      3040      3050
CCCTCCCCCGTGCCTTCCTTGACCCTGGAAGGTGCCACTCCCACTGTCCT
GGGAGGGGGCACGGAAGGAACTGGGACCTTCCACGGTGAGGGTGACAGGA
                           BGHPA                              >

3060      3070      3080      3090      3100
TTCCTAATAAAATGAGGAAATTGCATCGCATTGTCTGAGTAGGTGTCATT
AAGGATTATTTTACTCCTTTAACGTAGCGTAACAGACTCATCCACAGTAA
                           BGHPA                              >

3110      3120      3130      3140      3150
CTATTCTGGGGGGTGGGGTGGGGCAGGACAGCAAGGGGGAGGATTGGGAA
GATAAGACCCCCACCCCACCCCGTCCTGTCGTTCCCCCTCCTAACCCTT
                           BGHPA                              >

3160      3170      3180      3190      3200
GACAATAGCAGGCATGCTGGGGATCTGATAGCAGGCATGCTGGGGAGAGA
CTGTTATCGTCCGTACGACCCCTAGACTATCGTCCGTACGACCCCTCTCT
             BGHPA         >

3210      3220      3230      3240      3250
TCGATCTAGGAACCCCTAGTGATGGAGTTGGCCACTCCCTCTCTGCGCGC
AGCTAGATCCTTGGGGATCACTACCTCAACCGGTGAGGGAGAGACGCGCG
                           ITR                                 >

3260      3270      3280      3290      3300
TCGCTCGCTCACTGAGGCCGCCCGGGCAAAGCCCGGGCGTCGGGCGACCT
AGCGAGCGAGTGACTCCGGCGGGCCCGTTTCGGGCCCGCAGCCCGCTGGA
                           ITR                                 >

3310      3320      3330      3340      3350
TTGGTCGCCCGGCCTCAGTGAGCGAGCGAGCGCGCAGAGAGGGAGTGGCC
AACCAGCGGGCCGGAGTCACTCGCTCGCTCGCGCGTCTCTCCCTCACCGG
                           ITR                                 >

3360      3370      3380      3390      3400
AACCCCCCCCCCCCCCCCTGCATGCAGGCGATTCTCTTGTTTGCTCCA
TTGGGGGGGGGGGGGGGGACGTACGTCCGCTAAGAGAACAAACGAGGT
___>

3410      3420      3430      3440      3450
GACTCTCAGGCAATGACCTGATAGCCTTTGTAGAGACCTCTCAAAAATAG
```

FIG. 1C (continued)

CTGAGAGTCCGTTACTGGACTATCGGAAACATCTCTGGAGAGTTTTTATC

```
         3460      3470      3480      3490      3500
CTACCCTCTCCGGCATGAATTTATCAGCTAGAACGGTTGAATATCATATT
GATGGGAGAGGCCGTACTTAAATAGTCGATCTTGCCAACTTATAGTATAA 3510      3520      3530      3540      3550
GATGGTGATTTGACTGTCTCCGGCCTTTCTCACCCGTTTGAATCTTTACC
CTACCACTAAACTGACAGAGGCCGGAAAGAGTGGGCAAACTTAGAAATGG 3560      3570      3580      3590      3600
TACACATTACTCAGGCATTGCATTTAAAATATATGAGGGTTCTAAAAATT
ATGTGTAATGAGTCCGTAACGTAAATTTTATATACTCCCAAGATTTTTAA 3610      3620      3630      3640      3650
TTTATCCTTGCGTTGAAATAAAGGCTTCTCCCGCAAAAGTATTACAGGGT
AAATAGGAACGCAACTTTATTTCCGAAGAGGGCGTTTTCATAATGTCCCA 3660      3670      3680      3690      3700
CATAATGTTTTTGGTACAACCGATTTAGCTTTATGCTCTGAGGCTTTATT
GTATTACAAAAACCATGTTGGCTAAATCGAAATACGAGACTCCGAAATAA 3710      3720      3730      3740      3750
GCTTAATTTTGCTAATTCTTTGCCTTGCCTGTATGATTTATTGGATGTTG
CGAATTAAAACGATTAAGAAACGGAACGGACATACTAAATAACCTACAAC 3760      3770      3780      3790      3800
GAATTCCTGATGCGGTATTTTCTCCTTACGCATCTGTGCGGTATTTCACA
CTTAAGGACTACGCCATAAAAGAGGAATGCGTAGACACGCCATAAAGTGT 3810      3820      3830      3840      3850
CCGCATATGGTGCACTCTCAGTACAATCTGCTCTGATGCCGCATAGTTAA
GGCGTATACCACGTGAGAGTCATGTTAGACGAGACTACGGCGTATCAATT 3860      3870      3880      3890      3900
GCCAGCCCCGACACCCGCCAACACCCGCTGACGCGCCCTGACGGGCTTGT
CGGTCGGGGCTGTGGGCGGTTGTGGGCGACTGCGCGGGACTGCCCGAACA 3910      3920      3930      3940      3950
CTGCTCCCGGCATCCGCTTACAGACAAGCTGTGACCGTCTCCGGGAGCTG
GACGAGGGCCGTAGGCGAATGTCTGTTCGACACTGGCAGAGGCCCTCGAC 3960      3970      3980      3990      4000
CATGTGTCAGAGGTTTTCACCGTCATCACCGAAACGCGCGAGACGAAAGG
GTACACAGTCTCCAAAAGTGGCAGTAGTGGCTTTGCGCGCTCTGCTTTCC 4010      4020      4030      4040      4050
GCCTCGTGATACGCCTATTTTTATAGGTTAATGTCATGATAATAATGGTT
CGGAGCACTATGCGGATAAAAATATCCAATTACAGTACTATTATTACCAA 4060      4070      4080      4090      4100
TCTTAGACGTCAGGTGGCACTTTTCGGGGAAATGTGCGCGGAACCCCTAT
AGAATCTGCAGTCCACCGTGAAAAGCCCCTTTACACGCGCCTTGGGGATA 4110      4120      4130      4140      4150
```

FIG. 1C (continued)

```
TTGTTTATTTTTCTAAATACATTCAAATATGTATCCGCTCATGAGACAAT
AACAAATAAAAAGATTTATGTAAGTTTATACATAGGCGAGTACTCTGTTA 4160      4170      4180      4190      4200
AACCCTGATAAATGCTTCAATAATATTGAAAAAGGAAGAGTATGAGTATT
TTGGGACTATTTACGAAGTTATTATAACTTTTTCCTTCTCATACTCATAA
                                                  >
                                      ----------------
       4210      4220      4230      4240      4250
CAACATTTCCGTGTCGCCCTTATTCCCTTTTTTGCGGCATTTTGCCTTCC
GTTGTAAAGGCACAGCGGGAATAAGGGAAAAAACGCCGTAAAACGGAAGG
--------------------------AMPR--------------------->

4260      4270      4280      4290      4300
TGTTTTTGCTCACCCAGAAACGCTGGTGAAAGTAAAAGATGCTGAAGATC
ACAAAAACGAGTGGGTCTTTGCGACCACTTTCATTTTCTACGACTTCTAG
--------------------------AMPR--------------------->

4310      4320      4330      4340      4350
AGTTGGGTGCACGAGTGGGTTACATCGAACTGGATCTCAACAGCGGTAAG
TCAACCCACGTGCTCACCCAATGTAGCTTGACCTAGAGTTGTCGCCATTC
--------------------------AMPR--------------------->

4360      4370      4380      4390      4400
ATCCTTGAGAGTTTTCGCCCCGAAGAACGTTTTCCAATGATGAGCACTTT
TAGGAACTCTCAAAAGCGGGGCTTCTTGCAAAAGGTTACTACTCGTGAAA
--------------------------AMPR--------------------->

4410      4420      4430      4440      4450
TAAAGTTCTGCTATGTGGCGCGGTATTATCCCGTATTGACGCCGGGCAAG
ATTTCAAGACGATACACCGCGCCATAATAGGGCATAACTGCGGCCCGTTC
--------------------------AMPR--------------------->

4460      4470      4480      4490      4500
AGCAACTCGGTCGCCGCATACACTATTCTCAGAATGACTTGGTTGAGTAC
TCGTTGAGCCAGCGGCGTATGTGATAAGAGTCTTACTGAACCAACTCATG
--------------------------AMPR--------------------->

4510      4520      4530      4540      4550
TCACCAGTCACAGAAAAGCATCTTACGGATGGCATGACAGTAAGAGAATT
AGTGGTCAGTGTCTTTTCGTAGAATGCCTACCGTACTGTCATTCTCTTAA
--------------------------AMPR--------------------->

4560      4570      4580      4590      4600
ATGCAGTGCTGCCATAACCATGAGTGATAACACTGCGGCCAACTTACTTC
TACGTCACGACGGTATTGGTACTCACTATTGTGACGCCGGTTGAATGAAG
--------------------------AMPR--------------------->

4610      4620      4630      4640      4650
TGACAACGATCGGAGGACCGAAGGAGCTAACCGCTTTTTTGCACAACATG
ACTGTTGCTAGCCTCCTGGCTTCCTCGATTGGCGAAAAAACGTGTTGTAC
--------------------------AMPR--------------------->

4660      4670      4680      4690      4700
GGGGATCATGTAACTCGCCTTGATCGTTGGGAACCGGAGCTGAATGAAGC
```

FIG. 1C (continued)

```
          CCCCTAGTACATTGAGCGGAACTAGCAACCCTTGGCCTCGACTTACTTCG
                                 AMPR                          >

4710      4720      4730      4740      4750
          CATACCAAACGACGAGCGTGACACCACGATGCCTGTAGCAATGGCAACAA
          GTATGGTTTGCTGCTCGCACTGTGGTGCTACGGACATCGTTACCGTTGTT
                                 AMPR                          >

4760      4770      4780      4790      4800
          CGTTGCGCAAACTATTAACTGGCGAACTACTTACTCTAGCTTCCCGGCAA
          GCAACGCGTTTGATAATTGACCGCTTGATGAATGAGATCGAAGGGCCGTT
                                 AMPR                          >

4810      4820      4830      4840      4850
          CAATTAATAGACTGGATGGAGGCGGATAAAGTTGCAGGACCACTTCTGCG
          GTTAATTATCTGACCTACCTCCGCCTATTTCAACGTCCTGGTGAAGACGC
                                 AMPR                          >

4860      4870      4880      4890      4900
          CTCGGCCCTTCCGGCTGGCTGGTTTATTGCTGATAAATCTGGAGCCGGTG
          GAGCCGGGAAGGCCGACCGACCAAATAACGACTATTTAGACCTCGGCCAC
                                 AMPR                          >

4910      4920      4930      4940      4950
          AGCGTGGGTCTCGCGGTATCATTGCAGCACTGGGGCCAGATGGTAAGCCC
          TCGCACCCAGAGCGCCATAGTAACGTCGTGACCCCGGTCTACCATTCGGG
                                 AMPR                          >

4960      4970      4980      4990      5000
          TCCCGTATCGTAGTTATCTACACGACGGGGAGTCAGGCAACTATGGATGA
          AGGGCATAGCATCAATAGATGTGCTGCCCCTCAGTCCGTTGATACCTACT
                                 AMPR                          >

5010      5020      5030      5040      5050
          ACGAAATAGACAGATCGCTGAGATAGGTGCCTCACTGATTAAGCATTGGT
          TGCTTTATCTGTCTAGCGACTCTATCCACGGAGTGACTAATTCGTAACCA
                                 AMPR                          >

5060      5070      5080      5090      5100
          AACTGTCAGACCAAGTTTACTCATATATACTTTAGATTGATTTAAAACTT
          TTGACAGTCTGGTTCAAATGAGTATATATGAAATCTAACTAAATTTTGAA
          ....>

5110      5120      5130      5140      5150
          CATTTTTAATTTAAAAGGATCTAGGTGAAGATCCTTTTTGATAATCTCAT
          GTAAAAATTAAATTTTCCTAGATCCACTTCTAGGAAAAACTATTAGAGTA 5160      5170      5180      5190      5200
          GACCAAAATCCCTTAACGTGAGTTTTCGTTCCACTGAGCGTCAGACCCCG
          CTGGTTTTAGGGAATTGCACTCAAAAGCAAGGTGACTCGCAGTCTGGGGC 5210      5220      5230      5240      5250
          TAGAAAAGATCAAAGGATCTTCTTGAGATCCTTTTTTTCTGCGCGTAATC
          ATCTTTTCTAGTTTCCTAGAAGAACTCTAGGAAAAAAAGACGCGCATTAG
                                 PBR322 ORIGIN                  >
```

FIG. 1C (continued)

```
          5260      5270      5280      5290      5300
     TGCTGCTTGCAAACAAAAAAACCACCGCTACCAGCGGTGGTTTGTTTGCC
     ACGACGAACGTTTGTTTTTTTGGTGGCGATGGTCGCCACCAAACAAACGG
                       PBR322 ORIGIN                    >
          5310      5320      5330      5340      5350
     GGATCAAGAGCTACCAACTCTTTTTCCGAAGGTAACTGGCTTCAGCAGAG
     CCTAGTTCTCGATGGTTGAGAAAAGGCTTCCATTGACCGAAGTCGTCTC
                       PBR322 ORIGIN                    >
          5360      5370      5380      5390      5400
     CGCAGATACCAAATACTGTCCTTCTAGTGTAGCCGTAGTTAGGCCACCAC
     GCGTCTATGGTTTATGACAGGAAGATCACATCGGCATCAATCCGGTGGTG
                       PBR322 ORIGIN                    >
          5410      5420      5430      5440      5450
     TTCAAGAACTCTGTAGCACCGCCTACATACCTCGCTCTGCTAATCCTGTT
     AAGTTCTTGAGACATCGTGGCGGATGTATGGAGCGAGACGATTAGGACAA
                       PBR322 ORIGIN                    >
          5460      5470      5480      5490      5500
     ACCAGTGGCTGCTGCCAGTGGCGATAAGTCGTGTCTTACCGGGTTGGACT
     TGGTCACCGACGACGGTCACCGCTATTCAGCACAGAATGGCCCAACCTGA
                       PBR322 ORIGIN                    >
          5510      5520      5530      5540      5550
     CAAGACGATAGTTACCGGATAAGGCGCAGCGGTCGGGCTGAACGGGGGGT
     GTTCTGCTATCAATGGCCTATTCCGCGTCGCCAGCCCGACTTGCCCCCCA
                       PBR322 ORIGIN                    >
          5560      5570      5580      5590      5600
     TCGTGCACACAGCCCAGCTTGGAGCGAACGACCTACACCGAACTGAGATA
     AGCACGTGTGTCGGGTCGAACCTCGCTTGCTGGATGTGGCTTGACTCTAT
                       PBR322 ORIGIN                    >
          5610      5620      5630      5640      5650
     CCTACAGCGTGAGCTATGAGAAAGCGCCACGCTTCCCGAAGGGAGAAAGG
     GGATGTCGCACTCGATACTCTTTCGCGGTGCGAAGGGCTTCCCTCTTTCC
                       PBR322 ORIGIN                    >
          5660      5670      5680      5690      5700
     CGGACAGGTATCCGGTAAGCGGCAGGGTCGGAACAGGAGAGCGCACGAGG
     GCCTGTCCATAGGCCATTCGCCGTCCCAGCCTTGTCCTCTCGCGTGCTCC
                       PBR322 ORIGIN                    >
          5710      5720      5730      5740      5750
     GAGCTTCCAGGGGGAAACGCCTGGTATCTTTATAGTCCTGTCGGGTTTCG
     CTCGAAGGTCCCCCTTTGCGGACCATAGAAATATCAGGACAGCCCAAAGC
                       PBR322 ORIGIN                    >
          5760      5770      5780      5790      5800
     CCACCTCTGACTTGAGCGTCGATTTTTGTGATGCTCGTCAGGGGGGCGGA
     GGTGGAGACTGAACTCGCAGCTAAAAACACTACGAGCAGTCCCCCCGCCT
                       PBR322 ORIGIN                    >
```

FIG. 1C (continued)

```
         5810      5820      5830      5840      5850
GCCTATGGAAAAACGCCAGCAACGCGGCCTTTTTACGGTTCCTGGCCTTT
CGGATACCTTTTTGCGGTCGTTGCGCCGGAAAAATGCCAAGGACCGGAAA
         PBR322 ORIGIN          >

5860      5870      5880      5890      5900
TGCTGGCCTTTTGCTCACATGTTCTTTCCTGCGTTATCCCCTGATTCTGT
ACGACCGGAAAACGAGTGTACAAGAAAGGACGCAATAGGGGACTAAGACA 5910      5920      5930      5940      5950
GGATAACCGTATTACCGCCTTTGAGTGAGCTGATACCGCTCGCCGCAGCC
CCTATTGGCATAATGGCGGAAACTCACTCGACTATGGCGAGCGGCGTCGG 5960      5970      5980      5990      6000
GAACGACCGAGCGCAGCGAGTCAGTGAGCGAGGAAGCGGAAGAGCGCCCA
CTTGCTGGCTCGCGTCGCTCAGTCACTCGCTCCTTCGCCTTCTCGCGGGT 6010      6020      6030      6040
ATACGCAAACCGCCTCTCCCCGCGCGTTGGCCGATTCATTAATG
TATGCGTTTGGCGGAGAGGGGCGCGCAACCGGCTAAGTAATTAC
```

SEQ ID NO: 6

*CCTGCAGGCAGCTGCGCGCTCGCTCGCTCACTGAGGCCGCCCGGGCAAAGCCCG*
*GGCGTCGGGCGACCTTTGGTCGCCCGGCCTCAGTGAGCGAGCGAGCGCGCAGA*
*GAGGGAGTGGCCAACTCCATCACTAGGGGTTCCTGCGGCCGCGGTACCGGCGC*
GCCGGGGGAGGCTGCTGGTGAATATTAACCAAGGTCACCCCAGTTATCG
GAGGAGCAAACAGGGGCTAAGTCCACACGCGTGGTACCGTCTGTCTGCAC
ATTTCGTAGAGCGAGTGTTCCGATACTCTAATCTCCCTAGGCAAGGTTCATAT
TTGTGTAGGTTACTTATTCTCCTTTTGTTGACTAAGTCAATAATCAGAATCAG
CAGGTTTGGAGTCAGCTTGGCAGGGATCAGCAGCCTGGGTTGGAAGGAGGGG
GTATAAAAGCCCCTTCACCAGGAGAAGCCGTCACACAGATCCACAAGCTCCT
G*AAGAGGTAAGGGTTTAAGGGATGGTTGGTTGGTGGGNATTAATGTTTAATTACC*
*TGGAGCACCTGCCTGAAATCACTTTTTTTCAGGTTGG*CTAGTATGCAGATCGAG
CTGTCCACCTGCTTTTTTCTGTGCCTGCTGCGGTTCTGCTTCAGCGCCAC
CCGGCGGTACTACCTGGGCGCCGTGGAGCTGTCCTGGGACTACATGCAG
AGCGACCTGGGCGAGCTGCCCGTGGACGCCCGGTTCCCCCCCAGAGTG
CCCAAGAGCTTCCCCTTCAACACCAGCGTGGTGTACAAGAAAACCCTGT
TCGTGGAGTTCACCGACCACCTGTTCAATATCGCCAAGCCCAGGCCCCC
CTGGATGGGCCTGCTGGGCCCCACCATCCAGGCCGAGGTGTACGACACC
GTGGTGATCACCCTGAAGAACATGGCCAGCCACCCCGTGAGCCTGCACG
CCGTGGGCGTGAGCTACTGGAAGGCCAGCGAGGGCGCCGAGTACGACG
ACCAGACCAGCCAGCGGGAGAAAGAAGATGACAAGGTGTTCCCTGGCG
GCAGCCACACCTACGTGTGGCAGGTGCTGAAAGAAAACGGCCCCATGGC
CTCCGACCCCCTGTGCCTGACCTACAGCTACCTGAGCCACGTGGACCTG
GTGAAGGACCTGAACAGCGGCCTGATCGGCGCTCTGCTCGTCTGCCGGG
AGGGCAGCCTGGCCAAAGAGAAAACCCAGACCCTGCACAAGTTCATCCT
GCTGTTCGCCGTGTTCGACGAGGGCAAGAGCTGGCACAGCGAGACAAA
GAACAGCCTGATGCAGGACCGGGACGCCGCCTCTGCCAGAGCCTGGCC
CAAGATGCACACCGTGAACGGCTACGTGAACAGAAGCCTGCCCGGCCTG
ATTGGCTGCCACCGGAAGAGCGTGTACTGGCACGTGATCGGCATGGGCA
CCACACCCGAGGTGCACAGCATCTTTCTGGAAGGGCACACCTTTCTGGT
CCGGAACCACCGGCAGGCCAGCCTGGAAATCAGCCCTATCACCTTCCTG
ACCGCCCAGACACTGCTGATGGACCTGGGCCAGTTCCTGCTGTTTGCC
ACATCAGCTCTCACCAGCACGACGGCATGGAAGCCTACGTGAAGGTGGA
CTCTTGCCCCGAGGAACCCCAGCTGCGGATGAAGAACAACGAGGAAGCC
GAGGACTACGACGACGACCTGACCGACAGCGAGATGGACGTGGTGCGG
TTCGACGACGACAACAGCCCCAGCTTCATCCAGATCAGAAGCGTGGCCA
AGAAGCACCCCAAGACCTGGGTGCACTATATCGCCGCCGAGGAAGAGGA
CTGGGACTACGCCCCCCTGGTGCTGGCCCCCGACGACAGAAGCTACAAG
AGCCAGTACCTGAACAATGGCCCCAGCGGATCGGCCGGAAGTACAAGA
AAGTGCGGTTCATGGCCTACACCGACGAGACATTCAAGACCCGGGAGGC
CATCCAGCACGAGAGCGGCATCCTGGGCCCCCTGCTGTACGGCGAAGTG
GGCGACACACTGCTGATCATCTTCAAGAACCAGGCTAGCCGGCCCTACA

FIG. 6C (continued)

ACATCTACCCCCACGGCATCACCGACGTGCGGCCCCTGTACAGCAGGCG
GCTGCCCAAGGGCGTGAAGCACCTGAAGGACTTCCCCATCCTGCCCGGC
GAGATCTTCAAGTACAAGTGGACCGTGACCGTGGAGGACGGCCCCACCA
AGAGCGACCCCAGATGCCTGACCCGGTACTACAGCAGCTTCGTGAACAT
GGAACGGGACCTGGCCTCCGGGCTGATCGGACCTCTGCTGATCTGCTAC
AAAGAAAGCGTGGACCAGCGGGGCAACCAGATCATGAGCGACAAGCGG
AACGTGATCCTGTTCAGCGTGTTCGATGAGAACCGGTCCTGGTATCTGA
CCGAGAACATCCAGCGGTTTCTGCCCAACCCTGCCGGCGTGCAGCTGGA
AGATCCCGAGTTCCAGGCCAGCAACATCATGCACTCCATCAATGGCTAC
GTGTTCGACTCTCTGCAGCTCTCCGTGTGTCTGCACGAGGTGGCCTACT
GGTACATCCTGAGCATCGGCGCCCAGACCGACTTCCTGAGCGTGTTCTT
CAGCGGCTACACCTTCAAGCACAAGATGGTGTACGAGGACACCCTGACC
CTGTTCCCTTTCAGCGGCGAGACAGTGTTCATGAGCATGGAAAACCCCG
GCCTGTGGATTCTGGGCTGCCACAACAGCGACTTCCGGAACCGGGGCAT
GACCGCCCTGCTGAAGGTGTCCAGCTGCGACAAGAACACCGGCGACTAC
TACGAGGACAGCTACGAGGATATCAGCGCCTACCTGCTGTCCAAGAACA
ACGCCATCGAACCCCGGAGCTTCAGCCAGAACCCCCCGTGCTGACGCG
TCACCAGCGGGAGATCACCCGGACAACCCTGCAGTCCGACCAGGAAGAG
ATCGATTACGACGACACCATCAGCGTGGAGATGAAGAAGAGGATTTCG
ATATCTACGACGAGGACGAGAACCAGAGCCCCAGAAGCTTCCAGAAGAA
AACCCGGCACTACTTCATTGCCGCCGTGGAGAGGCTGTGGGACTACGGC
ATGAGTTCTAGCCCCCACGTGCTGCGGAACCGGGCCCAGAGCGGCAGC
GTGCCCCAGTTCAAGAAAGTGGTGTTCCAGGAATTCACAGACGGCAGCT
TCACCCAGCCTCTGTATAGAGGCGAGCTGAACGAGCACCTGGGGCTGCT
GGGGCCCTACATCAGGGCCGAAGTGGAGGACAACATCATGGTGACCTTC
CGGAATCAGGCCAGCAGACCCTACTCCTTCTACAGCAGCCTGATCAGCT
ACGAAGAGGACCAGCGGCAGGGCGCCGAACCCCGGAAGAACTTCGTGA
AGCCCAACGAAACCAAGACCTACTTCTGGAAAGTGCAGCACCACATGGC
CCCCACCAAGGACGAGTTCGACTGCAAGGCCTGGGCCTACTTCAGCGAC
GTGGATCTGGAAAAGGACGTGCACTCTGGACTGATTGGCCCACTCCTGG
TCTGCCACACTAACACCCTCAACCCCGCCCACGGCCGCCAGGTGACCGT
GCAGGAATTCGCCCTGTTCTTCACCATCTTCGACGAGACAAAGTCCTGG
TACTTCACCGAGAATATGGAACGGAACTGCAGAGCCCCCTGCAACATCC
AGATGGAAGATCCTACCTTCAAAGAGAACTACCGGTTCCACGCCATCAA
CGGCTACATCATGGACACCCTGCCTGGCCTGGTGATGGCCCAGGACCAG
AGAATCCGGTGGTATCTGCTGTCCATGGGCAGCAACGAGAATATCCACA
GCATCCACTTCAGCGGCCACGTGTTCACCGTGCGGAAGAAAGAAGAGTA
CAAGATGGCCCTGTACAACCTGTACCCCGGCGTGTTCGAGACAGTGGAG
ATGCTGCCCAGCAAGGCCGGCATCTGGCGGGTGGAGTGTCTGATCGGC
GAGCACCTGCACGCTGGCATGAGCACCCTGTTTCTGGTGTACAGCAACA
AGTGCCAGACCCCACTGGGCATGGCCTCTGGCCACATCCGGGACTTCCA
GATCACCGCCTCCGGCCAGTACGGCCAGTGGGCCCCCAAGCTGGCCAGA
CTGCACTACAGCGGCAGCATCAACGCCTGGTCCACCAAAGAGCCCTTCA
GCTGGATCAAGGTGGACCTGCTGGCCCCTATGATCATCCACGGCATTAA
GACCCAGGGCGCCAGGCAGAAGTTCAGCAGCCTGTACATCAGCCAGTTC

FIG. 6C (continued)

ATCATCATGTACAGCCTGGACGGCAAGAAGTGGCAGACCTACCGGGGCA
ACAGCACCGGCACCCTGATGGTGTTCTTCGGCAATGTGGACAGCAGCGG
CATCAAGCACAACATCTTCAACCCCCCCATCATTGCCCGGTACATCCGGC
TGCACCCCACCCACTACAGCATTAGATCCACACTGAGAATGGAACTGAT
GGGCTGCGACCTGAACTCCTGCAGCATGCCTCTGGGCATGGAAAGCAAG
GCCATCAGCGACGCCCAGATCACAGCCAGCAGCTACTTCACCAACATGT
TCGCCACCTGGTCCCCTCCAAGGCCAGGCTGCACCTGCAGGGCCGGTC
CAACGCCTGGCGGCCTCAGGTCAACAACCCCAAAGAATGGCTGCAGGTG
GACTTTCAGAAAACCATGAAGGTGACCGGCGTGACCACCCAGGGCGTGA
AAAGCCTGCTGACCAGCATGTACGTGAAAGAGTTTCTGATCAGCAGCTC
TCAGGATGGCCACCAGTGGACCCTGTTCTTTCAGAACGGCAAGGTGAAA
GTGTTCCAGGGCAACCAGGACTCCTTCACCCCCGTGGTGAACTCCCTGG
ACCCCCCCTGCTGACCCGCTACCTGAGAATCCACCCCAGTCTTGGGT
GCACCAGATCGCCCTCAGGATGGAAGTCCTGGGATGTGAGGCCCAGGAT
CTGTACTGATGAGGATCTAGGCTCGAC*ATGCTTTATTTGTGAAATTTGTGATG*
*CTATTGCTTTATTTGTAACCATTATAAGCTGCAATAAACAAGTTAACAACAACA*
*ATTGCATTCATTTTATGTTTCAGGTTCAGGGGGAGGTGTGGGAGGTTTTTTAAA*
CTCGAGATCCACGGCCGC*AGGAACCCCTAGTGATGGAGTTGGCCACTCCCTCTC*
*TGCGCGCTCGCTCGCTCACTGAGGCCGGGCGACCAAAGGTCGCCCGACGCCCG*
*GGCTTTGCCCGGGCGGCCTCAGTGAGCGAGCGAGCGCGCAGCTGCCTGCAGGG*
GCGCCTGATGCGGTATTTCTCCTTACGCATCTGTGCGGTATTTCACACCGCA
TACGTCAAAGCAACCATAGTACGCGCCCTGTAGCGGCGCATTAAGCGCGGCG
GGTGTGGTGGTTACGCGCAGCGTGACCGCTACACTTGCCAGCGCCCTAGCGC
CCGCTCCTTTCGCTTTCTTCCCTTCCTTTCTCGCCACGTTCGCCGGCTTTCCCC
GTCAAGCTCTAAATCGGGGGCTCCCTTTAGGGTTCCGATTTAGTGCTTTACGG
CACCTCGACCCCAAAAAACTTGATTTGGGTGATGGTTCACGTAGTGGGCCAT
CGCCCTGATAGACGGTTTTTCGCCCTTTGACGTTGGAGTCCACGTTCTTTAAT
AGTGGACTCTTGTTCCAAACTGGAACAACACTCAACCCTATCTCGGGCTATTC
TTTTGATTTATAAGGGATTTTGCCGATTTCGGCCTATTGGTTAAAAAATGAGC
TGATTTAACAAAAATTTAACGCGAATTTTAACAAAATATTAACGTTTACAATT
TTATGGTGCACTCTCAGTACAATCTGCTCTGATGCCGCATAGTTAAGCCAGCC
CCGACACCCGCCAACACCCGCTGACGCGCCCTGACGGGCTTGTCTGCTCCCG
GCATCCGCTTACAGACAAGCTGTGACCGTCTCCGGGAGCTGCATGTGTCAGA
GGTTTTCACCGTCATCACCGAAACGCGCGAGACGAAAGGGCCTCGTGATACG
CCTATTTTTATAGGTTAATGTCATGATAATAATGGTTTCTTAGACGTCAGGTG
GCACTTTTCGGGGAAATGTGCGCGGAACCCCTATTTGTTTATTTTTCTAAATA
CATTCAAATATGTATCCGCTCATGAGACAATAACCCTGATAAATGCTTCAATA
ATATTGAAAAAGGAAGAGTATGAGTATTCAACATTTCCGTGTCGCCCTTATTC
CCTTTTTTGCGGCATTTTGCCTTCCTGTTTTTGCTCACCCAGAAACGCTGGTGA
AAGTAAAAGATGCTGAAGATCAGTTGGGTGCACGAGTGGGTTACATCGAACT
GGATCTCAACAGCGGTAAGATCCTTGAGAGTTTTCGCCCCGAAGAACGTTTTC
CAATGATGAGCACTTTTAAAGTTCTGCTATGTGGCGCGGTATTATCCCGTATT
GACGCCGGGCAAGAGCAACTCGGTCGCCGCATACACTATTCTCAGAATGACT
TGGTTGAGTACTCACCAGTCACAGAAAAGCATCTTACGGATGGCATGACAGT
AAGAGAATTATGCAGTGCTGCCATAACCATGAGTGATAACACTGCGGCCAAC

FIG. 6C (continued)

TTACTTCTGACAACGATCGGAGGACCGAAGGAGCTAACCGCTTTTTTGCACA
ACATGGGGGATCATGTAACTCGCCTTGATCGTTGGGAACCGGAGCTGAATGA
AGCCATACCAAACGACGAGCGTGACACCACGATGCCTGTAGCAATGGCAAC
AACGTTGCGCAAACTATTAACTGGCGAACTACTTACTCTAGCTTCCCGGCAAC
AATTAATAGACTGGATGGAGGCGGATAAAGTTGCAGGACCACTTCTGCGCTC
GGCCCTTCCGGCTGGCTGGTTTATTGCTGATAAATCTGGAGCCGGTGAGCGTG
GGTCTCGCGGTATCATTGCAGCACTGGGGCCAGATGGTAAGCCCTCCCGTAT
CGTAGTTATCTACACGACGGGGAGTCAGGCAACTATGGATGAACGAAATAGA
CAGATCGCTGAGATAGGTGCCTCACTGATTAAGCATTGGTAACTGTCAGACC
AAGTTTACTCATATATACTTTAGATTGATTTAAAACTTCATTTTTAATTTAAAA
GGATCTAGGTGAAGATCCTTTTTGATAATCTCATGACCAAAATCCCTTAACGT
GAGTTTTCGTTCCACTGAGCGTCAGACCCCGTAGAAAAGATCAAAGGATCTT
CTTGAGATCCTTTTTTTCTGCGCGTAATCTGCTGCTTGCAAACAAAAAAACCA
CCGCTACCAGCGGTGGTTTGTTTGCCGGATCAAGAGCTACCAACTCTTTTTCC
GAAGGTAACTGGCTTCAGCAGAGCGCAGATACCAAATACTGTCCTTCTAGTG
TAGCCGTAGTTAGGCCACCACTTCAAGAACTCTGTAGCACCGCCTACATACCT
CGCTCTGCTAATCCTGTTACCAGTGGCTGCTGCCAGTGGCGATAAGTCGTGTC
TTACCGGGTTGGACTCAAGACGATAGTTACCGGATAAGGCGCAGCGGTCGGG
CTGAACGGGGGGTTCGTGCACACAGCCCAGCTTGGAGCGAACGACCTACACC
GAACTGAGATACCTACAGCGTGAGCTATGAGAAAGCGCCACGCTTCCCGAAG
GGAGAAAGGCGGACAGGTATCCGGTAAGCGGCAGGGTCGGAACAGGAGAGC
GCACGAGGGAGCTTCCAGGGGGAAACGCCTGGTATCTTTATAGTCCTGTCGG
GTTTCGCCACCTCTGACTTGAGCGTCGATTTTTGTGATGCTCGTCAGGGGGC
GGAGCCTATGGAAAAACGCCAGCAACGCGGCCTTTTACGGTTCCTGGCCTTT
TGCTGGCCTTTTGCTCACATGT

FIG. 6D

SEQ ID NO: 7
ATGCAGATCGAGCTGTCCACCTGCTTTTTTCTGTGCCTGCTGCGGTTCTGCTTCAG
CGCCACCCGGCGGTACTACCTGGGCGCCGTGGAGCTGTCCTGGGACTACATGCA
GAGCGACCTGGGCGAGCTGCCCGTGGACGCCCGGTTCCCCCCCAGAGTGCCCAA
GAGCTTCCCCTTCAACACCAGCGTGGTGTACAAGAAAACCCTGTTCGTGGAGTTCA
CCGACCACCTGTTCAATATCGCCAAGCCCAGGCCCCCTGGATGGGCCTGCTGGG
CCCCACCATCCAGGCCGAGGTGTACGACACCGTGGTGATCACCCTGAAGAACATG
GCCAGCCACCCCGTGAGCCTGCACGCCGTGGGCGTGAGCTACTGGAAGGCCAGC
GAGGGCGCCGAGTACGACGACCAGACCAGCCAGCGGGAGAAGAAGATGACAAG
GTGTTCCCTGGCGGCAGCCACACCTACGTGTGGCAGGTGCTGAAAGAAAACGGCC
CCATGGCCTCCGACCCCTGTGCCTGACCTACAGCTACCTGAGCCACGTGGACCT
GGTGAAGGACCTGAACAGCGGCCTGATCGGCGCTCTGCTCGTCTGCCGGGAGGG
CAGCCTGGCCAAAGAGAAACCCAGACCCTGCACAAGTTCATCCTGCTGTTCGCC
GTGTTCGACGAGGGCAAGAGCTGGCACAGCGAGACAAAGAACAGCCTGATGCAGG
ACCGGGACGCCGCCTCTGCCAGAGCCTGGCCCAAGATGCACACCGTGAACGGCT
ACGTGAACAGAAGCCTGCCCGGCCTGATTGGCTGCCACCGGAAGAGCGTGTACTG
GCACGTGATCGGCATGGGCACCACACCCGAGGTGCACAGCATCTTTCTGGAAGGG
CACACCTTTCTGGTCCGGAACCACCGGCAGGCCAGCCTGGAAATCAGCCCTATCA
CCTTCCTGACCGCCCAGACACTGCTGATGGACCTGGGCCAGTTCCTGCTGTTTGC
CACATCAGCTCTCACCAGCACGACGGCATGGAAGCCTACGTGAAGGTGGACTCTT
GCCCCGAGGAACCCCAGCTGCGGATGAAGAACAACGAGGAAGCCGAGGACTACG
ACGACGACCTGACCGACAGCGAGATGGACGTGGTGCGGTTCGACGACGACAACA
GCCCCAGCTTCATCCAGATCAGAAGCGTGGCCAAGAAGCACCCCAAGACCTGGGT
GCACTATATCGCCGCCGAGGAAGAGGACTGGGACTACGCCCCCCTGGTGCTGGC
CCCCGACGACAGAAGCTACAAGAGCCAGTACCTGAACAATGGCCCCCAGCGGATC
GGCCGGAAGTACAAGAAAGTGCGGTTCATGGCCTACACCGACGAGACATTCAAGA
CCCGGGAGGCCATCCAGCACGAGAGCGGCATCCTGGGCCCCCTGCTGTACGGCG
AAGTGGGCGACACACTGCTGATCATCTTCAAGAACCAGGCTAGCCGGCCCTACAA
CATCTACCCCCACGGCATCACCGACGTGCGGCCCCTGTACAGCAGGCGGCTGCCC
AAGGGCGTGAAGCACCTGAAGGACTTCCCCATCCTGCCCGGCGAGATCTTCAAGT
ACAAGTGGACCGTGACCGTGGAGGACGGCCCCACCAAGAGCGACCCCAGATGCC
TGACCCGGTACTACAGCAGCTTCGTGAACATGGAACGGGACCTGGCCTCCGGGCT
GATCGGACCTCTGCTGATCTGCTACAAAGAAAGCGTGGACCAGCGGGGCAACCAG
ATCATGAGCGACAAGCGGAACGTGATCCTGTTCAGCGTGTTCGATGAGAACCGGT
CCTGGTATCTGACCGAGAACATCCAGCGGTTTCTGCCCAACCCTGCCGGCGTGCA
GCTGGAAGATCCCGAGTTCCAGGCCAGCAACATCATGCACTCCATCAATGGCTACG
TGTTCGACTCTCTGCAGCTCTCCGTGTGTCTGCACGAGGTGGCCTACTGGTACATC
CTGAGCATCGGCGCCCAGACCGACTTCCTGAGCGTGTTCTTCAGCGGCTACACCT
TCAAGCACAAGATGGTGTACGAGGACACCCTGACCCTGTTCCCTTTCAGCGGCGA
GACAGTGTTCATGAGCATGGAAAACCCCGGCCTGTGGATTCTGGGCTGCCACAAC
AGCGACTTCCGGAACCGGGGCATGACCGCCCTGCTGAAGGTGTCCAGCTGCGACA
AGAACACCGGCGACTACTACGAGGACAGCTACGAGGATATCAGCGCCTACCTGCT
GTCCAAGAACAACGCCATCGAACCCCGGAGCTTCAGCCAGAACCCCCCGTGCTG
ACGCGTCACCAGCGGGAGATCACCCGGACAACCCTGCAGTCCGACCAGGAAGAG
ATCGATTACGACGACACCATCAGCGTGGAGATGAAGAAGGAGGATTTCGATATCTA
CGACGAGGACGAGAACCAGAGCCCCAGAAGCTTCCAGAAGAAACCCGGCACTAC
TTCATTGCCGCCGTGGAGAGGCTGTGGGACTACGGCATGAGTTCTAGCCCCCACG

FIG. 6D (continued)

```
TGCTGCGGAACCGGGCCCAGAGCGGCAGCGTGCCCCAGTTCAAGAAAGTGGTGTT
CCAGGAATTCACAGACGGCAGCTTCACCCAGCCTCTGTATAGAGGCGAGCTGAAC
GAGCACCTGGGGCTGCTGGGGCCCTACATCAGGGCCGAAGTGGAGGACAACATC
ATGGTGACCTTCCGGAATCAGGCCAGCAGACCCTACTCCTTCTACAGCAGCCTGAT
CAGCTACGAAGAGGACCAGCGGCAGGGCGCCGAACCCCGGAAGAACTTCGTGAA
GCCCAACGAAACCAAGACCTACTTCTGGAAAGTGCAGCACCACATGGCCCCACC
AAGGACGAGTTCGACTGCAAGGCCTGGGCCTACTTCAGCGACGTGGATCTGGAAA
AGGACGTGCACTCTGGACTGATTGGCCCACTCCTGGTCTGCCACACTAACACCCTC
AACCCCGCCCACGGCCGCCAGGTGACCGTGCAGGAATTCGCCCTGTTCTTCACCA
TCTTCGACGAGACAAAGTCCTGGTACTTCACCGAGAATATGGAACGGAACTGCAGA
GCCCCTGCAACATCCAGATGGAAGATCCTACCTTCAAAGAGAACTACCGGTTCCA
CGCCATCAACGGCTACATCATGGACACCCTGCCTGGCCTGGTGATGGCCCAGGAC
CAGAGAATCCGGTGGTATCTGCTGTCCATGGGCAGCAACGAGAATATCCACAGCAT
CCACTTCAGCGGCCACGTGTTCACCGTGCGGAAGAAGAAGAGTACAAGATGGCC
CTGTACAACCTGTACCCCGGCGTGTTCGAGACAGTGGAGATGCTGCCCAGCAAGG
CCGGCATCTGGCGGGTGGAGTGTCTGATCGGCGAGCACCTGCACGCTGGCATGA
GCACCCTGTTTCTGGTGTACAGCAACAAGTGCCAGACCCCACTGGGCATGGCCTC
TGGCCACATCGGGACTTCCAGATCACCGCCTCCGGCCAGTACGGCCAGTGGGCC
CCCAAGCTGGCCAGACTGCACTACAGCGGCAGCATCAACGCCTGGTCCACCAAAG
AGCCCTTCAGCTGGATCAAGGTGGACCTGCTGGCCCCTATGATCATCCACGGCATT
AAGACCCAGGGCGCCAGGCAGAAGTTCAGCAGCCTGTACATCAGCCAGTTCATCA
TCATGTACAGCCTGGACGGCAAGAAGTGGCAGACCTACCGGGGCAACAGCACCGG
CACCCTGATGGTGTTCTTCGGCAATGTGGACAGCAGCGGCATCAAGCACAACATCT
TCAACCCCCCCATCATTGCCCGGTACATCCGGCTGCACCCCACCCACTACAGCATT
AGATCCACACTGAGAATGGAACTGATGGGCTGCGACCTGAACTCCTGCAGCATGC
CTCTGGGCATGGAAAGCAAGGCCATCAGCGACGCCCAGATCACAGCCAGCAGCTA
CTTCACCAACATGTTCGCCACCTGGTCCCCTCCAAGGCCAGGCTGCACCTGCAG
GGCCGGTCCAACGCCTGGCGGCCTCAGGTCAACAACCCCAAAGAATGGCTGCAG
GTGGACTTTCAGAAAACCATGAAGGTGACCGGCGTGACCACCCAGGGCGTGAAAA
GCCTGCTGACCAGCATGTACGTGAAAGAGTTTCTGATCAGCAGCTCTCAGGATGGC
CACCAGTGGACCCTGTTCTTTCAGAACGGCAAGGTGAAAGTGTTCCAGGGCAACCA
GGACTCCTTCACCCCCGTGGTGAACTCCCTGGACCCCCCCTGCTGACCCGCTAC
CTGAGAATCCACCCCAGTCTTGGGTGCACCAGATCGCCCTCAGGATGGAAGTCC
TGGGATGTGAGGCCCAGGATCTGTACTGATGA
```

SEQ ID NO: 8

GGGGGAGGCTGCTGGTGAATATTAACCAAGGTCACCCCAGTTATCGGAGGAGCAA
ACAGGGGCTAAGTCCAC

F

SEQ ID NO: 9

GTCTGTCTGCACATTTCGTAGAGCGAGTGTTCCGATACTCTAATCTCCCTAGGCAA
GGTTCATATTTGTGTAGGTTACTTATTCTCCTTTTGTTGACTAAGTCAATAATCAGAA
TCAGCAGGTTTGGAGTCAGCTTGGCAGGGATCAGCAGCCTGGGTTGGAAGGAGGG
GGTATAAAAGCCCCTTCACCAGGAGAAGCCGTC

G

SEQ ID NO: 10

AAGAGGTAAGGGTTTAAGGGATGGTTGGTTGGTGGGGNATTAATGTTTAATTACCT
GGAGCACCTGCCTGAAATCACTTTTTTTCAGGTTGG

H

SEQ ID NO: 11

ATGCTTTATTTGTGAAATTTGTGATGCTATTGCTTTATTTGTAACCATTATAAGCTGC
AATAAACAAGTTAACAACAACAATTGCATTCATTTTATGTTTCAGGTTCAGGGGGAG
GTGTGGGAGGTTTTTTAAA

FIG. 8B

SEQ ID NO: 12

GACGGATCGGGAGATCTCCCGATCCCCTATGGTCGACTCTCAGTACAATCTGCTCTGATGCCG
CATAGTTAAGCCAGTATCTGCTCCCTGCTTGTGTGTTGGAGGTCGCTGAGTAGTGCGCGAGCA
AAATTTAAGCTACAACAAGGCAAGGCTTGACCGACAATTGCATGAAGAATCTGCTTAGGGTT
AGGCGTTTTGCGCTGCTTCGCGCGTGGAGCTAGTTATTAATAGTAATCAATTACGGGGTCATT
AGTTCATAGCCCATATATGGAGTTCCGCGTTACATAACTTACGGTAAATGGCCCGCCTGGCTG
ACCGCCCAACGACCCCGCCCATTGACGTCAATAATGACGTATGTTCCCATAGTAACGTCAAT
AGGGACTTTCCATTGACGTCAATGGGTGGAGTATTTACGGTAAACTGCCCACTTGGCAGTACA
TCAAGTGTATCATATGCCAAGTACGCCCCCTATTGACGTCAATGACGGTAAATGGCCCGCCTG
GCATTATGCCCAGTACATGACCTTATGGGACTTTCCTACTTGGCAGTACATCTACGTATTAGTC
ATCGCTATTACCATGGTGATGCGGTTTTGGCAGTACATCAATGGGCGTGGATAGCGGTTTGAC
TCACGGGGATTTCCAAGTCTCCACCCCATTGACGTCAATGGGAGTTTGTTTTGGCACCAAAAT
CAACGGGACTTTCCAAAATGTCGTAACAACTCCGCCCCATTGACGCAAATGGGCGGTAGGCGT
GTACGGTGGGAGGTCTATATAAGCAGAGCTCGTTTAGTGAACCGTCAGATCGCCTGGAGACG
CCATCCACGCTGTTTTGACCTCCATAGAAGACACCGGGACCGATCCAGCCTCCGCGGATTCGA
ATCCCGGCCGGGAACGGTGCATTGGAACGCGGATTCCCCGTGCCAAGAGTGACGTAAGTACC
GCCTATAGAGTCTATAGGCCCACAAAAAATGCTTTCTTCTTTTAATATACTTTTTTGTTTATCTT
ATTTCTAATACTTTCCCTAATCTCTTTCTTTCAGGGCAATAATGATACAATGTATCATGCCTCTT
TGCACCATTCTAAAGAATAACAGTGATAATTTCTGGGTTAAGGCAATAGCAATATTTCTGCAT
ATAAATATTTCTGCATATAAATTGTAACTGATGTAAGAGGTTTCATATTGCTAATAGCAGCTA
CAATCCAGCTACCATTCTGCTTTTATTTTATGGTTGGGATAAGGCTGGATTATTCTGAGTCCAA
GCTAGGCCCTTTTGCTAATCATGTTCATACCTCTTATCTTCCTCCCACAGCTCCTGGGCAACGT
GCTGGTCTGTGTGCTGGCCCATCACTTTGGCAAAGAATTGGGATTCGAACATCGATGCCGCCA
CCatgggcagcagcctggacgacgagcacatcctgagcgccctgctgcagagcgacgacgagctggtcggcgaggacagcgacagcgaggtgagc
gaccacgtgagcgaggacgacgtgcagtccgacaccgaggaggccttcatcgacgaggtgcacgaggtgcagcctaccagcagcggctccgagatcc
tggacgagcagaacgtgatcgagcagcccggcagctccctggccagcaacaggatcctgaccctgcccagaggaccatcaggggcaagaacaagca
ctgctggtccacctccaagcccaccaggcggagcagggtgtccgccctgaacatcgtgagaagccagaggggcccccaccaggatgtgcaggaacatct
acgaccccctgctgtgcttcaagctgttcttcaccgacgagatcatcagcgagatcgtgaagtggaccaacgccgatcagcctgaagaggcgggaga
gcatgaccagcgccaccttcagggacaccaacgaggacgagatctacgccttcttcggcatcctggtgatgaccgccgtgaggaaggacaaccacatga
gcaccgacgacctgttcgacagatccctgagcatggtgtacgtgagcgtgatgagcagggacagattcgacttcctgatcagatgcctgaggatggacga
caagagcatcaggcccaccctgcgggagaacgacgtgttcaccccccgtgagaaagatctgggacctgttcatccaccagtgcatccagaactacaccct
ggcgcccacctgaccatcgacgagcagctgctgggcttcaggggcaggtgcccttcagggtgtatatcccaacaagcccagcaagtacggcatcaag
atcctgatgatgtgcgacagcggcaccaagtacatgatcaacgcatgcccctacctgggcaggggcaccagaccaacggcgtgcccctgggcgagta
ctacgtgaaggagctgtccaagcccgtccacggcagctgcagaaacatcacctgcgacaactggttcaccagcatcccctgccaagaacctgctgca
ggagccctacaagctgaccatcgtgggcaccgtgagaagcaacaagagagagatccccgaggtcctgaagaacagcaggtccaggcccgtgggcacc
agcatgttctgcttcgacggccccctgaccctggtgtcctacaagcccaagcccgccaagatggtgtacctgctgtgccagctgcgacgaggacgccagcat
caacgagagcaccggcaagccccagatggtgatgtactacaaccagaccaaggggcggcgtggacaccctggaccagatgtgcagcgtgatgacctgca
gcagaaagaccaacaggtggcccatggccctgctgtacggcatgatcaacatcgcctgcatcaacagcttcatcatctacagccacaacgtgagcagcaa
gggcgagaaggtgcagagccggaaaaagttcatgcggaacctgtacatgggcctgacctccagcttcatgaggaagaggctggaggcccccaccctga
agagatacctgagggacaacatcagcaacatcctgcccaaggaggtgcccggcaccagcgacgacagcaccgaggagcccgtgatgaagaagagga
cctactgcacctactgtcccagcaagatcagaagaaaggccagcgccagctgcaagaagtgtaagaaggtcatctgccgggagcacaacatcgacatgt
gccagagctgtttctgaCTCGAGCATGCATCTAGAGGGCCCTATTCTATAGTGTCACCTAAATGCTAGAG
CTCGCTGATCAGCCTCGACTGTGCCTTCTAGTTGCCAGCCATCTGTTGTTTGCCCCTCCCCCGT
GCCTTCCTTGACCCTGGAAGGTGCCACTCCCACTGTCCTTTCCTAATAAAATGAGGAAATTGC
ATCGCATTGTCTGAGTAGGTGTCATTCTATTCTGGGGGGTGGGGTGGGGCAGGACAGCAAGG
GGGAGGATTGGGAAGACAATAGCAGGCATGCTGGGGATGCGGTGGGCTCTATGGCTTCTGAG
GCGGAAAGAACCAGCTGGGGCTCTAGGGGGTATCCCCACGCGCCCTGTAGCGGCGCATTAAG
CGCGGCGGGTGTGGTGGTTACGCGCAGCGTGACCGCTACACTTGCCAGCGCCCTAGCGCCCGC
TCCTTTCGCTTTCTTCCCTTCCTTTCTCGCCACGTTCGCCGGCTTTCCCCGTCAAGCTCTAAATC
GGGGCATCCCTTTAGGGTTCCGATTTAGTGCTTTACGGCACCTCGACCCCAAAAAACTTGATT FIG. 8B (continued)

```
AGGGTGATGGTTCACGTAGTGGGCCATCGCCCTGATAGACGGTTTTCGCCCTTTGACGTTGG
AGTCCACGTTCTTTAATAGTGGACTCTTGTTCCAAACTGGAACAACACTCAACCCTATCTCGGT
CTATTCTTTTGATTTATAAGGGATTTTGGGGATTTCGGCCTATTGGTTAAAAAATGAGCTGATT
TAACAAAAATTTAACGCGAATTAATTCTGTGGAATGTGTGTCAGTTAGGGTGTGGAAAGTCCC
CAGGCTCCCCAGGCAGGCAGAAGTATGCAAAGCATGCATCTCAATTAGTCAGCAACCAGGTG
TGGAAAGTCCCCAGGCTCCCCAGCAGGCAGAAGTATGCAAAGCATGCATCTCAATTAGTCAG
CAACCATAGTCCCGCCCCTAACTCCGCCCATCCCGCCCCTAACTCCGCCCAGTTCCGCCCATTC
TCCGCCCCATGGCTGACTAATTTTTTTATTTATGCAGAGGCCGAGGCCGCCTCTGCCTCTGAG
CTATTCCAGAAGTAGTGAGGAGGCTTTTTGGAGGCCTAGGCTTTTGCAAAAAGCTCCCGGGA
GCTTGTATATCCATTTTCGGATCTGATCAAGAGACAGGATGAGGATCGTTTCGCATGATTGAA
CAAGATGGATTGCACGCAGGTTCTCCGGCCGCTTGGGTGGAGAGGCTATTCGGCTATGACTGG
GCACAACAGACAATCGGCTGCTCTGATGCCGCCGTGTTCCGGCTGTCAGCGCAGGGGCGCCCG
GTTCTTTTTGTCAAGACCGACCTGTCCGGTGCCCTGAATGAACTGCAGGACGAGGCAGCGCGG
CTATCGTGGCTGGCCACGACGGGCGTTCCTTGCGCAGCTGTGCTCGACGTTGTCACTGAAGCG
GGAAGGGACTGGCTGCTATTGGGCGAAGTGCCGGGGCAGGATCTCCTGTCATCTCACCTTGCT
CCTGCCGAGAAAGTATCCATCATGGCTGATGCAATGCGGCGGCTGCATACGCTTGATCCGGCT
ACCTGCCCATTCGACCACCAAGCGAAACATCGCATCGAGCGAGCACGTACTCGGATGGAAGC
CGGTCTTGTCGATCAGGATGATCTGGACGAAGAGCATCAGGGGCTCGCGCCAGCCGAACTGTT
CGCCAGGCTCAAGGCGCGCATGCCCGACGGCGAGGATCTCGTCGTGACCCATGGCGATGCCT
GCTTGCCGAATATCATGGTGGAAAATGGCCGCTTTTCTGGATTCATCGACTGTGGCCGGCTGG
GTGTGGCGGACCGCTATCAGGACATAGCGTTGGCTACCCGTGATATTGCTGAAGAGCTTGGCG
GCGAATGGGCTGACCGCTTCCTCGTGCTTTACGGTATCGCCGCTCCCGATTCGCAGCGCATCG
CCTTCTATCGCCTTCTTGACGAGTTCTTCTGAGCGGGACTCTGGGGTTCGAAATGACCGACCA
AGCGACGCCCAACCTGCCATCACGAGATTTCGATTCCACCGCCGCCTTCTATGAAAGGTTGGG
CTTCGGAATCGTTTTCCGGGACGCCGGCTGGATGATCCTCCAGCGCGGGGATCTCATGCTGGA
GTTCTTCGCCCACCCCAACTTGTTTATTGCAGCTTATAATGGTTACAAATAAAGCAATAGCATC
ACAAATTTCACAAATAAAGCATTTTTTTCACTGCATTCTAGTTGTGGTTTGTCCAAACTCATCA
ATGTATCTTATCATGTCTGTATACCGTCGACCTCTAGCTAGAGCTTGGCGTAATCATGGTCATA
GCTGTTTCCTGTGTGAAATTGTTATCCGCTCACAATTCCACACAACATACGAGCCGGAAGCAT
AAAGTGTAAAGCCTGGGGTGCCTAATGAGTGAGCTAACTCACATTAATTGCGTTGCGCTCACT
GCCCGCTTTCCAGTCGGGAAACCTGTCGTGCCAGCTGCATTAATGAATCGGCCAACGCGCGGG
GAGAGGCGGTTTGCGTATTGGGCGCTCTTCCGCTTCCTCGCTCACTGACTCGCTGCGCTCGGTC
GTTCGGCTGCGGCGAGCGGTATCAGCTCACTCAAAGGCGGTAATACGGTTATCCACAGAATCA
GGGGATAACGCAGGAAAGAACATGTGAGCAAAAGGCCAGCAAAAGGCCAGGAACCGTAAAA
AGGCCGCGTTGCTGGCGTTTTTCCATAGGCTCCGCCCCCTGACGAGCATCACAAAAATCGAC
GCTCAAGTCAGAGGTGGCGAAACCCGACAGGACTATAAAGATACCAGGCGTTTCCCCCTGGA
AGCTCCCTCGTGCGCTCTCCTGTTCCGACCCTGCCGCTTACCGGATACCTGTCCGCCTTTCTCC
CTTCGGGAAGCGTGGCGCTTTCTCAATGCTCACGCTGTAGGTATCTCAGTTCGGTGTAGGTCGT
TCGCTCCAAGCTGGGCTGTGTGCACGAACCCCCCGTTCAGCCCGACCGCTGCGCCTTATCCGG
TAACTATCGTCTTGAGTCCAACCCGGTAAGACACGACTTATCGCCACTGGCAGCAGCCACTGG
TAACAGGATTAGCAGAGCGAGGTATGTAGGCGGTGCTACAGAGTTCTTGAAGTGGTGGCCTA
ACTACGGCTACACTAGAAGGACAGTATTTGGTATCTGCGCTCTGCTGAAGCCAGTTACCTTCG
GAAAAAGAGTTGGTAGCTCTTGATCCGGCAAACAAACCACCGCTGGTAGCGGTGGTTTTTTG
TTTGCAAGCAGCAGATTACGCGCAGAAAAAAAGGATCTCAAGAAGATCCTTTGATCTTTTCTA
CGGGGTCTGACGCTCAGTGGAACGAAAACTCACGTTAAGGGATTTTGGTCATGAGATTATCAA
AAAGGATCTTCACCTAGATCCTTTTAAATTAAAAATGAAGTTTTAAATCAATCTAAAGTATAT
ATGAGTAAACTTGGTCTGACAGTTACCAATGCTTAATCAGTGAGGCACCTATCTCAGCGATCT
GTCTATTTCGTTCATCCATAGTTGCCTGACTCCCCGTCGTGTAGATAACTACGATACGGGAGG
GCTTACCATCTGGCCCCAGTGCTGCAATGATACCGCGAGACCCACGCTCACCGGCTCCAGATT
TATCAGCAATAAACCAGCCAGCCGGAAGGGCCGAGCGCAGAAGTGGTCCTGCAACTTTATCC
GCCTCCATCCAGTCTATTAATTGTTGCCGGGAAGCTAGAGTAAGTAGTTCGCCAGTTAATAGT
TTGCGCAACGTTGTTGCCATTGCTACAGGCATCGTGGTGTCACGCTCGTCGTTTGGTATGGCTT
CATTCAGCTCCGGTTCCCAACGATCAAGGCGAGTTACATGATCCCCATGTTGTGCAAAAAG
CGGTTAGCTCCTTCGGTCCTCCGATCGTTGTCAGAAGTAAGTTGGCCGCAGTGTTATCACTCAT
```

FIG. 8B (continued)

GGTTATGGCAGCACTGCATAATTCTCTTACTGTCATGCCATCCGTAAGATGCTTTCTGTGACT
GGTGAGTACTCAACCAAGTCATTCTGAGAATAGTGTATGCGGCGACCGAGTTGCTCTTGCCCG
GCGTCAATACGGGATAATACCGCGCCACATAGCAGAACTTTAAAAGTGCTCATCATTGGAAA
ACGTTCTTCGGGGCGAAAACTCTCAAGGATCTTACCGCTGTTGAGATCCAGTTCGATGTAACC
CACTCGTGCACCCAACTGATCTTCAGCATCTTTTACTTTCACCAGCGTTTCTGGGTGAGCAAAA
ACAGGAAGGCAAAATGCCGCAAAAAAGGGAATAAGGGCGACACGGAAATGTTGAATACTCA
TACTCTTCCTTTTTCAATATTATTGAAGCATTTATCAGGGTTATTGTCTCATGAGCGGATACAT
ATTTGAATGTATTTAGAAAAATAAACAAATAGGGGTTCCGCGCACATTTCCCCGAAAAGTGCC
ACCTGACGTC

FIG. 8D

SEQ ID NO: 13

CTAAATTGTAAGCGTTAATATTTTGTTAAAATTCGCGTTAAATTTTTGTTAAATCAGCTCATTT
TTTAACCAATAGGCCGAAATCGGCAAAATCCCTTATAAATCAAAAGAATAGACCGAGATAGG
GTTGAGTGTTGTTCCAGTTTGGAACAAGAGTCCACTATTAAAGAACGTGGACTCCAACGTCAA
AGGGCGAAAAACCGTCTATCAGGGCGATGGCCCACTACGTGAACCATCACCCTAATCAAGTTT
TTTGGGGTCGAGGTGCCGTAAAGCACTAAATCGGAACCCTAAAGGGAGCCCCCGATTTAGAG
CTTGACGGGGAAAGCCGGCGAACGTGGCGAGAAAGGAAGGGAAGAAAGCGAAAGGAGCGG
GCGCTAGGGCGCTGGCAAGTGTAGCGGTCACGCTGCGCGTAACCACCACACCCGCCGCGCTT
AATGCGCCGCTACAGGGCGCGTCCCATTCGCCATTCAGGCTGCGCAACTGTTGGGAAGGGCG
ATCGGTGCGGGCCTCTTCGCTATTACGCCAGCTGGCGAAAGGGGATGTGCTGCAAGGCGATT
AAGTTGGGTAACGCCAGGGTTTTCCCAGTCACGACGTTGTAAAACGACGGCCAGTGAGCGCG
CTTAACCCTAGAAAGATAATCATATTGTGACGTACGTTAAAGATAATCATGCGTAAAATTGAC
GCATGTGTTTTATCGGTCTGTATATCGAGGTTTATTTATTAATTTGAATAGATATTAAGTTTTAT
TATATTTACACTTACATACTAATAATAAATTCAACAAACAATTTATTTATGTTTATTTATTTATT
AAAAAAAAACAAAAACTCAAAATTTCTTCTATAAAGTAACAAAACTTTTATCGATAACTTCGT
ATAATGTATGCTATACGAAGTTATagaggggcggaagggacgttaggagggaggcagggaggcagggaggcagggaggaac
ggagggagGCGGCCGCGGTACCGGCGCGCCGGGGGAGGCTGCTGGTGAATATTAACCAAGGTCA
CCCCAGTTATCGGAGGAGCAAACAGGGGCTAAGTCCACACGCGTGGTACCGTCTGTCTGCAC
ATTTCGTAGAGCGAGTGTTCCGATACTCTAATCTCCCTAGGCAAGGTTCATATTTGTGTAGGTT
ACTTATTCTCCTTTTGTTGACTAAGTCAATAATCAGAATCAGCAGGTTTGGAGTCAGCTTGGCA
GGGATCAGCAGCCTGGGTTGGAAGGAGGGGGTATAAAAGCCCCTTCACCAGGAGAAGCCGTC
ACACAGATCCACAAGCTCCTGAAGAGGTAAGGGTTTAAGGGATGGTTGGTTGGTGGGGNATT
AATGTTTAATTACCTGGAGCACCTGCCTGAAATCACTTTTTTTCAGGTTGGCTAGTATGCAGAT
CGAGCTGTCCACCTGCTTTTTCTGTGCCTGCTGCGGTTCTGCTTCAGCGCCACCCGGCGGTAC
TACCTGGGCGCCGTGGAGCTGTCCTGGACTACATGCAGAGCGACCTGGGCGAGCTGCCCGT
GGACGCCCGGTTCCCCCCCAGAGTGCCCAAGAGCTTCCCCTTCAACACCAGCGTGGTGTACAA
GAAAACCCTGTTCGTGGAGTTCACCGACCACCTGTTCAATATCGCCAAGCCCAGGCCCCCCTG
GATGGGCCTGCTGGGCCCCACCATCCAGGCCGAGGTGTACGACACCGTGGTGATCACCCTGA
AGAACATGGCCAGCCACCCCGTGAGCCTGCACGCCGTGGGCGTGAGCTACTGGAAGGCCAGC
GAGGGCGCCGAGTACGACGACCAGACCAGCCAGCGGGAGAAAGAAGATGACAAGGTGTTCC
CTGGCGGCAGCCACACCTACGTGTGGCAGGTGCTGAAAGAAAACGGCCCCATGGCCTCCGAC
CCCCTGTGCCTGACCTACAGCTACCTGAGCCACGTGGACCTGGTGAAGGACCTGAACAGCGGC
CTGATCGGCGCTCTGCTCGTCTGCCGGGAGGGCAGCCTGGCCAAAGAGAAAACCCAGACCCT
GCACAAGTTCATCCTGCTGTTCGCCGTGTTCGACGAGGGCAAGAGCTGGCACAGCGAGACAA
AGAACAGCCTGATGCAGGACCGGGACGCCGCCTCTGCCAGAGCCTGGCCCAAGATGCACACC
GTGAACGGCTACGTGAACAGAAGCCTGCCCGGCCTGATTGGCTGCCACCGGAAGAGCGTGTA
CTGGCACGTGATCGGCATGGGCACCACACCCGAGGTGCACAGCATCTTTCTGGAAGGGCACA
CCTTTCTGGTCCGGAACCACCGGCAGGCCAGCCTGGAAATCAGCCCTATCACCTTCCTGACCG
CCCAGACACTGCTGATGGACCTGGGCCAGTTCCTGCTGTTTTGCCACATCAGCTCTCACCAGC
ACGACGGCATGGAAGCCTACGTGAAGGTGGACTCTTGCCCCGAGGAACCCCAGCTGCGGATG
AAGAACAACGAGGAAGCCGAGGACTACGACGACGACCTGACCGACAGCGAGATGGACGTGG
TGCGGTTCGACGACGACAACAGCCCCAGCTTCATCCAGATCAGAAGCGTGGCCAAGAAGCAC
CCCAAGACCTGGGTGCACTATATCGCCGCCGAGGAAGAGGACTGGGACTACGCCCCCCTGGT
GCTGGCCCCCGACGACAGAAGCTACAAGAGCCAGTACCTGAACAATGGCCCCCAGCGGATCG
GCCGGAAGTACAAGAAAGTGCGGTTCATGGCCTACACCGACGAGACATTCAAGACCCGGGAG
GCCATCCAGCACGAGAGCGGCATCCTGGGCCCCCTGCTGTACGGCGAAGTGGGCGACACACT
GCTGATCATCTTCAAGAACCAGGCTAGCCGGCCCTACAACATCTACCCCCACGGCATCACCGA
CGTGCGGCCCCTGTACAGCAGGCGGCTGCCCAAGGGCGTGAAGCACCTGAAGGACTTCCCCA
TCCTGCCCGGCGAGATCTTCAAGTACAAGTGGACCGTGACCGTGGAGGACGGCCCCACCAAG
AGCGACCCCAGATGCCTGACCCGGTACTACAGCAGCTTCGTGAACATGGAACGGGACCTGGC FIG. 8D (continued)

CTCCGGGCTGATCGGACCTCTGCTGATCTGCTACAAAGAAAGCGTGGACCAGCGGGGCAACC
AGATCATGAGCGACAAGCGGAACGTGATCCTGTTCAGCGTGTTCGATGAGAACCGGTCCTGGT
ATCTGACCGAGAACATCCAGCGGTTTCTGCCCAACCCTGCCGGCGTGCAGCTGGAAGATCCCG
AGTTCCAGGCCAGCAACATCATGCACTCCATCAATGGCTACGTGTTCGACTCTCTGCAGCTCT
CCGTGTGTCTGCACGAGGTGGCCTACTGGTACATCCTGAGCATCGGCGCCCAGACCGACTTCC
TGAGCGTGTTCTTCAGCGGCTACACCTTCAAGCACAAGATGGTGTACGAGGACACCCTGACCC
TGTTCCCTTTCAGCGGCGAGACAGTGTTCATGAGCATGGAAAACCCCGGCCTGTGGATTCTGG
GCTGCCACAACAGCGACTTCCGGAACCGGGGCATGACCGCCCTGCTGAAGGTGTCCAGCTGC
GACAAGAACACCGGCGACTACTACGAGGACAGCTACGAGGATATCAGCGCCTACCTGCTGTC
CAAGAACAACGCCATCGAACCCCGGAGCTTCAGCCAGAACCCCCCGTGCTGACGCGTCACC
AGCGGGAGATCACCCGGACAACCCTGCAGTCCGACCAGGAAGAGATCGATTACGACGACACC
ATCAGCGTGGAGATGAAGAAAGAGGATTTCGATATCTACGACGAGGACGAGAACCAGAGCCC
CAGAAGCTTCCAGAAGAAAACCCGGCACTACTTCATTGCCGCCGTGGAGAGGCTGTGGGACT
ACGGCATGAGTTCTAGCCCCCACGTGCTGCGGAACCGGGCCCAGAGCGGCAGCGTGCCCCAG
TTCAAGAAAGTGGTGTTCCAGGAATTCACAGACGGCAGCTTCACCCAGCCTCTGTATAGAGGC
GAGCTGAACGAGCACCTGGGGCTGCTGGGGCCCTACATCAGGGCCGAAGTGGAGGACAACAT
CATGGTGACCTTCCGGAATCAGGCCAGCAGACCCTACTCCTTCTACAGCAGCCTGATCAGCTA
CGAAGAGGACCAGCGGCAGGGCGCCGAACCCCGGAAGAACTTCGTGAAGCCCAACGAAACC
AAGACCTACTTCTGGAAAGTGCAGCACCACATGGCCCCCACCAAGGACGAGTTCGACTGCAA
GGCCTGGGCCTACTTCAGCGACGTGGATCTGGAAAAGGACGTGCACTCTGGACTGATTGGCCC
ACTCCTGGTCTGCCACACTAACACCCTCAACCCCGCCCACGGCCGCCAGGTGACCGTGCAGGA
ATTCGCCCTGTTCTTCACCATCTTCGACGAGACAAAGTCCTGGTACTTCACCGAGAATATGGA
ACGGAACTGCAGAGCCCCCTGCAACATCCAGATGGAAGATCCTACCTTCAAAGAGAACTACC
GGTTCCACGCCATCAACGGCTACATCATGGACACCCTGCCTGGCCTGGTGATGGCCCAGGACC
AGAGAATCCGGTGGTATCTGCTGTCCATGGGCAGCAACGAGAATATCCACAGCATCCACTTCA
GCGGCCACGTGTTCACCGTGCGGAAGAAAGAAGAGTACAAGATGGCCCTGTACAACCTGTAC
CCCGGCGTGTTCGAGACAGTGGAGATGCTGCCCAGCAAGGCCGGCATCTGGCGGGTGGAGTG
TCTGATCGGCGAGCACCTGCACGCTGGCATGAGCACCCTGTTTCTGGTGTACAGCAACAAGTG
CCAGACCCCACTGGGCATGGCCTCTGGCCACATCCGGGACTTCCAGATCACCGCCTCCGGCCA
GTACGGCCAGTGGGCCCCCAAGCTGGCCAGACTGCACTACAGCGGCAGCATCAACGCCTGGT
CCACCAAAGAGCCCTTCAGCTGGATCAAGGTGGACCTGCTGGCCCCTATGATCATCCACGGCA
TTAAGACCCAGGGCGCCAGGCAGAAGTTCAGCAGCCTGTACATCAGCCAGTTCATCATCATGT
ACAGCCTGGACGGCAAGAAGTGGCAGACCTACCGGGGCAACAGCACCGGCACCCTGATGGTG
TTCTTCGGCAATGTGGACAGCAGCGGCATCAAGCACAACATCTTCAACCCCCCCATCATTGCC
CGGTACATCCGGCTGCACCCCACCCACTACAGCATTAGATCCACACTGAGAATGGAACTGATG
GGCTGCGACCTGAACTCCTGCAGCATGCCTCTGGGCATGGAAAGCAAGGCCATCAGCGACGC
CCAGATCACAGCCAGCAGCTACTTCACCAACATGTTCGCCACCTGGTCCCCCTCCAAGGCCAG
GCTGCACCTGCAGGGCCGGTCCAACGCCTGGCGGCCTCAGGTCAACAACCCCAAAGAATGGC
TGCAGGTGGACTTTCAGAAAACCATGAAGGTGACCGGCGTGACCACCCAGGGCGTGAAAAGC
CTGCTGACCAGCATGTACGTGAAAGAGTTTCTGATCAGCAGCTCTCAGGATGGCCACCAGTGG
ACCCTGTTCTTTCAGAACGGCAAGGTGAAAGTGTTCCAGGGCAACCAGGACTCCTTCACCCCC
GTGGTGAACTCCCTGGACCCCCCCCTGCTGACCCGCTACCTGAGAATCCACCCCCAGTCTTGG
GTGCACCAGATCGCCCTCAGGATGGAAGTCCTGGGATGTGAGGCCCAGGATCTGTACTGATG
AGGATCTAGGCTCGACATGCTTTATTTGTGAAATTTGTGATGCTATTGCTTTATTTGTAACCAT
TATAAGCTGCAATAAACAAGTTAACAACAACAATTGCATTCATTTTATGTTTCAGGTTCAGGG
GGAGGTGTGGGAGGTTTTTTAAACTCGAGACCGGTagaggggcggaagggacgttaggagggaggcagggaggcag
ggaggcagggaggaacggagggagATAACTTCGTATAATGTATGCTATACGAAGTTATGATATCTATAAC
AAGAAAATATATATATAATAAGTTATCACGTAAGTAGAACACGAAATAACAATATAATTATC
GTATGAGTTAAATCTTAAAAGTCACGTAAAAGATAATCATGCGTCATTTTGACTCACGCGGTT
GTTATAGTTCAAAATCAGTGACACTTACCGCATTGACAAGCACGCCTCACGGGAGCTCCAAGC
GGCGACTGAGATGTCCTAAATGCACAGCGACGGATTCGCGCTATTTAGAAAGAGAGCAAT
ATTTCAAGAATGCATGCGTCAATTTTACGCAGACTATCTTTCTAGGGTTAAGCGCGCTTGGCGT
AATCATGGTCATAGCTGTTTCCTGTGTGAAATTGTTATCCGCTCACAATTCCACACAACATACG
AGCCGGAAGCATAAAGTGTAAAGCCTGGGGTGCCTAATGAGTGAGCTAACTCACATTAATTG FIG. 8D (continued)

CGTTGCGCTCACTGCCCGCTTTCCAGTCGGGAAACCTGTCGTGCCAGCTGCATTAATGAATCG
GCCAACGCGCGGGGAGAGGCGGTTTGCGTATTGGGCGCTCTTCCGCTTCCTCGCTCACTGACT
CGCTGCGCTCGGTCGTTCGGCTGCGGCGAGCGGTATCAGCTCACTCAAAGGCGGTAATACGGT
TATCCACAGAATCAGGGGATAACGCAGGAAAGAACATGTGAGCAAAAGGCCAGCAAAAGGC
CAGGAACCGTAAAAAGGCCGCGTTGCTGGCGTTTTTCCATAGGCTCCGCCCCCCTGACGAGCA
TCACAAAAATCGACGCTCAAGTCAGAGGTGGCGAAACCCGACAGGACTATAAAGATACCAGG
CGTTTCCCCCTGGAAGCTCCCTCGTGCGCTCTCCTGTTCCGACCCTGCCGCTTACCGGATACCT
GTCCGCCTTTCTCCCTTCGGGAAGCGTGGCGCTTTCTCATAGCTCACGCTGTAGGTATCTCAGT
TCGGTGTAGGTCGTTCGCTCCAAGCTGGGCTGTGTGCACGAACCCCCCGTTCAGCCCGACCGC
TGCGCCTTATCCGGTAACTATCGTCTTGAGTCCAACCCGGTAAGACACGACTTATCGCCACTG
GCAGCAGCCACTGGTAACAGGATTAGCAGAGCGAGGTATGTAGGCGGTGCTACAGAGTTCTT
GAAGTGGTGGCCTAACTACGGCTACACTAGAAGGACAGTATTTGGTATCTGCGCTCTGCTGAA
GCCAGTTACCTTCGGAAAAAGAGTTGGTAGCTCTTGATCCGGCAAACAAACCACCGCTGGTAG
CGGTGGTTTTTTTGTTTGCAAGCAGCAGATTACGCGCAGAAAAAAAGGATCTCAAGAAGATCC
TTTGATCTTTTCTACGGGGTCTGACGCTCAGTGGAACGAAAACTCACGTTAAGGGATTTTGGT
CATGAGATTATCAAAAAGGATCTTCACCTAGATCCTTTTAAATTAAAAATGAAGTTTTAAATC
AATCTAAAGTATATATGAGTAAACTTGGTCTGACAGTTACCAATGCTTAATCAGTGAGGCACC
TATCTCAGCGATCTGTCTATTTCGTTCATCCATAGTTGCCTGACTCCCCGTCGTGTAGATAACT
ACGATACGGGAGGGCTTACCATCTGGCCCCAGTGCTGCAATGATACCGCGAGACCCACGCTC
ACCGGCTCCAGATTTATCAGCAATAAACCAGCCAGCCGGAAGGGCCGAGCGCAGAAGTGGTC
CTGCAACTTTATCCGCCTCCATCCAGTCTATTAATTGTTGCCGGGAAGCTAGAGTAAGTAGTTC
GCCAGTTAATAGTTTGCGCAACGTTGTTGCCATTGCTACAGGCATCGTGGTGTCACGCTCGTC
GTTTGGTATGGCTTCATTCAGCTCCGGTTCCCAACGATCAAGGCGAGTTACATGATCCCCCAT
GTTGTGCAAAAAAGCGGTTAGCTCCTTCGGTCCTCCGATCGTTGTCAGAAGTAAGTTGGCCGC
AGTGTTATCACTCATGGTTATGGCAGCACTGCATAATTCTCTTACTGTCATGCCATCCGTAAGA
TGCTTTTCTGTGACTGGTGAGTACTCAACCAAGTCATTCTGAGAATAGTGTATGCGGCGACCG
AGTTGCTCTTGCCCGGCGTCAATACGGGATAATACCGCGCCACATAGCAGAACTTTAAAAGTG
CTCATCATTGGAAAACGTTCTTCGGGGCGAAAACTCTCAAGGATCTTACCGCTGTTGAGATCC
AGTTCGATGTAACCCACTCGTGCACCCAACTGATCTTCAGCATCTTTTACTTTCACCAGCGTTT
CTGGGTGAGCAAAAACAGGAAGGCAAAATGCCGCAAAAAAGGGAATAAGGGCGACACGGAA
ATGTTGAATACTCATACTCTTCCTTTTTCAATATTATTGAAGCATTTATCAGGGTTATTGTCTCA
TGAGCGGATACATATTTGAATGTATTTAGAAAAATAAACAAATAGGGGTTCCGCGCACATTTC
CCCGAAAAGTGCCAC

FIG. 8F

SEQ ID NO:14

CTAAATTGTAAGCGTTAATATTTTGTTAAAATTCGCGTTAAATTTTTGTTAAATCAGCTCATTT
TTTAACCAATAGGCCGAAATCGGCAAAATCCCTTATAAATCAAAAGAATAGACCGAGATAGG
GTTGAGTGTTGTTCCAGTTTGGAACAAGAGTCCACTATTAAAGAACGTGGACTCCAACGTCAA
AGGGCGAAAAACCGTCTATCAGGGCGATGGCCCACTACGTGAACCATCACCCTAATCAAGTTT
TTTGGGGTCGAGGTGCCGTAAAGCACTAAATCGGAACCCTAAAGGGAGCCCCCGATTTAGAG
CTTGACGGGGAAAGCCGGCGAACGTGGCGAGAAAGGAAGGGAAGAAAGCGAAAGGAGCGG
GCGCTAGGGCGCTGGCAAGTGTAGCGGTCACGCTGCGCGTAACCACCACACCCGCCGCGCTT
AATGCGCCGCTACAGGGCGCGTCCCATTCGCCATTCAGGCTGCGCAACTGTTGGGAAGGGCG
ATCGGTGCGGGCCTCTTCGCTATTACGCCAGCTGGCGAAAGGGGGATGTGCTGCAAGGCGATT
AAGTTGGGTAACGCCAGGGTTTTCCCAGTCACGACGTTGTAAAACGACGGCCAGTGAGCGCG
CTTAACCCTAGAAAGATAATCATATTGTGACGTACGTTAAAGATAATCATGCGTAAAATTGAC
GCATGATAACTTCGTATAATGTATGCTATACGAAGTTATGCGGCCGCGGTACCGGCGCGCCGG
GGGAGGCTGCTGGTGAATATTAACCAAGGTCACCCCAGTTATCGGAGGAGCAAACAGGGGCT
AAGTCCACACGCGTGGTACCGTCTGTCTGCACATTTCGTAGAGCGAGTGTTCCGATACTCTAA
TCTCCCTAGGCAAGGTTCATATTTGTGTAGGTTACTTATTCTCCTTTTGTTGACTAAGTCAATA
ATCAGAATCAGCAGGTTTGGAGTCAGCTTGGCAGGGATCAGCAGCCTGGGTTGGAAGGAGGG
GGTATAAAAGCCCCTTCACCAGGAGAAGCCGTCACACAGATCCACAAGCTCCTGAAGAGGTA
AGGGTTTAAGGGATGGTTGGTTGGTGGGTATTAATGTTTAATTACCTGGAGCACCTGCCTGA
AATCACTTTTTTTCAGGTTGGGCTAGCCCACCATGCAGCGCGTGAACATGATCATGGCCGAGA
GCCCCGGCCTGATCACCATCTGCCTGCTGGGCTACCTGCTGAGCGCCGAGTGCACCGTGTTCC
TGGACCACGAGAACGCCAACAAGATCCTGAACCGCCCCAAGCGCTACAACAGCGGCAAGCTG
GAGGAGTTCGTGCAGGGCAACCTGGAGCGCGAGTGCATGGAGGAGAAGTGCAGCTTCGAGGA
GGCCCGCGAGGTGTTCGAGAACACCGAGCGCACCACCGAGTTCTGGAAGCAGTACGTGGACG
GCGACCAGTGCGAGAGCAACCCCTGCCTGAACGGCGGCAGCTGCAAGGACGACATCAACAGC
TACGAGTGCTGGTGCCCCTTCGGCTTCGAGGGCAAGAACTGCGAGCTGGACGTGACCTGCAAC
ATCAAGAACGGCCGCTGCGAGCAGTTCTGCAAGAACAGCGCCGACAACAAGGTGGTGTGCAG
CTGCACCGAGGGCTACCGCCTGGCCGAGAACCAGAAGAGCTGCGAGCCCGCCGTGCCCTTCC
CCTGCGGCCGCGTGAGCGTGAGCCAGACCAGCAAGCTGACCCGCGCCGAGGCCGTGTTCCCC
GACGTGGACTACGTGAACAGCACCGAGGCCGAGACCATCCTGGACAACATCACCCAGAGCAC
CCAGAGCTTCAACGACTTCACCCGCGTGGTGGGCGGCGAGGACGCCAAGCCCGGCCAGTTCC
CCTGGCAGGTGGTGCTGAACGGCAAGGTGGACGCCTTCTGCGGCGGCAGCATCGTGAACGAG
AAGTGGATCGTGACCGCCGCCCACTGCGTGGAGACCGGCGTGAAGATCACCGTGGTGGCCGG
CGAGCACAACATCGAGGAGACCGAGCACACCGAGCAGAAGCGCAACGTGATCCGCATCATCC
CCCACCACAACTACAACGCCGCCATCAACAAGTACAACCACGACATCGCCCTGCTGGAGCTG
GACGAGCCCCTGGTGCTGAACAGCTACGTGACCCCCATCTGCATCGCCGACAAGGAGTACAC
CAACATCTTCCTGAAGTTCGGCAGCGGCTACGTGAGCGGCTGGGGCCGCGTGTTCCACAAGGG
CCGCAGCGCCCTGGTGCTGCAGTACCTGCGCGTGCCCCTGGTGGACCGCGCCACCTGCCTGCG
CAGCACCAAGTTCACCATCTACAACAACATGTTCTGCGCCGGCTTCCACGAGGGCGGCCGCGA
CAGCTGCCAGGGCGACAGCGGCGGCCCCACGTGACCGAGGTGGAGGGCACCAGCTTCCTGA
CCGGCATCATCAGCTGGGGCGAGGAGTGCGCCATGAAGGGCAAGTACGGCATCTACACCAAG
GTGAGCCGCTACGTGAACTGGATCAAGGAGAAGACCAAGCTGACCTAATGAAAGATGGATTT
CCAAGGTTAATTCATTGGAATTGAAAATTAACAGCCCCCCCCCCCCCCCTGCAGATCTAG
AGCTCGCTGATCAGCCTCGACTGTGCCTTCTAGTTGCCAGCCATCTGTTGTTTGCCCCTCCCCC
GTGCCTTCCTTGACCCTGGAAGGTGCCACTCCCACTGTCCTTTCCTAATAAAATGAGGAAATT
GCATCGCATTGTCTGAGTAGGTGTCATTCTATTCTGGGGGGTGGGGTGGGCAGGACAGCAAG
GGGGAGGATTGGGAAGACAATAGCAGGCATGCTGGGGACCGGTATAACTTCGTATAATGTAT
GCTATACGAAGTTATGCATGCGTCAATTTTACGCAGACTATCTTTCTAGGGTTAAGCGCGCTTG
GCGTAATCATGGTCATAGCTGTTTCCTGTGTGAAATTGTTATCCGCTCACAATTCCACACAACA
TACGAGCCGGAAGCATAAAGTGTAAAGCCTGGGGTGCCTAATGAGTGAGCTAACTCACATTA

FIG. 8F (continued)

ATTGCGTTGCGCTCACTGCCCGCTTTCCAGTCGGGAAACCTGTCGTGCCAGCTGCATTAATGA
ATCGGCCAACGCGCGGGGAGAGGCGGTTTGCGTATTGGGCGCTCTTCCGCTTCCTCGCTCACT
GACTCGCTGCGCTCGGTCGTTCGGCTGCGGCGAGCGGTATCAGCTCACTCAAAGGCGGTAATA
CGGTTATCCACAGAATCAGGGGATAACGCAGGAAAGAACATGTGAGCAAAAGGCCAGCAAA
AGGCCAGGAACCGTAAAAAGGCCGCGTTGCTGGCGTTTTTCCATAGGCTCCGCCCCCCTGACG
AGCATCACAAAAATCGACGCTCAAGTCAGAGGTGGCGAAACCCGACAGGACTATAAAGATAC
CAGGCGTTTCCCCCTGGAAGCTCCCTCGTGCGCTCTCCTGTTCCGACCCTGCCGCTTACCGGAT
ACCTGTCCGCCTTTCTCCCTTCGGGAAGCGTGGCGCTTTCTCATAGCTCACGCTGTAGGTATCT
CAGTTCGGTGTAGGTCGTTCGCTCCAAGCTGGGCTGTGTGCACGAACCCCCCGTTCAGCCCGA
CCGCTGCGCCTTATCCGGTAACTATCGTCTTGAGTCCAACCCGGTAAGACACGACTTATCGCC
ACTGGCAGCAGCCACTGGTAACAGGATTAGCAGAGCGAGGTATGTAGGCGGTGCTACAGAGT
TCTTGAAGTGGTGGCCTAACTACGGCTACACTAGAAGGACAGTATTTGGTATCTGCGCTCTGC
TGAAGCCAGTTACCTTCGGAAAAAGAGTTGGTAGCTCTTGATCCGGCAAACAAACCACCGCTG
GTAGCGGTGGTTTTTTTGTTTGCAAGCAGCAGATTACGCGCAGAAAAAAAGGATCTCAAGAA
GATCCTTTGATCTTTTCTACGGGGTCTGACGCTCAGTGGAACGAAAACTCACGTTAAGGGATT
TTGGTCATGAGATTATCAAAAAGGATCTTCACCTAGATCCTTTTAAATTAAAAATGAAGTTTT
AAATCAATCTAAAGTATATATGAGTAAACTTGGTCTGACAGTTACCAATGCTTAATCAGTGAG
GCACCTATCTCAGCGATCTGTCTATTTCGTTCATCCATAGTTGCCTGACTCCCCGTCGTGTAGA
TAACTACGATACGGGAGGGCTTACCATCTGGCCCCAGTGCTGCAATGATACCGCGAGACCCAC
GCTCACCGGCTCCAGATTTATCAGCAATAAACCAGCCAGCCGGAAGGGCCGAGCGCAGAAGT
GGTCCTGCAACTTTATCCGCCTCCATCCAGTCTATTAATTGTTGCCGGGAAGCTAGAGTAAGT
AGTTCGCCAGTTAATAGTTTGCGCAACGTTGTTGCCATTGCTACAGGCATCGTGGTGTCACGCT
CGTCGTTTGGTATGGCTTCATTCAGCTCCGGTTCCCAACGATCAAGGCGAGTTACATGATCCCC
CATGTTGTGCAAAAAAGCGGTTAGCTCCTTCGGTCCTCCGATCGTTGTCAGAAGTAAGTTGGC
CGCAGTGTTATCACTCATGGTTATGGCAGCACTGCATAATTCTCTTACTGTCATGCCATCCGTA
AGATGCTTTTCTGTGACTGGTGAGTACTCAACCAAGTCATTCTGAGAATAGTGTATGCGGCGA
CCGAGTTGCTCTTGCCCGGCGTCAATACGGGATAATACCGCGCCACATAGCAGAACTTTAAAA
GTGCTCATCATTGGAAAACGTTCTTCGGGGCGAAAACTCTCAAGGATCTTACCGCTGTTGAGA
TCCAGTTCGATGTAACCCACTCGTGCACCCAACTGATCTTCAGCATCTTTTACTTTCACCAGCG
TTTCTGGGTGAGCAAAAACAGGAAGGCAAAATGCCGCAAAAAAGGGAATAAGGGCGACACG
GAAATGTTGAATACTCATACTCTTCCTTTTTCAATATTATTGAAGCATTTATCAGGGTTATTGT
CTCATGAGCGGATACATATTTGAATGTATTTAGAAAAATAAACAAATAGGGGTTCCGCGCACA
TTTCCCCGAAAAGTGCCAC

SEQ ID NO:15

CTAAATTGTAAGCGTTAATATTTTGTTAAAATTCGCGTTAAATTTTTGTTAAATCAGCTCATTT
TTTAACCAATAGGCCGAAATCGGCAAAATCCCTTATAAATCAAAAGAATAGACCGAGATAGG
GTTGAGTGTTGTTCCAGTTTGGAACAAGAGTCCACTATTAAAGAACGTGGACTCCAACGTCAA
AGGGGCGAAAAACCGTCTATCAGGGCGATGGCCCACTACGTGAACCATCACCCTAATCAAGTTT
TTTGGGGTCGAGGTGCCGTAAAGCACTAAATCGGAACCCTAAAGGGAGCCCCCGATTTAGAG
CTTGACGGGGAAAGCCGGCGAACGTGGCGAGAAAGGAAGGGAAGAAAGCGAAAGGAGCGG
GCGCTAGGGCGCTGGCAAGTGTAGCGGTCACGCTGCGCGTAACCACCACCCGCCGCGCTT
AATGCGCCGCTACAGGGCGCGTCCCATTCGCCATTCAGGCTGCGCAACTGTTGGGAAGGGCG
ATCGGTGCGGGCCTCTTCGCTATTACGCCAGCTGGCGAAAGGGGATGTGCTGCAAGGCGATT
AAGTTGGGTAACGCCAGGGTTTTCCCAGTCACGACGTTGTAAAACGACGGCCAGTGAGCGCG
CTTAACCCTAGAAAGATAATCATATTGTGACGTACGTTAAAGATAATCATGCGTAAAATTGAC
GCATGATAACTTCGTATAATGTATGCTATACGAAGTTATGCGGCCGCGGTACCGGCGCGCCGG
GGGAGGCTGCTGGTGAATATTAACCAAGGTCACCCCAGTTATCGGAGGAGCAAACAGGGGCT
AAGTCCACACGCGTGGTACCGTCTGTCTGCACATTTCGTAGAGCGAGTGTTCCGATACTCTAA
TCTCCCTAGGCAAGGTTCATATTTGTGTAGGTTACTTATTCTCCTTTTGTTGACTAAGTCAATA
ATCAGAATCAGCAGGTTTGGAGTCAGCTTGGCAGGGATCAGCAGCCTGGGTTGGAAGGAGGG
GGTATAAAAGCCCCTTCACCAGGAGAAGCCGTCACACAGATCCACAAGCTCCTGAAGAGGTA
AGGGTTTAAGGGATGGTTGGTTGGTGGGGTATTAATGTTTAATTACCTGGAGCACCTGCCTGA
AATCACTTTTTTTCAGGTTGGGCTAGCCCACCATGCAGCGCGTGAACATGATCATGGCCGAGA
GCCCCGGCCTGATCACCATCTGCCTGCTGGGCTACCTGCTGAGCGCCGAGTGCACCGTGTTCC
TGGACCACGAGAACGCCAACAAGATCCTGAACCGCCCCAAGCGCTACAACAGCGGCAAGCTG
GAGGAGTTCGTGCAGGGCAACCTGGAGCGCGAGTGCATGGAGGAGAAGTGCAGCTTCGAGGA
GGCCCGCGAGGTGTTCGAGAACACCGAGCGCACCACCGAGTTCTGGAAGCAGTACGTGGACG
GCGACCAGTGCGAGAGCAACCCCTGCCTGAACGGCGGCAGCTGCAAGGACGACATCAACAGC
TACGAGTGCTGGTGCCCCTTCGGCTTCGAGGGCAAGAACTGCGAGCTGGACGTGACCTGCAAC
ATCAAGAACGGCCGCTGCGAGCAGTTCTGCAAGAACAGCGCCGACAACAAGGTGGTGTGCAG
CTGCACCGAGGGCTACCGCCTGGCCGAGAACCAGAAGAGCTGCGAGCCCGCCGTGCCCTTCC
CCTGCGGCCGCGTGAGCGTGAGCCAGACCAGCAAGCTGACCCGCGCCGAGGCCGTGTTCCCC
GACGTGGACTACGTGAACAGCACCGAGGCCGAGACCATCCTGGACAACATCACCCAGAGCAC
CCAGAGCTTCAACGACTTCACCCGCGTGGTGGGCGGCGAGGACGCCAAGCCCGGCCAGTTCC
CCTGGCAGGTGGTGCTGAACGGCAAGGTGGACGCCTTCTGCGGCGGCAGCATCGTGAACGAG
AAGTGGATCGTGACCGCCGCCCACTGCGTGGAGACCGGCGTGAAGATCACCGTGGTGGCCGG
CGAGCACAACATCGAGGAGACCGAGCACACCGAGCAGAAGCGCAACGTGATCCGCATCATCC
CCCACCACAACTACAACGCCGCCATCAACAAGTACAACCACGACATCGCCCTGCTGGAGCTG
GACGAGCCCCTGGTGCTGAACAGCTACGTGACCCCCATCTGCATCGCCGACAAGGAGTACAC
CAACATCTTCCTGAAGTTCGGCAGCGGCTACGTGAGCGGCTGGGGCCGCGTGTTCCACAAGGG
CCGCAGCGCCCTGGTGCTGCAGTACCTGCGCGTGCCCCTGGTGGACCGCGCCACCTGCCTGCT
GAGCACCAAGTTCACCATCTACAACAACATGTTCTGCGCCGGCTTCCACGAGGGCGGCCGCGA
CAGCTGCCAGGGCGACAGCGGCGGCCCCCACGTGACCGAGGTGGAGGGCACCAGCTTCCTGA
CCGGCATCATCAGCTGGGGCGAGGAGTGCGCCATGAAGGGCAAGTACGGCATCTACACCAAG
GTGAGCCGCTACGTGAACTGGATCAAGGAGAAGACCAAGCTGACCTAATGAAAGATGGATTT
CCAAGGTTAATTCATTGGAATTGAAAATTAACAGCCCCCCCCCCCCCCTGCAGATCTAG
AGCTCGCTGATCAGCCTCGACTGTGCCTTCTAGTTGCCAGCCATCTGTTGTTTGCCCCTCCCCC
GTGCCTTCCTTGACCCTGGAAGGTGCCACTCCCACTGTCCTTTCCTAATAAAATGAGGAAATT
GCATCGCATTGTCTGAGTAGGTGTCATTCTATTCTGGGGGGTGGGGTGGGGCAGGACAGCAAG
GGGGAGGATTGGGAAGACAATAGCAGGCATGCTGGGGACCGGTATAACTTCGTATAATGTAT
GCTATACGAAGTTATGCATGCGTCAATTTTACGCAGACTATCTTTCTAGGGTTAAGCGCGCTTG
GCGTAATCATGGTCATAGCTGTTTCCTGTGTGAAATTGTTATCCGCTCACAATTCCACACAACA
TACGAGCCGGAAGCATAAAGTGTAAAGCCTGGGGTGCCTAATGAGTGAGCTAACTCACATTA

FIG. 8H (continued)

ATTGCGTTGCGCTCACTGCCCGCTTTCCAGTCGGGAAACCTGTCGTGCCAGCTGCATTAATGA
ATCGGCCAACGCGCGGGGAGAGGCGGTTTGCGTATTGGGCGCTCTTCCGCTTCCTCGCTCACT
GACTCGCTGCGCTCGGTCGTTCGGCTGCGGCGAGCGGTATCAGCTCACTCAAAGGCGGTAATA
CGGTTATCCACAGAATCAGGGGATAACGCAGGAAAGAACATGTGAGCAAAAGGCCAGCAAA
AGGCCAGGAACCGTAAAAAGGCCGCGTTGCTGGCGTTTTTCCATAGGCTCCGCCCCCCTGACG
AGCATCACAAAAATCGACGCTCAAGTCAGAGGTGGCGAAACCCGACAGGACTATAAAGATAC
CAGGCGTTTCCCCCTGGAAGCTCCCTCGTGCGCTCTCCTGTTCCGACCCTGCCGCTTACCGGAT
ACCTGTCCGCCTTTCTCCCTTCGGGAAGCGTGGCGCTTTCTCATAGCTCACGCTGTAGGTATCT
CAGTTCGGTGTAGGTCGTTCGCTCCAAGCTGGGCTGTGTGCACGAACCCCCCGTTCAGCCCGA
CCGCTGCGCCTTATCCGGTAACTATCGTCTTGAGTCCAACCCGGTAAGACACGACTTATCGCC
ACTGGCAGCAGCCACTGGTAACAGGATTAGCAGAGCGAGGTATGTAGGCGGTGCTACAGAGT
TCTTGAAGTGGTGGCCTAACTACGGCTACACTAGAAGGACAGTATTTGGTATCTGCGCTCTGC
TGAAGCCAGTTACCTTCGGAAAAAGAGTTGGTAGCTCTTGATCCGGCAAACAAACCACCGCTG
GTAGCGGTGGTTTTTTTGTTTGCAAGCAGCAGATTACGCGCAGAAAAAAAGGATCTCAAGAA
GATCCTTTGATCTTTTCTACGGGGTCTGACGCTCAGTGGAACGAAAACTCACGTTAAGGGATT
TTGGTCATGAGATTATCAAAAAGGATCTTCACCTAGATCCTTTTAAATTAAAAATGAAGTTTT
AAATCAATCTAAAGTATATATGAGTAAACTTGGTCTGACAGTTACCAATGCTTAATCAGTGAG
GCACCTATCTCAGCGATCTGTCTATTTCGTTCATCCATAGTTGCCTGACTCCCCGTCGTGTAGA
TAACTACGATACGGGAGGGCTTACCATCTGGCCCCAGTGCTGCAATGATACCGCGAGACCCAC
GCTCACCGGCTCCAGATTTATCAGCAATAAACCAGCCAGCCGGAAGGGCCGAGCGCAGAAGT
GGTCCTGCAACTTTATCCGCCTCCATCCAGTCTATTAATTGTTGCCGGGAAGCTAGAGTAAGT
AGTTCGCCAGTTAATAGTTTGCGCAACGTTGTTGCCATTGCTACAGGCATCGTGGTGTCACGCT
CGTCGTTTGGTATGGCTTCATTCAGCTCCGGTTCCCAACGATCAAGGCGAGTTACATGATCCCC
CATGTTGTGCAAAAAAGCGGTTAGCTCCTTCGGTCCTCCGATCGTTGTCAGAAGTAAGTTGGC
CGCAGTGTTATCACTCATGGTTATGGCAGCACTGCATAATTCTCTTACTGTCATGCCATCCGTA
AGATGCTTTTCTGTGACTGGTGAGTACTCAACCAAGTCATTCTGAGAATAGTGTATGCGGCGA
CCGAGTTGCTCTTGCCCGGCGTCAATACGGGATAATACCGCGCCACATAGCAGAACTTTAAAA
GTGCTCATCATTGGAAAACGTTCTTCGGGGCGAAAACTCTCAAGGATCTTACCGCTGTTGAGA
TCCAGTTCGATGTAACCCACTCGTGCACCCAACTGATCTTCAGCATCTTTTACTTTCACCAGCG
TTTCTGGGTGAGCAAAAACAGGAAGGCAAAATGCCGCAAAAAAGGGAATAAGGGCGACACG
GAAATGTTGAATACTCATACTCTTCCTTTTTCAATATTATTGAAGCATTTATCAGGGTTATTGT
CTCATGAGCGGATACATATTTGAATGTATTTAGAAAAATAAACAAATAGGGGTTCCGCGCACA
TTTCCCCGAAAAGTGCCAC

SEQ ID NO: 17

GACGGATCGGGAGATCTCCCGATCCCCTATGGTCGACTCTCAGTACAATCTGCTCTGATGCCG
CATAGTTAAGCCAGTATCTGCTCCCTGCTTGTGTGTTGGAGGTCGCTGAGTAGTGCGCGAGCA
AAATTTAAGCTACAACAAGGCAAGGCTTGACCGACAATTGCATGAAGAATCTGCTTAGGGTT
AGGCGTTTTGCGCTGCTTCGCGCGTGGAGCTAGTTATTAATAGTAATCAATTACGGGGTCATT
AGTTCATAGCCCATATATGGAGTTCCGCGTTACATAACTTACGGTAAATGGCCCGCCTGGCTG
ACCGCCCAACGACCCCCGCCCATTGACGTCAATAATGACGTATGTTCCCATAGTAACGTCAAT
AGGGACTTTCCATTGACGTCAATGGGTGGAGTATTTACGGTAAACTGCCCACTTGGCAGTACA
TCAAGTGTATCATATGCCAAGTACGCCCCCTATTGACGTCAATGACGGTAAATGGCCCGCCTG
GCATTATGCCCAGTACATGACCTTATGGGACTTTCCTACTTGGCAGTACATCTACGTATTAGTC
ATCGCTATTACCATGGTGATGCGGTTTTGGCAGTACATCAATGGGCGTGGATAGCGGTTTGAC
TCACGGGGATTTCCAAGTCTCCACCCCATTGACGTCAATGGGAGTTTGTTTTGGCACCAAAAT
CAACGGGACTTTCCAAAATGTCGTAACAACTCCGCCCCATTGACGCAAATGGGCGGTAGGCGT
GTACGGTGGGAGGTCTATATAAGCAGAGCTCGTTTAGTGAACCGTCAGATCGCCTGGAGACG
CCATCCACGCTGTTTTGACCTCCATAGAAGACACCGGGACCGATCCAGCCTCCGCGGATTCGA
ATCCCGGCCGGGAACGGTGCATTGGAACGCGGATTCCCCGTGCCAAGAGTGACGTAAGTACC
GCCTATAGAGTCTATAGGCCCACAAAAAATGCTTTCTTCTTTTAATATACTTTTTTGTTTATCTT
ATTTCTAATACTTTCCCTAATCTCTTTCTTTCAGGGCAATAATGATACAATGTATCATGCCTCTT
TGCACCATTCTAAAGAATAACAGTGATAATTTCTGGGTTAAGGCAATAGCAATATTTCTGCAT
ATAAATATTTCTGCATATAAATTGTAACTGATGTAAGAGGTTTCATATTGCTAATAGCAGCTA
CAATCCAGCTACCATTCTGCTTTTATTTTATGGTTGGGATAAGGCTGGATTATTCTGAGTCCAA
GCTAGGCCCTTTTGCTAATCATGTTCATACCTCTTATCTTCCTCCCACAGCTCCTGGGCAACGT
GCTGGTCTGTGTGCTGGCCCATCACTTTGGCAAAGAATTGGGATTCGAACATCGATGCCGCCA
CCATGGGAAAATCAAAAGAAATCAGCCAAGACCTCAGAAAAAGAATTGTAGACCTCCACAAG
TCTGGTTCATCCTTGGGAGCAATTTCCCGACGCCTGGCGGTACCACGTTCATCTGTACAAACA
ATAGTACGCAAGTATAAACACCATGGGACCACGCAGCCGTCATACCGCTCAGGAAGGAGACG
CGTTCTGTCTCCTAGAGATGAACGTACTTTGGTGCGAAAAGTGCAAATCAATCCCAGAACAAC
AGCAAAGGACCTTGTGAAGATGCTGGAGGAAACAGGTACAAAAGTATCTATATCCACAGTAA
AACGAGTCCTATATCGACATAACCTGAAAGGCCACTCAGCAAGGAAGAAGCCACTGCTCCAA
AACCGACATAAGAAAGCCAGACTACGGTTTGCAACTGCACATGGGACAAAGATCTAACTTT
TTGGAGAAATGTCCTCTGGTCTGATGAAACAAAAATAGAACTGTTTGGCCATAATGACCATCG
TTATGTTTGGAGGAAGAAGGGGGAGGCTTGCAAGCCGAAGAACACCATCCCAACCGTGAAGC
ACGGGGGTGGCAGCATCATGTTGTGGGGGTGCTTTGCTGCAGGAGGGACTGGTAAACTTGTCC
GAATAGAAGGCATCATGGACGCGGTGCAGTATGTGGATATATTGAAGCAACATCTCAAGACA
TCAGTCAGGAAGTTAAAGCTTGGTCGCAAATGGGTCTTCCAACACGACAATGACCCCAAGCAT
ACTTCCAAAGTTGTGGCAAAATGGCTTAAGGACAACAAAGTCAAGGTATTGGACTGGCCATC
ACAAAGCCCTGACCTCAATCCTATAGAAAATTTGTGGGCAGAACTGAAAAAGCGTGTGCGAG
CAAGGAGGCCTACAAACCTGACTCAGTTACACCAGCTCTGTCAGGAGGAATGGGCCAAAATT
CACCCAAATTATTGTGGGAAGCTTGTGGAAGGCTACCCGAAACGTTTGACCCAAGTTAAACAA
TTTAAAGGCAATGCTACCAAATACTAGCTCGAGCATGCATCTAGAGGGCCCTATTCTATAGTG
TCACCTAAATGCTAGAGCTCGCTGATCAGCCTCGACTGTGCCTTCTAGTTGCCAGCCATCTGTT
GTTTGCCCCTCCCCCGTGCCTTCCTTGACCCTGGAAGGTGCCACTCCCACTGTCCTTTCCTAAT
AAAATGAGGAAATTGCATCGCATTGTCTGAGTAGGTGTCATTCTATTCTGGGGGGTGGGGTGG
GGCAGGACAGCAAGGGGGAGGATTGGGAAGACAATAGCAGGCATGCTGGGGATGCGGTGGG
CTCTATGGCTTCTGAGGCGGAAAGAACCAGCTGGGGCTCTAGGGGGTATCCCCACGCGCCCTG
TAGCGGCGCATTAAGCGCGGCGGGTGTGGTGGTTACGCGCAGCGTGACCGCTACACTTGCCA
GCGCCCTAGCGCCCGCTCCTTTCGCTTTCTTCCCTTCCTTTCTCGCCACGTTCGCCGGCTTTCCC
CGTCAAGCTCTAAATCGGGGCATCCCTTTAGGGTTCCGATTTAGTGCTTTACGGCACCTCGACC
CCAAAAAACTTGATTAGGGTGATGGTTCACGTAGTGGGCCATCGCCCTGATAGACGGTTTTTC

FIG. 8K (continued)

```
GCCCTTTGACGTTGGAGTCCACGTTCTTTAATAGTGGACTCTTGTTCCAAACTGGAACAACACT
CAACCCTATCTCGGTCTATTCTTTTGATTTATAAGGGATTTTGGGGATTTCGGCCTATTGGTTA
AAAAATGAGCTGATTTAACAAAAATTTAACGCGAATTAATTCTGTGGAATGTGTGTCAGTTAG
GGTGTGGAAAGTCCCCAGGCTCCCCAGGCAGGCAGAAGTATGCAAAGCATGCATCTCAATTA
GTCAGCAACCAGGTGTGGAAAGTCCCCAGGCTCCCCAGCAGGCAGAAGTATGCAAAGCATGC
ATCTCAATTAGTCAGCAACCATAGTCCCGCCCCTAACTCCGCCCATCCCGCCCCTAACTCCGCC
CAGTTCCGCCCATTCTCCGCCCCATGGCTGACTAATTTTTTTATTTATGCAGAGGCCGAGGCC
GCCTCTGCCTCTGAGCTATTCCAGAAGTAGTGAGGAGGCTTTTTGGAGGCCTAGGCTTTTGC
AAAAAGCTCCCGGGAGCTTGTATATCCATTTTCGGATCTGATCAAGAGACAGGATGAGGATCG
TTTCGCATGATTGAACAAGATGGATTGCACGCAGGTTCTCCGGCCGCTTGGGTGGAGAGGCTA
TTCGGCTATGACTGGGCACAACAGACAATCGGCTGCTCTGATGCCGCCGTGTTCCGGCTGTCA
GCGCAGGGGCGCCCGGTTCTTTTTGTCAAGACCGACCTGTCCGGTGCCCTGAATGAACTGCAG
GACGAGGCAGCGCGGCTATCGTGGCTGGCCACGACGGGCGTTCCTTGCGCAGCTGTGCTCGAC
GTTGTCACTGAAGCGGGAAGGGACTGGCTGCTATTGGGCGAAGTGCCGGGGCAGGATCTCCT
GTCATCTCACCTTGCTCCTGCCGAGAAAGTATCCATCATGGCTGATGCAATGCGGCGGCTGCA
TACGCTTGATCCGGCTACCTGCCCATTCGACCACCAAGCGAAACATCGCATCGAGCGAGCACG
TACTCGGATGGAAGCCGGTCTTGTCGATCAGGATGATCTGGACGAAGAGCATCAGGGGCTCG
CGCCAGCCGAACTGTTCGCCAGGCTCAAGGCGCGCATGCCCGACGGCGAGGATCTCGTCGTG
ACCCATGGCGATGCCTGCTTGCCGAATATCATGGTGGAAAATGGCCGCTTTTCTGGATTCATC
GACTGTGGCCGGCTGGGTGTGGCGGACCGCTATCAGGACATAGCGTTGGCTACCCGTGATATT
GCTGAAGAGCTTGGCGGCGAATGGGCTGACCGCTTCCTCGTGCTTTACGGTATCGCCGCTCCC
GATTCGCAGCGCATCGCCTTCTATCGCCTTCTTGACGAGTTCTTCTGAGCGGGACTCTGGGGTT
CGAAATGACCGACCAAGCGACGCCCAACCTGCCATCACGAGATTTCGATTCCACCGCCGCCTT
CTATGAAAGGTTGGGCTTCGGAATCGTTTTCCGGGACGCCGGCTGGATGATCCTCCAGCGCGG
GGATCTCATGCTGGAGTTCTTCGCCCACCCCAACTTGTTTATTGCAGCTTATAATGGTTACAAA
TAAAGCAATAGCATCACAAATTTCACAAATAAAGCATTTTTTCACTGCATTCTAGTTGTGGTT
TGTCCAAACTCATCAATGTATCTTATCATGTCTGTATACCGTCGACCTCTAGCTAGAGCTTGGC
GTAATCATGGTCATAGCTGTTTCCTGTGTGAAATTGTTATCCGCTCACAATTCCACACAACATA
CGAGCCGGAAGCATAAAGTGTAAAGCCTGGGGTGCCTAATGAGTGAGCTAACTCACATTAAT
TGCGTTGCGCTCACTGCCCGCTTTCCAGTCGGGAAACCTGTCGTGCCAGCTGCATTAATGAAT
CGGCCAACGCGCGGGGAGAGGCGGTTTGCGTATTGGGCGCTCTTCCGCTTCCTCGCTCACTGA
CTCGCTGCGCTCGGTCGTTCGGCTGCGGCGAGCGGTATCAGCTCACTCAAAGGCGGTAATACG
GTTATCCACAGAATCAGGGGATAACGCAGGAAAGAACATGTGAGCAAAAGGCCAGCAAAAG
GCCAGGAACCGTAAAAAGGCCGCGTTGCTGGCGTTTTTCCATAGGCTCCGCCCCCCTGACGAG
CATCACAAAAATCGACGCTCAAGTCAGAGGTGGCGAAACCCGACAGGACTATAAAGATACCA
GGCGTTTCCCCCTGGAAGCTCCCTCGTGCGCTCTCCTGTTCCGACCCTGCCGCTTACCGGATAC
CTGTCCGCCTTTCTCCCTTCGGGAAGCGTGGCGCTTTCTCAATGCTCACGCTGTAGGTATCTCA
GTTCGGTGTAGGTCGTTCGCTCCAAGCTGGGCTGTGTGCACGAACCCCCCGTTCAGCCCGACC
GCTGCGCCTTATCCGGTAACTATCGTCTTGAGTCCAACCCGGTAAGACACGACTTATCGCCAC
TGGCAGCAGCCACTGGTAACAGGATTAGCAGAGCGAGGTATGTAGGCGGTGCTACAGAGTTC
TTGAAGTGGTGGCCTAACTACGGCTACACTAGAAGGACAGTATTTGGTATCTGCGCTCTGCTG
AAGCCAGTTACCTTCGGAAAAAGAGTTGGTAGCTCTTGATCCGGCAAACAAACCACCGCTGGT
AGCGGTGGTTTTTTGTTTGCAAGCAGCAGATTACGCGCAGAAAAAAAGGATCTCAAGAAGA
TCCTTTGATCTTTTCTACGGGGTCTGACGCTCAGTGGAACGAAAACTCACGTTAAGGGATTTTG
GTCATGAGATTATCAAAAAGGATCTTCACCTAGATCCTTTTAAATTAAAAATGAAGTTTTAAA
TCAATCTAAAGTATATATGAGTAAACTTGGTCTGACAGTTACCAATGCTTAATCAGTGAGGCA
CCTATCTCAGCGATCTGTCTATTTCGTTCATCCATAGTTGCCTGACTCCCCGTCGTGTAGATAA
CTACGATACGGGAGGGCTTACCATCTGGCCCCAGTGCTGCAATGATACCGCGAGACCCACGCT
CACCGGCTCCAGATTTATCAGCAATAAACCAGCCAGCCGGAAGGGCCGAGCGCAGAAGTGGT
CCTGCAACTTTATCCGCCTCCATCCAGTCTATTAATTGTTGCCGGGAAGCTAGAGTAAGTAGTT
CGCCAGTTAATAGTTTGCGCAACGTTGTTGCCATTGCTACAGGCATCGTGGTGTCACGCTCGTC
GTTTGGTATGGCTTCATTCAGCTCCGGTTCCCAACGATCAAGGCGAGTTACATGATCCCCCAT
GTTGTGCAAAAAAGCGGTTAGCTCCTTCGGTCCTCCGATCGTTGTCAGAAGTAAGTTGGCCGC
AGTGTTATCACTCATGGTTATGGCAGCACTGCATAATTCTCTTACTGTCATGCCATCCGTAAGA
```

FIG. 8K (continued)

TGCTTTTCTGTGACTGGTGAGTACTCAACCAAGTCATTCTGAGAATAGTGTATGCGGCGACCG
AGTTGCTCTTGCCCGGCGTCAATACGGGATAATACCGCGCCACATAGCAGAACTTTAAAAGTG
CTCATCATTGGAAAACGTTCTTCGGGGCGAAAACTCTCAAGGATCTTACCGCTGTTGAGATCC
AGTTCGATGTAACCCACTCGTGCACCCAACTGATCTTCAGCATCTTTTACTTTCACCAGCGTTT
CTGGGTGAGCAAAAACAGGAAGGCAAAATGCCGCAAAAAAGGGAATAAGGGCGACACGGAA
ATGTTGAATACTCATACTCTTCCTTTTTCAATATTATTGAAGCATTTATCAGGGTTATTGTCTCA
TGAGCGGATACATATTTGAATGTATTTAGAAAAATAAACAAATAGGGGTTCCGCGCACATTTC
CCCGAAAAGTGCCACCTGACGTC

A.

B

C

D

E.

F.

G.

H.

A.

B.

C.

D.

A.

B.

C.

D.

A

B

C

D

E

F

G

H

I

J

K

VECTORS FOR LIVER-DIRECTED GENE THERAPY OF HEMOPHILIA AND METHODS AND USE THEREOF

This application is a U.S. national phase application of International Patent Application No. PCT/EP2013/072450, filed Oct. 25, 2013, which claims the benefit of International Patent Application No. PCT/EP2012/071297, filed Oct. 26, 2012 and International Patent Application No. PCT/EP2013/064054, filed Jul. 3, 2013.

FIELD OF THE INVENTION

The invention relates to expression vectors for gene therapy with improved liver-specific expression capabilities, particularly for use as a gene therapy means for the treatment of hemophilia, more particularly for restoring coagulation factor IX (FIX) and/or coagulation factor VIII (FVIII) in liver-directed gene therapy of respectively, hemophilia B and hemophilia A.

BACKGROUND OF THE INVENTION

Hemophilia B is an X-linked, recessive bleeding disorder caused by deficiency of clotting factor IX (FIX). The clinical presentation for hemophilia B is characterized by episodes of spontaneous and prolonged bleeding. There are an estimated 1 in 20,000 individuals who suffer from hemophilia B. Currently, hemophilia B is treated with protein replacement therapy using either plasma-derived or recombinant FIX. Although FIX protein replacement markedly improved the life expectancy of patients suffering from hemophilia, they are still at risk for severe bleeding episodes and chronic joint damage, since prophylactic treatment is restricted by the short half-life, the limited availability and the high cost of purified FIX, which can approach 100.000$/patient/year. In addition, the use of plasma-derived factors obtained from contaminated blood sources increases the risk of viral transmission. Gene therapy offers the promise of a new method of treating hemophilia B, since the therapeutic window is relatively broad and levels slightly above 1% of normal physiologic levels are therapeutic. If successful, gene therapy could provide constant FIX synthesis which may lead to a cure for this disease. The different modalities for gene therapy of hemophilia have been extensively reviewed (Chuah et al., 2012a, 2012b, 2012c; VandenDriessche et al., 2012; High 2001, 2011; Matrai et al., 2010a, 2010b).

Hemophilia A is a serious bleeding disorder caused by a deficiency in, or complete absence of, the blood coagulation factor VIII (FVIII). The severity of hemophilia A and hemophilia B has been classified by the subcommittee on Factor VIII and Factor IX of the Scientific and Standardization Committee of the International Society on Thrombosis and Haemostasis into three forms, depending on respectively, the FVIII level and the FIX level: 1) severe form (FVIII or FIX level less than 0.01 international units (IU)/ml, i.e. less than 1% of normal FVIII or FIX level), 2) moderate form (FVIII or FIX level from 0.01 to 0.05 IU/ml, i.e. from 1 to 5% of normal FVIII or FIX level), and 3) mild from (FVIII or FIX level higher than 0.05 to 0.4 IU/ml, i.e. higher than 5 to 40% of normal FVIII or FIX level). Hemophilia A is the most common hereditary coagulation disorder with an incidence approaching approximately 1 in 5000 males.

Protein substitution therapy (PST) with purified or recombinant FVIII has significantly improved the patients' quality of life. However, PST is not curative and patients are still at risk of developing potentially life-threatening hemorrhages and crippling joint inflammation. Unfortunately, many patients suffering from hemophilia A (up to 40%) develop neutralizing antibodies to FVIII (i.e. "inhibitors") following PST. These inhibitors complicate the management of bleeding episodes and can render further PST ineffective. These limitations of PST, justify the development of gene therapy as a potential alternative for hemophilia treatment. Furthermore, only a modest increase in FVIII plasma concentration is needed for therapeutic benefit, with levels of more than 1% of normal levels able to achieve markedly reduced rates of spontaneous bleeding and long-term arthropathy.

The liver is the main physiological site of FIX and FVIII synthesis and hence, hepatocytes are well suited target cells for hemophilia gene therapy. From this location, FIX protein can easily enter into the circulation. Moreover, the hepatic niche may favor the induction of immune tolerance towards the transgene product (Annoni et al., 2007; Follenzi et al., 2004; Brown et al., 2007; Herzog et al., 1999; Matrai et al., 2011; Matsui et al., 2009). Liver-directed gene therapy for hemophilia can be accomplished with different viral vectors including retroviral (Axelrod et al., 1990; Kay et al., 1992; VandenDriessche et al., 1999, Xu et al., 2003, 2005), lentiviral (Ward et al., 2011, Brown et al., 2007, Matrai et al., 2011), adeno-associated viral (AAV) (Herzog et al., 1999) and adenoviral vectors (Brown et al., 2004)(Ehrhardt & Kay, 2002). In particular, AAV is a naturally occurring replication defective non-pathogenic virus with a single stranded DNA genome. AAV vectors have a favorable safety profile and are capable of achieving persistent transgene expression. Long-term expression is predominantly mediated by episomally retained AAV genomes. More than 90% of the stably transduced vector genomes are extra-chromosomal, mostly organized as high-molecular-weight concatamers. Therefore, the risk of insertional oncogenesis is minimal, especially in the context of hemophilia gene therapy where no selective expansion of transduced cells is expected to occur. Nevertheless, oncogenic events have been reported following AAV-based gene transfer (Donsante et al., 2007) but it has been difficult to reproduce these findings in other model systems (Li et al., 2011). The major limitation of AAV vectors is the limited packaging capacity of the vector particles (i.e. approximately 4.7 kb), constraining the size of the transgene expression cassette to obtain functional vectors (Jiang et al., 2006). Several immunologically distinct AAV serotypes have been isolated from human and non-human primates (Gao et al., 2002, Gao et al. 2004), although most vectors for hemophilia gene therapy were initially derived from the most prevalent AAV serotype 2. The first clinical success of AAV-based gene therapy for congenital blindness underscores the potential of this gene transfer technology (Bainbridge et al., 2008).

AAV-mediated hepatic gene transfer is an attractive alternative for gene therapy of hemophilia for both liver and muscle-directed gene therapy (Herzog et al., 1997, 1999, 2002; Arruda et al., 2010; Fields et al., 2001; Buchlis et al., 2012; Jiang et al., 2006; Kay et al., 2000). Preclinical studies with the AAV vectors in murine and canine models of hemophilia or non-human primates have demonstrated persistent therapeutic expression, leading to partial or complete correction of the bleeding phenotype in the hemophilic models (Snyder et al., 1997, 1999; Wang et al., 1999, 2000; Mount et al., 2002; Nathwani et al., 2002). Particularly, hepatic transduction conveniently induces immune tolerance to FIX that required induction of regulatory T cells (Tregs) (Mingozzi et al., 2003; Dobrzynski et al., 2006). Long-term correction of the hemophilia phenotype without inhibitor development was achieved in inhibitor-prone null mutation hemophilia B dogs treated with liver-directed AAV2-FIX gene therapy (Mount et al, 2002). In order to further reduce the vector dose, more potent FIX expression cassettes have been developed. This could be accomplished by using stronger promoter/enhancer elements, codon-optimized FIX or self-complementary, double-stranded AAV vectors (scAAV) that overcome one of the limiting steps in AAV transduction (i.e. single-stranded to double-stranded AAV conversion) (McCarty, 2001, 2003; Nathwani et al, 2002, 2006, 2011; Wu et al., 2008). Alternative AAV serotypes could be used (e.g. AAV8 or AAV5) that result in increased transduction into hepatocytes, improve intra-nuclear vector import and reduce the risk of T cell activation (Gao et al., 2002; Vandenberghe et al., 2006). Liver-directed gene therapy for hemophilia B with AAV8 or AAV9 is more efficient than when lentiviral vectors are used, at least in mice, and resulted in less inflammation (VandenDriessche et al., 2007, 2002). Furthermore, recent studies indicate that mutations of the surface-exposed tyrosine residues allow the vector particles to evade phosphorylation and subsequent ubiquitination and, thus, prevent proteasome-mediated degradation, which resulted in a 10-fold increase in hepatic expression of FIX in mice (Zhong et al., 2008).

These liver-directed preclinical studies paved the way toward the use of AAV vectors for clinical gene therapy in patients suffering from severe hemophilia B. Hepatic delivery of AAV-FIX vectors resulted in transient therapeutic FIX levels (maximum 12% of normal levels) in subjects receiving AAV-FIX by hepatic artery catheterization (Kay et al., 2000). However, the transduced hepatocytes were able to present AAV capsid-derived antigens in association with MHC class I to T cells (Manno et al., 2006, Mingozzi et al., 2007). Although antigen presentation was modest, it was sufficient to flag the transduced hepatocytes for T cell-mediated destruction. Recently, gene therapy for hemophilia made an important step forward (Nathwani et al., 2011; Commentary by VandenDriessche & Chuah, 2012). Subjects suffering from severe hemophilia B (<1% FIX) were injected intravenously with self-complementary (sc) AAV8 vectors expressing codon-optimized FIX from a liver-specific promoter. This AAV8 serotype exhibits reduced cross-reactivity with pre-existing anti-AAV2 antibodies. Interestingly, its uptake by dendritic cells may be reduced compared to conventional AAV2 vectors, resulting in reduced T cell activation (Vandenberghe et al., 2006). In mice, AAV8 allows for a substantial increase in hepatic transduction compared to AAV2, though this advantage may be lost in higher species, like dog, rhesus monkeys and man. Subjects received escalating doses of the scAAV8-FIX vector, with two participants per dose. All of the treated subjects expressed FIX above the therapeutic 1% threshold for several months after vector administration, yielding sustained variable expression levels (i.e. 2 to 11% of normal levels). The main difference with the previous liver-directed AAV trial is that for the first time sustained therapeutic FIX levels could be achieved after gene therapy. Despite this progress, T-cell mediated clearance of AAV-transduced hepatocytes remains a concern consistent with elevated liver enzyme levels in some of the patients. Transient immune suppression using a short course of glucocorticoids was used in an attempt to limit this vector-specific immune response.

One of the significant limitations in the generation of efficient viral gene delivery systems for the treatment of hemophilia A by gene therapy is the large size of the FVIII cDNA. Previous viral vector-based gene therapy studies for hemophilia A typically relied on the use of small but weak promoters, required excessively high vector doses that were not clinically relevant or resulted in severely compromised vector titers. Several other ad hoc strategies were explored, such as the use of split or dual vector design to overcome the packaging constraints of AAV, but these approaches were overall relatively inefficient and raised additional immunogenicity concerns (reviewed in Petrus et al., 2010). It has been found that the FVIII B domain is dispensable for procoagulant activity. Consequently, FVIII constructs in which the B domain is deleted are used for gene transfer purposes since their smaller size is more easily incorporated into vectors. Furthermore, it has been shown that deletion of the B domain leads to a 17-fold increase in mRNA and primary translation product. FVIII wherein the B domain is deleted and replaced by a short 14-amino acid linker is currently produced as a recombinant product and marketed as Refacto® for clinical use (Wyeth Pharma) (Sandberg et al., 2001). Miao et al. (2004) added back a short B domain sequence to a B domain deleted FVIII, optimally 226 amino acids and retaining 6 sites for N-linked glycosylation, to improve secretion. McIntosh et al. (2013) replaced the 226 amino-acid spacer of Miao et al. with a 17 amino-acid peptide in which six glycosylation triplets from the B-domain were juxtaposed. Yet, production was still not sufficient for therapeutic purposes.

Non-viral vectors typically rely on a plasmid-based gene delivery system, where only the naked DNA is delivered, potentially in conjunction with physicochemical methods that facilitate transfection. Consequently, the non-viral approach maybe less immunogenic and potentially safer than viral vectors, though innate immune response may still occur. The non-viral gene transfer method is simple, but the efficiency is generally low compared to most viral vector-mediated gene transfer approaches. Efficient in vivo gene delivery of non-viral vectors remains a bottleneck. Typically, for hepatic gene delivery, plasmids are administered by hydrodynamic injection. In this case, a hydrodynamic pressure is generated by rapid injection of a large volume of DNA solution into the circulation, in order to deliver the gene of interest in the liver (Miao et al., 2000). Efforts are being made to adapt hydrodynamic injection towards a clinically relevant modality by reducing the volume of injection along with maintaining localized hydrodynamic pressure for gene transfer. Alternative approaches based on targetable nanoparticles are being explored to achieve target specific delivery of FIX into hepatocytes. Expression could be prolonged by removing bacterial backbone sequences which interfere with long term expression (i.e. mini-circle DNA) Finally, to increase the stability of FIX expression after non-viral transfection, transposons could be used that result in stable genomic transgene integration. We and others have shown that transposons could be used to obtain stable clotting factor expression following in vivo gene therapy (Yant et al., 2000; Mates, Chuah et al., 2009, VandenDriessche et al., 2009; Kren et al., 2009; Ohlfest et al., 2004).

An exemplary state of the art vector for liver-specific expression of FIX is described in WO2009/130208 and is composed of a single-stranded AAV vector that contains the TTR/Serp regulatory sequences driving a factor cDNA. A FIX first intron was included in the vector, together with a polyadenylation signal. Using said improved vector yielded about 25-30% stable circulating factor IX.

In order to translate viral-vector based gene therapy for hemophilia to the clinic, the safety concerns associated with administering large vector doses to the liver and the need for manufacturing large amounts of clinical-grade vector must be addressed. Increasing the potency (efficacy per dose) of gene transfer vectors is crucial towards achieving these goals. It would allow using lower doses to obtain therapeutic benefit, thus reducing potential toxicities and immune activation associated with in vivo administration, and easing manufacturing needs.

One way to increase potency is to engineer the transgene sequence itself to maximize expression and biological activity per vector copy. We have shown that FIX transgenes optimized for codon usage and carrying an R338L amino acid substitution associated with clotting hyperactivity and thrombophilia (Simioni et al., 2009), increase the efficacy of gene therapy using lentiviral vector up to 15-fold in hemophilia B mice, without detectable adverse effects, substantially reducing the dose requirement for reaching therapeutic efficacy and thus facilitating future scale up and its clinical translation (Cantore et al., 2012).

Also codon optimization of human factor VIII cDNAs leads to high-level expression. Significantly greater levels (up to a 44-fold increase and in excess of 200% normal human levels) of active FVIII protein were detected in the plasma of neonatal hemophilia A mice transduced with lentiviral vector expressing FVIII from a codon-optimized cDNA sequence, thereby successfully correcting the disease model (Ward et al., 2011).

It is an object of the present invention to increase the efficiency and safety of liver-directed gene therapy for hemophilia A and B.

SUMMARY OF THE INVENTION

It is an object of the present invention to increase the efficiency and safety of liver-directed gene therapy for hemophilia B. The above objective is accomplished by providing a vector, either a viral vector, in particular an AAV-based vector, or a non-viral vector, in particular a transposon-based vector, comprising a nucleic acid expression cassette with specific regulatory elements that enhance liver-directed gene expression, while retaining tissue specificity, in conjunction with the use of a human FIX gene containing a hyper-activating mutation and/or a codon-optimized transgene.

The resulting vector and nucleic acid expression cassette results in unexpectedly high expression levels of FIX in the liver, due to its unique combination of regulatory elements and the choice of vector type and transgene. The combined effect of these elements could not have been predicted. In WO2009/130208 for example, the given AAV-based vector yielded about 25-30% stable circulating factor IX. In the current application the new vector obtained 500-600% of stable circulating factor IX levels. This represents a more than 20-fold increase in FIX levels due to the unique combination of elements of the nucleic acid expression cassette and vector of the present invention. In particular, the inventors demonstrated in Example 7 that specific combinations of the Serpin enhancer (called "Serp" or "SerpEnh" herein) with codon-optimized hFIX transgene or the Serpin enhancer with transgene encoding hFIX containing the Padua mutation provide for synergistic effects on FIX activity. The highest hFIX activity was measured in mice hydrodynamically injected with a plasmid comprising the unique combination of the Serpin enhancer with a codon-optimized transgene encoding hFIX containing the Padua mutation. hFIX activity in these mice was up to 265-fold higher as compared to hFIX activity in mice injected with a corresponding hFIX plasmid without the Serpin enhancer, the codon-optimization and the Padua mutation. This increase in hFIX activity was shown to be synergistic.

It is another object of the present invention to increase the efficiency and safety of liver-directed gene therapy for hemophilia A. As shown in the experimental section, this objective is accomplished by providing a vector either a viral vector, in particular an AAV-based vector, or a non-viral vector, in particular a transposon-based vector, comprising a nucleic acid expression cassette with specific regulatory elements that enhance liver-directed gene expression, while retaining tissue specificity, in particular the Serpin enhancer, in conjunction with the use of a codon-optimized human FVIII construct, in particular a codon-optimized B domain deleted FVIII construct.

The resulting AAV-based vector and nucleic acid expression cassette resulted in unprecedented, supra-physiologic FVIII expression levels (i.e. more than 200% of normal level) using relatively low vector doses ($5 \times 10^9$ vg/mouse). This constitutes a robust 50-fold improvement in FVIII expression levels, when compared to AAV vectors that expressed a codon-optimized B domain deleted FVIII cDNA from a truncated liver-specific promoter (McInthosh et al. 2013). This represents a significant improvement over the latest generation AAV-FVIII vectors and an important step towards clinical translation. The inventors demonstrated in Example 6 that the specific combination of the Serpin enhancer with the codon-optimized B domain deleted FVIII transgene provides for a synergistic effect on FVIII expression levels compared to expression cassettes containing either the Serpin enhancer or the codon-optimized B domain deleted FVIII transgene.

The inventors further demonstrated in Example 5 that the inclusion of the MVM intron into the nucleic acid expression cassettes disclosed herein provides for unexpectedly increased expression of the transgene operably linked thereto.

The invention therefore provides the following aspects:

Aspect 1. A vector comprising a nucleic acid expression cassette comprising a liver-specific regulatory element, a promoter, optionally a minute virus of mouse (MVM) intron, a transgene, preferably a codon-optimized transgene, and a transcriptional termination signal.

Aspect 2. The vector according to aspect 1, wherein said transgene encodes for factor VIII or factor IX.

Aspect 3. The vector according to aspect 2, wherein said coagulation factor VIII has a deletion of the B domain.

Aspect 4. The vector according to aspect 3, wherein said B domain of said FVIII is replaced by a linker having SEQ ID NO:16.

Aspect 5. The vector according to aspect 2, wherein said coagulation factor IX contains a hyper-activating mutation.

Aspect 6. The vector according to aspect 5, wherein said hyper-activating mutation in coagulation factor IX corresponds to an R338L amino acid substitution.

Aspect 7. The vector according to any one of aspects 2 to 6, wherein said transgene encoding for coagulation factor VIII or IX is codon-optimized.

Aspect 8. The vector according to any one of aspects 1 to 4, or 7, wherein said transgene encoding for coagulation factor VIII has SEQ ID NO:7.

Aspect 9. The vector according to any one of aspects 1 to 8, wherein said liver-specific regulatory element contains sequences from the serpin promoter.

Aspect 10. The vector according to any one of aspects 1 to 9, wherein said liver-specific regulatory element comprises or consists of SEQ ID NO:8, or a sequence having 95% identity to said sequence, preferably wherein said liver-specific regulatory element is the Serpin enhancer.

Aspect 11. The vector according to any one of aspects 1 to 10, wherein said promoter is derived from the transthyretin (TTR) promoter, preferably the minimal TTR promoter.

Aspect 12. The vector according to any one of aspects 1 to 11, wherein said transcriptional termination signal is derived from the bovine growth hormone polyadenylation signal or from the Simian virus 40 polyadenylation signal.

Aspect 13. The vector according to any one of aspects 1 to 12, wherein said vector is a viral vector.

Aspect 14. The vector according to aspect 13, wherein said vector is derived from an adeno-associated virus (AAV), preferably AAV serotype 9.

Aspect 15. The vector according to aspect 14, wherein said vector is a single-stranded AAV, preferably single-stranded AAV serotype 9.

Aspect 16. The vector according to any one of aspects 1 to 4, 7 to 15, having SEQ ID NO: 6, or the vector according to any one of aspects 1, 2, 5 to 7, 9 to 15, or 17, having SEQ ID NO: 1 or 2.

Aspect 17. The vector according to aspect 14, wherein said vector is a self-complementary AAV, preferably self-complementary AAV serotype 9.

Aspect 18. The vector according to any one of aspects 1 to 12, wherein said vector is a non-viral vector.

Aspect 19. The vector according to aspect 18, wherein said vector is a transposon-based vector.

Aspect 20. The vector according to aspect 19, wherein said vector is a PiggyBac(PB)-based vector, such as the PB-based vector having SEQ ID NO:13, preferably a PiggyBac-based vector comprising micro inverted repeats, more preferably the PB-based vector having SEQ ID NO: 14 or 15, or a Sleeping Beauty(SB)-based vector, preferably the SB-based vector having SEQ ID NO:16.

Aspect 21. A method to obtain levels of factor VIII in plasma equal to or higher than the therapeutic threshold concentration of 10 mU/ml plasma in a subject, comprising the transduction or transfection of the vector according to any one of aspects 1 to 4, 7 to 20 into a subject.

Aspect 22. The method according to aspect 21, wherein the transduction of the vector according to any one of aspects 1 to 4, 7 to 17 into the subject is done at a dose lower than $2.5 \times 10^{11}$ vg/kg.

Aspect 23. A method to obtain levels of factor IX in plasma equal to or higher than the therapeutic threshold concentration of 10 mU/ml plasma in a subject, comprising the transduction or transfection of the vector according to any one of aspects 1, 2, 5 to 15, 17 to 20 into a subject.

Aspect 24. The method according to aspect 23, wherein the transduction of the vector according to any one of aspects 1, 2, 5 to 15, 17 into the subject is done at a dose lower than $2 \times 10^{11}$ vg/kg.

Aspect 24. The method according to aspect 23, used to obtain levels of factor IX in plasma equal to or higher than the therapeutic concentration of 100 mU/ml in a subject, wherein the transduction of the vector according to any one of aspects 1, 2, 5 to 15, 17 into the subject is done at a dose lower than or equal than $6 \times 10^{11}$ vg/kg.

Aspect 25. The method according to aspect 23, used to obtain levels of factor IX in plasma equal to or higher than the therapeutic concentration of 50 mU/ml in a subject, wherein the transduction of the vector according to any one of aspects 1, 2, 5 to 15, 17 into the subject is done at a dose lower than or equal than $6 \times 10^{11}$ vg/kg.

Aspect 26. The method according to aspect 23, used to obtain levels of factor IX in plasma equal to or higher than the therapeutic concentration of 200 mU/ml in a subject, wherein the transduction of the vector according to any one of aspects 1, 2, 5 to 15, 17 into the subject is done at a dose lower than or equal than $2 \times 10^{12}$ vg/kg.

Aspect 27. The method according to aspect 23, used to obtain levels of factor IX in plasma equal to or higher than the therapeutic concentration of 150 mU/ml in a subject, wherein the transduction of the vector according to any one of aspects 1, 2, 5 to 15, 17 into the subject is done at a dose lower than or equal than $2 \times 10^{12}$ vg/kg.

Aspect 28. The method according to any one of aspects 21 to 27, wherein said transduction or transfection is by intravenous administration.

Aspect 29. The method according to any one of aspects 21 or 23, wherein said transfection is by hydrodynamic transfection.

Aspect 30. The method according to any one of aspects 21, 23, 28 or 29, wherein a vector according to any one of aspects 19 or 20 is administered in combination with a vector encoding a transposase, preferably a hyperactive transposase.

Aspect 31. The method according to any one of aspects 21 to 30, wherein said subject is a mammalian subject, preferably a human subject.

Aspect 32. A method for treating hemophilia A in a mammalian subject, comprising performing the method according to any one of aspects 21, 22, 28 to 31.

Aspect 33. The use of the vector according to any one of aspects 1 to 4, 7 to 20 for the manufacture of a medicament to treat hemophilia A.

Aspect 34. The vector according to any one of aspects 1 to 4, 7 to 20 for use in the treatment of hemophilia A.

Aspect 35. A method for treating hemophilia B in a mammalian subject, comprising performing the method according to any one of aspects 23 to 31.

Aspect 36. The use of the vector according to any one of aspects 1, 2, 5 to 15, 17 to 20 for the manufacture of a medicament to treat hemophilia B.

Aspect 37. The vector according to any one of aspects 1, 2, 5 to 15, 17 to 20 for use in the treatment of hemophilia B.

Aspect 38. A pharmaceutical composition comprising a vector according to any one of aspects 1 to 4, 7 to 20 and a pharmaceutically acceptable carrier, optionally further comprising an active ingredient for treating hemophilia A.

Aspect 39. The pharmaceutical composition according to aspect 38 for use in treating hemophilia A.

Aspect 40. The pharmaceutical composition for use according to aspect 39, or the vector for use according to aspect 34, wherein said treatment results in levels of factor VIII in plasma of the treated subject that are equal to or higher than the therapeutic threshold concentration of 10 mU/ml plasma in a subject.

Aspect 41. The pharmaceutical composition for use according to any one of aspects 39 or 40, or the vector for use according to any one of aspects 34 or 40, wherein said treatment comprises the transduction of the vector according to any one of aspects 1 to 4, 7 to 17 into the subject at a dose lower than or equal than $2.5 \times 10^{11}$ vg/kg.

Aspect 42. A pharmaceutical composition comprising a vector according to any one of aspects 1, 2, 5 to 15, 17 to 20 and a pharmaceutically acceptable carrier, optionally further comprising an active ingredient for treating hemophilia B.

Aspect 43. The pharmaceutical composition according to aspect 42, for use in treating hemophilia B.

Aspect 44. The pharmaceutical composition for use according to aspect 43, or the vector for use according to aspect 37, wherein said treatment results in levels of factor IX in plasma of the treated subject that are equal to or higher than the therapeutic threshold concentration of 10 mU/ml plasma in a subject, preferably equal to or higher than the therapeutic concentration of 50 mU/ml plasma in a subject, more preferably equal to or higher than the therapeutic concentration of 100 mU/ml plasma in a subject, even more preferably equal to or higher than the therapeutic concentration of 150 mU/ml plasma in a subject and even more preferably equal to or higher than the therapeutic concentration of 200 mU/ml plasma in a subject.

Aspect 45. The pharmaceutical composition for use according to aspect 43 or 44, or the vector for use according to aspect 37 or 44, wherein said treatment comprises the transduction of the vector according to any one of aspects 1, 2, 5 to 15, 17 to 20 into the subject at a dose lower than or equal than $2 \times 10^{12}$ vg/kg, preferably at a dose lower than or equal than $6 \times 10^{11}$ vg/kg, more preferably at a dose lower than or equal than $2 \times 10^{11}$ vg/kg.

BRIEF DESCRIPTION OF THE FIGURES

The present invention is illustrated by the following figures which are to be considered for illustrative purposes only and in no way limit the invention to the embodiments disclosed therein.

DETAILED DESCRIPTION OF THE INVENTION

Figure 1A:
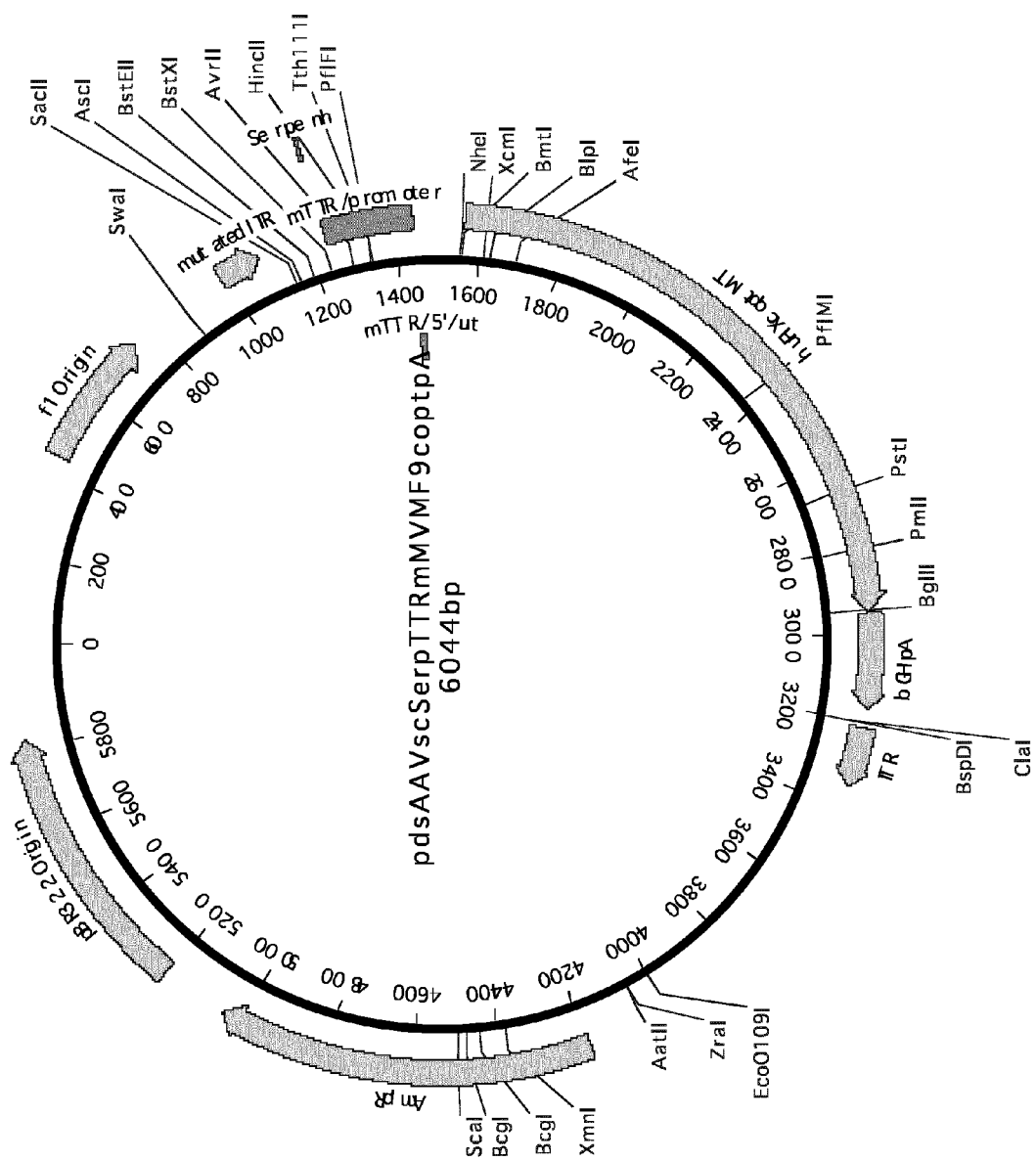
FIG. 1 A) shows a schematic diagram of the AAV9-SerpEnh-TTRm-MVM-co-hFIX construct (pdsAAVsc SerpTTRmMVMF9coptpA) with indication where the liver-specific Serpin regulatory element ("Serp" or "SerpEnh") is inserted upstream of the transthyretin minimal promoter (TTRm). Abbreviations used are: ITR: viral inverted terminal repeat; mTTR: minimal transthyretin promoter; MVM: minute virus mouse; huFIXcoptMT: codon-optimized FIX; bGHpA: polyadenylation signal of bovine growth hormone; B) shows the sequence of the AAV9-SerpEnh-TTRm-MVM-co-hFIX construct (SEQ ID No. 1) and C) shows the sequence of the AAV9-SerpEnh-TTRm-MVM-co-hFIX-R338L construct (SEQ ID No. 2).

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes.

Where the term "comprising" is used in the present description and claims, it does not exclude other elements or steps. The term "comprising" also encompasses the more specific embodiments defined as "consisting of" and "consisting essentially of".

Where an indefinite or definite article is used when referring to a singular noun e.g. "a" or "an", "the", this includes a plural of that noun unless something else is specifically stated. Furthermore, the terms first, second, third and the like in the description and in the claims, are used for distinguishing between similar elements and not necessarily for describing a sequential or chronological order.

It is to be understood that the terms so used are interchangeable under appropriate circumstances and that the embodiments of the invention described herein are capable of operation in other sequences than described or illustrated herein.

The following terms or definitions are provided to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, 2nd ed., Cold Spring Harbor Press, Plainsview, N.Y. (1989); and Ausubel et al., Current Protocols in Molecular Biology (Supplement 47), John Wiley & Sons, New York (1999), for definitions and terms of the art.

The definitions provided herein should not be construed to have a scope less than understood by a person of ordinary skill in the art.

The term "coagulation factor IX" has the meaning as known in the art. Synonyms of coagulation factor IX are "FIX" or "Christmas factor" or "F9" and can be used interchangeably. In particular, the term "coagulation factor IX" encompasses the human protein encoded by the mRNA sequence as defined in Genbank accession number NM_000133.

Preferably, said FIX is a mutated FIX, which is hyperactive or hyper-functional as compared to the wild type FIX. Modifying functional activity of human coagulation factor can be done by bioengineering e.g. by introduction of point mutations. By this approach a hyperactive R338A variant was reported, which showed a 3 fold increased clotting activity compared to the wild type human FIX in an in vitro activated partial thromboplastin time assay (APPT) (Chang et al., 1998) and a 2 to 6-fold higher specific activity in hemophilia B mice transduced with the mutant FIX gene (Schuettrumpf et al., 2005). Further exemplary FIX point-mutants or domain exchange mutants with even higher clotting activities have been described: FIX, with the EGF-1 domain replaced with the EGF-1 domain from FVII, alone or in combination with a R338A point mutation (Brunetti-Pierri et al., 2009), the V86A/E277A/R338A triple mutant (Lin et al., 2010), the Y259F, K265T, and/or Y345T single, double or triple mutants (Milanov, et al., 2012), and the G190V point mutant (Kao et al., 2010), all incorporated herein by reference. In a particularly preferred embodiment, the FIX mutant is the one described by Simioni et al., in 2009 and denominated as the "factor IX Padua" mutant, causing X-linked thrombophilia. Said mutant factor IX is hyperactive and carries an R338L amino acid substitution. In a preferred embodiment of the present invention, the FIX transgene used in expression vector encodes the human FIX protein, most preferably the FIX transgene encodes for the Padua mutant of the human FIX protein.

The term "coagulation factor VIII" has the meaning as known in the art. Synonyms of coagulation factor VIII are "FVIII" or "antihemophilic factor" or "AHF" and can be used interchangeably herein. The term "coagulation factor VIII" encompasses, for example, the human protein having the amino acid sequence as defined in Uniprot accession number P00451.

In embodiments, said FVIII is a FVIII wherein the B domain is deleted (i.e. B domain deleted FVIII, also referred to as BDD FVIII or FVIIIAB herein). The term "B domain deleted FVIII" encompasses for example, but without limitation, FVIII mutants wherein whole or a part of the B domain is deleted and FVIII mutants wherein the B domain is replaced by a linker. Non-limiting examples of B domain deleted FVIII are described in Ward et al. (2011) and WO 2011/005968, which are specifically incorporated by reference herein.

In preferred embodiments, said FVIII is B domain deleted FVIII wherein the B domain is replaced by a linker having the following sequence: SFSQNPPVLTRHQR (SEQ ID NO: 16) (i.e. SQ FVIII as defined in Ward et al. (2011)). In particularly preferred embodiments, said FVIII has SEQ ID NO:7 (i.e. codon-optimized B domain deleted human FVIII or hFVIIIcopt), as disclosed also in WO 2011/0059.

A "regulatory element" as used herein refers to transcriptional control elements, in particular non-coding cis-acting transcriptional control elements, capable of regulating and/or controlling transcription of a gene, in particular tissue-specific transcription of a gene. Regulatory elements comprise at least one transcription factor binding site (TFBS), more in particular at least one binding site for a tissue-specific transcription factor, most particularly at least one binding site for a liver-specific transcription factor. Typically, regulatory elements as used herein increase or enhance promoter-driven gene expression when compared to the transcription of the gene from the promoter alone, without the regulatory elements. Thus, regulatory elements particularly comprise enhancer sequences, although it is to be understood that the regulatory elements enhancing transcription are not limited to typical far upstream enhancer sequences, but may occur at any distance of the gene they regulate. Indeed, it is known in the art that sequences regulating transcription may be situated either upstream (e.g. in the promoter region) or downstream (e.g. in the 3'UTR) of the gene they regulate in vivo, and may be located in the immediate vicinity of the gene or further away. Of note, although regulatory elements as disclosed herein typically are naturally occurring sequences, combinations of (parts of) such regulatory elements or several copies of a regulatory element, i.e. non-naturally occurring sequences, are themselves also envisaged as regulatory element. Regulatory elements as used herein may be part of a larger sequence involved in transcriptional control, e.g. part of a promoter sequence. However, regulatory elements alone are typically not sufficient to initiate transcription, but require a promoter to this end.

The regulatory elements contained in the nucleic acid expression cassettes and vectors disclosed herein are preferably liver-specific. Non-limiting examples of liver-specific regulatory elements are disclosed in WO 2009/130208, which is specifically incorporated by reference herein.

In preferred embodiments, the regulatory element in the nucleic acid expression cassettes and vectors disclosed herein is a liver-specific regulatory element derived from the serpin gene promoter. Said regulatory element comprises the sequence as defined in SEQ ID NO:8, a sequence having at least 85%, preferably at least 90%, more preferably at least 95%, such as 96%, 97%, 98% or 99%, identity to said sequence, or a functional fragment thereof. Said regulatory element is herein referred to as "the Serpin enhancer", "SerpEnh", or "Serp".

In further embodiments, the regulatory element in the nucleic acid expression cassettes and vectors disclosed herein consists of the sequence defined by SEQ ID NO:8 (i.e. the Serpin enhancer, also called "SerpEnh", or "Serp" herein).

'Liver-specific expression', as used in the application, refers to the preferential or predominant expression of a (trans)gene (as RNA and/or polypeptide) in the liver as compared to other tissues. According to particular embodiments, at least 50% of the (trans)gene expression occurs within the liver. According to more particular embodiments, at least 60%, at least 70%, at least 75%, at least 80%, at least 85%, at least 90%, at least 95%, at least 97%, at least 99% or 100% of the (trans)gene expression occurs within the liver. According to a particular embodiment, liver-specific expression entails that there is no 'leakage' of expressed gene product to other organs, such as spleen, muscle, heart and/or lung. The same applies mutatis mutandis for hepatocyte-specific expression, which may be considered as a particular form of liver-specific expression. Throughout the application, where liver-specific is mentioned in the context of expression, hepatocyte-specific expression is also explicitly envisaged. Similarly, where tissue-specific expression is used in the application, cell-type specific expression of the cell type(s) predominantly making up the tissue is also envisaged.

The term "functional fragment" as used in the application refers to fragments of the sequences disclosed herein that retain the capability of regulating liver-specific expression, i.e. they still confer tissue specificity and they are capable of regulating expression of a (trans)gene in the same way (although possibly not to the same extent) as the sequence from which they are derived. Fragments comprise at least 10 contiguous nucleotides from the sequence from which they are derived. In further particular embodiments, fragments comprise at least 15, at least 20, at least 25, at least 30, at least 35 or at least 40 contiguous nucleotides from the sequence from which they are derived.

As used herein, the term "nucleic acid expression cassette" refers to nucleic acid molecules that include one or more transcriptional control elements (such as, but not limited to promoters, enhancers and/or regulatory elements, polyadenylation sequences, and introns) that direct (trans) gene expression in one or more desired cell types, tissues or organs. Typically, they will also contain the FIX transgene or the FVIII transgene as defined herein.

The term "operably linked" as used herein refers to the arrangement of various nucleic acid molecule elements relative to each such that the elements are functionally connected and are able to interact with each other. Such elements may include, without limitation, a promoter, an enhancer and/or a regulatory element, a polyadenylation sequence, one or more introns and/or exons, and a coding sequence of a gene of interest to be expressed (i.e., the transgene). The nucleic acid sequence elements, when properly oriented or operably linked, act together to modulate the activity of one another, and ultimately may affect the level of expression of the transgene. By modulate is meant increasing, decreasing, or maintaining the level of activity of a particular element. The position of each element relative to other elements may be expressed in terms of the 5' terminus and the 3' terminus of each element, and the distance between any particular elements may be referenced by the number of intervening nucleotides, or base pairs, between the elements.

As used in the application, the term "promoter" refers to nucleic acid sequences that regulate, either directly or indirectly, the transcription of corresponding nucleic acid coding sequences to which they are operably linked (e.g. a transgene or endogenous gene). A promoter may function alone to regulate transcription or may act in concert with one or more other regulatory sequences (e.g. enhancers or silencers). In the context of the present application, a promoter is typically operably linked to regulatory elements to regulate transcription of a transgene.

When a regulatory element as described herein is operably linked to both a promoter and a transgene, the regulatory element can (1) confer a significant degree of liver specific expression in vivo (and/or in hepatocytes/hepatic cell lines in vitro) of the transgene, and/or (2) can increase the level of expression of the transgene in the liver (and/or in hepatocytes/hepatocyte cell lines in vitro).

According to a particular embodiment, the promoter contained in the nucleic acid expression cassettes and vectors disclosed herein is a liver-specific promoter. According to a further particular embodiment, the liver-specific promoter is from the transthyretin (TTR) gene. According to yet a further particular embodiment, the TTR promoter is a minimal promoter (also referred to as TTRm, mTTR or TRRmin herein), most particularly the minimal TTR promoter as defined in SEQ ID NO: 9.

According to another particular embodiment, the promoter in the nucleic acid expression cassettes and vectors disclosed herein is a minimal promoter.

A 'minimal promoter' as used herein is part of a full-size promoter still capable of driving expression, but lacking at least part of the sequence that contributes to regulating (e.g. tissue-specific) expression. This definition covers both promoters from which (tissue-specific) regulatory elements have been deleted—that are capable of driving expression of a gene but have lost their ability to express that gene in a tissue-specific fashion and promoters from which (tissue-specific) regulatory elements have been deleted that are capable of driving (possibly decreased) expression of a gene but have not necessarily lost their ability to express that gene in a tissue-specific fashion. Minimal promoters have been extensively documented in the art, a non-limiting list of minimal promoters is provided in the specification.

Typically, the nucleic acid expression cassette in the expression vector according to the invention comprises a plasmid origin, a promoter and/or enhancer, a (trans)gene, a transcription terminator, and a selection gene.

In embodiments, the nucleic acid expression cassette in the expression vector according to the invention comprises the following elements:
  a plasmid origin such as the f1 origin,
  an Inverted Terminal Repeat sequence (ITR), sometimes mutated,
  an enhancer, preferably the Serpin enhancer ("Serp" or "SerpEnh"),
  a promoter, preferably the minimal TTR promoter (TTRm),
  the MVM intron,
  a (trans)gene, preferably a codon-optimized transgene
  a transcription terminator, preferably a polyadenylation signal such as the bGHpA,
  an Inverted Terminal Repeat sequence (ITR),
  a selection gene (e.g. an antibiotic resistance gene such as an ampicillin resistance gene), and
  a plasmid origin such as the pBR322 origin.

The cloning of the MVM intron into a nucleic acid expression cassette described herein was shown to unexpectedly high expression levels of the transgene operably linked thereto.

In a typical embodiment of the present invention, said nucleic acid expression cassette in the expression vector comprises the following elements (cf. FIG. 1):
  an plasmid origin such as the f1 origin,
  an Inverted Terminal Repeat sequence (ITR), sometimes mutated,
  an enhancer, preferably the Serpin enhancer ("Serp" or "SerpEnh"),
  a promoter, preferably the minimal TTR promoter (TTRm),
  an intron sequence, preferably the MVM intron,
  a (trans)gene, preferably the FIX encoding gene, or its Padua mutant form,
  a transcription terminator, preferably a polyadenylation signal such as the bGHpA,
  an Inverted Terminal Repeat sequence (ITR), a selection gene (e.g. an antibiotic resistance gene such as an ampicillin resistance gene), and a plasmid origin such as the pBR322 origin.

The combination of said elements results in an unexpectedly high expression level of FIX and in particular of the Padua mutant thereof in the liver of subjects. Preferably, the vector is an adeno-associated virus-derived vector, in combination with the Padua-mutant FIX gene.

In another typical embodiment of the present invention, said nucleic acid expression cassette in the vector comprises the following elements:

a plasmid origin, such as the f1 Origin, an Inverted Terminal Repeat sequence (ITR), optionally mutated, a liver-specific regulatory element, preferably the Serpin enhancer, a promoter, preferably the minimal TTR promoter, an intron sequence, preferably the MVM intron, a (trans)gene, preferably codon-optimized factor VIII cDNA, even more preferably codon-optimized B domain deleted factor VIII cDNA, a transcription terminator, preferably a polyadenylation signal such as the Simian vacuolating virus 40 or Simian virus 40 (SV40) polyadenylation signal, an Inverted Terminal Repeat sequence (ITR), a selection gene (e.g. an antibiotic resistance gene such as an ampicillin resistance gene), and a plasmid origin, such as the pBR322 origin.

The combination of said elements results in an unexpectedly high expression level of FVIII specifically in the liver of subjects. Preferably, the vector is an adeno-associated virus(AAV)-derived vector in combination with codon-optimized B domain deleted FVIII cDNA.

In typical embodiment of the invention, said nucleic acid expression cassette in the vectors disclosed herein comprises:

a liver-specific regulatory element, preferably the Serpin enhancer, a promoter, preferably the minimal TTR promoter, the MVM intron a (trans)gene, preferably a codon-optimized transgene a transcription terminator, preferably a polyadenylation signal such as the bovine growth hormone polyadenylation signal.

In another typical embodiment of the present invention, said nucleic acid expression cassette in the vectors disclosed herein comprises:

a liver-specific regulatory element, preferably the Serpin enhancer, a promoter, preferably the minimal TTR promoter, an intron sequence, preferably the MVM intron, a (trans)gene, preferably codon-optimized factor IX cDNA, even more preferably codon-optimized factor IX Padua cDNA, a transcription terminator, preferably a polyadenylation signal such as the bovine growth hormone polyadenylation signal, In yet another typical embodiment of the present invention, said nucleic acid expression cassette in the vectors disclosed herein comprises:

a liver-specific regulatory element, preferably the Serpin enhancer, a promoter, preferably the minimal TTR promoter, an intron sequence, preferably the MVM intron, a (trans)gene, preferably codon-optimized factor VIII cDNA, even more preferably codon-optimized B domain deleted factor VIII cDNA, a transcription terminator, preferably a polyadenylation signal such as the Simian vacuolating virus 40 or Simian virus 40 (SV40) polyadenylation signal, The term "transgene" or "(trans)gene" as used herein refers to particular nucleic acid sequences encoding a polypeptide or a portion of a polypeptide to be expressed in a cell into which the nucleic acid sequence is inserted. However, it is also possible that transgenes are expressed as RNA, typically to lower the amount of a particular polypeptide in a cell into which the nucleic acid sequence is inserted. These RNA molecules include but are not limited to molecules that exert their function through RNA interference (shRNA, RNAi), micro-RNA regulation (miR), catalytic RNA, antisense RNA, RNA aptamers, etc. How the nucleic acid sequence is introduced into a cell is not essential to the invention, it may for instance be through integration in the genome or as an episomal plasmid. Of note, expression of the transgene may be restricted to a subset of the cells into which the nucleic acid sequence is inserted. The term 'transgene' is meant to include (1) a nucleic acid sequence that is not naturally found in the cell (i.e., a heterologous nucleic acid sequence); (2) a nucleic acid sequence that is a mutant form of a nucleic acid sequence naturally found in the cell into which it has been introduced; (3) a nucleic acid sequence that serves to add additional copies of the same (i.e., homologous) or a similar nucleic acid sequence naturally occurring in the cell into which it has been introduced; or (4) a silent naturally occurring or homologous nucleic acid sequence whose expression is induced in the cell into which it has been introduced. By 'mutant form' is meant a nucleic acid sequence that contains one or more nucleotides that are different from the wild-type or naturally occurring sequence, i.e., the mutant nucleic acid sequence contains one or more nucleotide substitutions, deletions, and/or insertions. In some cases, the transgene may also include a sequence encoding a leader peptide or signal sequence such that the transgene product will be secreted from the cell.

The term 'vector' as used in the application refers to nucleic acid molecules, usually double-stranded DNA, which may have inserted into it another nucleic acid molecule (the insert nucleic acid molecule) such as, but not limited to, a cDNA molecule. The vector is used to transport the insert nucleic acid molecule into a suitable host cell. A vector may contain the necessary elements that permit transcribing the insert nucleic acid molecule, and, optionally, translating the transcript into a polypeptide. The insert nucleic acid molecule may be derived from the host cell, or may be derived from a different cell or organism. Once in the host cell, the vector can replicate independently of, or coincidental with, the host chromosomal DNA, and several copies of the vector and its inserted nucleic acid molecule may be generated.

The term "vector" may thus also be defined as a gene delivery vehicle that facilitates gene transfer into a target cell. This definition includes both non-viral and viral vectors. Non-viral vectors include but are not limited to cationic lipids, liposomes, nanoparticles, PEG, PEI, etc. Viral vectors are derived from viruses including but not limited to: retrovirus, lentivirus, adeno-associated virus, adenovirus, herpesvirus, hepatitis virus or the like. Typically, but not necessarily, viral vectors are replication-deficient as they have lost the ability to propagate in a given cell since viral genes essential for replication have been eliminated from the viral vector. However, some viral vectors can also be adapted to replicate specifically in a given cell, such as e.g. a cancer cell, and are typically used to trigger the (cancer) cell-specific (onco)lysis.

Preferred vectors are derived from adeno-associated virus, adenovirus, retroviruses and Antiviruses. Alternatively, gene delivery systems can be used to combine viral and non-viral components, such as nanoparticles or virosomes (Yamada et al., 2003). Retroviruses and Antiviruses are RNA viruses that have the ability to insert their genes into host cell chromosomes after infection. Retroviral and lentiviral vectors have been developed that lack the genes encoding viral proteins, but retain the ability to infect cells and insert their genes into the chromosomes of the target cell (Miller, 1990; Naldini et al., 1996, VandenDriessche et al., 1999). The difference between a lentiviral and a classical Moloney-murine leukemia-virus (MLV) based retroviral vector is that lentiviral vectors can transduce both dividing and non-dividing cells whereas MLV-based retroviral vectors can only transduce dividing cells.

Adenoviral vectors are designed to be administered directly to a living subject. Unlike retroviral vectors, most of the adenoviral vector genomes do not integrate into the chromosome of the host cell. Instead, genes introduced into cells using adenoviral vectors are maintained in the nucleus as an extrachromosomal element (episome) that persists for an extended period of time. Adenoviral vectors will transduce dividing and nondividing cells in many different tissues in vivo including airway epithelial cells, endothelial cells, hepatocytes and various tumors (Trapnell, 1993; Chuah et al., 2003). Another viral vector is derived from the herpes simplex virus, a large, double-stranded DNA virus. Recombinant forms of the vaccinia virus, another dsDNA virus, can accommodate large inserts and are generated by homologous recombination.

Adeno-associated virus (AAV) is a small ssDNA virus which infects humans and some other primate species, not known to cause disease and consequently causing only a very mild immune response. AAV can infect both dividing and non-dividing cells and may incorporate its genome into that of the host cell. These features make AAV a very attractive candidate for creating viral vectors for gene therapy, although the cloning capacity of the vector is relatively limited. In a preferred embodiment of the invention, the vector used is therefore derived from adeno-associated virus (i.e. AAV vector).

Different serotypes of AAVs have been isolated and characterized, such as, for example AAV serotype 2, AAV serotype 5, AAV serotype 8, and AAV serotype 9, and all AAV serotypes are contemplated herein. In a preferred embodiment, the vector used is AAV serotype 9.

The AAV vectors disclosed herein may be single-stranded (i.e. ssAAV vectors) or self-complementary (i.e. scAAV vectors). In particular, AAV vectors that comprise a FIX transgene as disclosed herein are preferably self-complementary, and AAV vectors that comprise a FVIII transgene as disclosed herein are preferably single-stranded. With the term "self-complementary AAV" is meant herein a recombinant AAV-derived vector wherein the coding region has been designed to form an intra-molecular double-stranded DNA template.

Gene therapy with adeno-associated viral vectors disclosed herein was shown to induce immune tolerance towards the transgene comprised in the vector.

In another aspect, the vector is a transposon-based vector. Preferably, said transposon-based vectors are preferably derived from Sleeping Beauty (SB) or PiggyBac (PB). A preferred SB transposon has been described in Ivics et al. (1997).

In preferred embodiments, said transposon-based vectors comprise the nucleic acid expression cassettes disclosed herein.

In embodiments, said transposon-based vectors are PiggyBac-based transposons. Such vectors are safe in that they do no enhance the tumorigenic risk. Furthermore, liver-directed gene therapy with these vectors was shown to induce immune tolerance towards the transgene, in particular hFIX, comprised in the vector.

In further embodiments, said PiggyBac-based vectors comprise micro inverted repeats, preferably inverted repeats having SEQ ID NO:29 and SEQ ID NO:30. With "micro inverted repeats" is meant herein inverted repeats wherein the majority of the native sequence has been removed. Exemplary micro inverted repeats have been described in Meir et al. (2011. BMC Biotechnology 11:28) and are characterized by the sequences ttaaccctagaaagataatcatattgtgacgtacgttaaagataatcatgcgtaaaattgacgcatg (SEQ ID NO:29) and gcatgcgtcaattttacgcagactatctttctagggttaa (SEQ ID NO:30). Such micro inverted repeats advantageously increase the expression level of the transgene comprised in the vector.

In a particularly preferred embodiment, said transposon-based vector is a PiggyBac-based transposon comprising the Serpin enhancer, the minimal transthyretin promoter, the minute virus of mouse intron, the codon-optimized human FIX Padua mutant, and the bovine growth hormone polyadenylation signal, such as, e.g., the transposon defined by SEQ ID NO:15. In further embodiments, said transposon-based vector comprises micro inverted repeats.

In another particularly preferred embodiment, said transposon-based vector is a PiggyBac-based transposon comprising the Serpin enhancer, the minimal transthyretin promoter, the minute virus of mouse intron, codon-optimized human FIX cDNA, and the bovine growth hormone polyadenylation signal, such as, e.g., the transposon defined by SEQ ID NO:14. In further embodiments, said transposon-based vector comprises micro inverted repeats.

In another particularly preferred embodiment, said transposon-based vector is a PiggyBac-based transposon comprising the Serpin enhancer, the minimal transthyretin promoter, the minute virus of mouse intron, a codon-optimized human B domain deleted FVIII cDNA, and the SV40 polyadenylation signal, such as, e.g., the transposon defined by SEQ ID NO:13. In further embodiments, said transposon-based vector comprises micro inverted repeats.

In yet another particularly preferred embodiment, said transposon-based vector is a Sleeping Beauty-based transposon comprising the Serpin enhancer, the minimal transthyretin promoter, the minute virus of mouse intron, codon-optimized human FIX cDNA, and the bovine growth hormone polyadenylation signal (FIG. 8I).

The transposon-based vectors disclosed herein are preferably administered in combination with a vector encoding a transposase for gene therapy. For example, the PiggyBac-derived transposon-based vector can be administered with wild-type PiggyBac transposase (Pbase) or mouse codon-optimized PiggyBac transposase (mPBase) Preferably, said transposases are hyperactive transposases, such as, for example, SBmax transposase and hyperactive PB (hyPB) transposase containing seven amino acid substitutions (I30V, S103P, G165S, M282V, S509G, N538K, N570S) as described in Yusa et al. (2011), which is specifically incorporated by reference herein.

Transposon/transposase constructs can be delivered by hydrodynamic injection or using non-viral nanoparticles to transfect hepatocytes.

In a further particular aspect, the nucleic acid regulatory elements, the nucleic acid expression cassettes and the vectors described herein can be used in gene therapy. Gene therapy protocols, intended to achieve therapeutic gene product expression in target cells, in vitro, but also particularly in vivo, have been extensively described in the art. These include, but are not limited to, intramuscular injection of plasmid DNA (naked or in liposomes), interstitial injection, instillation in airways, application to endothelium, intra-hepatic parenchyme, and intravenous or intra-arterial administration (e.g. intra-hepatic artery, intra-hepatic vein). Various devices have been developed for enhancing the availability of DNA to the target cell. A simple approach is to contact the target cell physically with catheters or implantable materials containing DNA. Another approach is to utilize needle-free, jet injection devices which project a column of liquid directly into the target tissue under high pressure. These delivery paradigms can also be used to deliver viral vectors. Another approach to targeted gene delivery is the use of molecular conjugates, which consist of protein or synthetic ligands to which a nucleic acid- or DNA-binding agent has been attached for the specific targeting of nucleic acids to cells (Cristiano et al., 1993).

According to a particular embodiment, the use of the nucleic acid regulatory elements, nucleic acid expression cassettes or vectors as described herein is envisaged for gene therapy of liver cells. According to a further particular embodiment, the use of the regulatory elements, expression cassettes or vectors is for gene therapy in vivo. According to yet a further particular embodiment, the use is for a method of gene therapy to treat hemophilia, in particular to treat hemophilia B or hemophilia A.

Gene transfer into mammalian hepatocytes has been performed using both ex vivo and in vivo procedures. The ex vivo approach requires harvesting of the liver cells, in vitro transduction with long-term expression vectors, and reintroduction of the transduced hepatocytes into the portal circulation (Kay et al., 1992; Chowdhury et al., 1991). In vivo targeting has been done by injecting DNA or viral vectors into the liver parenchyma, hepatic artery, or portal vein, as well as via transcriptional targeting (Kuriyama et al., 1991; Kistner et al., 1996). Recent methods also include intraportal delivery of naked DNA (Budker et al., 1996) and hydrodynamic tail vein transfection (Liu et al., 1999; Zhang et al., 1999).

According to a further aspect, methods for expressing a protein in liver cells are provided, comprising the steps of introducing in liver cells the nucleic acid expression cassette (or a vector) as described herein and expressing the transgene protein product in the liver cells. These methods may be performed both in vitro and in vivo.

Methods of gene therapy for a subject in need thereof are also provided, comprising the steps of introducing in the liver of the subject a nucleic acid expression cassette containing a transgene encoding a therapeutic protein, and expressing a therapeutic amount of the therapeutic protein in the liver. According to a further embodiment, the method comprises the steps of introducing in the liver of the subject a vector comprising the nucleic acid expression cassette containing a transgene encoding a therapeutic protein, and expressing a therapeutic amount of the therapeutic protein in the liver. According to a very specific embodiment, the therapeutic protein encoded by the transgene in the nucleic acid expression cassette is factor IX, and the method is a method for treating hemophilia B. By expressing factor IX in the liver via gene therapy, hemophilia B can be treated (Snyder et al., 1999).

According to another very specific embodiment, the therapeutic protein encoded by the transgene in the nucleic acid expression cassette is factor VIII, and the method is a method for treating hemophilia A.

Except when noted differently, the terms "subject" or "patient" are used interchangeably and refer to animals, preferably vertebrates, more preferably mammals, and specifically includes human patients and non-human mammals. "mammalian" subjects include, but are not limited to, humans, domestic animals, commercial animals, farm animals, zoo animals, sport animals, pet and experimental animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. Accordingly, "subject" or "patient" as used herein means any mammalian patient or subject to which the compositions of the invention can be administered. Preferred patients or subjects are human subjects.

As used herein, the terms "treat" or "treatment" refer to both therapeutic treatment and prophylactic or preventative measures, wherein the object is to prevent or slow down (lessen) an undesired physiological change or disorder, such as the development or spread of proliferative disease, e.g., cancer. Beneficial or desired clinical results include, but are not limited to, alleviation of symptoms, diminishment of extent of disease, stabilised (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

As used herein, a phrase such as "a subject in need of treatment" includes subjects, such as mammalian subjects, that would benefit from treatment of a given condition, such as, hemophilia B. Such subjects will typically include, without limitation, those that have been diagnosed with the condition, those prone to have or develop the said condition and/or those in whom the condition is to be prevented.

The term "therapeutically effective amount" refers to an amount of a compound or pharmaceutical composition of the invention effective to treat a disease or disorder in a subject, i.e., to obtain a desired local or systemic effect and performance. In a particular embodiment, the term implies that levels of factor IX in plasma equal to or higher than the therapeutic threshold concentration of 10 mU/ml (milli-units per milliliter) plasma, 50 mU/ml plasma, 100 mU/ml plasma, 150 mU/ml or 200 mU/ml plasma in a subject can be obtained by transduction or transfection of the vector according to any one the embodiments described herein into a subject. Due to the very high efficiency of the vector and nucleic acid expression cassette of the present invention, this high physiological level of factor IX in the subject can be obtained even by administering relatively low doses of vector. In another particular embodiment, the term implies that levels of factor VIII in plasma equal to or higher than the therapeutic threshold concentration of 10 mU/ml (milli-units per milliliter) plasma, 50 mU/ml plasma, 100 mU/ml plasma, 150 mU/ml plasma, 200 mU/ml plasma or higher can be obtained by transduction or transfection of any of the vectors disclosed herein into a subject. Due to the very high efficiency of the vectors and nucleic acid expression cassettes disclosed herein, these high physiological levels of factor VIII in the subject can be obtained even by administering relatively low doses of vector. The term thus refers to the quantity of compound or pharmaceutical composition that elicits the biological or medicinal response in a tissue, system, animal, or human that is being sought by a researcher, veterinarian, medical doctor or other clinician, which includes alleviation of the symptoms of the hemophilia being treated. In particular, these terms refer to the quantity of compound or pharmaceutical composition according to the invention which is necessary to prevent, cure, ameliorate, or at least minimize the clinical impairment, symptoms, or complications associated with hemophilia, in particular hemophilia B or hemophila A, in either a single or multiple dose.

In particular, the transduction of the vector according to any one of the embodiments defined herein into the subject can be done at a dose lower than $2\times10^{11}$ vg/kg (viral genomes per kilogram) to obtain a physiological factor IX level of 10 mU/ml plasma or of 50 mU/ml plasma in a subject.

Alternatively, if a level of factor IX of 100 mU/ml plasma needs to be reached in a subject, the transduction of the vector according to any one of the embodiments defined herein into the subject can be done at a dose lower than or equal to $6\times10^{11}$ vg/kg.

Further, if a level of factor IX equal to 150 mU/ml plasma or higher needs to be reached, the transduction of the vector according to any one of the embodiments defined herein into the subject can be done at a dose lower than or equal than $2\times10^{12}$ vg/kg. In a preferred embodiment, a level of factor IX of 200 mU/ml plasma or higher can be reached in a subject, when the transduction of the vector according to any one of the embodiments defined herein into the subject is done at a dose lower than or equal to $2\times10^{12}$ vg/kg.

In particular, the transduction of the vector according to any one of the embodiments defined herein into the subject can be done at a dose lower than or equal to $2\times10^{12}$ vg/kg (viral genomes per kilogram), such as lower than or equal to $1\times10^{12}$ vg/kg, $5\times10^{11}$ vg/kg, $2.5\times10^{11}$ vg/kg, $1\times10^{11}$ vg/kg, $5\times10^{10}$ vg/kg, $1\times10^{10}$ vg/kg, $5\times10^{9}$ vg/kg, or $1\times10^{9}$ vg/kg preferably at a dose lower than or equal to $2.5\times10^{11}$ vg/kg, to obtain a physiological factor VIII level of 10 mU/ml plasma, 50 mU/ml plasma, 100 mU/ml plasma, 150 mU/ml plasma, 200 mU/ml plasma, or higher in a subject.

For hemophilia therapy, efficacy of the treatment can, for example, be measured by assessing the hemophilia-caused bleeding in the subject. In vitro tests such as, but not limited to the in vitro actved partial thromboplastin time assay (APPT), test factor IX chromogenic activity assays, blood clotting times, factor IX or human factor VIII-specific ELISAs are also available. Any other tests for assessing the efficacy of the treatment known in the art can of course be used.

The compound or the pharmaceutical composition of the invention may be used alone or in combination with any of the know hemophilia therapies, such as the administration of recombinant or purified clotting factors. The compound or the pharmaceutical composition of the invention can thus be administered alone or in combination with one or more active compounds. The latter can be administered before, after or simultaneously with the administration of the said agent(s).

A further object of the invention are pharmaceutical preparations which comprise a therapeutically effective amount of the expression vector of the invention as defined herein, and a pharmaceutically acceptable carrier, i.e., one or more pharmaceutically acceptable carrier substances and/or additives, e.g., buffers, carriers, excipients, stabilisers, etc.

The term "pharmaceutically acceptable" as used herein is consistent with the art and means compatible with the other ingredients of a pharmaceutical composition and not deleterious to the recipient thereof. The term "pharmaceutically acceptable salts" as used herein means an inorganic acid addition salt such as hydrochloride, sulfate, and phosphate, or an organic acid addition salt such as acetate, maleate, fumarate, tartrate, and citrate. Examples of pharmaceutically acceptable metal salts are alkali metal salts such as sodium salt and potassium salt, alkaline earth metal salts such as magnesium salt and calcium salt, aluminum salt, and zinc salt. Examples of pharmaceutically acceptable ammonium salts are ammonium salt and tetramethylammonium salt. Examples of pharmaceutically acceptable organic amine addition salts are salts with morpholine and piperidine. Examples of pharmaceutically acceptable amino acid addition salts are salts with lysine, glycine, and phenylalanine. The pharmaceutical composition according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The pharmaceutical composition can be prepared in a manner known per se to one of skill in the art. For this purpose, the expression vector according to the invention as defined herein, one or more solid or liquid pharmaceutically acceptable excipients and, if desired, in combination with other pharmaceutical active compounds, are brought into a suitable administration form or dosage form which can then be used as a pharmaceutical in human medicine or veterinary medicine.

According to another aspect, a pharmaceutical composition is provided comprising a nucleic acid expression cassette containing a transgene encoding a therapeutic protein, and a pharmaceutically acceptable carrier. According to another embodiment, the pharmaceutical composition comprises a vector containing the nucleic acid expression cassette containing a transgene encoding a therapeutic protein, and a pharmaceutically acceptable carrier. According to further particular embodiments, the transgene encodes factor IX and the pharmaceutical composition is for treating hemophilia B or the transgene encodes factor VIII and the pharmaceutical composition is for treating hemophilia A.

The use of the nucleic acid expression cassette, its regulatory elements and the vector components as disclosed herein for the manufacture of these pharmaceutical compositions for use in treating hemophilia, preferably hemophilia B or hemophilia A, is also envisaged.

It is to be understood that although particular embodiments, specific constructions and configurations, as well as materials, have been discussed herein for methods and applications according to the present invention, various changes or modifications in form and detail may be made without departing from the scope and spirit of this invention.

The following examples are provided to better illustrate particular embodiments, and they should not be considered limiting the application. The application is limited only by the claims.

EXAMPLES

Example 1: In Vivo Validation of Liver-Specific Regulatory Enhancer Sequences Expressing Hyper-Active FIX Via AAV Vector Gene Delivery Materials and Methods
Vector Construction AAV-based vectors were constructed that express either the codon-optimized factor IX or the codon-optimized factor IX with the Padua R338L mutation from the TTRm promoter operably linked to the Serpin regulatory sequence. The Serpin regulatory sequence has been identified and described under patent application WO2009/130208.

Figure 10:
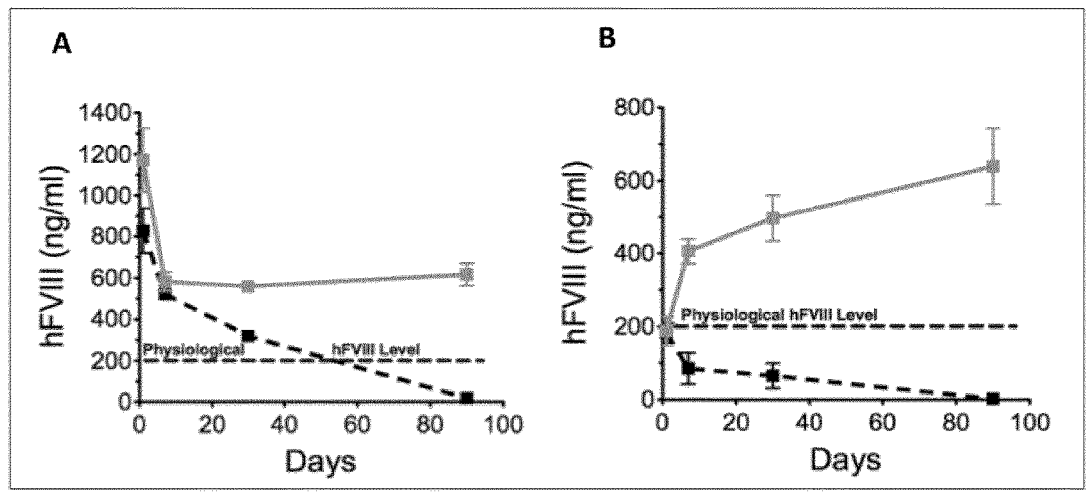
FIG. 10. FVIII expression levels in SCID mice treated by liver-directed gene therapy using hyperactive PB transposon systems: 1 μg pcDNA3_mouseCO_hyPiggyBac_Transposase_MT plasmid (hyPB plasmid)+5 μg PB_Minimal_T_(T53C-C136T)_D4Z4_TTRminSerpMVM_ hFVIIIcopt_SV40 pA_D4Z4 transposon (A); or 1 μg hyPB plasmid+500 ng PB_Minimal_T_(T53C-C136T)_D4Z4_TTRminSerpMVM_hFVIIIcopt_SV40 pA_D4Z4 transposon (B). (lines: with hyPB, broken lines: without hyPB control). Physiologic FVIII concentration (100%=200 ng/ml plasma) is indicated. Human FVIII levels were detected by ELISA.

An intron and poly-A sequence were also provided. The full sequence of the construct containing the codon-optimized factor IX is given in SEQ ID No.1 (FIG. 1B) and the construct containing the codon-optimized factor IX with the Padua R338L mutation in SEQ ID No.2 (FIG. 10). The vectors were constructed by conventional cloning and DNA synthesis. A schematic overview of the AAV vector containing the codon-optimized huFIX is shown in FIG. 1A. The vector with the Padua R338L is identical except for the specific R338L mutation that results in FIX hyper-activity.

Cell Lines and Culture Conditions 293T cells were cultured in Dulbecco's modified Eagle's medium (DMEM) supplemented with 2 mM L-glutamine (Gln), 100 IU/ml penicillin, 100 µg/ml streptomycin and 10% heat-inactivated fetal bovine serum (FBS, Invitrogen, Merelbeke, Belgium).

AAV Vector Production

As an example, the AAV serotype 9 viral vector was chosen to package the construct, known to be a promising vector for gene therapy (Vandendriessche et al. 2007). AAV vectors expressing human FIX were produced at high-titer by calcium phosphate transfection according to the manufacturer's instruction (Calcium phosphate transfection kit, Invitrogen) of 293 cells with AAV2-vector DNA (26 µg/10 cm dish), an adenoviral helper plasmid (52 µg/10 cm dish) and AAV helper plasmids expressing Rep2 and Cap9 (26 µg/10 cm dish) for production of AAV9 serotypes, as described in Gao et al. (2002), Mingozzi et al. (2003) and Gehrke (2003).

Two days post-transfection, cells were lysed by successive freeze-thaw cycles and sonication. Lysates were treated with benzonase (Merck) and deoxycholate (Sigma-Aldrich) and subsequently subjected to three successive rounds of cesium chloride density ultracentrifugation. The fractions containing the AAV particles were concentrated using an Amicon filter (Millipore) and washed with PBS 1 mM MgCl2. Vector genome titers were determined by quantitative polymerase chain reaction (qPCR) using TaqMan® probes and primers specific for the polyadenylation signal

```
(forward primer: 5'GCCTTCTAGTTGCCAGCCAT (SEQ ID No. 3), probe: 5'TGTTTGCCCCTCCCCCGTGC (SEQ ID No. 4), reverse primer:

5'GGCACCTTCCAGGGTCAAG (SEQ ID No.5)).
```

Animal Studies

Animal procedures were approved by the animal Ethical Commission of the VUB. Animals were housed under Biosafety Level II conditions. Mice were injected with the AAV9 vectors as described in Vandendriessche et al. (2007). Briefly, $10^9$ vg, $5\times10^9$ vg, $2\times10^{10}$ vg (vector genomes=vg) were injected (i.v.) into the tail vein of adult hemophilia B mice (3 mice/group). Blood was collected by retro-orbital bleeds under general anesthesia. Human FIX expression was determined in citrated mouse plasma using a chromogenic FIX activity assay, according to the manufacturer (Hyphen Biomed, Neuville-sur-Oise, France) using serially diluted hFIX standards for calibration.

Results

Figure 2:
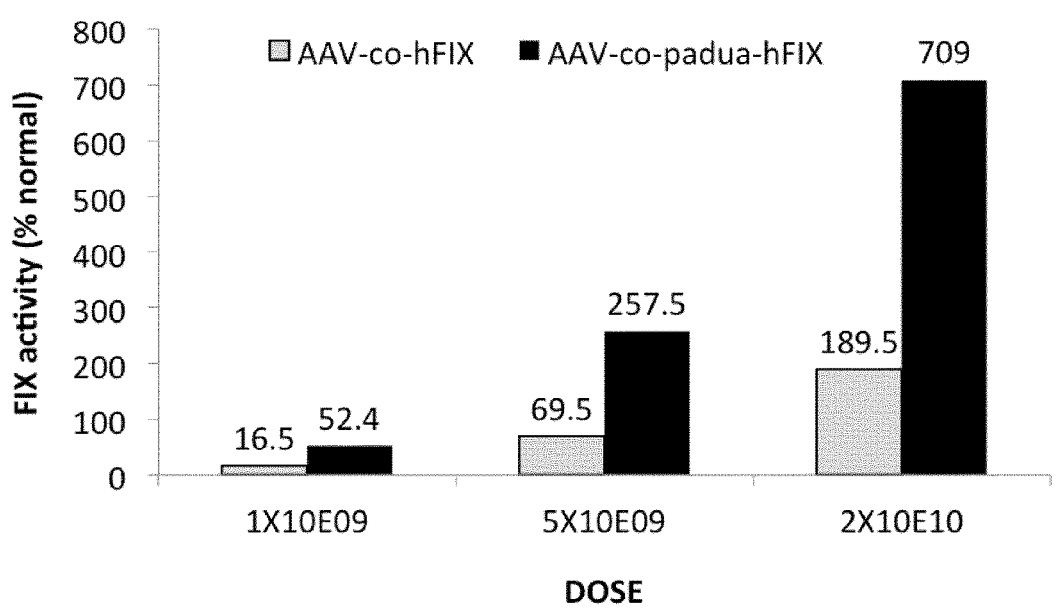
FIG. 2 shows FIX activity after intravenous injection of AAV9-SerpEnh-TTRm-MVM-co-hFIX construct (pdsAAVsc SerpTTRmMVMF9coptpA) or AAV9-SerpEnh-TTRm-MVM-co-hFIX-R338L construct in FIX-deficient hemophilia B mice. AAV vectors expressing either the human codon-optimized FIX cDNA were designated as AAV-co-hFIX or the human codon-optimized FIX-R338L cDNA as AAV-co-padua-hFIX. hFIX activity levels were determined using a chromogenic activity assay on citrated plasma. Mice were injected with different vectors dose of the cognate self-complementary AAV9 vectors ($10^9$ vg, $5 \times 10^9$ vg, $2 \times 10^{10}$ vg).

AAV vectors expressing either the human codon-optimized FIX cDNA (designated as AAV-co-hFIX in FIG. 2) or the human codon-optimized FIX-R338L cDNA (designated as AAV-co-padua-hFIX in FIG. 2) from a chimeric liver-specific promoter (SerpEnh/TTRm) were injected into FIX-deficient hemophilic mice that suffered from hemophilia B. A dose-response was observed and the AAV vector expressing the codon-optimized FIX-R338L yielded significantly higher FIX activity than the codon-optimized FIX control without the hyper-activating mutation. Remarkably, the AAV9-SerpEnh-TTRm-MVM-co-hFIX-R338L vector reached therapeutic FIX levels at a relatively low dose (>50% of normal FIX levels at $1\times10^9$ gc/mouse, >250% of normal FIX levels at $5\times10^9$ gc/mouse and >700% of normal FIX levels at $2\times10^{10}$ gc/mouse after 5 days), which underscores its potency. These levels typically increase more than 2-fold to stable levels in subsequent weeks, reaching respectively approximately >100%, >500% and >1400% FIX at doses of respectively, $1\times10^9$ gc/mouse, $5\times10^9$ gc/mouse and $2\times10^{10}$ gc/mouse. These levels were still increasing in subsequent days following vector injection. Hence, this new vector produced unprecedented, high levels of human IX and can be used at much lower doses than described in the art to cure hemophilia B in a clinically relevant animal model.

Example 2: Enhanced, Liver-Specific Expression of FIX Via AAV Vector Gene Delivery Materials and Methods
Vector Constructs A FIX construct comprising human FIX cDNA (hFIX), was cloned downstream of a liver-specific minimal transthyretin (TTRm) promoter in an adeno-associated viral vector 9 (AAV9) backbone. This vector was further improved to AAV9-SerpEnh-TTRm-hFIX, which comprised an additional hepatocyte-specific regulatory element, namely the Serpin regulatory sequence ("Serp" or "SerpEnh"), upstream of the TTRm promoter. To improve the function of this vector, a minute virus of mice (MVM) intron was cloned in between the TTRm promoter and the hFIX transgene (AAV9-SerpEnh-TTRm-MVM-hFIX). Next, the hFIX transgene was codon-optimized in order to augment the expression of the protein (AAV9-SerpEnh-TTRm-MVM-co-hFIX). A further improvement encompassed a mutation, namely the R338L, Padua mutation (FIG. 3C), of the co-hFIX fragment (AAV9-SerpEnh-TTRm-MVM-co-hFIX-R338L).

Figure 3:
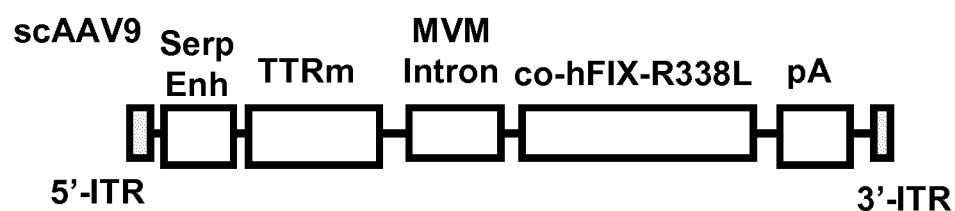
FIG. 3 A) shows a schematic representation of the AAV9sc-SerpEnh-TTRm-MVM-co-hFIX-R338L vector. The expression cassette was packaged in a self-complimentary (sc) adeno-associated virus serotype 9 (AAV9), flanked by the 5' and 3' AAV inverted terminal repeats (ITR). The liver-specific minimal transthyretin (TTRm) promoter drives the codon-optimized human FIX with R338L mutation (co-hFIX-R338L) transgene. The hepatocyte-specific regulatory elements ("Serp" or "SerpEnh") are located upstream of the TTRm promoter. The minute virus of mouse mini-intron (MVM) intron and bovine growth hormone polyadenylation site (pA) are also indicated. B) shows a schematic representation of a control vector AAV9-SerpEnh-TTRm-MVM-co-hFIX, which is identical to the AAV9-SerpEnh-TTRm-MVM-co-hFIX-R338L vector, but the transgene, codon-optimized hFIX, does not contain the R338L mutation. C) compares the R338L or Padua mutation in human FIX fragment (SEQ ID NO:23), making hFIX hyper-functional, with human FIX fragment (SEQ ID NO:24).
Figure 3:
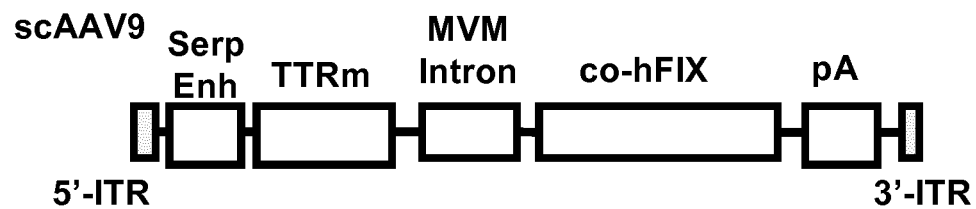
Figure 3:
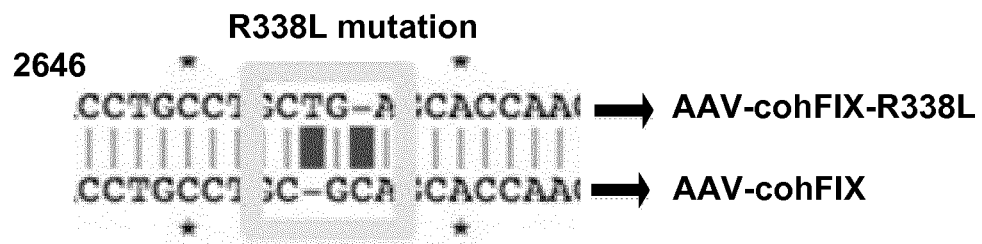

Vectors:
-AAV9-TTRm-hFIX
-AAV9-SerpEnh-TTRm-hFIX
-AAV9-SerpEnh-TTRm-MVM-hFIX
-AAV9-SerpEnh-TTRm-MVM-co-hFIX (FIG. 3B)
-AAV9-SerpEnh-TTRm-MVM-co-hFIX-R338L (FIG. 3A,C)

Vector Production and Purification

Calcium phosphate (Invitrogen Corp, Carlsbad, Calif., USA) co-transfection of AAV-293 cells with the AAV plasmid of interest, a chimeric packaging construct and an adenoviral helper plasmid, were used to produce AAV vectors as described in VandenDriessche T et al. (2007, VandenDriessche T., Thorrez L, Acosta-Sanchez, Petrus I, Wang L, Ma L, De Waele L, Iwasaki Y, Giillijns V, Wilson J M, Collen D, Chuah M K; Efficacy and safety of adeno-associated viral vectors based on serotype 8 and 9 vs. lentiviral vectors for hemophilia B gene therapy. J Thromb Haemost, 2007. 5(1): p. 16-24), which is specifically incorporated by reference herein. Cells were harvested two days after transfection and lysed by freeze/thaw cycles and sonication, followed by bezonase (Novagen, Madison, Wis., USA) and deoxycholic acid (Sigma-Aldrich, St Louis, Mo., USA) treatments and 3 consecutive rounds of cesium chloride (Invitrogen Corp, Carlsbad, Calif., USA) density gradient ultracentrifugation. AAV vector containing fractions were collected and concentrated in Dulbecco's phosphate buffered saline (PBS) (Gibco, BRL) containing 1 mM $MgCl_2$.

Quantitative real-time PCR with SYBR® Green and primers for the bovine growth hormone polyadenylation sequence (bGHpolyA) was used to determine vector titers. The forward primer sequence was 5'-GCCTTCTAGTTGC-CAGCCAT-3' (SEQ ID NO:3). The reverse primer used was 5'-GGCACCTTCCAGGGTCAAG-3' (SEQ ID NO:5). To generate standard curves, known copy numbers ($10^2$-$10^7$) of the corresponding vector plasmids were used.

Animal Experiments and Clotting Assays

Vector administration was carried out by tail vein injection on adult hemophilia B mice at doses of $1\times10^9$ vg/mouse, $5\times10^9$ vg/mouse and $2\times10^{10}$ vg/mouse. Whole blood was collected into buffered citrate by phlebotomy of the retro-orbital plexus. Human FIX antigen concentration in citrated plasma was determined by enzyme-linked immunosorbent assay (ELISA) specific for hFIX antigen (Diagnostica Stago, France) using manufacturer's protocol. FIX activity was assessed using BIOPHEN Factor IX chromogenic assay (Hyphen BioMed, Neuville-sur-Oise, France) according to the manufacturer's protocol. For both assays, serially diluted hFIX standards were used for calibration.

D-dimer levels were determined by ELISA, according to the manufacturers instructions (Hyphen Biomed, Neuville-sur-Oise, France).

Tail-clipping assay was performed. Mice were anesthetized and tail was placed in pre-warmed 37° C. normal saline solution for 2 minutes and subsequently cut at 2-3 mm diameter. Tail was then immediately placed in 37° C. normal saline solution and monitored for bleeding and survival.

Immunizations and Detection of Anti-FIX Antibodies

Immunizations were carried out by subcutaneous injection of 5 μg of recombinant human (rh)FIX protein (BeneFix, Pfizer, Italy) in incomplete Freund's adjuvant (IFA) (Sigma-Aldrich, USA). Briefly, 96-well microtiter plates were coated with hFIX (1 μg/ml) and serially diluted standards made of purified mouse IgG (Invitrogen, Europe). The plate was incubated overnight at 4° C. On day 2, the samples of mouse plasma were diluted in dilution buffer, loaded on the pre-coated plates and incubated overnight at 4° C. Experimental plasma samples were obtained from mice injected with AAV9-SerpEnh-TTRm-MVM-co-hFIX-R338L. Plasma from phosphate-buffered saline (PBS)-injected mice immunized with rhFIX was used as control. The plate was then incubated with horseradish peroxidase (HRP)-goat anti-mouse IgG (Invitrogen, Europe) secondary antibody. Anti-hFIX antibody levels were measured following incubation with detection buffer constituting 12 ml 0.01M sodium citrate, 12 mg o-phenylenediamine and 2.5 μl hydrogen peroxide (Invitrogen, Europe). The chromogenic reaction was monitored by determining the absorbance at 450 nm.

Vector DNA and mRNA Quantification

Genomic DNA was extracted from different tissues using the DNeasy Blood & Tissue Kit (Qiagen, Chatsworth, Calif., USA). 100 ng DNA was analyzed using qPCR ABI Prism 7900HT (Applied Biosystems, Foster City/CA, USA) with bGHPolyA specific primers 5'-GCCTTCTAGTTGCCAGC-CAT-3' (SEQ ID NO:3) (forward) and 5'-GGCACCTTC-CAGGGTCAAG-3' (SEQ ID NO:4) (Reverse). To generate standard curves, known copy numbers of the corresponding vector plasmid was used.

The mRNA was isolated from different organs using a NucleoSpin RNA extraction kit (Machery-Nagel, Germany). Using a cDNA synthesis kit (Invitrogen corp, Carlsbad, Calif., USA), RNA from each organ was reverse transcribed to cDNA. cDNA was then analyzed by qPCR ABI Prism 7900HT (Applied Biosystems, Foster City/CA, USA) using bGHPolyA specific primers 5'-GCCTTCTAGTTGCCAGC-CAT-3' (SEQ ID NO:3) (forward) and 5'-GGCACCTTC-CAGGGTCAAG-3' (SEQ ID NO:4) (Reverse). To expression levels were normalized to glyceraldehyde-3-phosphate dehydrogenase (GAPDH) mRNA expression, obtained by using the forward primer 5'-GAAGGTGAAGGTCG-GAGTC-3' (SEQ ID NO:18) and reverse primer 5'-GAAGATGGTGATGGGATTTC-3' (SEQ ID NO:19).

Statistics

Data were analyzed using Microsoft Excel Statistics package. Values shown in the figures are the mean+SEM. Specific values were obtained by comparison using t-test.

Results

Figure 4:
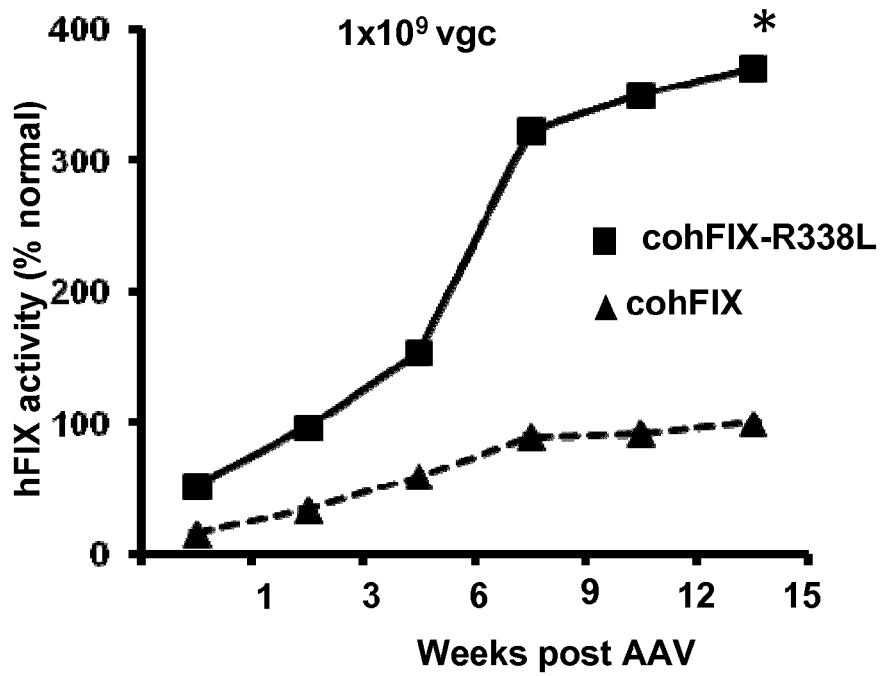
FIG. 4. Evaluation of codon-optimized and hyper-functional FIX transgenes by AAV9 delivery in hemophilic mice. Mice were intravenously administered $1 \times 10^9$ vg/mouse (A,B), $5 \times 10^9$ vg/mouse (C,D) or $2 \times 10^{10}$ vg/mouse (E,F) of AAV9sc-SerpEnh-TTRm-MVM-co-hFIX-R338L (indicated as cohFIX-R338L) or AAV9sc-SerpEnh-TTRm-MVM-co-hFIX- (indicated as cohFIX) vector. hFIX activity (A, C, E) and hFIX protein (B, D, F) were measured by clotting activity using chromogenic FIX activity assays (n=3) and by ELISA (n=3), respectively, on plasma samples collected at the indicated times after AAV administration. (G, H, I) Hemophilic mice were intravenously administered $1 \times 10^9$ vg/mouse (G), $5 \times 10^9$ vg/mouse (H) or $2 \times 10^{10}$ vg/mouse (I) of AAV9-SerpEnh-TTRm-MVM-co-hFIX-R338L (n=3). For each dose, hFIX expression (hFIX protein) was compared to the corresponding FIX clotting activity. (J) D-dimer levels and hFIX activity were determined in mice injected with AAV9sc-SerpEnh-TTRm-MVM-co-hFIX-R338L (indicated as AAV cohFIX R338L) or AAV9sc-SerpEnh-TTRm-MVM-co-hFIX (indicated as AAV cohFIX) vector at the indicated doses and compared to non-injected control mice. D-dimer levels were determined by ELISA and hFIX activity was analyzed by chromogenic assay. The D-dimer positive control is shown. Results are presented as mean±SEM. *: p<0.05, : p<0.01, *: p<0.001 (t-test). (K) Analysis of immune tolerance induction in hemophilia B mice injected with $5 \times 10^9$ vg/mouse of AAV9sc-SerpEnh-TTRm-MVM-co-hFIX-R338L (indicated as cohFIX-R338L, n=4). FIX-specific antibodies were measured by ELISA at week 2 (w2), w4, w6 and w8 after immunization with hFIX protein, as indicated. The immunizations were initiated 2 weeks after vector administration. Immunized PBS-injected hemophilia B mice (n=4) were used as control.
Figure 4:
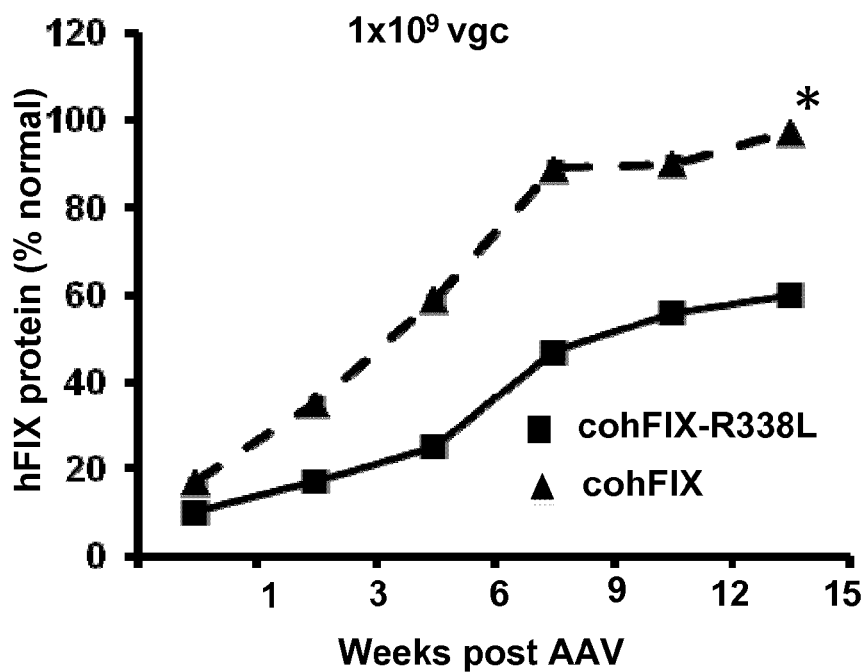
Figure 4:
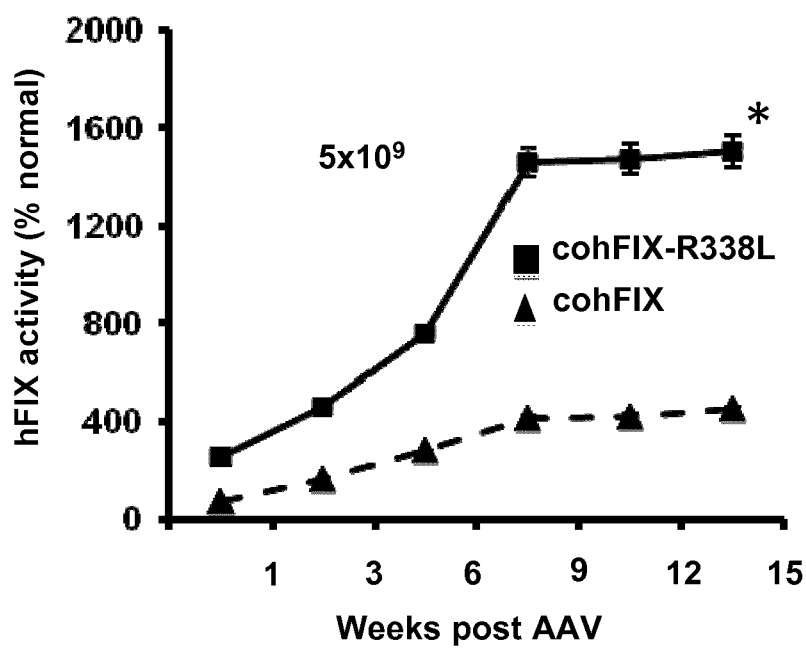
Figure 4:
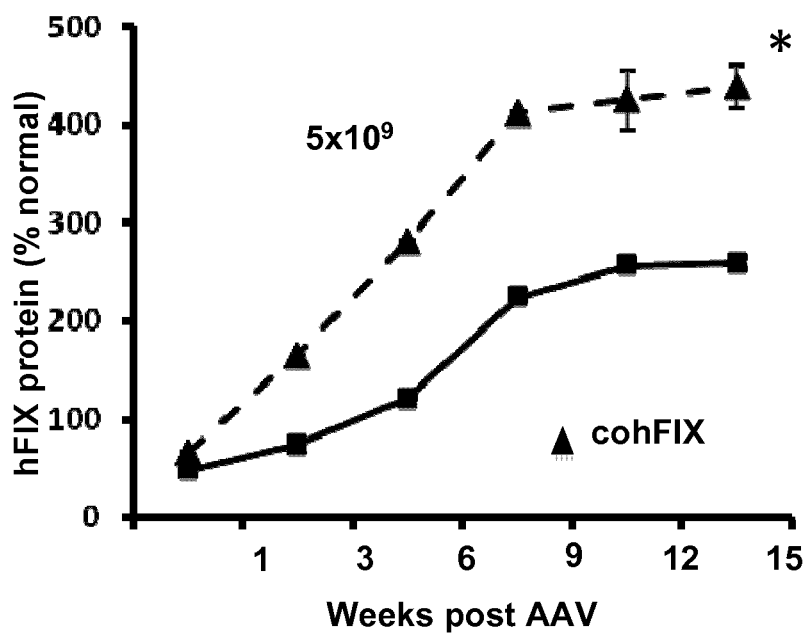
Figure 4:
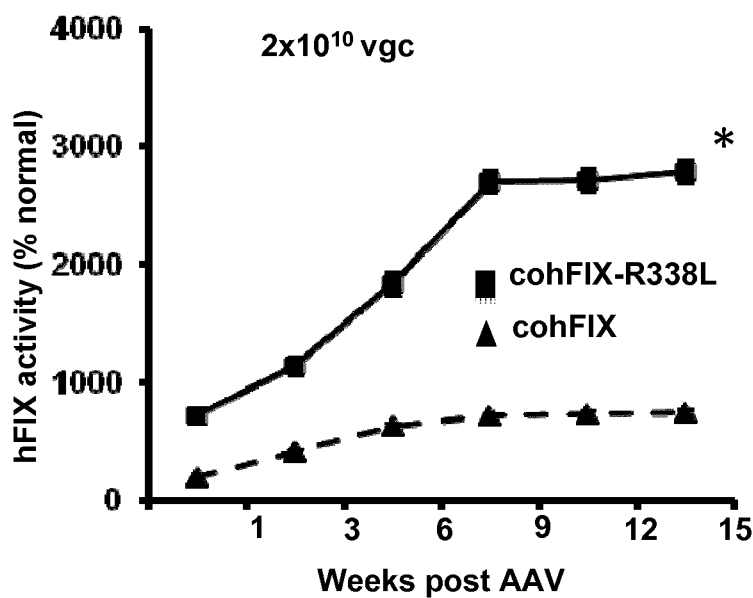
Figure 4:
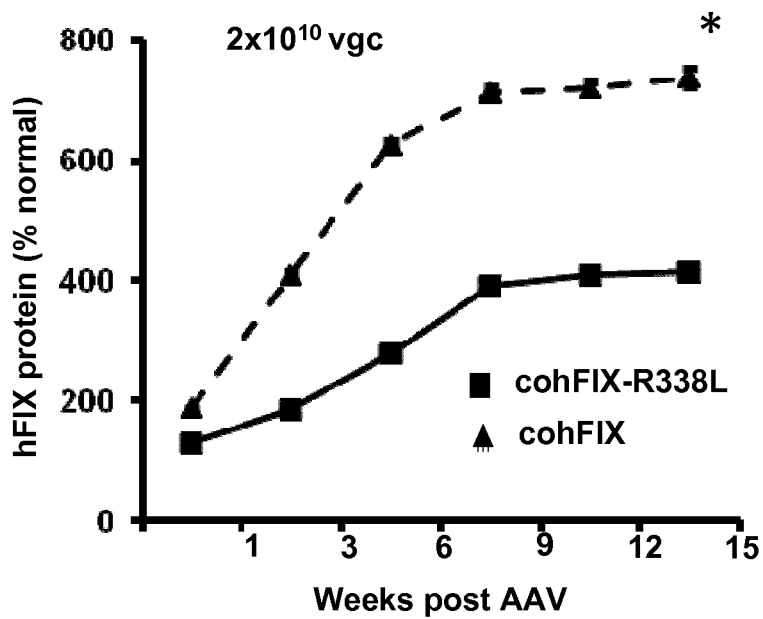
Figure 4:
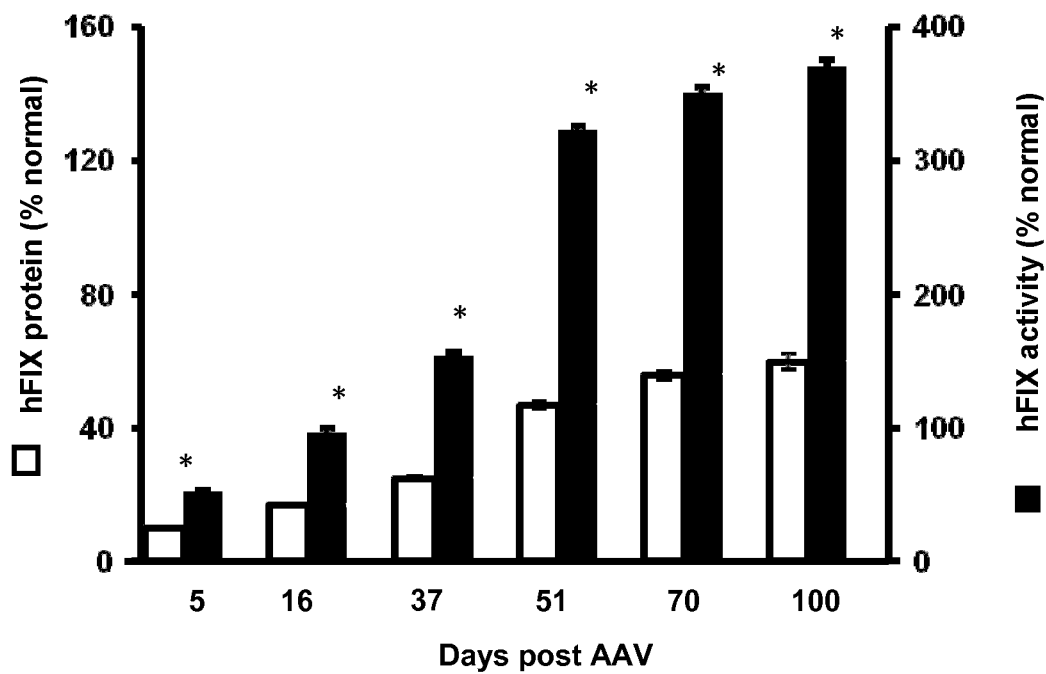
Figure 4:
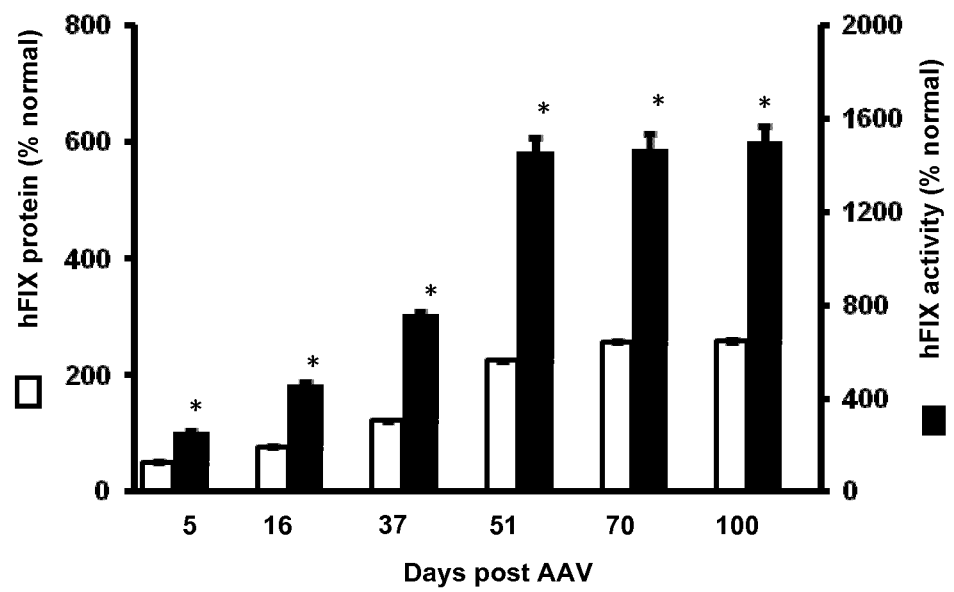
Figure 4:
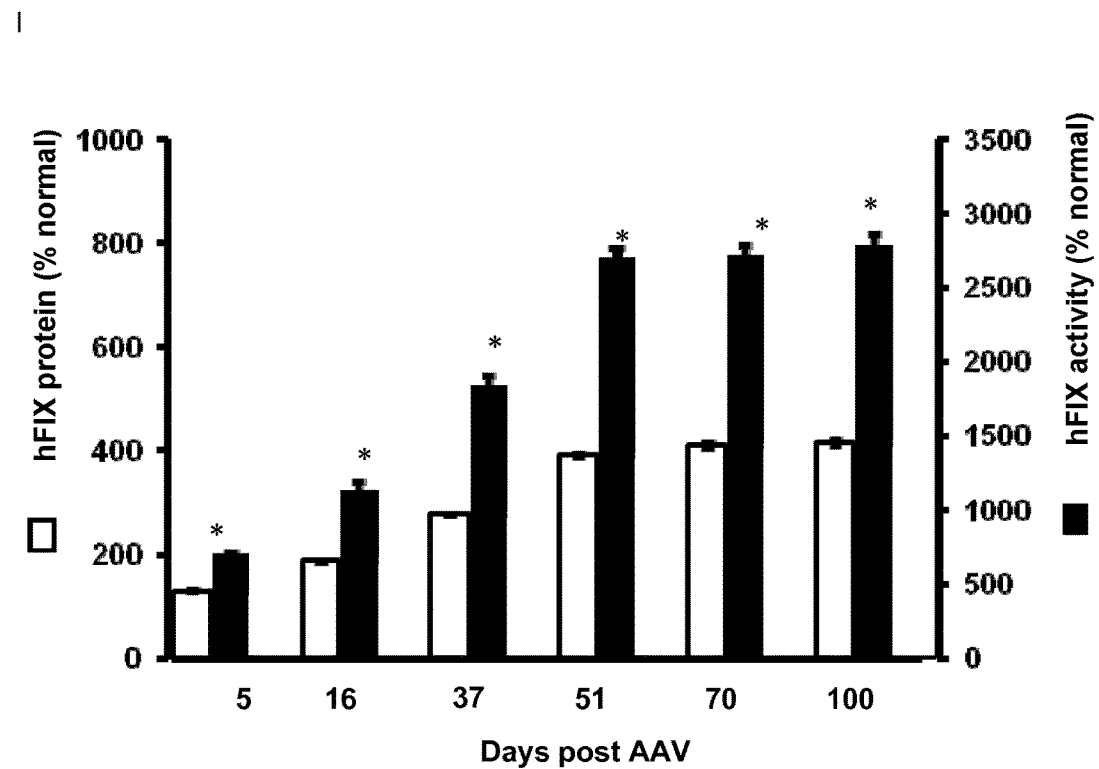
Figure 4:
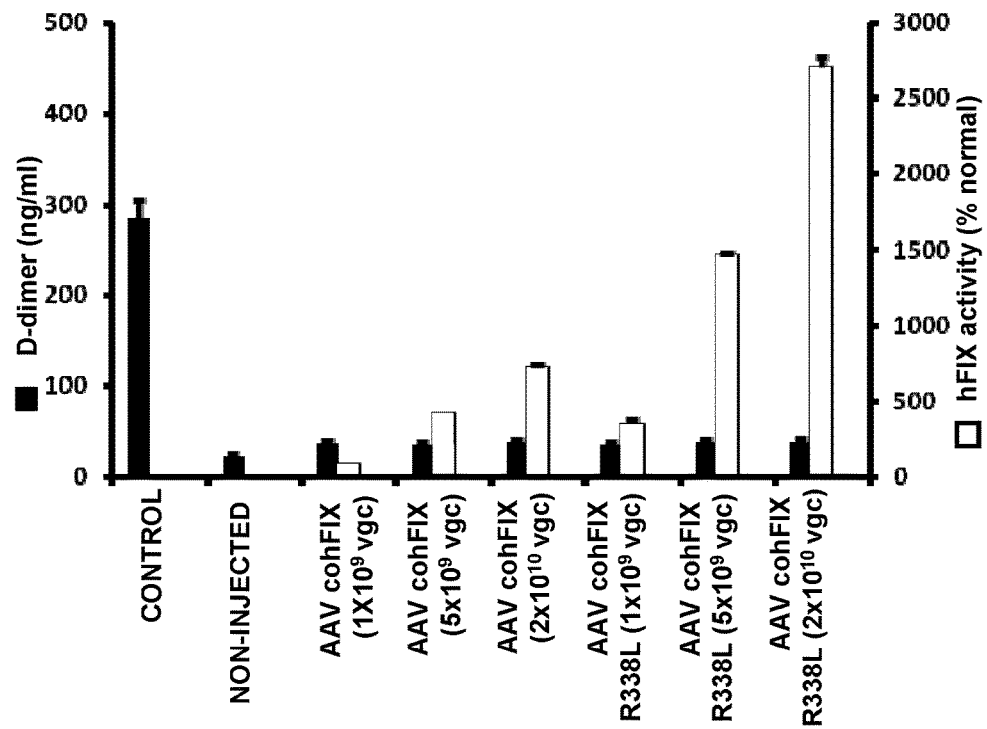
Figure 4:
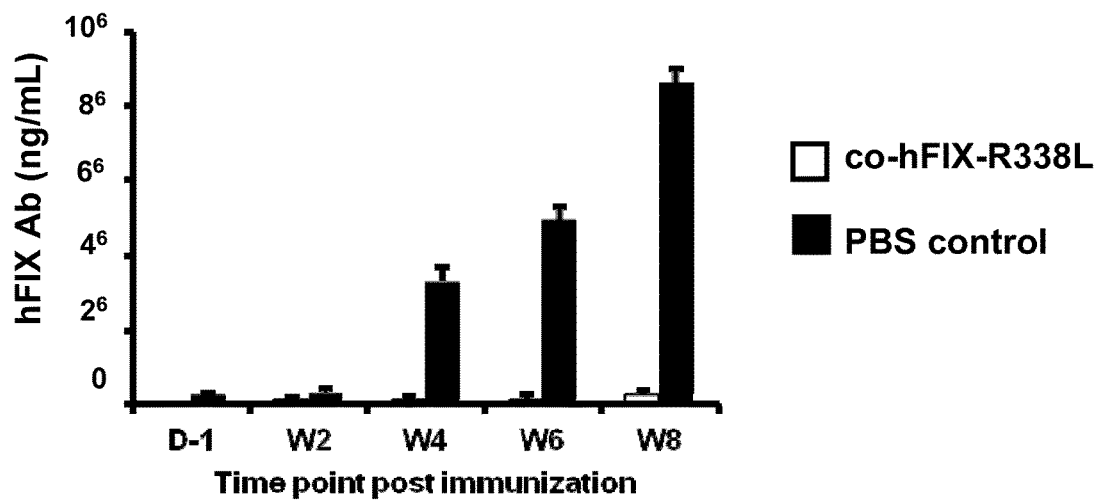
Figure 5:
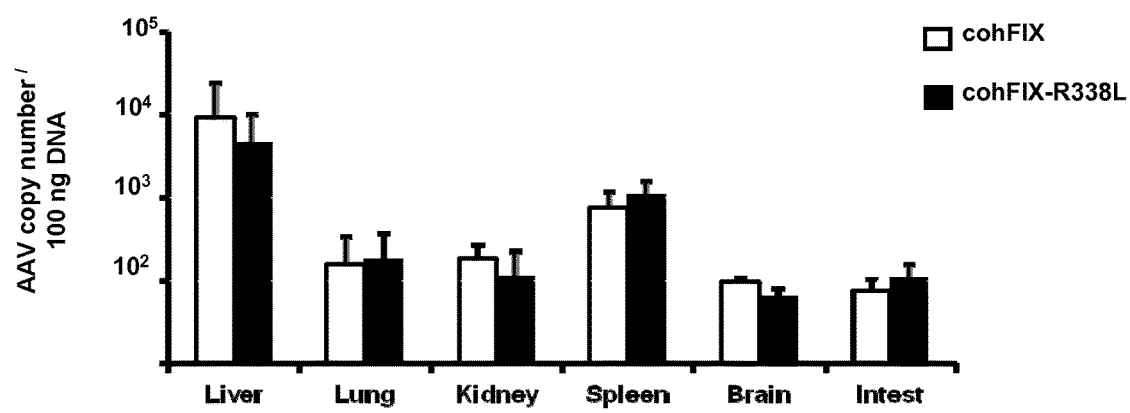
FIG. 5. Biodistribution and transduction efficiency in different organs of mice injected with AAV9sc-SerpEnh-TTRm-MVM-co-hFIX-R338L (indicated as cohFIX-R338L, n=3) or AAV9sc-SerpEnh-TTRm-MVM-co-hFIX (indicated as cohFIX, n=3). (A, B) AAV copy number relative to 100 ng of genomic DNA was determined for both constructs at a dose of $1 \times 10^9$ vg/mouse (A) and $5 \times 10^9$ vg/mouse (B). (C, D) Quantitative reverse transcriptase (qRT)-PCR analysis of hFIX mRNA levels in the different organs expressed relative to hFIX mRNA levels in the liver for both constructs at a dose of $1 \times 10^9$ vg/mouse (C) and $5 \times 10^9$ vg/mouse (D). GAPDH was used for normalization. Results are presented as mean±SEM. *: p<0.05, : p<0.01, *: p<0.001 (t-test).
Figure 5:
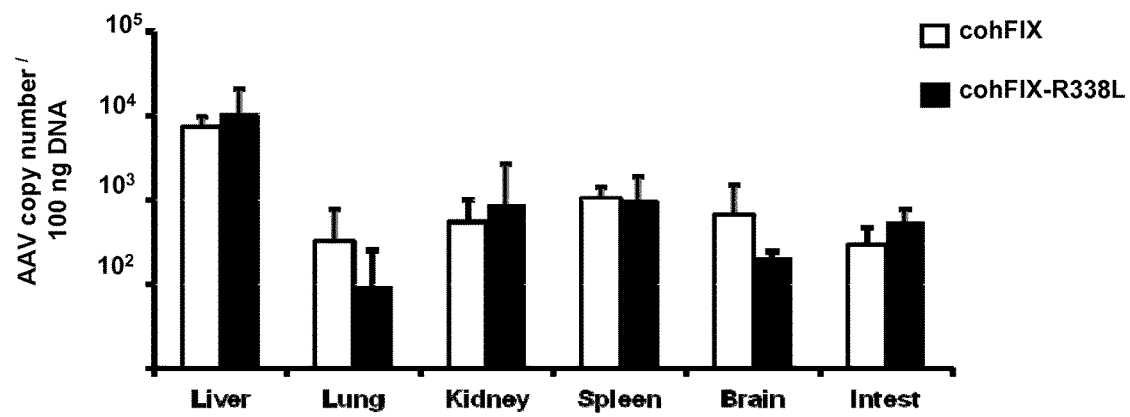
Figure 5:
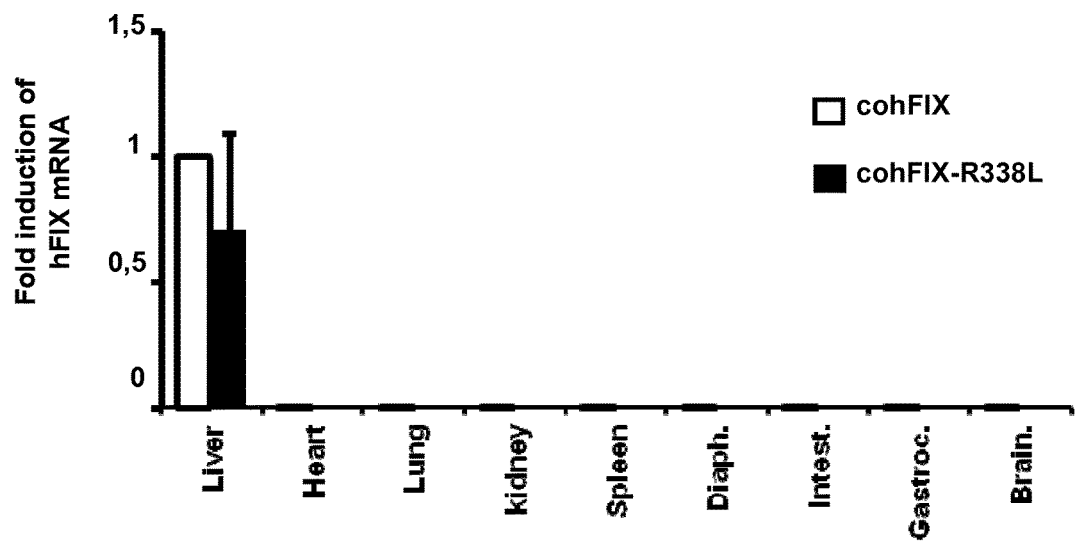
Figure 5:
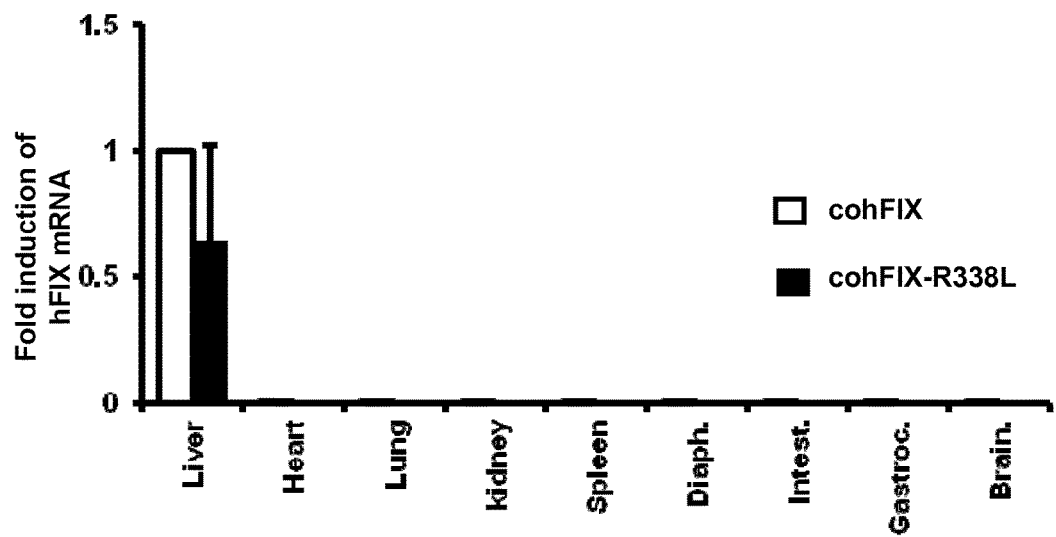

FIG. 4 shows that administration of the AAV9-SerpEnh-TTRm-MVM-co-hFIX-R338L vector to hemophilia B mice provides for significantly higher FIX levels and activity compared to the AAV9-SerpEnh-TTRm-MVM-co-hFIX vector. The FIX response was dose-dependent. Therapeutic FIX levels could be attained at relatively low vector doses of $1\times10^9$ vgc/mouse, $5\times10^9$ vgc/mouse, and $2\times10^{10}$ vgc/mouse. Furthermore, these vector doses are safe as no thrombolysis was observed (FIG. 4J). FIG. 5 shows that FIX was specifically expressed in the liver (FIG. 5 C-D), despite transduction of the vector in other organs (FIG. 5 A-B).

To further assess the clinical relevance of the AAV9-SerpEnh-TTRm-MVM-co-hFIX-R338L vector, a tail-clipping assay was performed on hemophilia B mice treated with $1\times10^9$ vg/mouse of the vector (n=5). Wild-type (C57BL6) (n=4) and untreated hemophilia B (HemoB) mice (n=4) were used as controls. Survival rate for each cohort was monitored and the FIX clotting activity were analyzed. The results are summarized in Table 1 and show that administration of the AAV9-SerpEnh-TTRm-MVM-co-hFIX-R338L vector allows for correcting the bleeding phenotype.

TABLE 1

| Tail-clipping assay | | |
|---|---|---|
| | Survival | FIX activity |
| Wild-type mice | 4/4 | — |
| untreated HemoB mice | 0/4 | 0.0013% |
| treated HemoB mice | 5/5 | 33% |

To assess the immune consequences of expressing the hyper-functional FIX Padua at high levels, the anti-FIX antibody response before and after active immunization with wild-type FIX protein and adjuvant was analyzed. The results show that immune tolerance could be achieved since none of the mice treated with the AAV9-SerpEnh-TTRm-MVM-co-hFIX-R338L vectors developed anti-FIX antibodies, in contrast to the controls that were not treated with this vector (FIG. 4K).

Example 3: Liver-Specific Expression of FVIII Via AAV Vector Gene Delivery

Materials and Methods
Vector Construction

AAV-based vectors were constructed that express a codon-optimized B domain-deleted human coagulation factor VIII (hFVIIIcopt) cDNA (Ward et al., 2011) from the minimal TTR (TTRm) promoter operably linked to the nucleic acid regulatory element Serpin enhancer ("Serp" or "SerpEnh") described in WO 2009/130208, which is specifically incorporated by reference herein. The codon-optimized B domain-deleted human FVIII cDNA was PCR amplified and subcloned into a pGEM-T easy plasmid (Promega, Belgium) and after restriction with SpeI-BamHI, the FVIII cDNA was cloned into the NheI-BglII restricted pAAV-SerpEnh-TTRm vector to generate AAV9ss-SerpEnh-TTRm-MVM-hFVIIIcopt-SV40 pA (also indicated as AAVss-SerpTTRm-MVM-FVIIIcopt-sv40 pA herein). This vector also contained a small intron from minute virus of mouse (MVM) to boost FVIII expression levels.

Vector Production

For titration of the AAV9ss-SerpEnh-TTRm-MVM-hFVIIIcopt-SV40 pA vector, primers binding the SV40 polyA region were used, including 5'-TGATGCTATTGCTT-TATTTGTAACC-3' (SEQ ID NO:20) as forward primer, 5'-CCTGAACCTGAAACATAAAATGA-3' (SEQ ID NO:21) as reverse primer and 5'-FAM-AGCTG-CAATAAACAAGTTAACAACAACAATTGCA-TAMRA-3' (SEQ ID NO:22) as probe. Titers were achieved in the normal range of 2-5×10$^{12}$ vg/ml. Briefly, reactions were performed in TaqMan® Universal PCR Master Mix (Applied Biosystems, Foster City, Calif., USA), on an ABI 7500 Real-Time PCR System (Applied Biosystems, Foster City, Calif., USA). Known copy numbers ($10^2$-$10^7$) of the vector plasmid used to generate the AAV vector were used to generate the standard curves.

Animal Studies

The AAV9ss-SerpEnh-TTRm-MVM-hFVIIIcopt-SV40 pA vectors were injected intravenously into adult male SCID mice (CB17/lcrTac/Prkdc scid) at a dose of 5×10$^9$ vg/mouse or 2.5×10$^{11}$ vg/kg.

FVIII Expression Analysis

Human (h) FVIII antigen levels were assayed in citrated mouse plasma using a hFVIII-specific enzyme-linked immunosorbent assay (ELISA) (Asserachrom® VIII:Ag, Diagnostica Stago, France), as per the manufacturer's instructions. Samples were diluted in sample diluent provided and analyzed in triplicate. Standard curves in percentage FVIII antigen activity were constructed by diluting normal control plasma. In brief, 200 ml diluted samples and standards were pipetted into the wells of the strips precoated with mouse monoclonal anti-human FVIII Fab fragments and incubated for 2 hours at room temperature for antigen immobilization. The wells were then washed with the wash buffer for 5 times before adding 200 ml mouse monoclonal anti-hFVIII antibody coupled with peroxidase for immobilization of immunoconjugate. After incubation for 2 hr at room temperature and washing, 200 ml of TMB substrate was added to the wells for color development. This mixture was incubated at room temperature for exactly 5 minutes. The reaction was then stopped by 50 ml 1M H$_2$SO$_4$ and then read at 450 nm within 1 h.

Results

Figure 6:
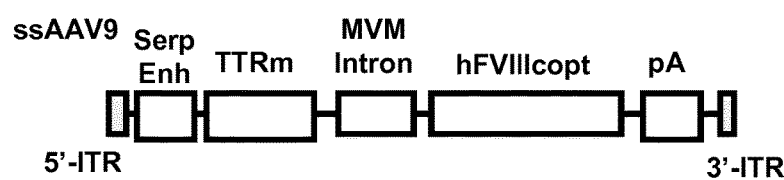
FIG. 6 A) shows a schematic representation of AAVss-SerpEnh-TTRm-MVM-hFVIIIcopt-sv40 pA vector. The expression cassette was packaged in a single-stranded (ss) adeno-associated virus, flanked by the 5' and 3' AAV inverted terminal repeats (ITR). The liver-specific minimal transthyretin (TTRm) promoter regulates transcription of the human codon-optimized B-domain deleted FVIII cDNA (hFVIIIcopt). The Serpin enhancer ("Serp" or "SerpEnh") is cloned upstream of the TTRm promoter. The minute virus of mouse mini-intron (MVM) and SV40 polyadenylation site (pA) are indicated. B) shows a schematic of the AAVss-SerpEnh-TTRm-MVM-hFVIIIcopt-sv40pA construct (AAVss-SerpTTRm-MVM-FVIIIcopt-sv40 pA) with indication where the liver-specific Serpin enhancer ("Serp" or "SerpEnh") is inserted upstream of the transthyretin minimal promoter (TTRm). Abbreviations used are: ITR: viral inverted terminal repeat; MVM intron: minute virus mouse intron; FVIIIcopt: codon-optimized B domain deleted human FIX; SvpolyA: polyadenylation signal of SV40. C) shows the sequence of the AAVss-SerpEnh-TTRm-MVM-hFVIIIcopt-sv40 pA construct (SEQ ID NO. 6). The flanking inverted terminal repeat sequences are indicated in italics, the Serpin enhancer ("Serp" or "SerpEnh") in bold (72 bp), the minimal transthyretin promoter (TTRm) is underlined (202 bp), the mTTR/5' untranslated region is boxed (21 bp), the MVM intron is in italics and underlined (92 bp), the codon-optimized B domain deleted hFVIII (hFVIIIcopt) underlined and in bold (4377 bp), and the SV40 polyadenylation sequence is in italics and bold and underlined (134 bp). D) Nucleotide sequence of codon-optimized B domain deleted FVIII (SEQ ID NO: 7). E) Nucleotide sequence of the Serpin enhancer ("Serp" or "SerpEnh") (SEQ ID NO: 8). F) Nucleotide sequence of the minimal transthyretin promoter (TTRm) (SEQ ID NO: 9). G) Nucleotide sequence of the minute virus mouse (MVM) intron (SEQ ID NO: 10). H) Nucleotide sequence of the SV40 polyadenylation signal (SV40polyA) (SEQ ID NO: 11).
Figure 6:
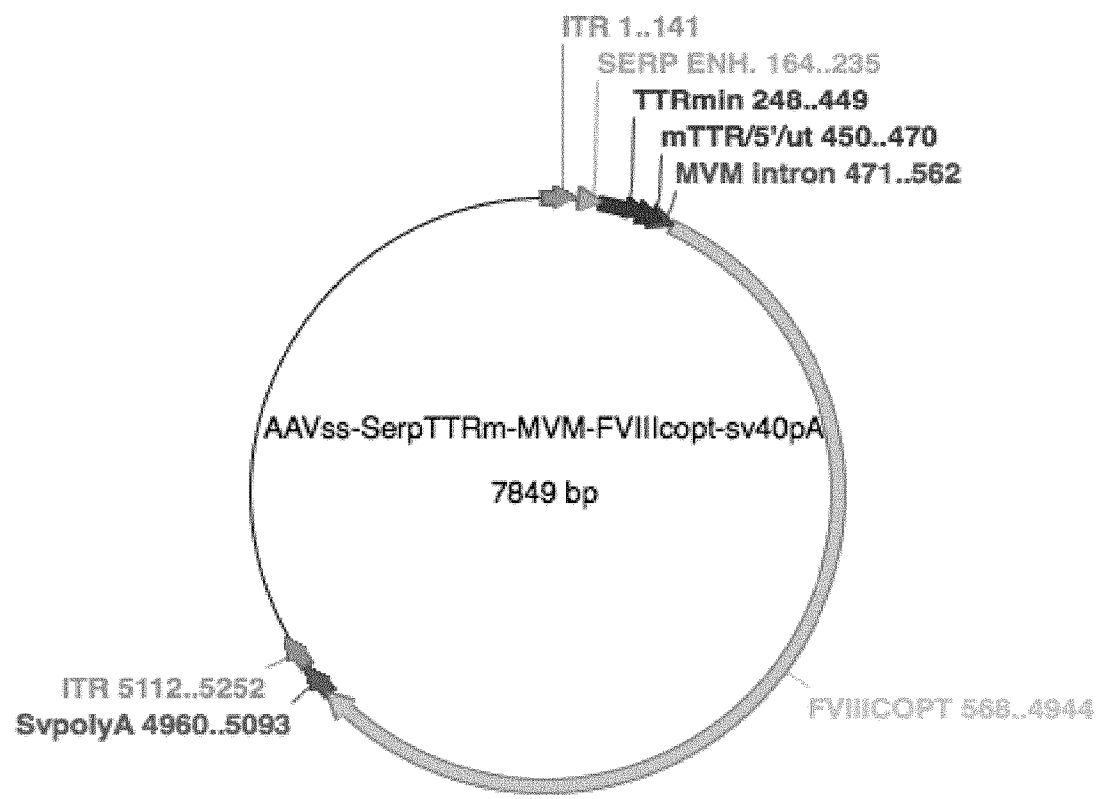
Figure 7:
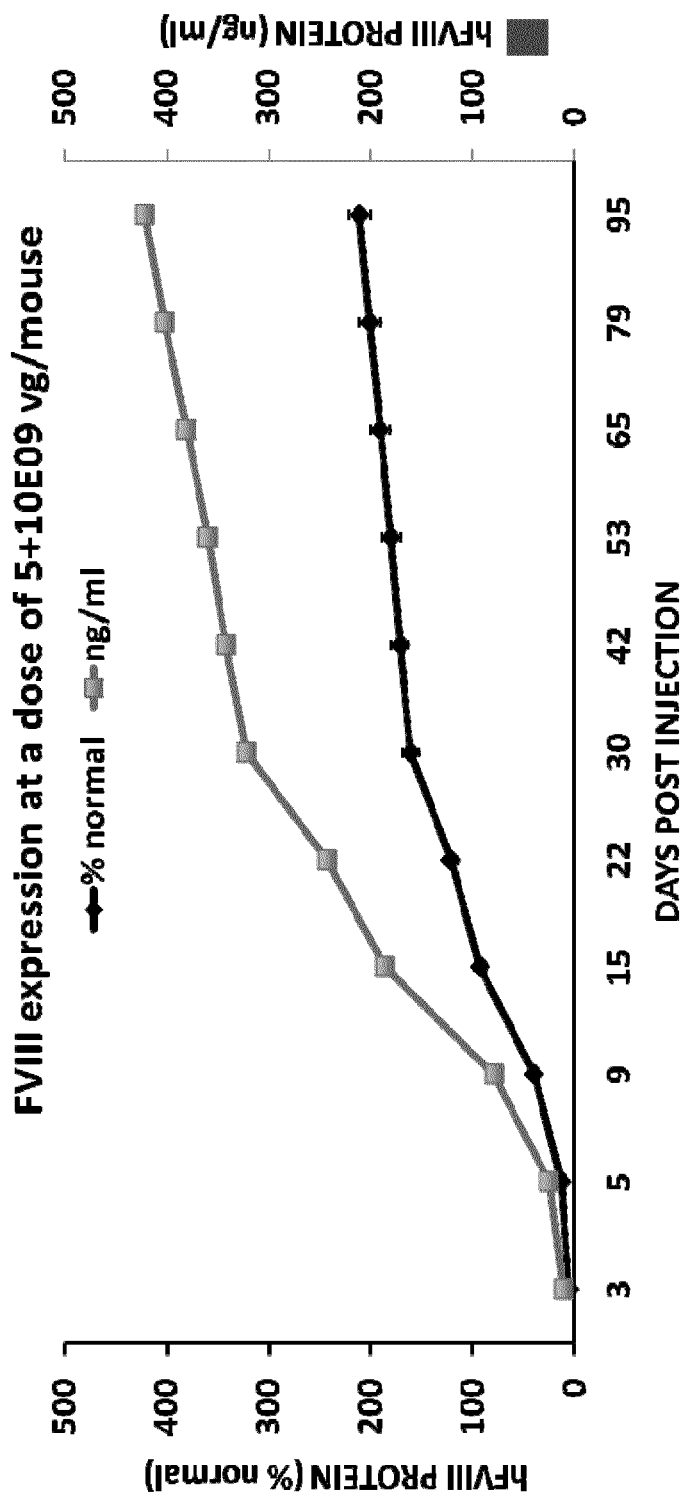
FIG. 7 shows FVIII expression levels in CB17.SCID mice in function of time (days) following intravenous injection with AAVss-SerpEnh-TTRm-MVM-hFVIIIcopt-sv40 pA ($5 \times 10^9$ vg/mouse). FVIII levels were determined using a hFVIII-specific ELISA and are expressed as a percentage of normal levels (i.e. physiological level of human FVIII of 200 ng/ml or 1 IU/ml of FVIII in a normal individual) and in ng/ml plasma.

High-titer AAV9ss-SerpEnh-TTRm-MVM-hFVIIIcopt-SV40 pA vectors expressing a codon-optimized B-domain deleted human FVIII cDNA (hFVIIIcopt) from a liver-specific promoter (TTRm) operably linked to a regulatory element ("Serp" or "SerpEnh") could be produced with a total insert size of 4913 bp (excluding ITR) (FIG. 6). Intravenous injection of a very low vector dose (5×10$^9$ vg/mouse) resulted in therapeutic FVIII levels approximating 421.8±4.9 ng/ml (i.e. 210.9±3.1% of normal levels) (FIG. 7). To our knowledge, AAV9ss-SerpEnh-TTRm-MVM-hFVIIIcopt-SV40 pA vector is the most robust AAV-FVIII vector design to date.

Figure 8A:
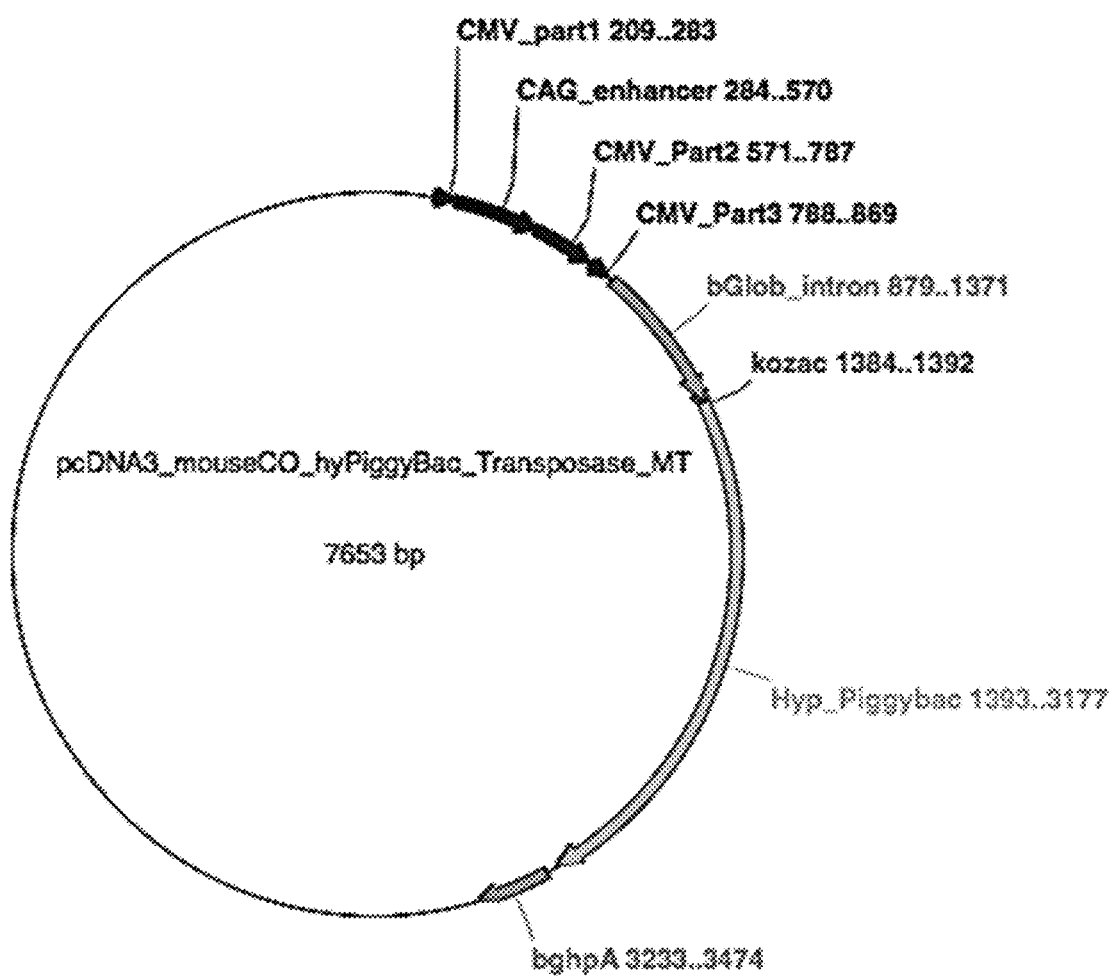
FIG. 8 A) shows a schematic of the plasmid pcDNA3_mouseCO_hyPiggyBac_Transposase_MT encoding codon-optimized hyperactive PiggyBac (PB) transposase. B) Nucleotide sequence of the pcDNA3_mouseCO_hyPiggyBac_Transposase_MT plasmid (SEQ ID NO:12). C) shows a schematic of the PB_Minimal_T_(T53C-C136T)_D4Z4_ TTRminSerpMVM_ hFVIIIcopt_SV40 pA_D4Z4 transposon. The liver-specific minimal transthyretin (TTRm) promoter is operably linked to the Serpin enhancer ("Serp" or "SerpEnh") to regulate transcription of the human codon-optimized B-domain deleted FVIII cDNA (FVIIIcopt). The minute virus of mouse mini-intron (MVM) and SV40 polyadenylation signal (SV40 pA) are indicated. D) Nucleotide sequence of the PB_Minimal_T_(T53C-C136T)_D4Z4TTRminSerpMVM_ hFVIIIcopt_SV40 pA_D4Z4 transposon (SEQ ID NO:13). E) schematically shows the PB_micro_T_No_ins_TTRmin-SerpMVM_FIXco_bghpA transposon. Codon-optimized human FIX expression is driven from the liver-specific minimal transthyretin (TTRm) promoter operably linked to the Serpin enhancer ("Serp" or "SerpEnh"). The minute virus of mouse mini-intron (MVM) and bovine growth hormone polyadenylation signal (bghpA) are indicated. F) Nucleotide sequence of the PB_micro_T_No_ins_TTRmin-SerpMVM_FIXco_bghpA transposon (SEQ ID NO:14). G) schematically shows the PB_micro_T_No_ins_TTRmin-SerpMVM_FIXco_Padua_bghpA transposon. Codon-optimized human Padua FIX expression is driven from the liver-specific minimal transthyretin (TTRm) promoter operably linked to the Serpin enhancer ("Serp" or "SerpEnh"). The minute virus of mouse mini-intron (MVM) and bovine growth hormone polyadenylation signal (bghpA) are indicated. H) Nucleotide sequence of the PB_micro_T_No_ins_TTRminSerpMVM_FIXco_Padua_bghpA transposon (SEQ ID NO:15). I) shows the Sleeping Beauty (SB) transposon pT2BH_TTRminSerpMVM_hFIXco_bghpA transposon. Codon-optimized human FIX expression is driven from the liver-specific minimal transthyretin (TTRm) promoter operably linked to the Serpin enhancer ("Serp" or "SerpEnh"). The minute virus of mouse mini-intron (MVM) and bovine growth hormone polyadenylation signal (bghpA) are indicated. J) shows a schematic of the plasmid pCDNA3_CMVBGI_SBMAX_bghpA encoding the hyperactive SBmax transposase. K) Nucleotide sequence of the pCDNA3_CMVBGI_SBMAX_bghpA plasmid (SEQ ID NO:17).
Figure 8C:
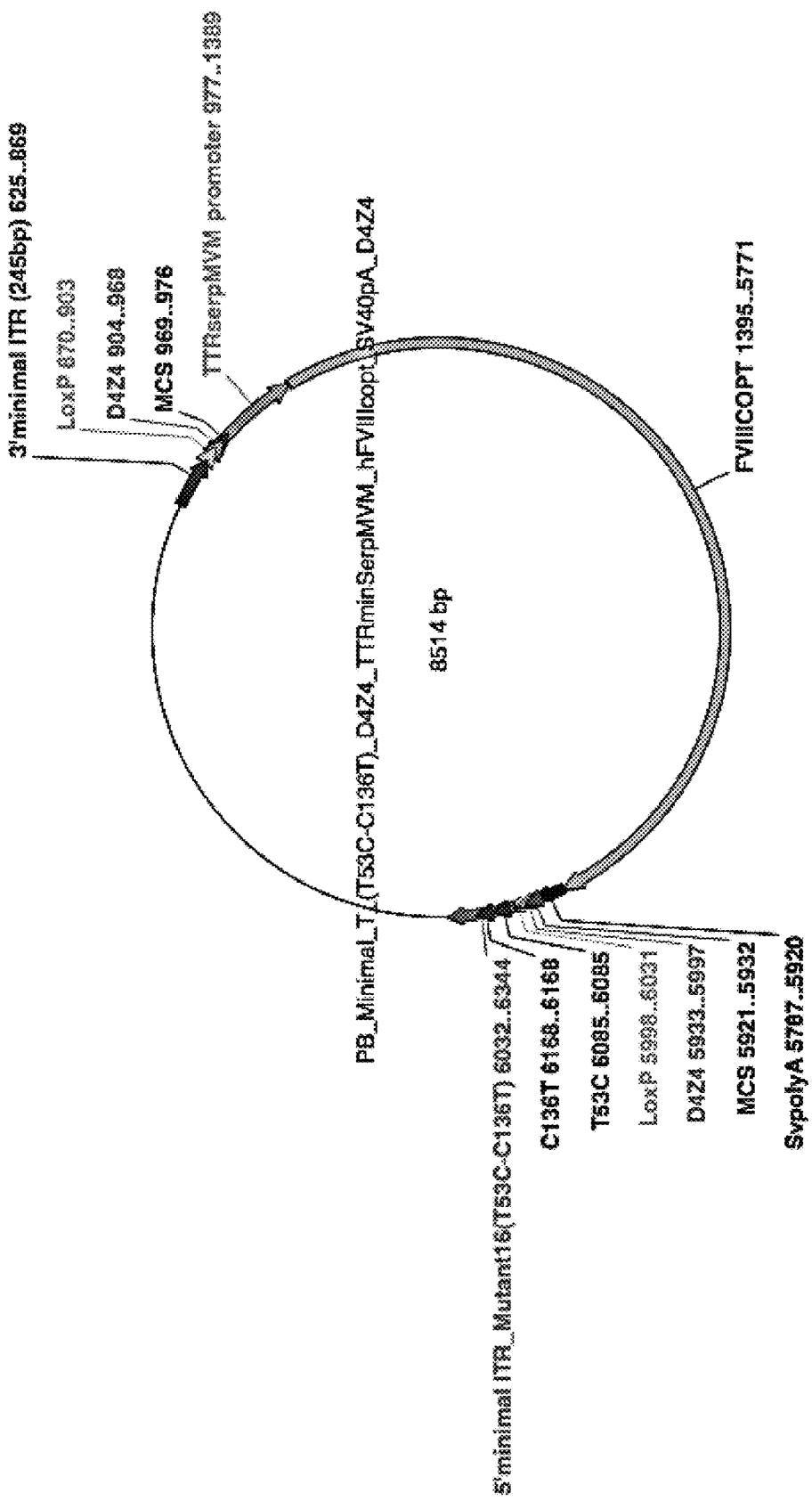
Figure 8E:
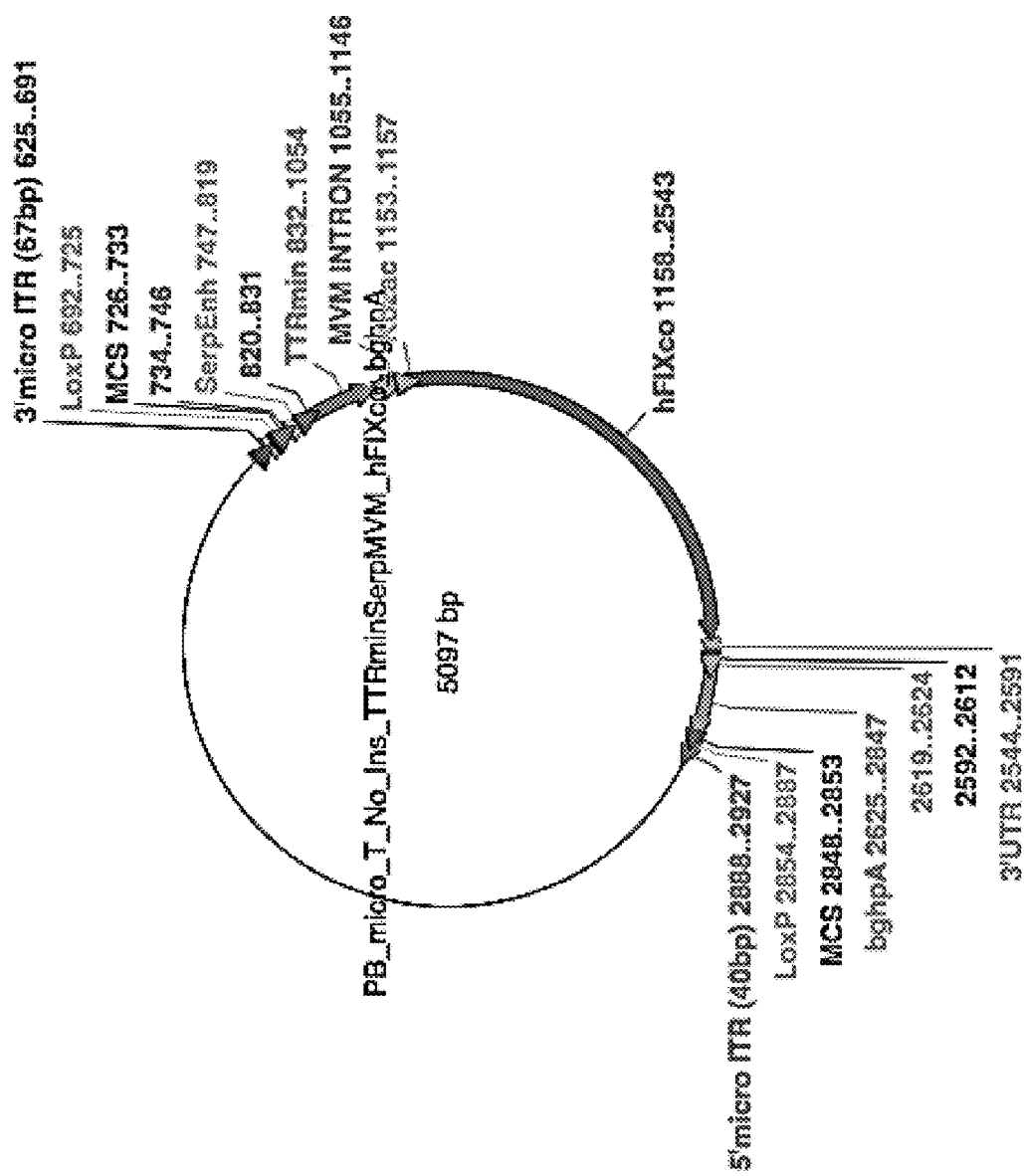
Figure 8:
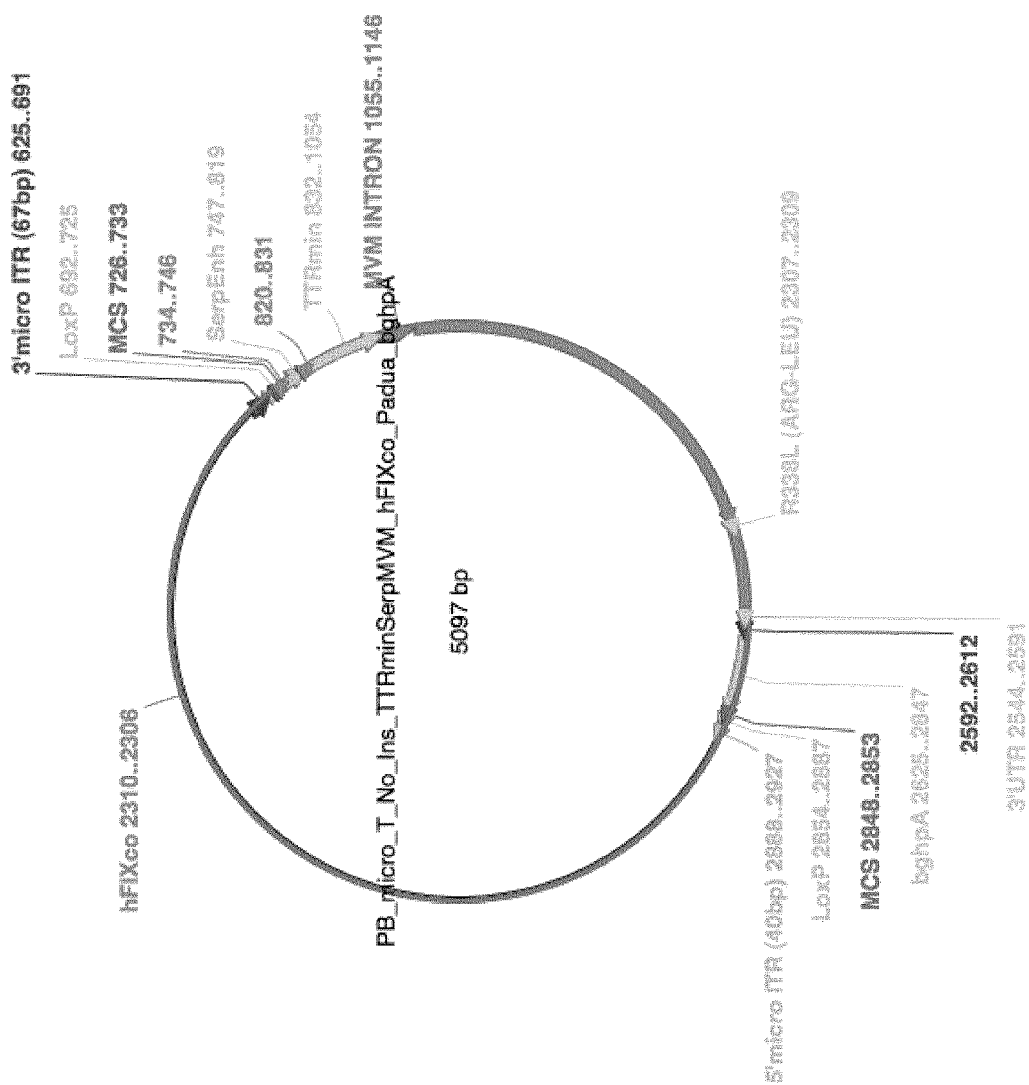
Figure 8:
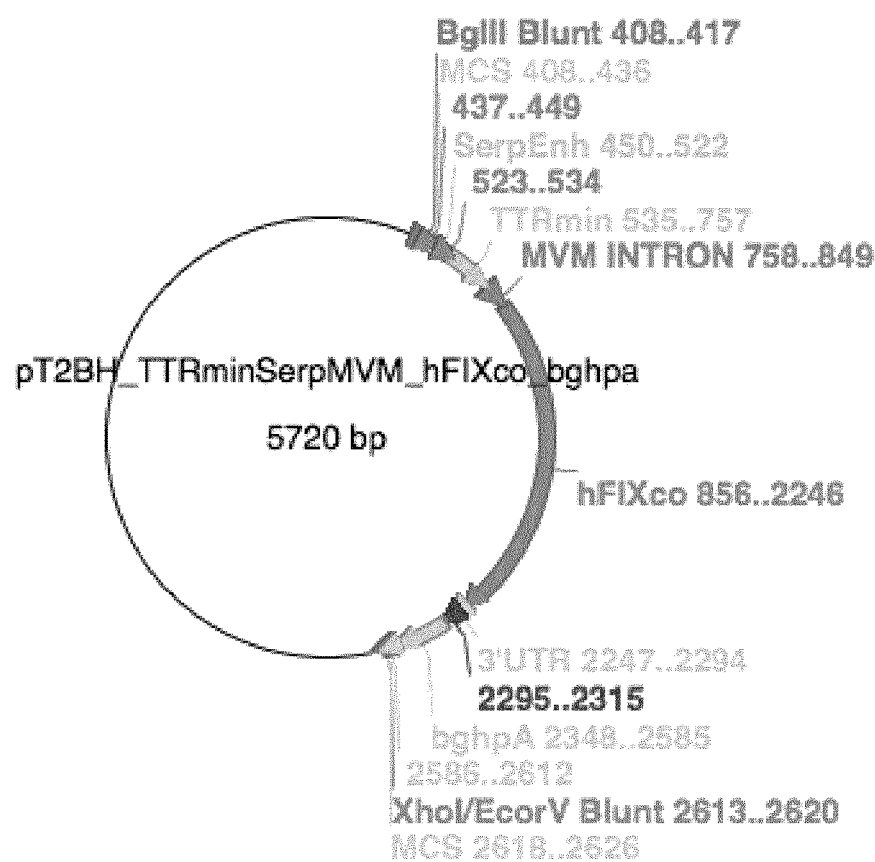
Figure 8:
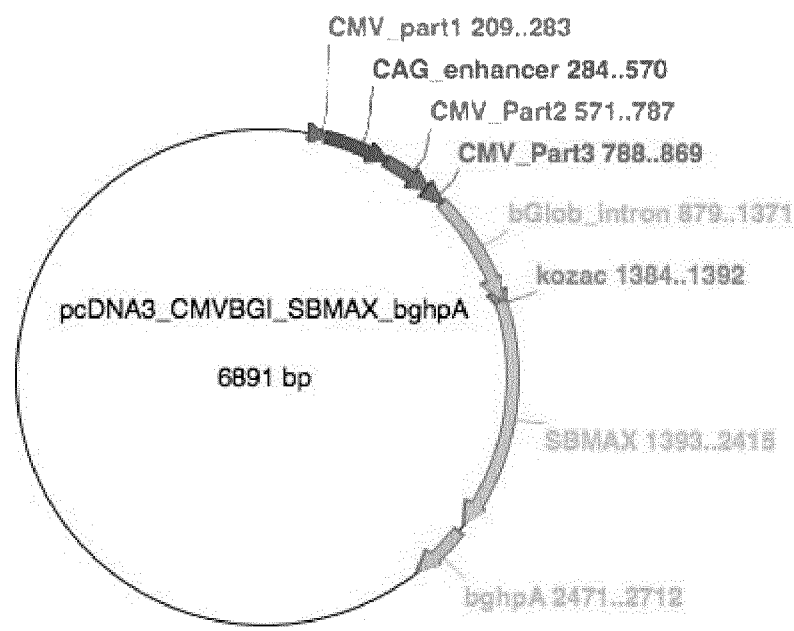

Example 4: Enhanced, Liver-Specific Expression of FVIII and FIX Via Transposon-Based Gene Delivery Materials and Methods The codon-optimized hyperactive PB transposase (huPB) was cloned into pcDNA3 and expressed from the CAG promoter (FIG. 8A,B). The hyperactive SBmax transposase was cloned into pcDNA3 and expressed from the CAG promoter (FIG. 8K,L). A codon-optimized B-domain deleted FVIII (hFVIIIcopt), described as SQ FVIII (co) in Ward et al. (2011) was cloned by conventional cloning techniques into a PB transposon to generate the PB_Minimal_T_(T53C-C136T)_D4Z4_TTRminSerpMVM_hFVIIIcopt_SV40 pA-D4Z4 (FIG. 8C,D). The human codon-optimized FIX cDNA and the codon-optimized FIX cDNA with the hyperactivating Padua mutation were cloned by conventional cloning techniques into a PB transposon to generate the PB_micro_T_No_Ins_TTRminSerpMVM_hFIXco_b-ghpA (FIG. 8E,F) and PB_micro_T_No_Ins_TTRminSerp-MVM_hFIXco_Padua_bghpA (FIG. 8G,H), respectively. The human codon-optimized FIX cDNA was cloned by conventional cloning techniques into an SB-based vector to generate pT2BH_TTRminSerpMVM_hFIXco_bghpA (FIG. 8I,J).

The transgenes were expressed from a liver-specific minimal transthyretin (TTRm) promoter along with the Serpin enhancer ("Serp" or "SerpEnh"). The constructs also contained a mouse mini-intron (MVM) and a polyadenylation site. The recombinant clones were verified by restriction analysis and sequencing.

The different FVIII-transposons and matching plasmids encoding the cognate hyperactive transposases (i.e. hyPB and SBmax, respectively) were purified by ion exchange chromatography and transfected by hydrodynamic transfection at varying transposon/transposase ratios and concentrations into adult mice. Controls without transposase were employed. The FIX expression was monitored by ELISA or using chromogenic activity assays in hemophilia B mice. FVIII expression in SCID mice was assessed using a human FVIII-specific ELISA.

Results

Figure 9:
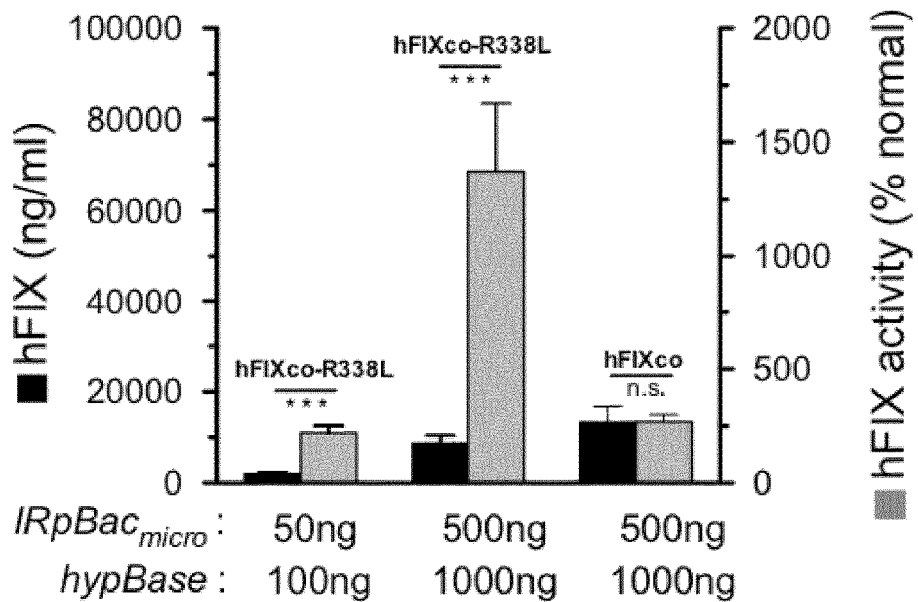
FIG. 9. FIX expression levels in hemophilia B mice treated by liver-directed gene therapy using hyperactive PB transposon expressing either codon-optimized FIX or the hyperactive codon-optimized FIX-R338L mutant. The amount of transposon (IRpBAc$_{micro}$) and transposase plasmid (hypBase) is indicated. Human FIX levels were determined using activity assays.

Incorporation of the Serpin enhancer into the PB transposons resulted in robust, stable gene transfer efficiencies in hepatocytes yielding high unprecedented activity of the codon-optimized FIX Padua (hFIXco-R338L), when the hyperactive hyPB transposase was employed (FIG. 9A). Conversely, in the absence of the hyperactive hyPB transposase, expression declined gradually to basal levels, consistent with our previous observations that transposition is required for stable gene expression in the liver. Molecular analysis, performed 1 year post-transfection, confirmed stable genomic integration of the FIX-transposons. Moreover, side-by-side comparisons revealed a nearly 100-fold increase in FIX expression with this optimized FIX transposon compared to early-generation transposon design.

FIG. 10 demonstrates that the use of the liver-specific Serpin enhancer ("Serp" or "SerpEnh") in conjunction with codon-optimized B-domain deleted FVIII (hFVIIIcopt), and the hyperactive hyPB system resulted in robust, stable gene transfer efficiencies in hepatocytes, yielding high unprecedented expression levels of FVIII. Conversely, in the absence of the hyperactive hyPB transposase, expression declined gradually to basal levels. This confirms that stable genomic integration by transposition is required for stable hepatic FVIII gene expression.

Figure 11:
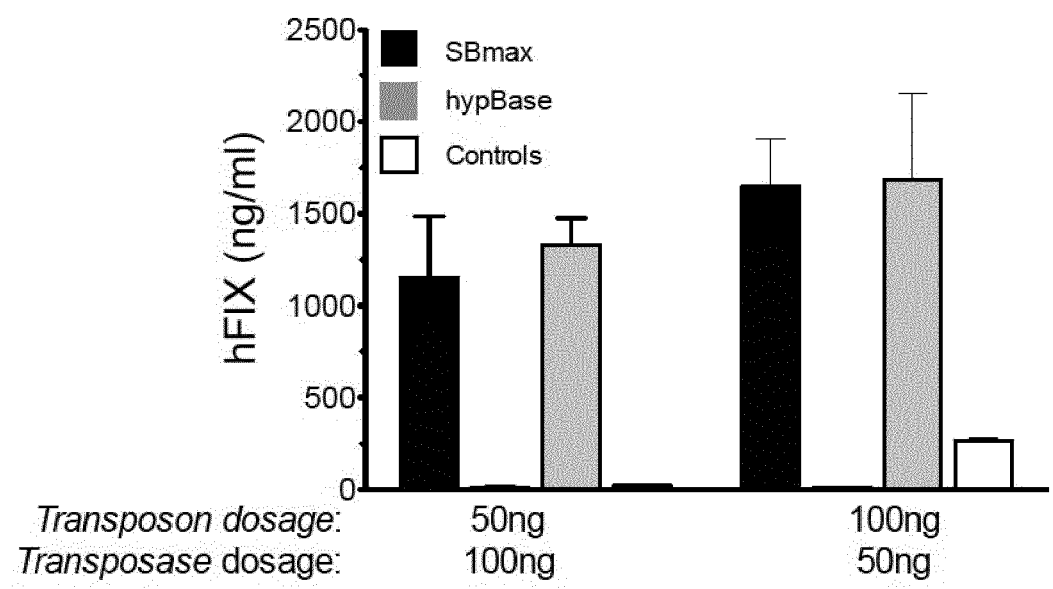
FIG. 11. Comparison of Sleeping Beauty transposon and PiggyBac transposon for codon-optimized hFIX hepatic gene delivery. Sleeping Beauty transposon (pT2BH_TTRminSerpMVM_hFIXco_bghpA) and PiggyBac transposon (PB_micro_T_No_Ins_SerpTTrminMVM_hFIXco_BGHpA) were injected in immunodeficient (NOD SCID) mice along with plasmid encoding codon-optimized hyperactive PB transposase (pcDNA3_mouseCO_hyPiggyBac_Transposase_MT) or hyperactive SBmax transposase (pCDNA3_CMVBGI_SBMAX_bghpA), respectively using the doses as indicated. One month post-injection FIX plasma levels were determined in plasma by ELISA.

Sleeping Beauty (SB) transposon (pT2BH_TTRminSerpMVM_hFIXco_bghpa) was compared side by side with the PiggyBac (PB) transposon (PB_micro_T_No_Ins_SerpTTrminMVM_hFIXco_B-GHpA)) in immunodeficient NOD SCID mice using two different doses as indicated (FIG. 11). One month post-injection of the transposon and transposase plasmids, blood was collected. FIX ELISA was performed to determine the amount of FIX expression. About 1500-2000 ng/ml of FIX antigen was detected in both, SB and PB, transposons. These data show that the SB and PB vectors are equally potent and can induce high therapeutic level of FIX expression amounting to about 30-40% of normal FIX.

No adverse events were noted in the different mouse models with any of the transposons, regardless of the transgene, that could be ascribed to the transposition or to the transient transposase expression.

To further ascertain the safety of the PB transposons we administered the transposons by hydrodynamic transfection into a tumor prone mouse model. In this model, mice were injected repeatedly with the carcinogen N,N-diethylnitrosamine (DEN) and developed hepatocellular carcinoma. The tumor burden was assessed 36 weeks post-DEN injection. We did not observe any statistically significant difference in tumor mass or number of tumor nodules in mice treated with the transposons vs. controls without transposition. These data indicate that PB transposition in itself does not significantly increase tumorigenicity, even in an HCC tumor-prone mouse model, which supports its safety.

Example 5: Enhanced Expression of FVIII and FIX by Cloning the MVM Intron into the Nucleic Acid Expression Cassette Materials and Methods A piggyBac transposon plasmid was constructed that comprises human FIX cDNA cloned downstream of a liver-specific minimal transthyretin (TTRmin) promoter operably linked to the Serpin regulatory sequence ("Serp" or "SerpEnh" or "HSH8"). The bovine growth hormone poly A (bghpA) was provided as a transcription termination signal. Human FIX cDNA comprises a truncated 1.4 kb intron A between exons 1 and the following exons 2-8. A schematic representation of said transposon, denoted as pB_hFIXIA, is shown in FIG. 12A.

A piggyBac transposon plasmid was constructed that contains a synthetic codon-optimized human FIX cDNA without intron A. Said codon-optimized hFIX cDNA was cloned downstream of a liver-specific minimal transthyretin (TTRmin) promoter operably linked to the Serpin regulatory sequence ("Serp" or "SerpEnh" or "HSH8"). A minute virus of mice (MVM) intron was cloned between the TTRmin promoter and the hFIXco transgene. The bovine growth hormone poly A (bghpA) was provided as a transcription termination signal. A schematic representation of said transposon, denoted as pB_hFIXco, is shown in FIG. 12B. The plasmids were constructed by conventional cloning and DNA synthesis.

Hemophilia B mice were hydrodynamically injected with 10 µg transposon plasmid and 2 µg of mouse transposase plasmid mpBase (FIG. 12C) or empty control plasmid (FIG. 12D) diluted in 2 ml of PBS into the tail vein. Typically, the injection took less than 10 s for each mouse. Determination of hFIX levels and activity occurred as described in Example 2.

Transposon Genome Copy Number Quantification

Genomic DNA was extracted from frozen liver samples according to DNeasy Blood & Tissue Kit protocol (Qiagen, Chatsworth, Calif., USA). RNase A (Qiagen, Chatsworth, Calif., USA) treatment was carried out to eliminate carry-over RNA. Transposon copy numbers were quantified by qPCR using a primer set against a specific region common to both transposon constructs using forward primer 5'-AACAGGGGCTAAGTCCACAC-3' (SEQ ID NO: 25) and reverse primer 5'-GAGCGAGTGTTCCGATACTCT-3' (SEQ ID NO: 26). Briefly, 50 ng of genomic DNA from each sample was subjected to qPCR in triplicate using an ABI Prism 7500 Fast Real-Time PCR System (Applied Biosystems, Foster City/CA, USA) and Power SYBR® Green PCR Master Mix (Applied Biosystems, Foster City/CA, USA). Copy number was determined comparing the amplification signal with a standard curve consisting of serial dilutions over a 6 log range of the corresponding linearized plasmid spiked with 50 ng of liver genomic DNA from saline-injected mouse (slope≈−3,3, intercept≈35, efficiency %≈100). Average copies per diploid genome were calculated taking into account that one murine diploid genome=5.92 pg.

hFIX mRNA Expression Analysis

Total RNA was extracted from frozen liver samples using a miRCURY™ RNA isolation kit (Exiqon, Denmark). DNase (Thermo Scientific, USA) treatment was carried out. The reverse transcription reaction was performed starting from 1 µg of total RNA from each sample using the SuperScript® III First Strand cDNA Synthesis Kit (Life Technologies, USA). Next, a cDNA amount corresponding to 10 ng of total RNA from each sample was analyzed in triplicate by quantitative (q)PCR using an ABI Prism 7500 Fast Real-Time PCR System (Applied Biosystems, Foster City/CA, USA) and Power SYBR® Green PCR Master Mix (Applied Biosystems, Foster City/CA, USA). The following primer set was used: forward primer 5'-GCCTTCTAGTT-GCCAGCCAT-3' (SEQ ID NO:3), reverse primer 5'-GGCACCTTCCAGGGTCAAG-3' (SEQ ID NO:4). The hFIX mRNA levels were normalized using a primer set against the mRNA of the housekeeping gene glyceraldehyde-3-phosphate dehydrogenase (mGAPDH) which is uniformly and constantly expressed in all samples (i.e. forward primer 5'-ATCAAGAAGGTGGTGAAGCAGGCA-3' (SEQ ID NO:27) and reverse primer 5'-TG-GAAGAGTGGGAGTTGCTGTTGA-3' (SEQ ID NO:28)). RNA samples were amplified with and without reverse transcriptase to exclude genomic DNA amplification. The $2^{-\Delta\Delta Ct}$ relative quantification method was used to determine the relative changes in hFIX mRNA expression level. The ΔCt was calculated by subtracting the Ct of mGAPDH mRNA from the Ct of the hFIX mRNA ($Ct_{hFIX}-Ct_{GAPDH}$). The ΔΔCt was calculated by subtracting the ΔCt of the reference sample (highest Ct) from the ΔCt of each sample ($\Delta Ct_{sample}-\Delta Ct_{reference}$). Fold-change was determined by using the equation $2^{-\Delta\Delta Ct}$.

Results

Figure 12:
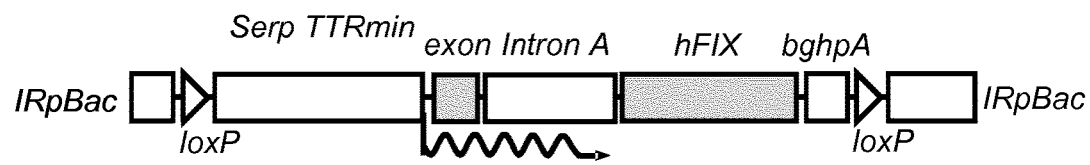
FIG. 12. Evaluation of effect of cloning MVM intron into nucleic acid constructs on in vivo expression of transgenes. (A) Schematic representation of the piggyBac transposon encoding for a wild-type hFIX (denoted as pB_hFIXIA) The expression cassette is flanked by the wild-type piggyBac transposon invert repeat (IRpBac). The liver-specific minimal transthyretin (TTRm) promoter drives the human FIX transgene comprising a truncated 1; 4 kb hFIX intron A between exon 1 and the following exons 2-8. The hepatocyte-specific regulatory element ("Serp" or "SerpEnh") is located upstream of the TTRm promoter. Bovine growth hormone polyadenylation site (pA) is also indicated. (B) Schematic representation of the piggyBac transposon encoding for a codon-optimized hFIX (denoted as pB_ hFIXco). The expression cassette is the same as pB_hFIXIA, except for the transgene. The hFIX transgene is codon-optimized (hFIXco) and contains no intron A. MVM intron is cloned upstream of the FIXco transgene. (C) Schematic representation of the mouse piggyBac transposase plasmid (denoted as mpBase). The mouse codon-optimized native piggyBac transposase (mpB) driven by the cytomegalovirus (CMV) promoter is cloned upstream of a β-globin intron (βGI). Bovine growth hormone polyadenylation site (bghpA) is also indicated. (D) Schematic representation of the empty control plasmid (denoted as empty) without a transposase gene. The plasmid contains a multiple cloning site (MCS) between the CMV promoter and the bghpa polyadenylation signal. (E, F) Hemophilia B mice were hydrodynamically injected with 10 µg of transposon plasmids comprising wild-type hFIX transgene and truncated intron A (pB_h-FIXIA, E) or codon-optimized hFIX transgene and MVM intron (pB_MVM-FIXco, F) in conjunction with 2 µg of plasmids encoding mouse piggyBac transposase (+ mpBase, full lines) or an empty control plasmid (+ empty, dashed lines) hFIX antigen expression (black squares) and hFIX clotting activity (grey squares) were measured on plasma samples collected at the indicated times by ELISA and a chromogenic hFIX activity assay, respectively. Transposon copies per diploid genome (G) and hFIX mRNA levels (H) were measured by a quantitative RT-PCR method (qRT-PCR) at the end of the experiments from total RNA extracted from liver biopsies. hFIX mRNA levels relative to FIXIA mRNA levels are shown in H. The pB hFIXco plasmid showed more than 57-fold expression of mRNA as compared to the pB FIXIA plasmid. Results were presented as mean±standard error of the mean. n.s. indicates not significant, *: $p<0.05$, : $p<0.01$, *: $p<0.001$ (n=3 mice/group).
Figure 12:
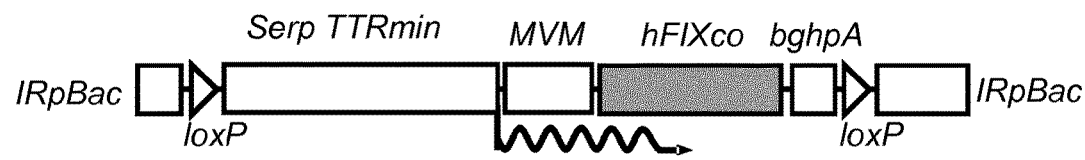
Figure 12:
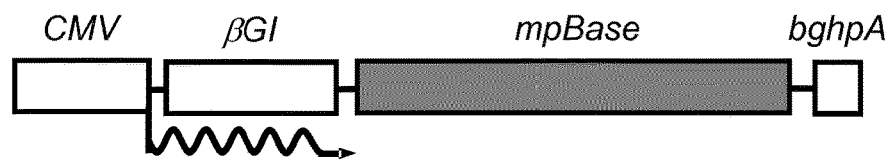
Figure 12:
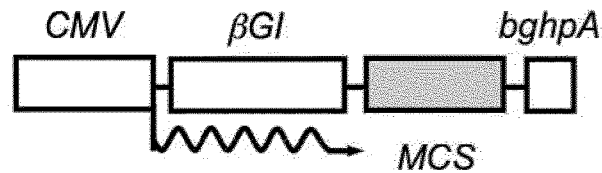
Figure 12:
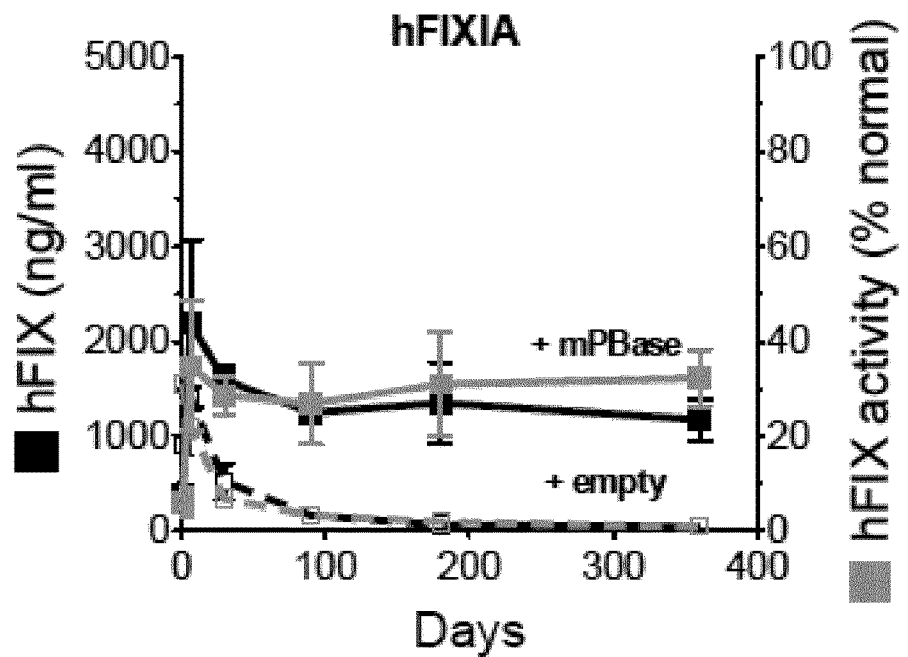
Figure 12:
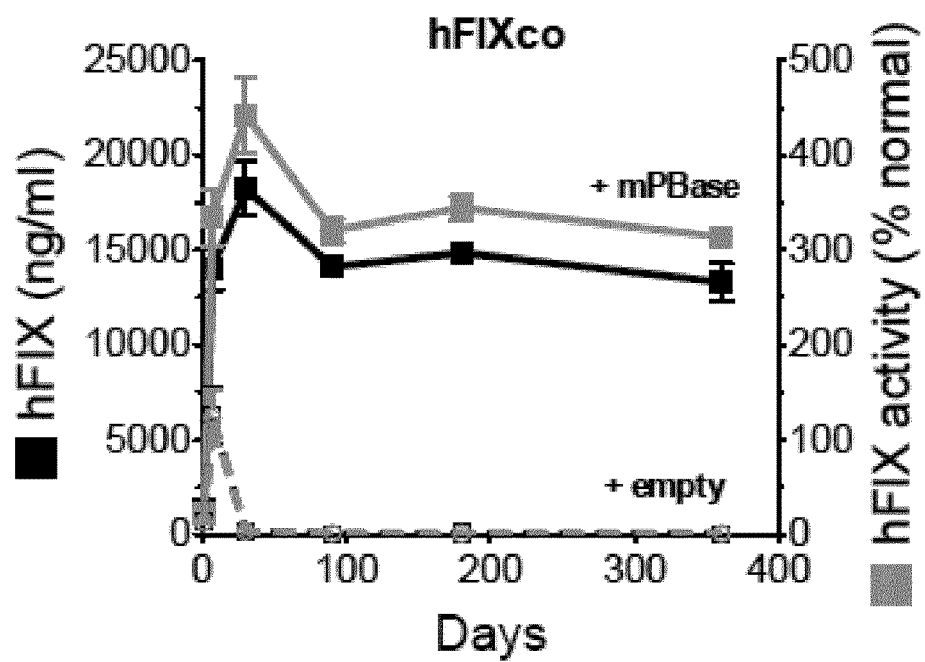
Figure 12:
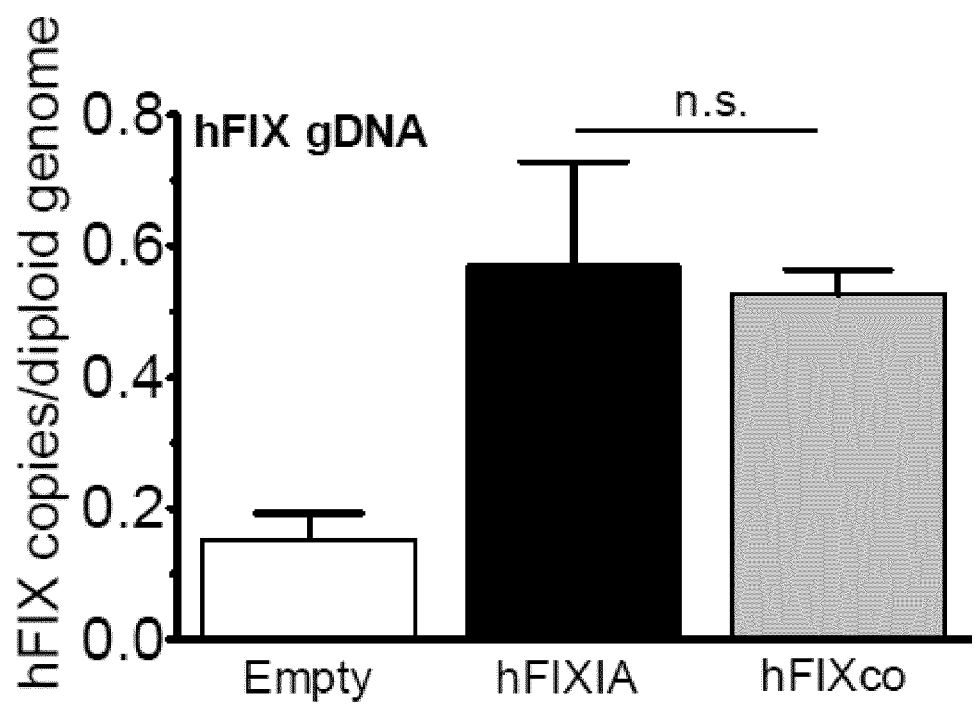
Figure 12:
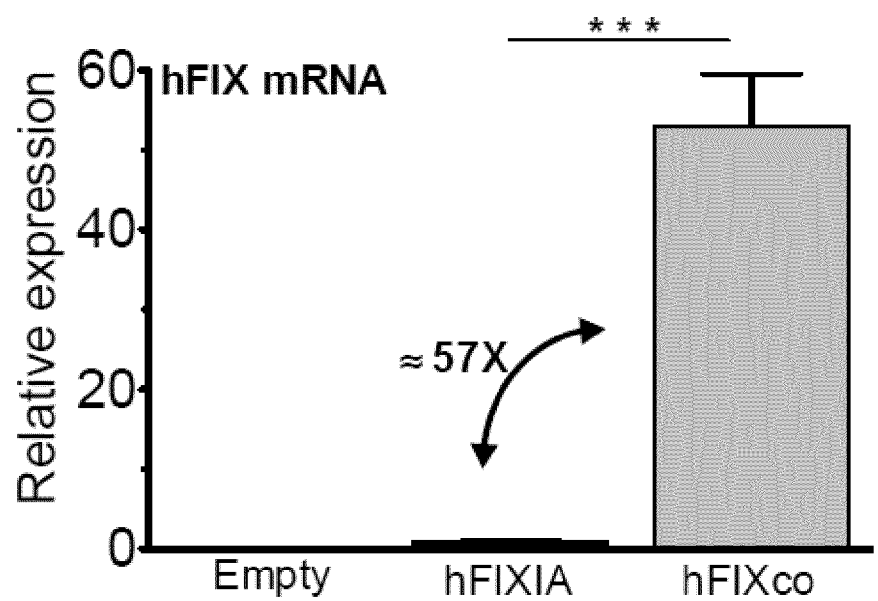

As shown in FIGS. 12E and F, hFIX expression and activity is transient and gradually declines to basal levels in mice that were co-injected with the empty control plasmid (FIG. 12E: pB_hFIXIA+empty plasmid: 46±13 ng/ml hFIX, 0.87±0.2% normal clotting activity and FIG. 12F: pB_hFIXco+empty plasmid: 48±22 ng/ml hFIX, 0.97±0.49% normal clotting activity). These results indicate that stable transposition is necessary for sustained expression, but the non-integrated pB-hFIXIA or pB-hFIXco plasmids may have contributed to the initial surge in hFIX expression The transposon plasmid comprising the MVM intron yielded significantly higher hFIX levels and activity as compared to the plasmid without MVM intron when co-delivered with the mouse transposase plasmid (FIG. 12E,F). Liver-directed hydrodynamic co-transfection of the pB-hFIXIA transposon without MVM intron (10 μg) along with 2 μg mPB plasmid, resulted in stable therapeutic hFIX antigen and activity levels for at least up to 12 months in hemophilic FIX-deficient mice (FIG. 12E, 1168±218 ng/ml hFIX and 32±6% normal clotting activity). Similarly, liver-directed co-transfection of the pB_hFIXco transposon with MVM intron and mPB plasmid resulted in a significant ≈12-fold higher (p<0.001) hFIX protein and activity level that stabilized in the supra-physiologic range (FIG. 12F: 13290±990 ng/ml hFIX and 313±7% normal clotting activity). The increase in hFIX protein levels was consistent with a more than 57-fold increase in hFIX mRNA levels when comparing the transposon with and without the MVM intron (FIG. 12 H), although the transposon copies per genome content were similar in the liver of mice that were injected with pB hFIXIA and pB hFIXco (FIG. 12G).

Example 6: Comparison of Expression Cassettes Comprising a FVIII Transgene

Material and Methods

The AAV9ss-SerpEnh-TTRm-MVM-hFVIIIcopt-SV40 pA plasmid of Example 3 was compared to:

(a) AAV9ss-TTRm-MVM-hFVIII-SV40 pA, (b) AAV9ss-SerpEnh-TTRm-MVM-hFVIII-SV40 pA, and (c) AAV9ss-TTRm-MVM-hFVIIIcopt-SV40 pA.

AAV9ss-TTRm-MVM-hFVIIIcopt-SV40 pA plasmid (c) was constructed by excising the Serpin enhancer from AAV9ss-SerpEnh-TTRm-MVM-hFVIIIcopt-SV40 pA plasmid.

Mice were hydrodynamically injected with 2 μg or 5 μg of the plasmid DNA diluted in 2 ml of phosphate buffered saline (PBS) and injected into the tail vein. Typically, the injection took less than 10 s for each mouse. FVIII expression analysis was carried out as described in Example 3.

Results

The AAV9ss-TTRm-MVM-hFVIIIcopt-SV40 pA (c) and AAV9ss-SerpEnh-TTRm-MVM-hFVIIIcopt-SV40 pA (d) constructs were hydrodynamically injected in mice at 2 μg and 5 μg DNA, and human FVIII levels were measured 1, 2 and 6 days post-transfection.

The effect of cloning the Serpin enhancer into the expression cassette on hFVIII levels can be calculated by dividing the hFVIII levels measured in mice injected with construct (d) by the levels measured in mice injected with construct (c). 3- to 6-fold higher hFVIII levels can be obtained by cloning the Serpin enhancer into the expression cassette (Table 2).

The codon-optimized B domain-deleted human coagulation factor VIII (hFVIIIcopt) cDNA was reported to achieve 29- to 44-fold increase in expression (Ward et al. 2011). We used the average increase in expression of 36.5 to predict the hFVIII levels in mice that are transfected with AAV9ss-SerpEnh-TTRm-MVM-hFVIII-SV40 pA construct (b), namely by dividing the hFVIII levels measured in mice transfected with construct (d) by 36.5.

Based on said predicted hFVIII levels in mice that are hydrodynamically injected with AAV9ss-SerpEnh-TTRm-MVM-hFVIII-SV40 pA construct (b), we can further predict the hFVIII levels in mice that are hydrodynamically injected with AAV9ss-TTRm-MVM-hFVIII-SV40 pA construct (a) by dividing said predicted hFVIII levels by the calculated effect of cloning the Serpin enhancer into the expression cassette on hFVIII levels.

Figure 13:
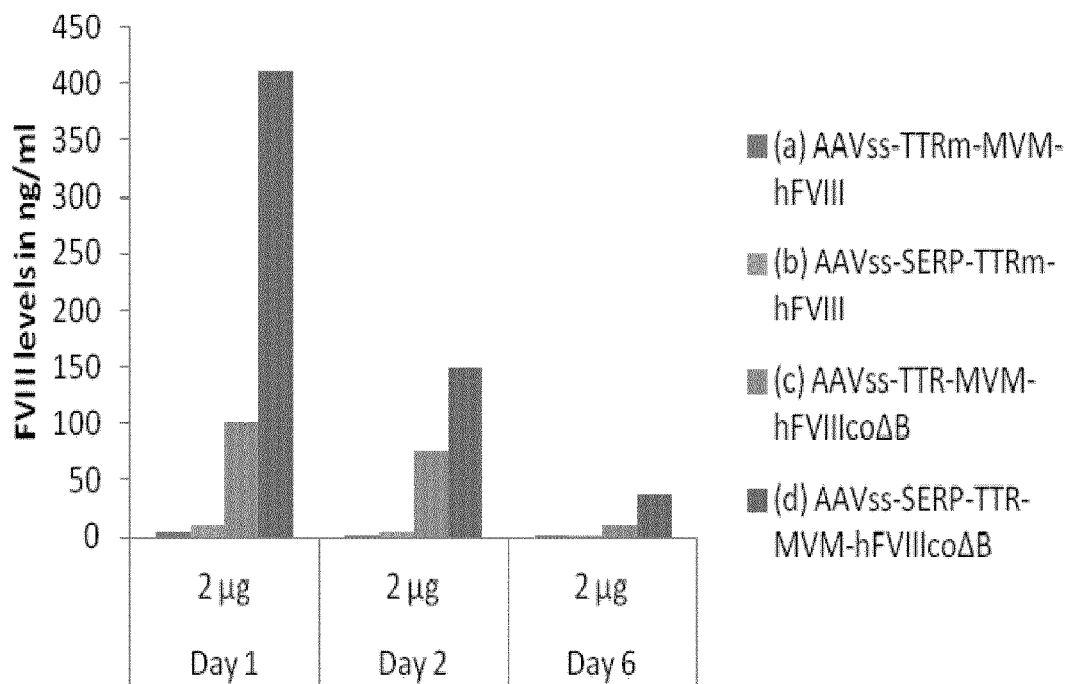
FIG. 13. Comparison of nucleic acid expression cassettes comprising hFVIII transgene. (A,B) Predicted (a,b) and measured (c,d) hFVIII levels in mice hydrodynamically injected with, from left to right, (a) AAV9ss-TTRm-MVM-hFVIII-SV40 pA plasmid, (b) AAV9ss-SerpEnh-TTRm-MVM-hFV111-SV40 pA plasmid, (c) AAV9ss-TTRm-MVM-hFVIIIcopt-SV40 pA plasmid, or (d) AAV9ss-SerpEnh-TTRm-MVM-hFVIIIcopt-SV40 pA plasmid, at 2 µg DNA (A) or 5 µg DNA (B). (C,D) Bars showing from left to right, predicted hFVIII levels in mice hydrodynamically injected with (b) AAV9ss-SerpEnh-TTRm-MVM-hFVIII-SV40 pA plasmid; measured hFVIII levels in mice injected with (c) AAV9ss-TTRm-MVM-hFVIIIcopt-SV40 pA plasmid; sum of hFVIII levels predicted in mice injected with (b) and hFVIII levels measured in mice injected with (c); and hFVIII levels measured in mice transfected with (d) AAV9ss-SerpEnh-TTRm-MVM-hFVIIIcopt-SV40 pA plasmid. (C) shows the data for mice that were injected with 2 µg DNA, (D) shows the data for mice that were injected with 5 µg DNA.
Figure 13:
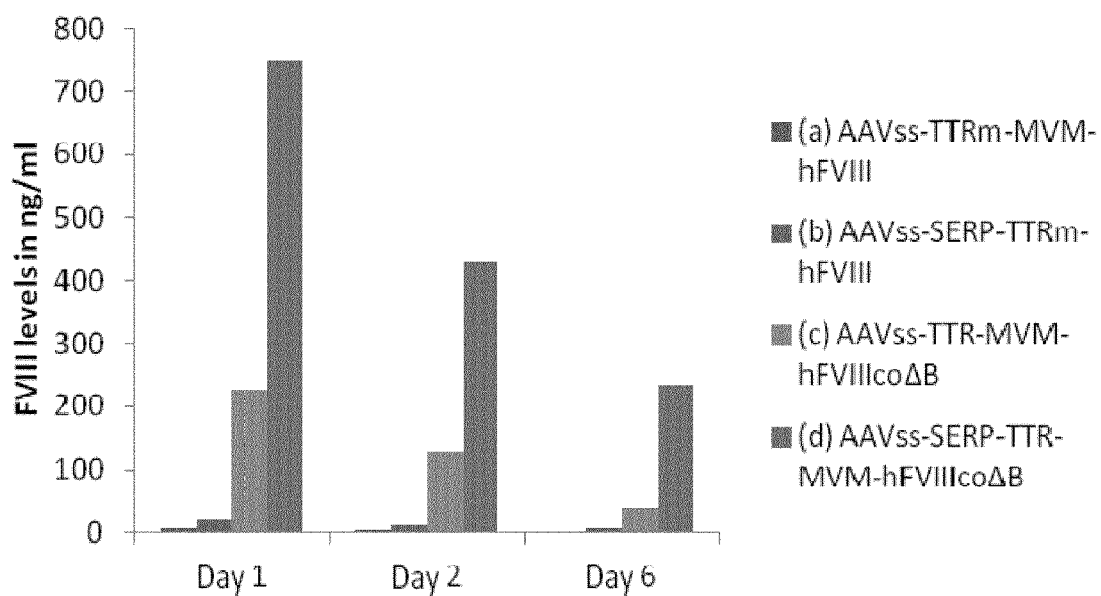
Figure 13:
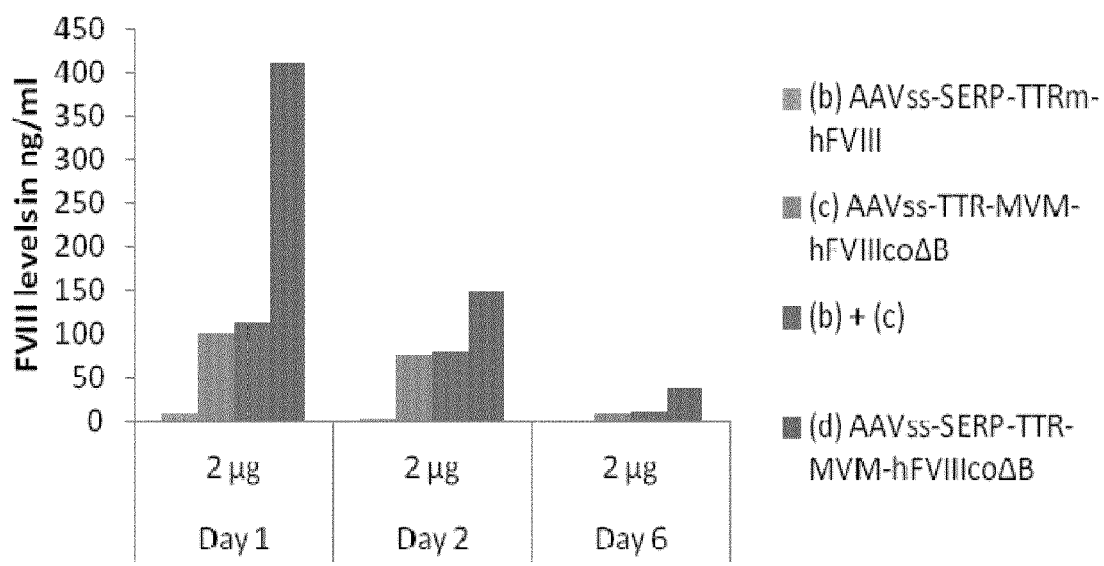
Figure 13:
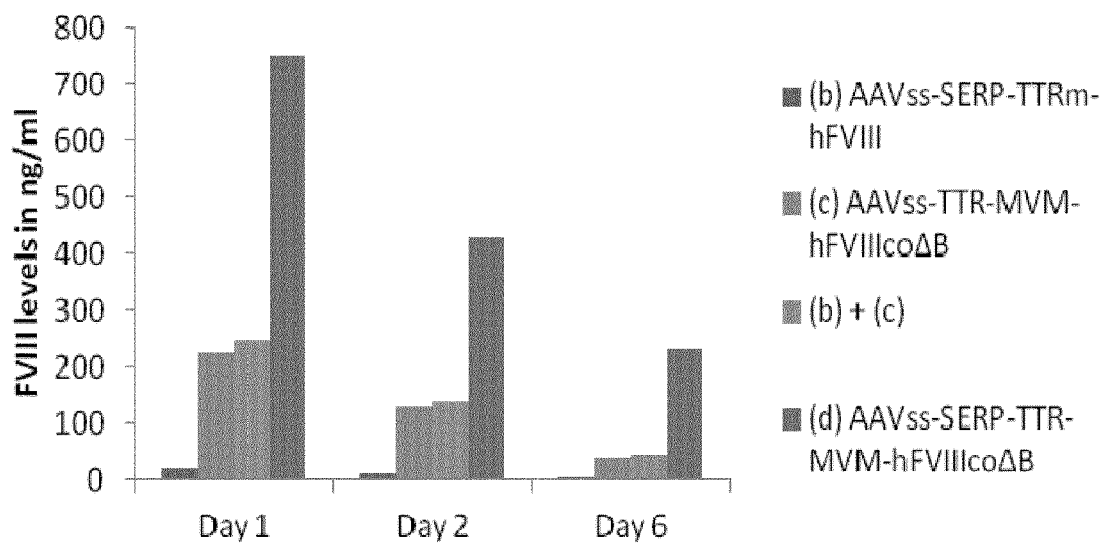

The measured and predicted hFVIII levels in mice hydrodynamically injected with the different constructs a-d are summarized in Table 3 and FIGS. 13A and 13B.

TABLE 3 hFVIII levels in mice hydrodynamically injected with 2 or 5 μg of plasmids (a) AAV9ss-TTRm-MVM-hFVIII-SV40pA, (b) AAV9ss-SerpEnh-TTRm-MVM-hFVIII-SV40pA, (c) AAV9ss-TTRm-MVM-hFVIIIcopt-SV40pA, and (d) AAV9ss-SerpEnh-TTRm-MVM-hFVIIIcopt-SV40pA.

|  | (a) AAVss-TTRm-MVM-hFVIII Predicted level: (a) = (b):[(d):(c)] no SERP, no codon-optimization | (b) AAVss-SERP-TTRm-hFVIII Predicted level: (b) = (d):36.5x SERP | (c) AAVss-TTR-MVM-hFVIIIcopt Measured level codon-optimization | (d) AAVss-SERP-TTR-MVM-hFVIIIcopt Measured level SERP + codon-optimization |
|---|---|---|---|---|
| Day 1 | 2 μg = 11/4 = 3 ng/ml | 2 μg = 11 ng/ml | 2 μg = 102 ng/ml | 2 μg = 412 ng/ml |
|  | 5 μg = 20/3.3 = 6 ng/ml | 5 μg = 20 ng/ml | 5 μg = 227 ng/ml | 5 μg = 751 ng/ml |
| Day 2 | 2 μg = 4.1/1.9 = 2 ng/ml | 2 μg = 4.1 ng/ml | 2 μg = 77 ng/ml | 2 μg = 150 ng/ml |
|  | 5 μg = 11.7/3.3 = 3.5 ng/ml | 5 μg = 11.7 ng/ml | 5 μg = 129 ng/ml | 5 μg = 429 ng/ml |
| Day 6 | 2 μg = 1/3.5 = 0.28 ng/ml | 2 μg = 1 ng/ml | 2 μg = 11 ng/ml | 2 μg = 39 ng/ml |
|  | 5 μg = 6.4/5.9 = 1 ng/ml | 5 μg = 6.4 ng/ml | 5 μg = 39 ng/ml | 5 μg = 233 ng/ml |

The data shows that expression cassettes comprising the specific combination of the codon-optimized B domain-deleted human coagulation factor VIII (hFVIIIcopt) cDNA described in Ward et al. (2011) and the Serpin enhancer can induce hFVIII levels that are significantly higher as compared to the sum of the hFVIII levels that are obtained by expression cassettes comprising each of these elements alone (Table 4, FIGS. 13C and 13D). In other words, said specific combination of hFVIIIcopt cDNA and the Serpin enhancer provides for a synergistic effect on hFVIII levels.

Figure 14:
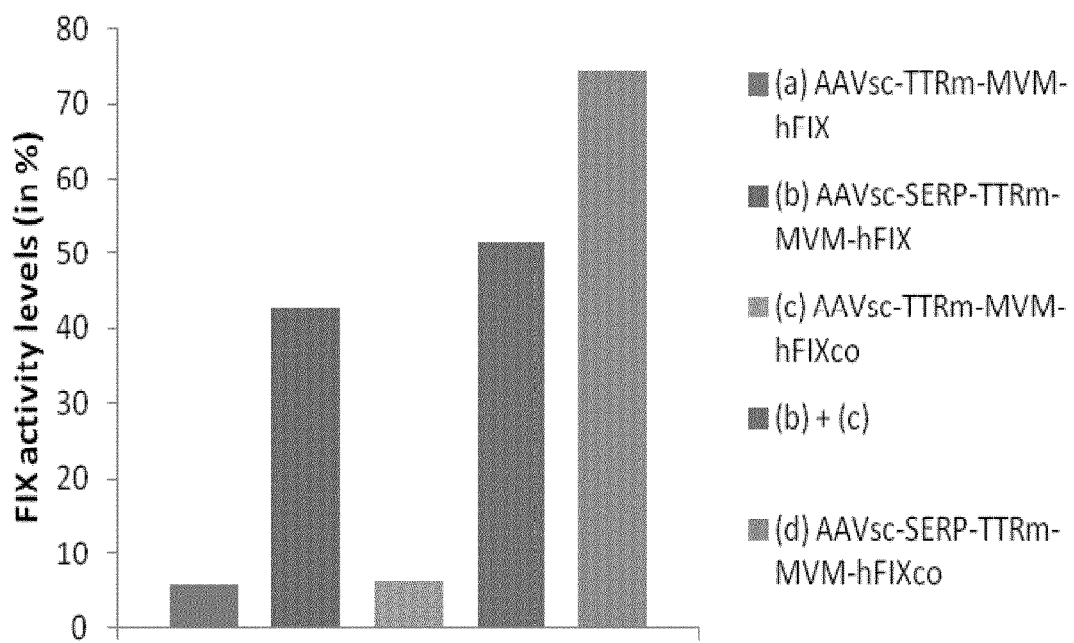
FIG. 14. Comparison of nucleic acid expression cassettes comprising hFIX transgene. (A,B) Bars showing from left to right, hFIX activity in mice hydrodynamically injected with (a) AAVsc-TTRm-MVM-hFIX-SV40 pA plasmid; (b) AAVsc-SerpEnh-TTRm-MVM-hFIX-SV40 pA plasmid; (c) AAVsc-TTRm-MVM-hFIXco-SV40 pA plasmid; (b) and (c) calculated as the sum of hFIX activity measured in mice injected with (b) and (c); and (d) AAVsc-SerpEnh-TTRm-MVM-hFIXco-SV40 pA plasmid at day 2 (A) and day 6 (B) post-injection. (C,D) Bars showing from left to right, hFIX activity in mice hydrodynamically injected with (c) AAVsc-TTRm-MVM-hFIXco-SV40 pA plasmid; (d) AAVsc-SerpEnh-TTRm-MVM-hFIXco-SV40 pA plasmid; (e) AAVsc-TTRm-MVM-hFIXcoPadua-SV40 pA plasmid; (d) and (e) calculated as the sum of hFIX activity measured in mice injected with (d) and (e); and (f) AAVsc-SerpEnh-TTRm-MVM-hFIXcoPadua-SV40 pA plasmid at day 2 (C) and day 6 (D) post-injection.
Figure 14:
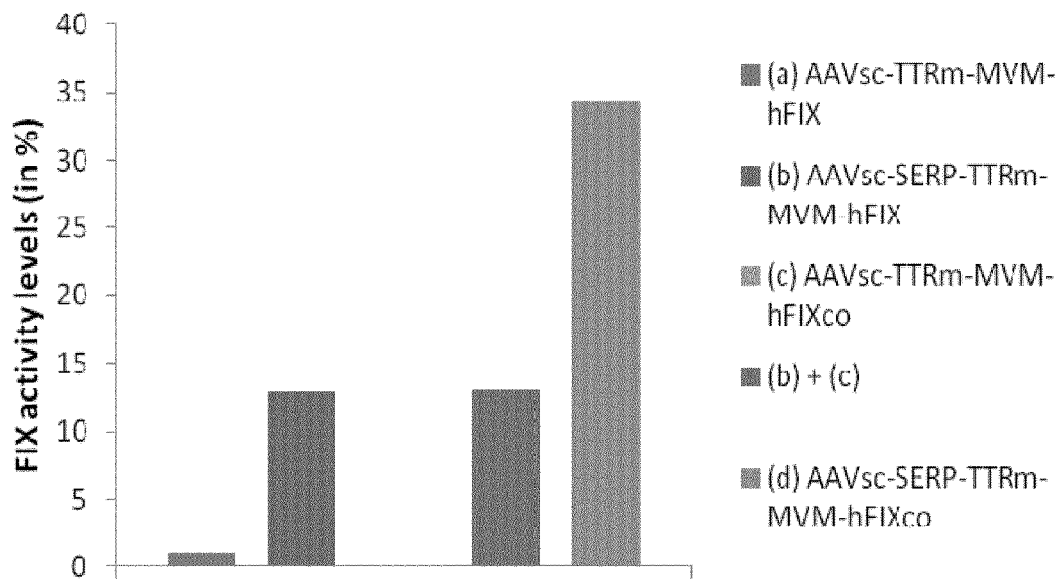
Figure 14:
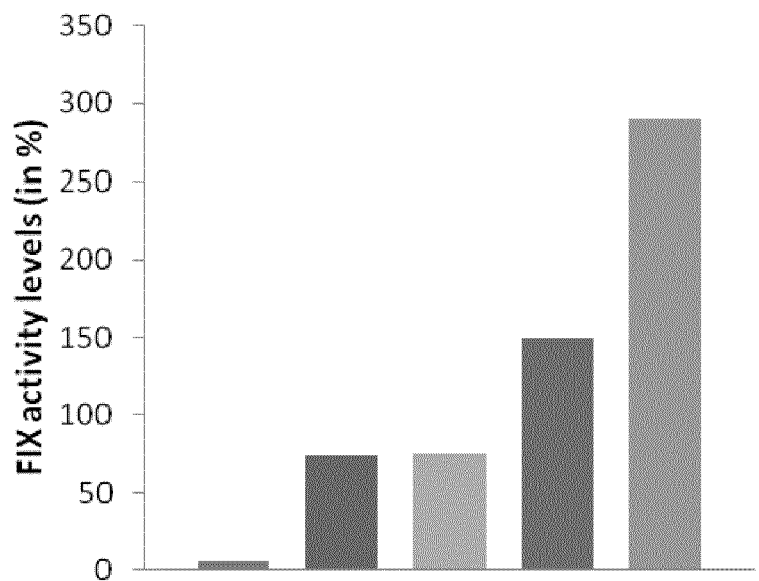
Figure 14:
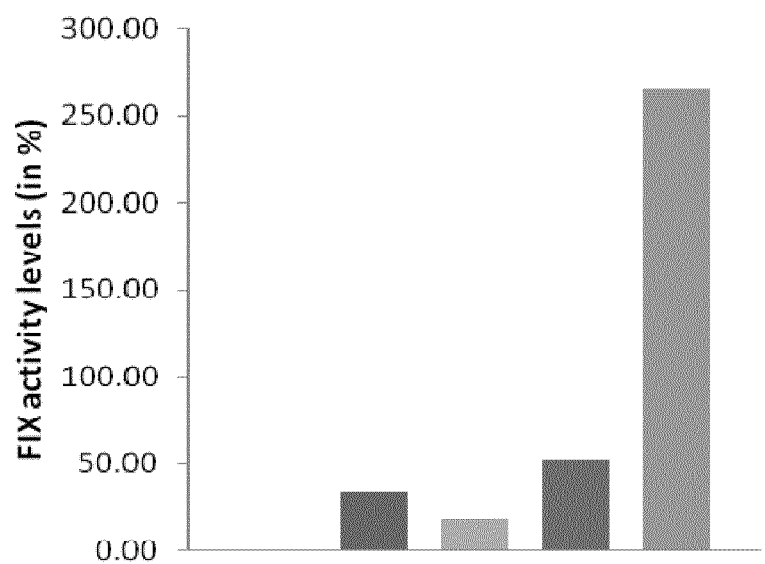

The data shows that the specific combination of codon-optimized human coagulation factor IX (hFIXco) cDNA and the Serpin enhancer results in hFIX activity that is higher than would have been predicted based on the sum of the hFIX activity determined in mice hydrodynamiclly injected with plasmids (b) and (c) comprising either a Serpin enhancer (b) or a codon-optimized hFIX transgene (c) (Table 6, FIGS. 14A and 14B). In other words, said specific combination of hFIXco cDNA and the Serpin enhancer provides for a synergistic effect on hFIX activity.

TABLE 4

Comparison of hFVIII levels induced by AAV9ss-SerpEnh-TTRm-MVM-hFVIIIcopt-SV40pA construct (d) as compared to the levels induced by (b) AAV9ss-SerpEnh-TTRm-MVM-hFVIII-SV40pA construct and (c) AAV9ss-TTRm-MVM-hFVIIIcopt-SV40pA construct, and as compared to the levels induced by (a) AAV9ss-TTRm-MVM-hFVIII-SV40pA construct.

|  | (b) + (c) | (d)/[(b) + (c)] | (d)/(a) |
|---|---|---|---|
| Day 1 | 2 µg = 11 + 102 = 113 ng/ml | 2 µg = 412/113 = 3.6x >>> | 2 µg = 412 13 = 137x >>> |
|  | 5 µg = 20 + 227 = 247 ng/ml | 5 µg = 751/247 = 3x >>> | 5 µg = 751/6 = 125x >>> |
| Day 2 | 2 µg = 77 + 4 = 81 ng/ml | 2 µg = 150/81 = 1.8x >>> | 2 µg = 150/2 = 75x >>> |
|  | 5 µg = 11 + 129 = 140 ng/ml | 5 µg = 429/140 = 3x >>> | 5 µg = 429/3.5 = 122x >>> |
| Day 6 | 2 µg = 11 + 1 = 12 ng/ml | 2 µg = 39/12 = 3.25x >>> | 2 µg = 39/0.28 = 139x >>> |
|  | 5 µg = 39 + 6.4 = 45.4 ng/ml | 5 µg = 233/45.4 = 5.1x >>> | 5 µg = 233/1 = 223x >>> |

Example 7: Comparison of Expression Cassettes Comprising a FIX Transgene

Material and Methods

AAV-based plasmids comprising a FIX transgene were constructed as described in Example 2.

FIX knockout mice were hydrodynamically injected with 2 µg of each of the following FIX plasmids diluted in 2 ml of phosphate buffered saline (PBS) into the tail vein:
(a): AAVsc-TTRm-MVM-hFIX-pA;
(b): AAVsc-SerpEnh-TTRm-MVM-hFIX-pA;
(c): AAVsc-TTRm-MVM-hFIXco-pA
(d): AAVsc-SerpEnh-TTRm-MVM-hFIXco-pA
(e): AAVsc-TTRm-MVM-hFIXcoPadua-pA
(f): AAVsc-SerpEnh-TTRm-MVM-hFIXcoPadua-pA Blood was collected from these mice at day 2 and day 6 post-injection. FIX activity was determined as described in Example 2.

Results

FIX activity as measured in the different mice is summarized in Table 5.

To evaluate the combination of the Serpin enhancer and the Padua mutation on hFIX activity, hFIX activity in mice hydrodynamically injected with (f) AAVsc-SerpEnh-TTRm-MVM-hFIXcoPadua-pA plasmid was compared versus hFIX activity in mice hydrodynamically injected with (d) AAVsc-SerpEnh-TTRm-MVM-hFIXco-pA plasmid and (e) AAVsc-TTRm-MVM-hFIXcoPadua-pA plasmid (Table 6, FIGS. 14C and 14D). The combination of the Serpin enhancer and the Padua mutation provides for a synergistic effect on hFIX activity.

Also the combination of the Serpin enhancer with codon-optimized transgene encoding hFIX containing the Padua mutation shows synergy on hFIX activity, as revealed by comparing hFIX activity in mice injected with (f) AAVsc-SerpEnh-TTRm-MVM-hFIXcoPadua-pA plasmid versus hFIX activity in mice injected with (b) AAVsc-SerpEnh-TTRm-MVM-hFIX-pA plasmid, and (e) AAVsc-TTRm-MVM-hFIXcoPadua-pA plasmid.

TABLE 5 hFIX activity at days 2 and 6 post-injection in mice hydrodynamically injected with 2 µg of (a) AAVsc-TTRm-MVM-hFIX-pA plasmid, (b) AAVsc-SerpEnh-TTRm-MVM-hFIX-pA plasmid, (c) AAVsc-TTRm-MVM-hFIXco-pA plasmid, (d) AAVsc-SerpEnh-TTRm-MVM-hFIXco-pA plasmid, (e) AAVsc-TTRm-MVM-hFIXcoPadua-pA plasmid, and (f) AAVsc-SerpEnh-TTRm-MVM-hFIXcoPadua-pA plasmid.

|  | (a) AAVsc-TTRm-MVM-hFIX-pA no SERP, no codon-optimization, no Padua | (b) AAVsc-SerpEnh-TTRm-MVM-hFIX-pA SERP | (c) AAVsc-TTRm-MVM-hFIXco-pA codon-optimization | (d) AAVsc-SerpEnh-TTRm-MVM-hFIXco-pA SERP + codon-optimization | (e) AAVsc-TTRm-MVM-hFIXcoPadua-pA codon-optimization + Padua | (f) AAVsc-SerpEnh-TTRm-MVM-hFIXcoPadua-pA SERP + codon-optimization + Padua |
|---|---|---|---|---|---|---|
| Day 2 | 5.92% | 42.99% | 6.36% | 74.25% | 75.09% | 289.34% |
| Day 6 | 1.00% | 12.90% | 0.23% | 34.32% | 18.48% | 265.71% |

TABLE 6

Comparison of hFIX activity induced by the different FIX plasmids: (a) AAVsc-TTRm-MVM-hFIX-pA plasmid, (b) AAVsc-SerpEnh-TTRm-MVM-hFIX-pA plasmid, (c) AAVsc-TTRm-MVM-hFIXco-pA plasmid, (d) AAVsc-SerpEnh-TTRm-MVM-hFIXco-pA plasmid, (e) AAVsc-TTRm-MVM-hFIXcoPadua-pA plasmid, and (f) AAVsc-SerpEnh-TTRm-MVM-hFIXcoPadua-pA plasmid.

| (b) + (c) | (d)/(b) + (c) SERP + codon-optimization | (d) + (e) | (f)/(d) + (e) SERP + Padua | (b) + (e) | (f)/(b) + (e) SERP + codon-optimization + Padua | (d)/(a) | (f)/(a) |
|---|---|---|---|---|---|---|---|
| 42.99 + | 74.25/ | 74.25 + | 289.34/ | 42.99 + | 289.34/ | 74.25/ | 289.34/ |
| 6.36 = | 49.35 = | 75.09 = | 149.34 = | 75.09 = | 118.08 = | 5.92 = | 5.92 = |
| 49.35% | 1.5x ↑ | 149.34% | 1.9x ↑ | 118.08% | 2.5x↑ | 12.5x | 48.9x |
| 12.90 + | 34.32/ | 34.32 + | 265.71/ | 12.90 + | 265.71/ | 34.32/ | 265.71/ |
| 0.23 = | 13.13 = | 18.48 = | 52.80 = | 18.48 = | 31.38 = | 1 = | 1 = |
| 13.13% | 2.6x ↑ | 52.80% | 5.0x ↑ | 31.38% | 8.5x↑ | 34.32x | 265.71x |

Example 8: Evaluation of the piggyBac Transposon System

Materials and Methods Transposon Constructs pB_hFIXIA (FIG. 12A) and pB_hFIXco (FIG. 12B) plasmids were constructed as described in Example 5.

A terminal inverted repeat of pB_hFIXco ($IR_{wt}$) was replaced by a terminal inverted repeat containing T53C and C136T point mutation ($IR_{mut16}$) to generate pB_hFIXco/$IR_{mut16}$ (FIG. 15A).

The terminal inverted repeats of pB_hFIXco were replaced by micro terminal inverted repeats as described in Meir et al. (2011) (IRmicro) to yield pB_hFIXco/$IR_{micro}$ (FIG. 15B). pB_hFIX-R338L plasmid (FIG. 15C) containing hyper-functional, codon-optimized hFIX transgene with Padua mutation was constructed by site-directed mutagenesis using pB_hFIXco/$IR_{micro}$ as template.

Hydrodynamic Injection, Analysis of hFIX Levels and Activity and Anti-hFIX Antibodies Plasmids were diluted in 2 ml of Dulbecco's PBS and hydrodynamically delivered to adult mice (6-7-week-old) by rapid tail vein injection. At different time intervals, we collected whole blood (≈200 µl) by phlebotomy of the retro-orbital plexus in eppendorf tubes pre-filled with 20% citrate buffer that were centrifuged at 14000 r.p.m. for 5 min at 4° C. The citrated plasma was stored at −80° C. for future analysis.

hFIX antigen levels and activity and antibodies directed against hFIX were analyzed as described in Example 2.

Tail Clipping Assay

A tail-clipping assay was used on hemophilic mice to assess phenotypic correction of the bleeding phenotype. Briefly, the tails of mice were transected (1 cm from the end) and mice were monitored for clotting and survival. Tail clip was performed on immobilized mice, allowing continuous blood collection at room temperature and total blood volume, bleeding time and survival rate were monitored.

Results

To assess the immune consequences of treating hemophilia B mice with piggyBac transposons expressing hFIXIA, hFIXco or hFIXco-R338L, the anti-FIX antibody response was analyzed after active immunization with recombinant hFIX antigen and adjuvant. None of the hemophilia B mice treated with the PB transposons expressing hFIXIA, hFIXco or hFIXco-R338L (Padua) developed an anti-hFIX specific antibody response (FIG. 15E). This indicates that liver-directed gene therapy using the various PB transposons encoding either hFIXIA, hFIXco or hFIXco-R338L (Padua) induced immune tolerance to the hFIX protein.

A tail-clip assay showed that the bleeding diathesis of hemophilia B mice transfected with pB-hFIXIA or pB-hFIXco and plasmid encoding mPBase was phenotypically corrected 1 year post-transfection (Table 7). Bleeding time and volume were lower in mice transfected with plasmid comprising codon-optimized hFIX transgene and MVM intron compared to mice transfected with wild-type hFIX transgene.

TABLE 7

Phenotypic correction of murine hemophilia B following tail clipping 48 weeks after gene transfer. 2 µg plasmid encoding mPBase was co-delivered with the indicated transposon plasmids via hydrodynamic injection. hFIX concentration (ng/ml) at the time of tail clipping is indicated. Bleeding time and volume were assayed following clipping of a section of tail 1 cm in length. Values represent means ± SEM

| Group | Transposon plasmid | hFIX (ng/ml) | Bleeding time (min) | Bleeding volume (µl) | Survival |
|---|---|---|---|---|---|
| C57BL/6 | none | 0 | 30 ± 5 | 146 ± 31 | 3/3 |
| FIX$^{-/-}$ | none | 0 | 294 ± 50 | 1433 ± 57 | 0/3 |
| FIX$^{-/-}$ | pB_hFIXIA | 1168 ± 218 | 109 ± 10 | 677 ± 52 | 3/3 |
| FIX$^{-/-}$ | pB_hFIXco | 13290 ± 990 | 57 ± 12 | 500 ± 45 | 3/3 |

The efficiency of the piggyBac platform could be improved by using the hyperactive PB transposase (hyPBase) described in Yusa et al. (2011) (FIG. 15D), allowing the use of lower transposon/transposase doses. This hyPBase contained several mutated residues compared to the mouse codon-usage optimized mPBase (compare FIG. 15D with 12C). Liver-directed hydrodynamic transfection of immune deficient SCID mice with 500 ng of pB-hFIXco transposon along with 1000 ng hyPB resulted in stable supra-physiologic hFIX levels corresponding to 200% of normal hFIX levels (FIG. 15F). These FIX levels were significantly higher (p<0.001) than what could be achieved with the original mPB transposase. Similarly, liver-directed transfection of SCID mice with 50 ng of pB-hFIXco transposon plasmid along with 100 ng hyPB resulted in a dose-dependent effect yielding therapeutic hFIX levels corresponding to 20% of normal levels. This represented a significant 20-fold increase (p<0.001) in FIX levels compared to when the mPB transposase was used (FIG. 15G).

To evaluate the effect of the terminal repeats $IR_{micro}$ and $IR_{mut16}$ on the in vivo potency of the PB transposons, mice were hydrodynamically injected with pB-hFIXco (FIG. 12B), pB-hFIXco/$IR_{mut16}$ (FIG. 15A) or B-hFIXco/$IR_{micro}$ (FIG. 15B) along with hyPBase. A significant 1.5-fold increase in hFIX expression was apparent when the $IR_{micro}$ was used compared to its wild-type counterpart (FIG. 15

Figure 15:
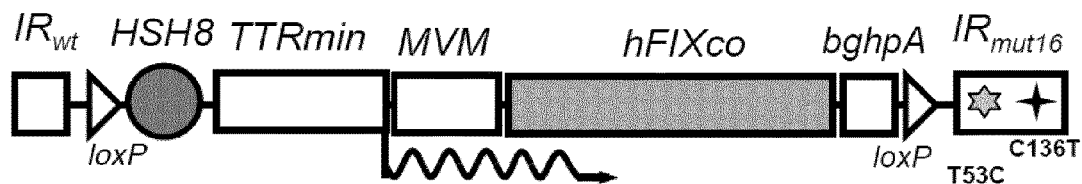
FIG. 15. (A) Schematic representation of the piggyBac transposon pB_hFIXco/IR$_{mut16}$, wherein the expression cassette is flanked by a wild-type piggyBac transposon inverted repeat (IRwt) and a piggybac transposon inverted repeat containing the indicated point mutations (IRmut16). The liver-specific minimal transthyretin (TTRmin) promoter drives a codon-optimized hFIX (hFIXco). Minute virus of mouse (MVM) intron is cloned upstream of the FIXco transgene. The Serpin enhancer (denoted as HSH8) is located upstream of the TTRmin promoter. Bovine growth hormone polyadenylation site (pA) is also indicated. (B) Schematic representation of the piggybac transposon pB_h-FIXco/IR$_{micro}$. The transposon is the same as pB_hFIXco/IR$_{mut16}$, except for the inverted repeats, w micro inverted repeats (IRmicro). (C) Schematic representation of the piggybac transposon pB_hFIXco-R338L. The transposon is the same as pB_hFIXco/IR$_{micro}$, except for the transgene which is codon-optimized human FIX containing the Padua mutation (hFIXco-R338L). (D) Schematic representation of the hyperactive piggyBac transposase (hyPBase) plasmid. The hyperactive piggyBac transposase (hyPBase) driven by the cytomegalovirus (CMV) promoter is cloned upstream of a β-globin intron (βGI). The hyperactiving mutations are indicated. Bovine growth hormone polyadenylation site (bghpA) is also indicated. (E) Three months after transfection with pB transposons pB_hFIXIA, pB_hFIXco, or pB_hFIXco-R338L, mice were subjected to immunization with recombinant hFIX antigen and adjuvant. Anti-hFIX specific antibodies were measured by ELISA at week 2 (black) and week 4 (grey) post-immunization (p.i). PBS-injected hemophilia B mice that were immunized with recombinant hFIX and adjuvant were used as positive control. Results are presented as mean±standard error of the mean. n.s. indicates not significant, *: $p<0.05$, : $p<0.01$, *: $p<0.001$ (n=3 mice/group). (F,G,H,I,J,K) CB17/lcrTac/Prkdc$^{scid}$ mice were hydrodynamically transfected with 500 ng (F,H,J) or 50 ng (G,I,K) of pB-hFIXco (F-K), pB-hFIXco/IR$_{micro}$ (H,I; triangle) or pB-hFIXco/IR$_{micro}$ (J,K; triangle) transposon plasmids along with 1000 ng (F,H,J) or 100 ng (G,I,K) mPB (triangle F,G) or hyPB-expressing plasmid (F,G; square and H-K) or empty control plasmid (hatched lines). hFIX expression was measured on plasma samples collected at the indicated times by a specific ELISA assay. Results were presented as mean±standard error of the mean. n.s. indicates not significant, *: $p<0.05$, : $p<0.01$, *: $p<0.001$ (n=3 mice/group).
Figure 15:
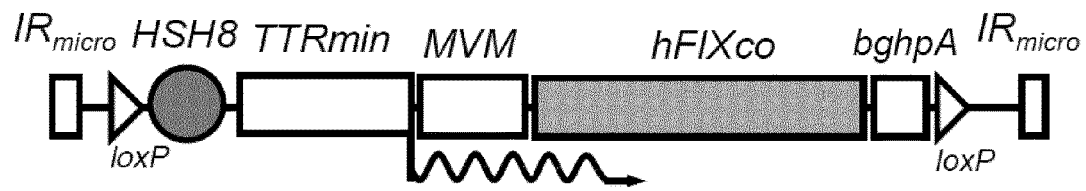
Figure 15:
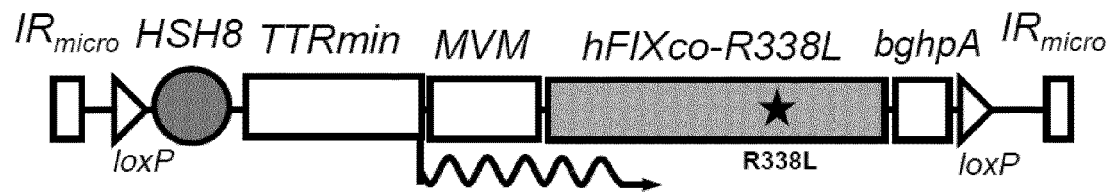
Figure 15:
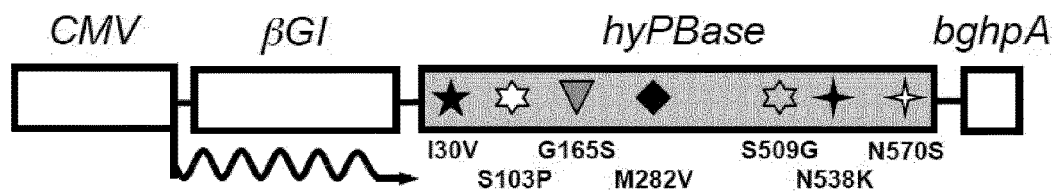
Figure 15:
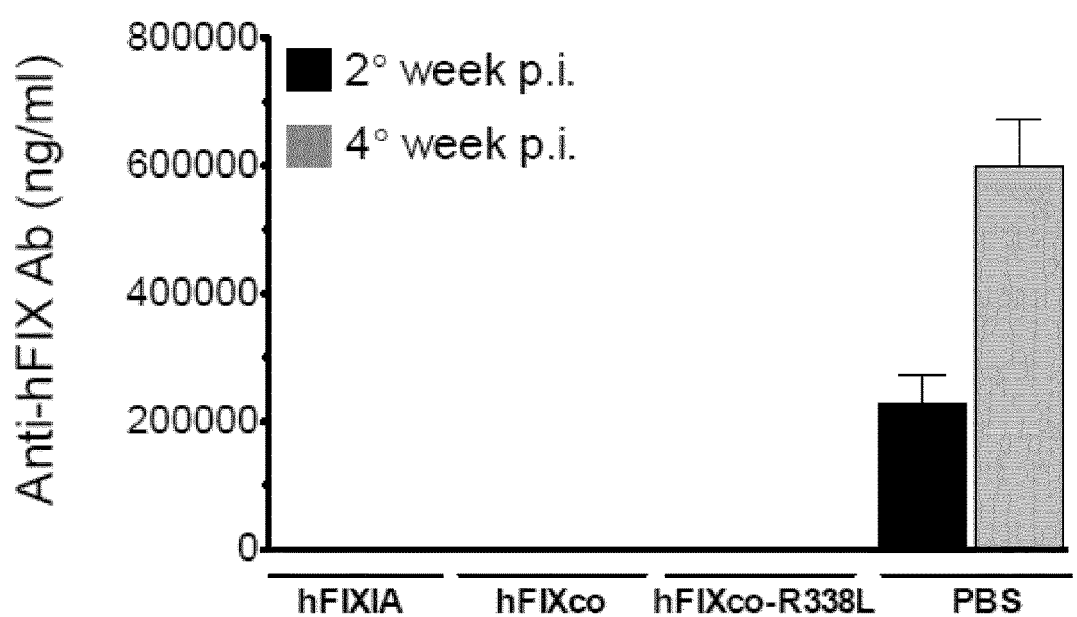
Figure 15:
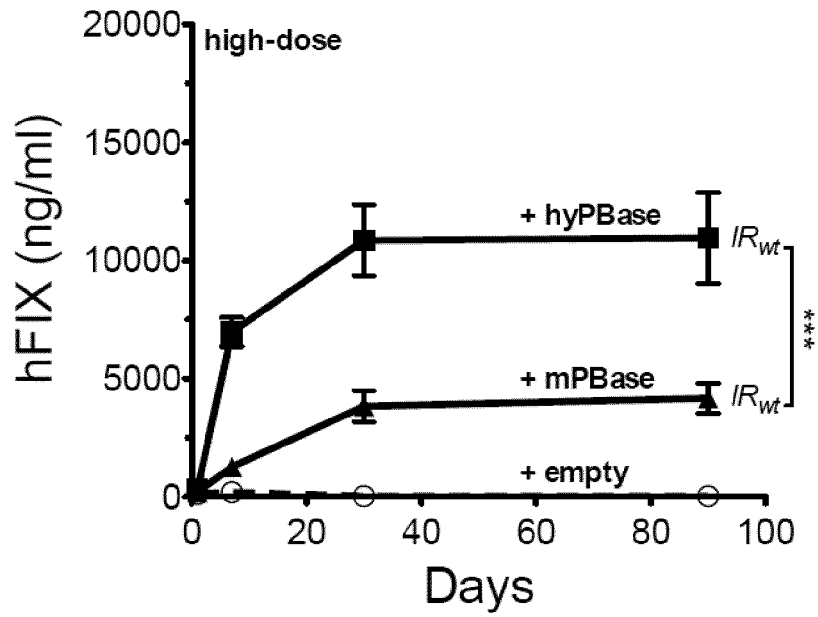
Figure 15:
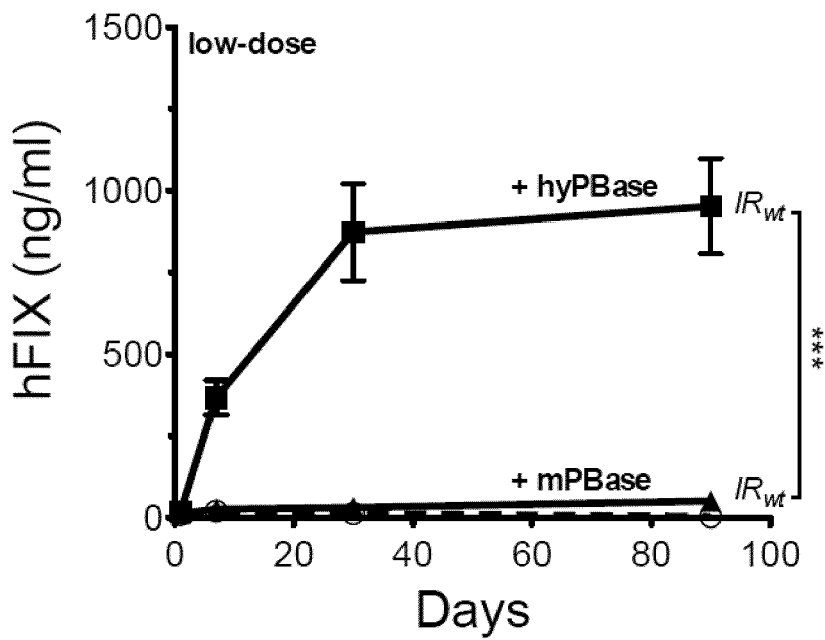
Figure 15:
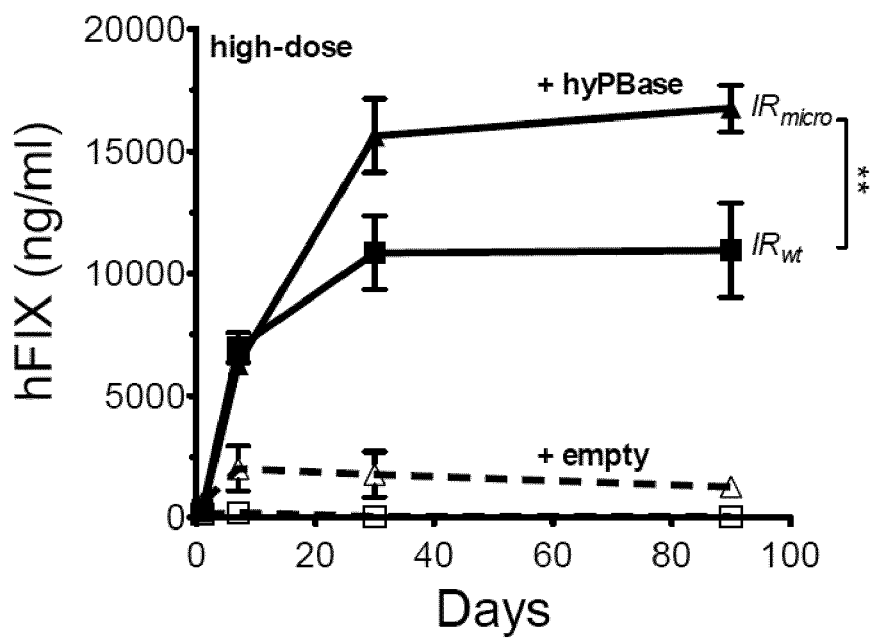
Figure 15:
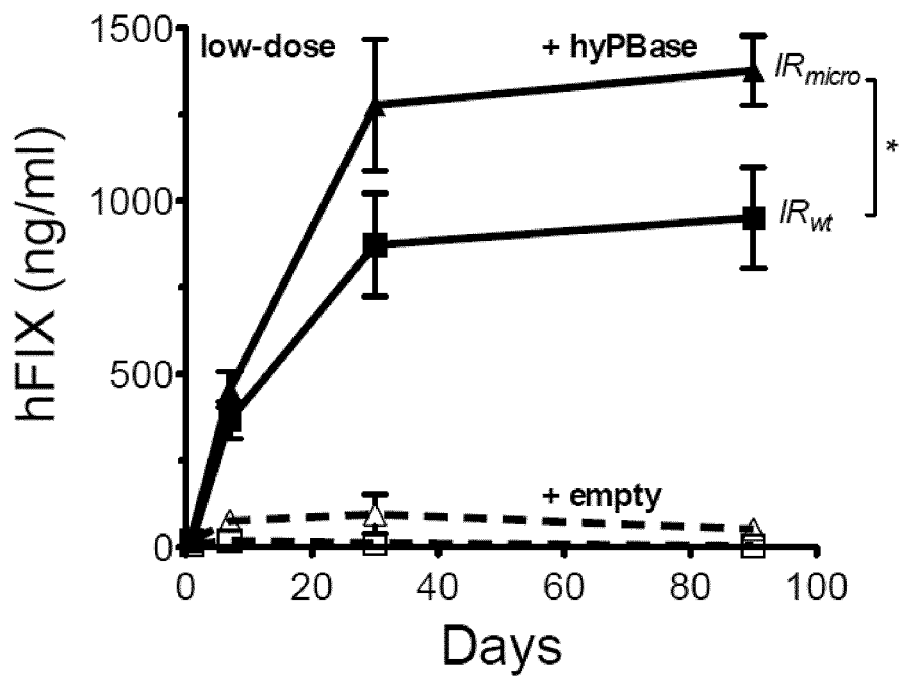
Figure 15:
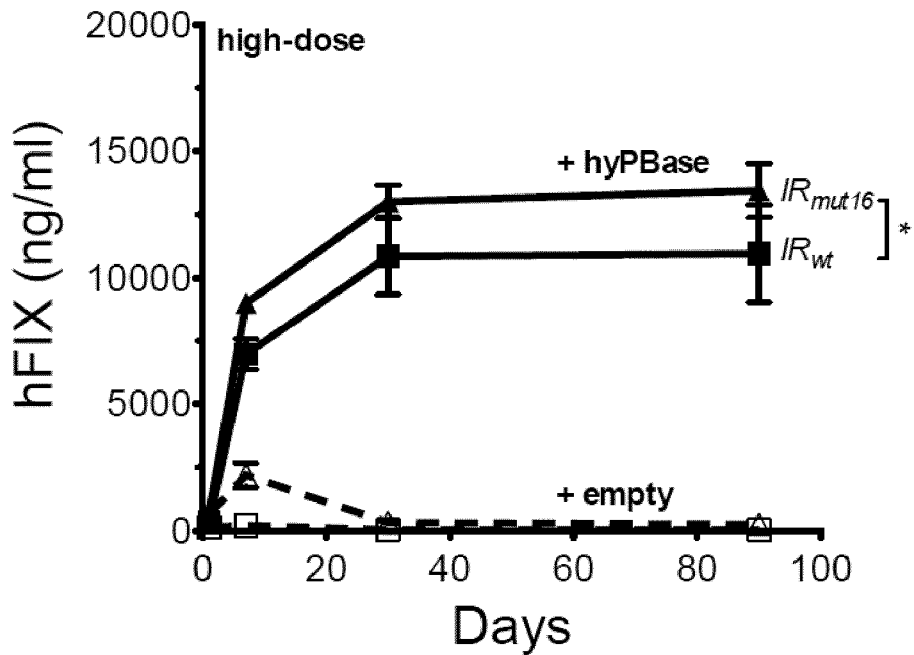
Figure 15:
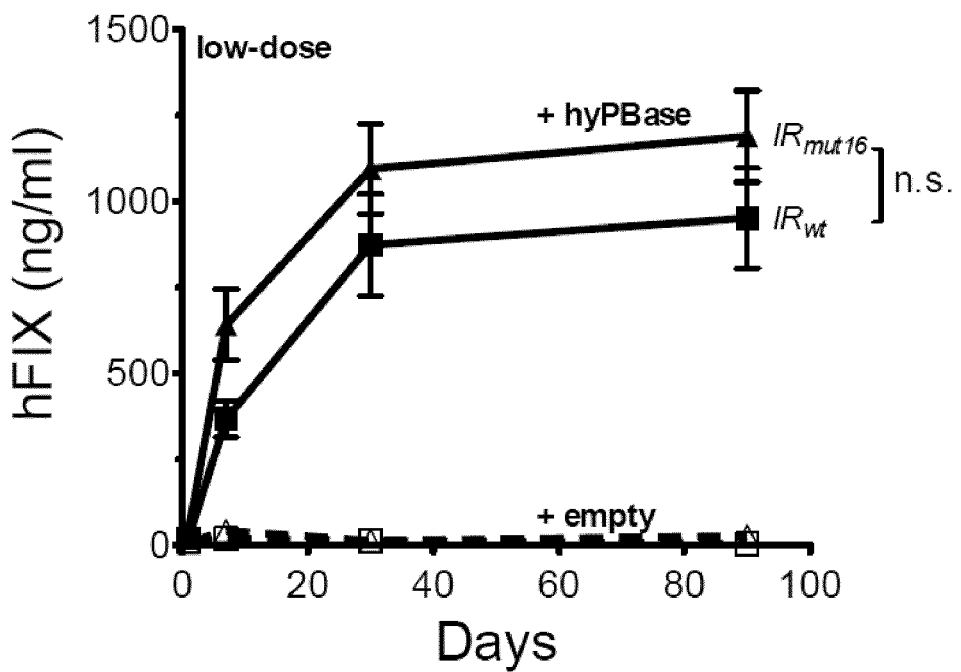

H-I). Liver-directed transfection of the PB-hFIXco/IR$_{micro}$ transposon (500 ng) along with 1000 ng hyPB transposase-encoding plasmid resulted in stable FIX levels reaching approximately 300% of normal hFIX levels (FIG. 15H). Similarly, at 10-fold lower PB-hFIXco/IR$_{micro}$ and hyPB doses a dose-dependent decrease in hFIX expression was apparent, yielding 30% of normal hFIX levels (FIG. 15I). In contrast, FIX expression was not or only slightly increased when the IR$_{mut16}$ was used compared to the IR$_{wt}$. (FIG. 15 J-K).

REFERENCES

ANNONI A, BROWN B D, CANTORE A, SERGI L S, NALDINI L, and RONCAROLO M G. (2009). In vivo delivery of a microRNA-regulated transgene induces antigen-specific regulatory T cells and promotes immunologic tolerance. Blood 114, 5152-5161

ARRUDA V R, STEDMAN H H, HAURIGOT V, and BUCHLIS G. (2010). Peripheral transvenular delivery of adeno-associated viral vectors to skeletal muscle as a novel therapy for hemophilia B. Blood 115, 4678-88.

AXELROD J H, READ M S, BRINKHOUS K M, and VERMA I M. (1990). Phenotypic correction of factor IX deficiency in skin fibroblasts of hemophilic dogs. Proc Natl Acad Sci USA; 87, 5173-7.

BROWN B D, SHI C X, POWELL S HURLBUT D, GRAHAM F L, and LILLICRAP D. (2004). Helper-dependent adenoviral vectors mediate therapeutic factor VIII expression for several months with minimal accompanying toxicity in a canine model of severe hemophilia A. Blood 103, 804-10.

BROWN B D, CANTORE A, ANNONI A, SERGI L S, LOMBARDO A, DELLA VALLE P, D'ANGELO A, and NALDINI L. (2007). A microRNA-regulated lentiviral vector mediates stable correction of hemophilia B mice. Blood 110, 4144-52.

Brunetti-Pierri N, Grove N C, Zuo Y, Edwards R, Palmer D, Cerullo V, Teruya J, Ng P. Bioengineered factor IX molecules with increased catalytic activity improve the therapeutic index of gene therapy vectors for hemophilia B. Hum Gene Ther. 2009 May; 20(5):479-85.

BUCHLIS G, PODSAKOFF G M, RADU A, HAWK S M, FLAKE A W, MINGOZZI F, and HIGH K A. (2012). Factor IX expression in skeletal muscle of a severe hemophilia B patient 10 years after AAV-mediated gene transfer. Blood 119, 3038-41.

BUDKER V, ZHANG G, KNECHTLE S, WOLFF J A. Naked DNA delivered intraportally expresses efficiently in hepatocytes. (1996) Gene Ther. July; 3(7):593-8.

CANTORE A, NAIR N, DELLA VALLE P, D I MATTED M, MÁTRAI J, SANVITO F, BROMBIN C, D I SERIO C, D'ANGELO A, CHUAH M, NALDINI L, VANDENDRIESSCHE T. Hyper-functional coagulation factor IX improves the efficacy of gene therapy in hemophilic mice. Blood. 2012. October 4.

CHANG, J., JIN, J., LOLLAR, P., BODE, W., BRANDSTETTER, H., HAMAGUCHI, N., STRAIGHT, D. L. & STAFFORD, D. W. (1998). Changing residue 338 in human factor IX from arginine to alanine causes an increase in catalytic activity. J Biol Chem 273(20): 12089-12094.

CHOWDHURY J R, GROSSMAN M, GUPTA S, CHOWDHURY N R, BAKER J R J R, WILSON J M. (1991) Long-term improvement of hypercholesterolemia after ex vivo gene therapy in LDLR-deficient rabbits. Science. December 20; 254(5039):1802-5.

CHUAH M K, SCHIEDNER G, THORREZ L, BROWN B, JOHNSTON M, GILLIJNS V, HERTEL S, VAN ROOIJEN N, LILLICRAP D, COLLEN D, VANDENDRIESSCHE T, and KOCHANEK S. (2003). Therapeutic factor VIII levels and negligible toxicity in mouse and dog models of hemophilia A following gene therapy with high-capacity adenoviral vectors. Blood 101, 1734-43.

Chuah M K, Nair N, VandenDriessche T. Recent progress in gene therapy for hemophilia. Hum Gene Ther. 2012a June; 23(6):557-65.

Chuah M K, Nair N, VandenDriessche T. Recent progress in gene therapy for hemophilia.

Hum Gene Ther. 2012b June; 23(6):557-65.

Chuah M K, VandenDriessche T. Platelet-directed gene therapy overcomes inhibitory antibodies to factor VIII. J Thromb Haemost. 2012c August; 10(8):1566-9

DONSANTE A, MILLER D G, L I Y, VOGLER C, BRUNT E M, RUSSELL D W, and SANDS M S. (2007). AAV vector integration sites in mouse hepatocellular carcinoma. Science 317, 477.

DOBRZYNSKI E, FITZGERALD J C, CAO O, MINGOZZI F, WANG L, and HERZOG R W (2006) Prevention of cytotoxic T lymphocyte responses to factor IX-expressing hepatocytes by gene transfer-induced regulatory T cells. Proc Natl Acad Sci USA 103, 4592-4597.

EHRHARDT A, and KAY M A. (2002). A new adenoviral helper-dependent vector results in long-term therapeutic levels of human coagulation factor IX at low doses in vivo. Blood 99, 3923-30.

FIELDS P A, ARRUDA V R, ARMSTRONG E, KIRK CHU, MINGOZZI, F. HAGSTROM, J., HERZOG R, HIGH K A. (2001). Risk and prevention of anti-factor IX formation in AAV-mediated gene transfer in the context of a large deletion of F9. Mol. Ther. 4, 201-210.

FOLLENZI A, BATTAGLIA M, LOMBARDO A, ANNONI A, RONCAROLO M G, and NALDINI L. (2004). Targeting lentiviral vector expression to hepatocytes limits transgene-specific immune response and establishes long-term expression of human antihemophilic factor IX in mice. Blood 103, 3700-9.

GAO G P, ALVIRA M R, WANG L, JOHNSTON J, WILSON J M. (2002). Novel adeno-associated viruses from rhesus monkeys as vectors for human gene therapy. Proc Natl Acad Sci USA 99, 11854-9.

GAO G, VANDENBERGH L H, ALVIRA M R L U Y, CALCEDO R, ZHOU X, and WILSON J M. (2004). Clades of Adeno-associated viruses are widely disseminated in human tissues. J. Viro 178, 6381-6388.

HERZOG R W, YANG E Y, COUTO L B, HAGSTROM J N, ELWELL D, FIELDS P A, BURTON M, BELLINGER D A, READ M S, BRINKHOUS K M, PODSAKOFF G M, NICHOLS T C, KURTZMAN G J, and HIGH K A. (1999). Long-term correction of canine hemophilia B by gene transfer of blood coagulation factor IX mediated by adeno-associated viral vector. Nat Med. 5, 56-63.

HERZOG R W, MOUNT J D, ARRUDA V R, HIGH K A, and LOTHROP C D Jr. (2001). Muscle-directed gene transfer and transient immune suppression result in sustained partial correction of canine hemophilia B caused by a null mutation. Mol Ther. 4, 192-200.

HERZOG R W, HAGSTROM J N, KUNG S H, TAI S J, WILSON J M, FISHER K J, and HIGH K A. (1997) Stable gene transfer and expression of human blood coagulation factor IX after intramuscular injection of recombinant adeno-associated virus. Proc Natl Acad Sci USA. 94, 5804-5809.

HERZOG R W, FIELDS P A, ARRUDA V R, BRUBAKER J O, ARMSTRONG E, MCCLINTOCK D, BELLINGER D A, COUTO L B, NICHOLS T C, HIGH K A (2002) Influence of vector dose on factor IX-specific T and B cell responses in muscle-directed gene therapy. Hum Gene Ther 13, 1281-1291.

HIGH K A. (2001). Gene Transfer as an approach to treating Hemophilia. Circ Res. 88, 137-144.

HIGH K A. (2011) Gene therapy for hemophilia: a long and winding road. J Thromb Haemost. 9 Suppl. 1: 2-11.

BAINBRIDGE J, SMITH A J, BARKER S, et al. (2008) Effect of Gene Therapy on Visual Function in Leber's Congenital Amaurosis. N Engl J Med. 358, 2231-2239.

JIANG H, LILLICRAP D, and PATARROYO-WHITE S. (2006). Multiyear therapeutic benefit of AAV serotypes 2, 6, and 8 delivering factor VIII to hemophilia A mice and dogs. Blood. 108, 107-15.

KAO, C. Y., LIN, C. N., YU, I. S., TAO, M. H., WU, H. L., SHI, G. Y., YANG, Y. L., KAO, J. T. & LIN, S. W. (2010). FIX-Triple, a gain-of-function factor IX variant, improves haemostasis in mouse models without increased risk of thrombosis. Thromb Haemost 104(2): 355-365.

KAY M A, BALEY P, ROTHENBERG S, LELAND F, FLEMING L, PONDER K P, LIU T, FINEGOLD M, DARLINGTON G, POKORNY W, WOO SLC. (1992) Expression of human alpha 1-antitrypsin in dogs after autologous transplantation of retroviral transduced hepatocytes. Proc Natl Acad Sci USA. January 1; 89(1): 89-93.

KAY M A, MANNO C S, RAGNI M V, COUTO L B, MCCLELLAND A, GLADER B, CHEW A J, TAI S J, HERZOG R W, ARRUDA V, JOHNSON F, SCALLAN C, SKARSGARD E, FLAKE A W, and HIGH K A. (2000). Evidence for gene transfer and expression of factor IX in hemophilia B patients treated with an AAV vector. Nat Genet. 24, 257-61.

KISTNER A, GOSSEN M, ZIMMERMANN F, JERECIC J, ULLMER C, LYBBERT H, BUJARD H. (1996) Doxycycline-mediated quantitative and tissue-specific control of gene expression in transgenic mice. Proc Natl Acad Sci USA. October 1; 93(20): 10933-8.

KREN B T, UNGER G M, SJEKLOCHA L, TROSSEN A A, KORMAN V, DIETHELEM-OKITA B M, REDING M T, and STEER C J. (2009). Nanocapsule-delivered Sleeping Beauty mediates therapeutic Factor VIII expression in liver sinusoidal endothelial cells of hemophilia A mice. J Clin Invest. 19, 2086-99.

KURIYAMA S, YOSHIKAWA M, ISHIZAKA S, TSUJII T, LKENAKA K, KAGAWA T, MORITA N, MIKOSHIBA K. (1991) A potential approach for gene therapy targeting hepatoma using a liver-specific promoter on a retroviral vector. Cell Struct Funct. December; 16(6):503-10.

L I H, MALANI N, HAMILTON S R, SCHLACHTERMAN A, BUSSADORI G, EDMONSON S E, SHAH R, ARRUDA V R, MINGOZZI F, WRIGHT J F, BUSHMAN F D, and HIGH K A. (2011). Assessing the potential for AAV vector genotoxicity in a murine model. Blood. 117, 3311-9.

LIN, C. N., KAO, C. Y., MIAO, C. H., HAMAGUCHI, N., WU, H. L., SHI, G. Y., LIU, Y. L., HIGH, K. A. & LIN, S. W. (2010). Generation of a novel factor IX with augmented clotting activities in vitro and in vivo. J Thromb Haemost 8(8): 1773-1783.

LIU F, SONG Y, LIU D. (1999) Hydrodynamics-based transfection in animals by systemic administration of plasmid DNA. Gene Ther. July; 6(7):1258-66.

MANNO C S, PIERCE G F, and ARRUDA V R. (2006). Successful transduction of liver in hemophilia by AAV-Factor IX and limitations imposed by the host immune response. Nat Med. 12, 342-7.

MATES L, CHUAH M K, BELAY E, JERCHOW B, MANOJ N, ACOSTA-SANCHEZ A, GRZELA D P, SCHMITT A, BECKER K, MÁTRAI J, M A L, SAMARA-KUKO E, GYSEMANS C, PRYPUTNIEWICZ D, MISKEY C, FLETCHER B, VANDENDRIESSCHE T, IVICS Z, and IZSVAK Z. (2009). Molecular evolution of a novel hyperactive Sleeping Beauty transposase enables robust stable gene transfer in vertebrates. Nat Genet. 41, 753-61.

MÁTRAI J, CHUAH M K, and VANDENDRIESSCHE T. (2010a). Pre clinical and clinical progress in hemophilia gene therapy. Curr Opin Hematol. 17, 387-92.

MÁTRAI J, CHUAH M K, and VANDENDRIESSCHE T. (2010b). Recent advances in lentiviral vector development and applications. Mol Ther. 18, 477-90.

MÁTRAI J, CANTORE A, BARTHOLOMAE C C, ANNONI A, WANG W, ACOSTA-SANCHEZ A, SAMARA-KUKO E, D E WAELE L, M A L, GENOVESE P, DAMO M, ARENS A, GOUDY K, NICHOLS T C, VON KALLE C, L CHUAH M K, RONCAROLO M G, SCHMIDT M, VANDENDRIESSCHE T, and NALDINI L. (2011). Hepatocyte-targeted expression by integrase-defective lentiviral vectors induces antigen-specific tolerance in mice with low genotoxic risk. Hepatology 53, 1696-707.

MATSUI H, SHIBATA M, BROWN B, LABELLE A, HEGADRON C, ANDREWS C, CHUAH M, VANDENDRIESSCHE T, MIAO C H, HOUGH C, and LILLICRAP D. (2009). A murine model for induction of long-term immunologic tolerance to factor VIII does not require persistent detectable levels of plasma factor VIII and involves contributions from Foxp3+T regulatory cells. Blood. 114, 677-85.

MATSUI H, HEGADORN C, OZELO M, BURNETT E, TUTTLE A, LABELLE A, McCARY P B Jr., NALDINI L, BROWN B, HOUGH C, and LILLICRAP D. (2011). A microRNA-regulated and GP64-pseudotyped lentiviral vector mediates stable expression of FVIII in a murine model of Hemophilia A. Mol Ther. 19, 723-30.

McCARTY D M, MONAHAN P E, and SAMULSKI R J. (2001). Self-complementary recombinant adeno-associated virus (scAAV) vectors promote efficient transduction independently of DNA synthesis. Gene Ther. 8, 1248-54.

McCARTY D M, FU H, MONAHAN P E, TOULSON C E, NAIK P, and SAMULSKI R J. (2003). Adeno-associated virus terminal repeat (TR) mutant generates self-complementary vectors to overcome the rate-limiting step to transduction in vivo. Gene Ther. 10, 2112-8.

McIntosh, J. et al. Therapeutic levels of FVIII following a single peripheral vein administration of rAAV vector encoding a novel human factor VIII variant. Blood (2013).

MIAO C H, OHASHI K, PATIJN G A, MEUSE L, Y EX, THOMPSON A R, and KAY M A. (2000). Inclusion of the hepatic locus control region, an intron, and untranslated region increases and stabilizes hepatic factor IX gene expression in vivo but not in vitro. Mol Ther. 1, 522-32.

MIAO H. Z., SIRACHAINAN N., PALMER L., et al. (2004). Bioengineering of coagulation factor VIII for improved secretion. Blood 103(9):3412-3419.

MILANOV, ET AL., 2012 Engineered factor IX variants bypass FVIII and correct hemophilia A phenotype in mice Blood 119:602-611.

MILLER A D. (1990) Retrovirus packaging cells. Hum Gene Ther. Spring; 1 (1):5-14.

MINGOZZI F, LIU Y L, DOBRZYNSKI E, KAUFHOLD A, LIU J H, WANG Y, ARRUDA V R, HIGH K A, and HERZOG R W. (2003). Induction of immune tolerance to coagulation factor IX antigen by in vivo hepatic gene transfer. J Clin Invest. 111, 1347-56.

MINGOZZI F, MAUS M V, HUI D J, SABATINO D E, MURPHY S L, RASKO J E, RAGINI M V, MANNO C S, SOMMER J, JIANG H, PIERCE G F, ERTL H C, and HIGH K A. (2007). CD8(+) T-cell responses to adeno-associated virus capsid in humans. Nat Med. 13, 419-22.

MOUNT J D, HERZOG R W, TILLSON D M, GOODMAN S A, ROBINSON N, MCCLELAND M L, BELLINGER D, NICHOLS T C, ARRUDA V R, LOTHROP C D J R, and HIGH K A. (2002). Sustained phenotypic correction of hemophilia B dogs with a factor IX null mutation by liver-directed gene therapy. Blood 99, 2670-6.

NALDINI L, BLOMER U, GALLAY P, ORY D, MULLIGAN R, GAGE F H, VERMA I M, TRONO D. (1996) In vivo gene delivery and stable transduction of nondividing cells by a lentiviral vector. Science. April 12; 272(5259): 263-7.

NATHWANI A C, DAVIDOFF A M, HANAWA H, YUNYU H U, HOFFER F A, NIKANOROV A, SLAUGHTER C, N G CYC, ZHOU J, LOZIER J, MANDRELL T D, VANIN E F, and NIENHUIS A W. (2002). Sustained high-level expression of human factor IX (hFIX) after liver-targeted delivery of recombinant adeno-associated virus encoding the hFIX gene in rhesus macaques. Blood 100, 1662-1669.

NATHWANI A C, GRAY J T, NG C Y, ZHOU J, SPENCE Y, WADDINGTON S N, TUDDENHAM E G, KEMBALL COOK G, McINTOSH J, BOON-SPIJKER M, MERTENS K, DAVIDOFF A M. (2006). Self-complementary adeno-associated virus vectors containing a novel liver-specific human factor IX expression cassette enable highly efficient transduction of murine and non-human primate liver. Blood 107, 2653-61.

NATHWANI A C, TUDDENHAM E G, RANGARAJAN S, ROSALES C, MCINTOSH J, LINCH D C, CHOWDARY P, RIDDELL A, PIE A J, HARRINGTON C, O'BEIRNE J, SMITH K, PASI J, GLADER B, RUSTAGI P, NG C Y, KAY M A, ZHOU J, SPENCE Y, MORTON C L, ALLAY J, COLEMAN J, SLEEP S, CUNNINGHAM J M, SRIVASTAVA D, BASNER-TSCHAKARJAN E, MINGOZZI F, HIGH K A, GRAY J T, REISS U M, NIENHUIS A W, and DAVIDOFF A M. (2011). Adenovirus-associated virus vector-mediated gene transfer in hemophilia B. N Engl J Med. 365, 2357-2365.

OHLFEST J R, FRANDSEN J L, FRITZ S, LOBITZ P D, PERKINSON S G, CLARK K J, NELSESTUEN G, KEY N S, MCLVOR R S, HACKETT P B, and LARGAESPADA D A. (2004). Phenotypic correction and long-term expression of factor VIII in hemophilic mice by immunotolerization and nonviral gene transfer using the Sleeping Beauty transposon system. Blood 105, 2691-8.

Petrus, I., Chuah, M. & VandenDriessche, T. Gene therapy strategies for hemophilia: benefits versus risks. *J Gene Med* 12, 797-809 (2010). SANDBERG H, ALMSTEDT A, BRANDT J, et al. (2001). Structural and functional characteristics of the B domain-deleted recombinant factor VIII protein, r-VIII SQ. Thromb Haemost. 85(1): 93-100.

SCHUETTRUMPF, J., HERZOG, R. W., SCHLACHTERMAN, A., KAUFHOLD, A., STAFFORD, D. W. & ARRUDA, V. R. (2005). Factor IX variants improve gene therapy efficacy for hemophilia B. Blood 105(6): 2316-2323.

SIMIONI, P., TORMENE, D., TOGNIN, G., GAVASSO, S., BULATO, C., IACOBELLI, N. P., FINN, J. D., SPIEZIA, L., RADU, C. & ARRUDA, V. R. (2009). X-linked thrombophilia with a mutant factor IX (factor IX Padua). N Engl J Med 361(17): 1671-1675.

SNYDER R O, MIAO C H, PATIJN G A, SPRATT S K, DANOS O, NAGY D, GOWN A M, WINTHER B, MEUSE L, COHEN L K, THOMPSON A R, and KAY M A. (1997). Persistent and therapeutic concentrations of human factor IX in mice after hepatic gene transfer of recombinant AAV vectors. Nat Genet. 16, 270-276.

SNYDER R O, MIAO C, MEUSE L, TUBB J, DONAHUE B A, HUI-FENG LIN, STAFFORD D W, PATEL S, THOMPSON A R, NICHOLS T, READ M S, BELLINGER D A, BRINKHOUS K M, and KAY M A. (1999). Correction of hemophilia B in canine and murine models using recombinant adeno-associated viral vectors. Nat Med. 5, 64-70.

TRAPNELL B C. (1993) Adenoviral vectors for gene transfer. Adv. Drug Del. Rev. 12: 185-199.

VANDENBERGHE L H, WANG L, SOMANATHAN S, ZHI Y, FIGUEREDO J, CALCEDO R, SANMIGUEL J, DESAI R A, CHEN C S, JOHNSTON J, GRANT R L, GAO G, and WILSON J M. (2006). Heparin binding directs activation of T cells against adeno-associated virus serotype 2 capsid. Nat Med. 12, 967-71.

VANDENDRIESSCHE T, VANSLEMBROUCK V, GOOVAERTS I, ZWINNEN H, VANDERHAEGHEN M L, COLLEN D, and CHUAH M K. (1999). Long-term expression of human coagulation factor VIII and correction of hemophilia A after in vivo retroviral gene transfer in factor VIII-deficient mice. Proc Natl Acad Sci USA. 96, 10379-84.

VANDENDRIESSCHE T, THORREZ L, NALDINI L, FOLLENZI A, MOONS L, ZWI BERNEMAN, COLLEN D, and CHUAH M K. (2002). Lentiviral vectors containing the human immunodeficiency virus type-1 central polypurine tract can efficiently transduce nondividing hepatocytes and antigen-presenting cells in vivo. Blood 100, 813-22.

VANDENDRIESSCHE T, THORREZ L, ACOSTA-SANCHEZ A, PETRUS I, WANG L, M A L, D E WAELE L, IWASAKI Y, GILLIJNS V, WILSON J M, COLLEN D, and CHUAH M K. (2007). Efficacy and safety of adeno-associated viral vectors based on serotype 8 and 9 vs. lentiviral vectors for hemophilia B gene therapy. J Thromb Haemost. 5, 16-24.

VANDENDRIESSCHE T, IVICS Z, IZSVAK Z, and CHUAH M K. (2009). Emerging potential of transposons for gene therapy and generation of induced pluripotent stem cells. Blood 114, 1461-8.

VANDENDRIESSCHE T, and CHUAH M K. (2012). Clinical progress in gene therapy: sustained partial correction of the bleeding disorder in patients suffering from severe hemophilia B. Hum Gene Ther. 23, 4-6.

WANG L, TAKABE K, BIDLINGMAIER S M, ILL C R, and VERMA I M. (1999). Sustained correction of bleeding disorder in hemophilia B mice by gene therapy. Proc Natl Acad Sci USA 96, 3906-3910.

WANG L, NICHOLS T C, READ M S, BELLINGER D A, and VERMA I M. (2000). Sustained expression of therapeutic level of factor IX in hemophilia B dogs by AAV-mediated gene therapy in liver. Mol Ther. 1, 154-158.

WANG L, CAO O, SWALM B, DOBRZYNSKI E, MINGOZZI F, and HERZOG R W (2005) Major role of local immune responses in antibody formation to factor IX in AAV gene transfer. Gene Ther 12, 1453-1464.

WARD N J, BUCKLEY S M, WADDINGTON S N, VANDENDRIESSCHE T, CHUAH M K, NATHWANI A C, McLNTOSH J, TUDDENHAM E G, KINNON C, THRASHER A J, and McVEY J H (2010) Codon optimization of human factor VIII cDNAs leads to high-level expression. Blood 117, 798-807.

Ward, N. J. et al. Codon optimization of human factor VIII cDNAs leads to high-level expression. *Blood* 117, 798-807 (2011).

WU Z, SUN J, ZHANG T, YIN C, YIN F, VAN DYKE T, SAMULSKI R J, and MONAHAN P E. (2008). Optimization of self-complementary AAV vectors for liver-directed expression results in sustained correction of hemophilia B at low vector dose. Mol Ther. 16, 280-9.

XU L, GAO C, and SANDS M S. (2003). Neonatal or hepatocyte growth factor-potentiated adult gene therapy with a retroviral vector results in therapeutic levels of canine factor IX for hemophilia B. Blood 101, 3924-3932.

XU L, NICHOLS T C, SARKAR R, Mc CORQUODALE S, BELLINGER D A, PONDER K P. (2005). Absence of a desmopressin response after therapeutic expression of factor VIII in hemophilia A dogs with liver-directed neonatal gene therapy. Proc Natl Acad Sci USA 102, 6080-6085.

YAMADA T, IWASAKI Y, TADA H, IWABUKI H, CHUAH M K, VANDENDRIESSCHE T, FUKUDA H, KONDO A, UEDA M, SENO M, TANIZAWA K, KURODA S. (2003) Nanoparticles for the delivery of genes and drugs to human hepatocytes. Nat Biotechnol. August; 21 (8):885-90.

YANT S R, MEUSE L, CHIU W, IVICS Z, IZSVAK Z, and KAY M A. (2000). Somatic integration and long-term transgene expression in normal and haemophilic mice using a DNA transposon system. Nat Genet. 25, 35-41.

Yusa et al. A hyperactive piggyBac transposase for mammalian applications. Proc Natl Acad Sci USA. 2011; 108(4):1531-6.

ZHANG G, BUDKER V, WOLFF J A. (1999) High levels of foreign gene expression in hepatocytes after tail vein injections of naked plasmid DNA. Hum Gene Ther. July 1; 10(10):1735-7.

ZHONG L, LI B, MAH C S, GOVINDASAMY L, AGBANDJE-MCKENNA, COOPER M, HERZOG R W, ZOLOTUKHIN I, WARRINGTON JR. K H, WEIGEL-VAN AKEN K, HOBBS J A, ZOLOTUKHIN S, MUZYCZKA N, and SRIVASTAVA A (2008). Next generation of adeno-associated virus 2 vectors: point mutations in tyrosines lead to high-efficiency transduction at lower doses. Proc Natl Acad Sci USA 105, 7827-32.

```

The invention claimed is:

1. A single stranded or self-complementary adeno-associated viral (AAV) vector comprising a nucleic acid expression cassette comprising a Serpin enhancer consisting of the nucleic acid sequence of SEQ ID NO: 8, a minimal transthyretin promoter, a minute virus of mice intron, a codon-optimized coagulation factor IX R338L hyper-activating mutant, and a transcriptional termination signal.

2. The vector according to claim 1, comprising the nucleic acid sequence of SEQ ID NO: 2.

3. The vector according to claim 1, wherein said transcriptional termination signal is the Simian virus 40 polyadenylation signal or the bovine growth hormone polyadenylation signal.

4. A pharmaceutical composition comprising the vector according to claim 1 and a pharmaceutically acceptable carrier, optionally further comprising an active ingredient for treating hemophilia B.

* * * * *

                        SEQUENCE LISTING

<160> NUMBER OF SEQ ID NOS: 30

<210> SEQ ID NO 1
<211> LENGTH: 6044
<212> TYPE: DNA
<213> ORGANISM: Artificial
<220> FEATURE:
<223> OTHER INFORMATION: Adenoviral expression vector pdsAAVsc SerpEnh
      TTRmin MVM FIXcoptMT-bghpA

<400> SEQUENCE: 1
cagcagctgg cgtaatagcg aagaggcccg caccgatcgc ccttcccaac agttgcgcag      60
cctgaatggc gaatgaatt ccagacgatt gagcgtcaaa atgtaggtat ttccatgagc     120 gttttcctg ttgcaatggc tggcggtaat attgttctgg atattaccag caaggccgat    180
agtttgagtt cttctactca ggcaagtgat gttattacta atcaaagaag tattgcgaca    240
acggttaatt tgcgtgatgg acagactctt ttactcggtg gcctcactga ttataaaaac    300
acttctcagg attctggcgt accgttcctg tctaaaatcc ctttaatcgg cctcctgttt    360
agctcccgct ctgattctaa cgaggaaagc acgttatacg tgctcgtcaa agcaaccata    420
gtacgcgccc tgtagcggcg cattaagcgc ggcgggtgtg gtggttacgc gcagcgtgac    480
cgctacactt gccagcgccc tagcgcccgc tcctttcgct ttcttccctt cctttctcgc    540
cacgttcgcc ggctttcccc gtcaagctct aaatcggggg ctccctttag ggttccgatt    600
tagtgcttta cggcacctcg accccaaaaa acttgattag ggtgatggtt cacgtagtgg    660
gccatcgccc tgatagacgg ttttcgccc tttgacgttg gagtccacgt tctttaatag    720
tggactcttg ttccaaactg gaacaacact caaccctatc tcggtctatt cttttgattt    780
ataagggatt ttgccgattt cggcctattg gttaaaaaat gagctgattt aacaaaaatt    840
taacgcgaat tttaacaaaa tattaacgtt tacaatttaa atatttgctt atacaatctt    900
```

```
cctgttttg gggcttttct gattatcaac cggggtacat atgattgaca tgctagtttt     960
acgattaccg ttcatcgcct gcactgcgcg ctcgctcgct cactgaggcc gcccgggcaa    1020
agcccgggcg tcgggcgacc tttggtcgcc cggcctcagt gagcgagcga gcgcgcagag    1080
agggagtgga attcacgcgt ggtacgatct gaattcggta caattcacgc gtggtacggc    1140
cgcggtaccg gcgcgccggg ggaggctgct ggtgaatatt aaccaaggtc accccagtta    1200
tcggaggagc aaacagggc  taagtccaca cgcgtggtac cgtctgtctg cacatttcgt    1260
agagcgagtg ttccgatact ctaatctccc taggcaaggt tcatatttgt gtaggttact    1320
tattctcctt ttgttgacta agtcaataat cagaatcagc aggtttggag tcagcttggc    1380
agggatcagc agcctgggtt ggaaggaggg ggtataaaag ccccttcacc aggagaagcc    1440
gtcacacaga tccacaagct cctgaagagg taagggttta agggatggtt ggttggtggg    1500
gtattaatgt ttaattacct ggagcacctg cctgaaatca ctttttttca ggttggctag    1560
catgcagcgc gtgaacatga tcatggccga gagccccggc ctgatcacca tctgcctgct    1620
gggctacctg ctgagcgccg agtgcaccgt gttcctggac cacgagaacg ccaacaagat    1680
cctgaaccgc cccaagcgct acaacagcgg caagctggag gagttcgtgc agggcaacct    1740
ggagcgcgag tgcatggagg agaagtgcag cttcgaggag gcccgcgagg tgttcgagaa    1800
caccgagcgc accaccgagt tctggaagca gtacgtggac ggcgaccagt gcgagagcaa    1860
ccctgcctg  aacggcggca gctgcaagga cgacatcaac agctacgagt gctggtgccc    1920
cttcggcttc gagggcaaga actgcgagct ggacgtgacc tgcaacatca gaacggccg    1980
ctgcgagcag ttctgcaaga cagcgccga  caacaaggtg gtgtgcagct gcaccgaggg    2040
ctaccgcctg gccgagaacc agaagagctg cgagcccgcc gtgcccttcc cctgcggccg    2100
cgtgagcgtg agccagacca gcaagctgac ccgcgccgag gccgtgttcc ccgacgtgga    2160
ctacgtgaac agcaccgagg ccgagaccat cctggacaac atcacccaga gcacccagag    2220
cttcaacgac ttcacccgcg tggtgggcgg cgaggacgcc aagcccggcc agttcccctg    2280
gcaggtggtg ctgaacggca aggtggacgc cttctgcggc ggcagcatcg tgaacgagaa    2340
gtggatcgtg accgccgccc actgcgtgga gaccggcgtg aagatcaccg tggtggccgg    2400
cgagcacaac atcgaggaga ccgagcacac cgagcagaag cgcaacgtga tccgcatcat    2460
cccccaccac aactacaacg ccgccatcaa caagtacaac cacgacatcg ccctgctgga    2520
gctggacgag cccctggtgc tgaacagcta cgtgaccccc atctgcatcg ccgacaagga    2580
gtacaccaac atcttcctga agttcggcag cggctacgtg agcggctggg gccgcgtgtt    2640
ccacaagggc cgcagcgccc tggtgctgca gtacctgcgc gtgcccctgg tggaccgcgc    2700
cacctgcctg cgcagcacca agttcaccat ctacaacaac atgttctgcg ccggcttcca    2760
cgagggcggc cgcgacagct gccagggcga cagcggcggc cccacgtga  ccgaggtgga    2820
gggcaccagc ttcctgaccg gcatcatcag ctggggcgag gagtgcgcca tgaagggcaa    2880
gtacggcatc tacaccaagg tgagccgcta cgtgaactgg atcaaggaga agaccaagct    2940
gacctggaga tctgatcagc ctcgactgtg ccttctagtt gccagccatc tgttgtttgc    3000
ccctcccccg tgccttcctt gaccctggaa ggtgccactc ccactgtcct ttcctaataa    3060
aatgaggaaa ttgcatcgca ttgtctgagt aggtgtcatt ctattctggg gggtggggtg    3120
ggcaggaca  gcaaggggga ggattggaa  gacaatagca ggcatgctgg ggatctgata    3180
gcaggcatgc tggggagaga tcgatctagg aaccctagt  gatggagttg ccactccct    3240
ctctgcgcgc tcgctcgctc actgaggccg cccgggcaaa gcccgggcgt cgggcgacct    3300
```

```
ttggtcgccc ggcctcagtg agcgagcgag cgcgcagaga gggagtggcc aaccccccccc      3360
ccccccccccc tgcatgcagg cgattctctt gtttgctcca gactctcagg caatgacctg      3420
atagcctttg tagagacctc tcaaaaatag ctaccctctc cggcatgaat ttatcagcta      3480
gaacggttga atatcatatt gatggtgatt tgactgtctc cggcctttct cacccgtttg      3540
aatctttacc tacacattac tcaggcattg catttaaaat atatgagggt tctaaaaatt      3600
tttatccttg cgttgaaata aaggcttctc ccgcaaaagt attacagggt cataatgttt      3660
ttggtacaac cgatttagct ttatgctctg aggctttatt gcttaatttt gctaattctt      3720
tgccttgcct gtatgattta ttggatgttg aattcctga tgcggtattt tctccttacg       3780
catctgtgcg gtatttcaca ccgcatatgg tgcactctca gtacaatctg ctctgatgcc      3840
gcatagttaa gccagccccg cacccgccca cacccgctg acgcgccctg acgggcttgt       3900
ctgctcccgg catccgctta cagacaagct gtgaccgtct ccgggagctg catgtgtcag      3960
aggttttcac cgtcatcacc gaaacgcgcg agacgaaagg gcctcgtgat acgcctattt      4020
ttataggtta atgtcatgat aataatggtt tcttagacgt caggtggcac ttttcgggga      4080
aatgtgcgcg gaacccctat ttgttttattt tctaaatac attcaaatat gtatccgctc      4140
atgagacaat aaccctgata aatgcttcaa taatattgaa aaaggaagag tatgagtatt      4200
caacatttcc gtgtcgccct tattcccttt tttgcggcat tttgccttcc tgttttttgct     4260
cacccagaaa cgctggtgaa agtaaaagat gctgaagatc agttgggtgc acgagtggg       4320
tacatcgaac tggatctcaa cagcggtaag atccttgaga gttttcgccc cgaagaacgt      4380
tttccaatga tgagcacttt taaagttctg ctatgtggcg cggtattatc ccgtattgac      4440
gccgggcaag agcaactcgg tcgccgcata cactattctc agaatgactt ggttgagtac      4500
tcaccagtca cagaaaagca tcttacggat ggcatgacag taagagaatt atgcagtgct      4560
gccataacca tgagtgataa cactgcggcc aacttacttc tgacaacgat cggaggaccg      4620
aaggagctaa ccgcttttt gcacaacatg ggggatcatg taactcgcct tgatcgttgg       4680
gaaccggagc tgaatgaagc cataccaaac gacgagcgtg acaccacgat gcctgtagca      4740
atggcaacaa cgttgcgcaa actattaact ggcgaactac ttactctagc ttcccggcaa      4800
caattaatag actggatgga ggcggataaa gttgcaggac cacttctgcg ctcggccctt      4860
ccggctggct ggtttattgc tgataaatct ggagccggtg agcgtgggtc tcgcggtatc      4920
attgcagcac tggggccaga tggtaagccc tcccgtatcg tagttatcta cacgacgggg      4980
agtcaggcaa ctatggatga acgaaataga cagatcgctg agataggtgc ctcactgatt      5040
aagcattggt aactgtcaga ccaagtttac tcatatatac tttagattga tttaaaactt      5100
catttttaat ttaaaaggat ctaggtgaag atccttttg ataatctcat gaccaaaatc       5160
ccttaacgtg agttttcgtt ccactgagcg tcagacccc g tagaaaagat caaaggatct     5220
tcttgagatc ctttttttct gcgcgtaatc tgctgcttgc aaacaaaaaa accaccgcta      5280
ccagcggtgg tttgtttgcc ggatcaagag ctaccaactc ttttttccgaa ggtaactggc     5340
ttcagcagag cgcagatacc aaatactgtc cttctagtgt agccgtagtt aggccaccac      5400
ttcaagaact ctgtagcacc gcctacatac ctcgctctgc taatcctgtt accagtggct      5460
gctgccagtg gcgataagtc gtgtcttacc gggttggact caagacgata gttaccggat      5520
aaggcgcagc ggtcgggctg aacggggggt tcgtgcacac agcccagctt ggagcgaacg      5580
acctacaccg aactgagata cctacagcgt gagctatgag aaagcgccac gcttcccgaa      5640
gggagaaagg cggacaggta tccggtaagc ggcagggtcg gaacaggaga gcgcacgagg      5700
```

-continued

```
gagcttccag ggggaaacgc ctggtatctt tatagtcctg tcgggtttcg ccacctctga      5760
cttgagcgtc gattttttgtg atgctcgtca ggggggcgga gcctatggaa aaacgccagc      5820
aacgcggcct ttttacggtt cctggccttt tgctggcctt ttgctcacat gttctttcct      5880
gcgttatccc ctgattctgt ggataaccgt attaccgcct ttgagtgagc tgataccgct      5940
cgccgcagcc gaacgaccga gcgcagcgag tcagtgagcg aggaagcgga agagcgccca      6000
atacgcaaac cgcctctccc cgcgcgttgg ccgattcatt aatg                       6044
```

<210> SEQ ID NO 2
<211> LENGTH: 6044
<212> TYPE: DNA
<213> ORGANISM: Artificial
<220> FEATURE:
<223> OTHER INFORMATION: Adenoviral expression vector pdsAAVsc SerpEnh
      TTRmin MVM FIXcopt-PADUA-bghpA

<400> SEQUENCE: 2

```
cagcagctgg cgtaatagcg aagaggcccg caccgatcgc ccttcccaac agttgcgcag        60
cctgaatggc gaatggaatt ccagacgatt gagcgtcaaa atgtaggtat ttccatgagc       120 gttttttcctg ttgcaatggc tggcggtaat attgttctgg atattaccag caaggccgat      180
agtttgagtt cttctactca ggcaagtgat gttattacta atcaaagaag tattgcgaca       240
acggttaatt tgcgtgatgg acagactctt ttactcggtg gcctcactga ttataaaaac       300
acttctcagg attctggcgt accgttcctg tctaaaatcc ctttaatcgg cctcctgttt       360
agctcccgct ctgattctaa cgaggaaagc acgttatacg tgctcgtcaa agcaaccata       420
gtacgcgccc tgtagcggcg cattaagcgc ggcgggtgtg tggttacgc gcagcgtgac        480 cgctacactt gccagcgccc tagcgcccgc tcctttcgct ttcttccctt cctttctcgc       540
cacgttcgcc ggctttcccc gtcaagctct aaatcggggg ctccctttag ggttccgatt      600
tagtgcttta cggcacctcg accccaaaaa acttgattag ggtgatggtt cacgtagtgg       660
gccatcgccc tgatagacgg ttttttcgccc tttgacgttg gagtccacgt tctttaatag      720
tggactcttg ttccaaactg gaacaacact caaccctatc tcggtctatt cttttgattt      780
ataagggatt ttgccgattt cggcctattg gttaaaaaat gagctgattt aacaaaaatt       840
taacgcgaat tttaacaaaa tattaacgtt tacaatttaa atatttgctt atacaatctt       900
cctgtttttg ggcttttct gattatcaac cggggtacat atgattgaca tgctagtttt      960
acgattaccg ttcatcgcct gcactgcgcg ctcgctcgct cactgaggcc gcccgggcaa      1020
agcccgggcg tcgggcgacc tttggtcgcc cggcctcagt gagcgagcga gcgcgcagag      1080
agggagtgga attcacgcgt ggtacgatct gaattcggta caattcacgc gtggtacggc      1140
cgcggtaccg gcgcgccggg ggaggctgct ggtgaatatt aaccaaggtc accccagtta      1200
tcggaggagc aaacagggc taagtccaca cgcgtggtac cgtctgtctg cacatttcgt      1260
agagcgagtg ttccgatact ctaatctccc taggcaaggt tcatatttgt gtaggttact      1320
tattctcctt tgttgactaa agtcaataat cagaatcagc aggtttggag tcagcttggc      1380
agggatcagc agcctgggtt ggaaggaggg ggtataaaag ccccttcacc aggagaagcc      1440
gtcacacaga tccacaagct cctgaagagg taagggttta agggatggtt ggttggtggg      1500
gtattaatgt ttaattacct ggagcacctg cctgaaatca cttttttttca ggttggctag      1560 catgcagcgc gtgaacatga tcatggccga gagccccggc ctgatcacca tctgcctgct      1620
gggctacctg ctgagcgccg agtgcaccgt gttcctggac cacgagaacg ccaacaagat      1680
```

```
cctgaaccgc cccaagcgct acaacagcgg caagctggag gagttcgtgc agggcaacct   1740
ggagcgcgag tgcatggagg agaagtgcag cttcgaggag gcccgcgagg tgttcgagaa   1800
caccgagcgc accaccgagt tctggaagca gtacgtggac ggcgaccagt gcgagagcaa   1860
cccctgcctg aacggcggca gctgcaagga cgacatcaac agctacgagt gctggtgccc   1920
cttcggcttc gagggcaaga actgcgagct ggacgtgacc tgcaacatca agaacggccg   1980
ctgcgagcag ttctgcaaga acagcgccga caacaaggtg gtgtgcagct gcaccgaggg   2040
ctaccgcctg gccgagaacc agaagagctg cgagcccgcc gtgcccttcc cctgcggccg   2100
cgtgagcgtg agccagacca gcaagctgac ccgcgccgag gccgtgttcc ccgacgtgga   2160
ctacgtgaac agcaccgagg ccgagaccat cctggacaac atcacccaga gcacccagag   2220
cttcaacgac ttcacccgcg tggtgggcgg cgaggacgcc aagcccggcc agttcccctg   2280
gcaggtggtg ctgaacggca aggtggacgc cttctgcggc ggcagcatcg tgaacgagaa   2340
gtggatcgtg accgccgccc actgcgtgga gaccggcgtg aagatcaccg tggtggccgg   2400
cgagcacaac atcgaggaga ccgagcacac cgagcagaag cgcaacgtga tccgcatcat   2460 ccccccaccac aactacaacg ccgccatcaa caagtacaac cacgacatcg ccctgctgga   2520
gctggacgag ccccctggtgc tgaacagcta cgtgacccc atctgcatcg ccgacaagga   2580
gtacaccaac atcttcctga agttcggcag cggctacgtg agcggctggg gccgcgtgtt   2640
ccacaagggc cgcagcgccc tggtgctgca gtacctgcgc gtgcccctgg tggaccgcgc   2700
cacctgcctg ctgagcacca agttcaccat ctacaacaac atgttctgcg ccggcttcca   2760
cgagggcggc cgcgacagct gccagggcga cagcggcggc ccccacgtga ccgaggtgga   2820
gggcaccagc ttcctgaccg gcatcatcag ctggggcgag gagtgcgcca tgaagggcaa   2880
gtacggcatc tacaccaagg tgagccgcta cgtgaactgg atcaaggaga agaccaagct   2940
gacctggaga tctgatcagc ctcgactgtg ccttctagtt gccagccatc tgttgtttgc   3000
ccctcccccg tgccttcctt gaccctggaa ggtgccactc ccactgtcct ttcctaataa   3060
aatgaggaaa ttgcatcgca ttgtctgagt aggtgtcatt ctattctggg gggtggggtg   3120
gggcaggaca gcaaggggga ggattgggaa gacaatagca ggcatgctgg ggatctgata   3180
gcaggcatgc tggggagaga tcgatctagg aaccccctagt gatggagttg ccactccct   3240 ctctgcgcgc tcgctcgctc actgaggccg cccgggcaaa gcccgggcgt cgggcgacct   3300
ttggtcgccc ggcctcagtg agcgagcgag cgcgcagaga gggagtggcc aaccccccc   3360 ccccccccc tgcatgcagg cgattctctt gtttgctcca gactctcagg caatgacctg   3420
atagcctttg tagagacctc tcaaaaatag ctaccctctc cggcatgaat ttatcagcta   3480
gaacggttga atatcatatt gatggtgatt tgactgtctc cggcctttct cacccgtttg   3540
aatctttacc tacacattac tcaggcattg catttaaaat atatgagggt tctaaaaatt   3600
tttatccttg cgttgaaata aaggcttctc ccgcaaaagt attacagggt cataatgttt   3660
ttggtacaac cgatttagct ttatgctctg aggctttatt gcttaatttt gctaattctt   3720
tgccttgcct gtatgattta ttggatgttg gaattcctga tgcggtattt tctccttacg   3780
catctgtgcg gtatttcaca ccgcatatgg tgcactctca gtacaatctg ctctgatgcc   3840
gcatagttaa gccagccccg acacccgcca acacccgctg acgcgccctg acgggcttgt   3900
ctgctcccgg catccgctta cagacaagct gtgaccgtct ccgggagctg catgtgtcag   3960
aggttttcac cgtcatcacc gaaacgcgcg agacgaaagg gcctcgtgat acgcctattt   4020
ttataggtta atgtcatgat aataatggtt tcttagacgt caggtggcac ttttcgggga   4080
```

-continued

```
aatgtgcgcg gaaccccctat ttgtttattt ttctaaatac attcaaatat gtatccgctc    4140
atgagacaat aaccctgata aatgcttcaa taatattgaa aaaggaagag tatgagtatt    4200
caacatttcc gtgtcgccct tattcccttt tttgcggcat tttgccttcc tgtttttgct    4260
cacccagaaa cgctggtgaa agtaaaagat gctgaagatc agttgggtgc acagtgggt    4320 tacatcgaac tggatctcaa cagcggtaag atccttgaga gttttcgccc cgaagaacgt    4380
tttccaatga tgagcacttt taaagttctg ctatgtggcg cggtattatc ccgtattgac    4440
gccgggcaag agcaactcgg tcgccgcata cactattctc agaatgactt ggttgagtac    4500
tcaccagtca cagaaaagca tcttacggat ggcatgacag taagagaatt atgcagtgct    4560
gccataacca tgagtgataa cactgcggcc aacttacttc tgacaacgat cggaggaccg    4620
aaggagctaa ccgcttttt gcacaacatg ggggatcatg taactcgcct tgatcgttgg    4680
gaaccggagc tgaatgaagc cataccaaac gacgagcgtg acaccacgat gcctgtagca    4740
atggcaacaa cgttgcgcaa actattaact ggcgaactac ttactctagc ttcccggcaa    4800
caattaatag actggatgga ggcggataaa gttgcaggac cacttctgcg ctcggccctt    4860
ccggctggct ggtttattgc tgataaatct ggagccggtg agcgtgggtc tcgcggtatc    4920
attgcagcac tggggccaga tggtaagccc tcccgtatcg tagttatcta cacgacgggg    4980
agtcaggcaa ctatggatga acgaaataga cagatcgctg agataggtgc ctcactgatt    5040
aagcattggt aactgtcaga ccaagtttac tcatatatac tttagattga tttaaaactt    5100
catttttaat ttaaaaggat ctaggtgaag atccttttg ataatctcat gaccaaaatc    5160
ccttaacgtg agttttcgtt ccactgagcg tcagaccccg tagaaaagat caaaggatct    5220
tcttgagatc cttttttct gcgcgtaatc tgctgcttgc aaacaaaaaa accaccgcta    5280
ccagcggtgg tttgtttgcc ggatcaagag ctaccaactc ttttccgaa ggtaactggc    5340 ttcagcagag cgcagatacc aaatactgtc cttctagtgt agccgtagtt aggccaccac    5400
ttcaagaact ctgtagcacc gcctacatac ctcgctctgc taatcctgtt accagtggct    5460
gctgccagtg gcgataagtc gtgtcttacc gggttggact caagacgata gttaccggat    5520
aaggcgcagc ggtcgggctg aacggggggt tcgtgcacac agcccagctt ggagcgaacg    5580
acctacaccg aactgagata cctacagcgt gagctatgag aaagcgccac gcttcccgaa    5640
gggagaaagg cggacaggta tccggtaagc ggcagggtcg aacaggaga gcgcacgagg    5700 gagcttccag ggggaaacgc ctggtatctt tatagtcctg tcgggtttcg ccacctctga    5760
cttgagcgtc gatttttgtg atgctcgtca ggggggcgga gcctatggaa aaacgccagc    5820
aacgcggcct ttttacggtt cctggccttt tgctggcctt ttgctcacat gttctttcct    5880
gcgttatccc ctgattctgt ggataaccgt attaccgcct ttgagtgagc tgataccgct    5940
cgccgcagcc gaacgaccga gcgcagcgag tcagtgagcg aggaagcgga agagcgccca    6000
atacgcaaac cgcctctccc cgcgcgttgg ccgattcatt aatg                    6044
```

<210> SEQ ID NO 3
<211> LENGTH: 20
<212> TYPE: DNA
<213> ORGANISM: Artificial
<220> FEATURE:
<223> OTHER INFORMATION: primer

<400> SEQUENCE: 3
gccttctagt tgccagccat                                                  20

<210> SEQ ID NO 4
<211> LENGTH: 20
<212> TYPE: DNA
<213> ORGANISM: Artificial
<220> FEATURE:
<223> OTHER INFORMATION: probe

<400> SEQUENCE: 4
tgtttgcccc tcccccgtgc                                                     20

<210> SEQ ID NO 5
<211> LENGTH: 19
<212> TYPE: DNA
<213> ORGANISM: Artificial
<220> FEATURE:
<223> OTHER INFORMATION: primer

<400> SEQUENCE: 5
ggcaccttcc agggtcaag                                                      19

<210> SEQ ID NO 6
<211> LENGTH: 7849
<212> TYPE: DNA
<213> ORGANISM: Artificial
<220> FEATURE:
<223> OTHER INFORMATION: Adenoviral expression vector
      AAVss-SerpEnh-TTRm-MVM-hFVIIIcopt-sv40pA
<220> FEATURE:
<221> NAME/KEY: misc_feature
<222> LOCATION: (508)..(508)
<223> OTHER INFORMATION: n is a, c, g, or t

<400> SEQUENCE: 6
cctgcaggca gctgcgcgct cgctcgctca ctgaggccgc ccgggcaaag cccgggcgtc         60
gggcgacctt tggtcgcccg gcctcagtga gcgagcgagc gcgcagagag ggagtggcca       120
actccatcac taggggttcc tgcggccgcg gtaccggcgc gccggggag gctgctggtg        180 aatattaacc aaggtcaccc cagtatcgg aggagcaaac aggggctaag tccacacgcg        240
tggtaccgtc tgtctgcaca tttcgtagag cgagtgttcc gatactctaa tctccctagg       300
caaggttcat atttgtgtag gttacttatt ctccttttgt tgactaagtc aataatcaga       360
atcagcaggt ttggagtcag cttggcaggg atcagcagcc tgggttggaa ggaggggta        420 taaaagcccc ttcaccagga gaagccgtca cacagatcca caagctcctg aagaggtaag       480
ggtttaaggg atggttggtt ggtggggnat taatgtttaa ttacctggag cacctgcctg       540
aaatcacttt ttttcaggtt ggctagtatg cagatcgagc tgtccacctg ctttttctg       600 tgcctgctgc ggttctgctt cagcgccacc cggcggtact acctgggcgc cgtggagctg       660
tcctgggact acatgcagag cgacctgggc gagctgcccg tggacgcccg gttccccccc       720
agagtgccca gagcttccc cttcaacacc agcgtggtgt acaagaaaac cctgttcgtg        780
gagttcaccg accacctgtt caatatcgcc aagcccaggc ccccctggat gggcctgctg       840
ggccccacca tccaggccga ggtgtacgac accgtggtga tcaccctgaa gaacatggcc       900 agccacccg tgagcctgca cgccgtgggc gtgagctact ggaaggccag cgagggcgcc        960
gagtacgacg accagaccag ccagcgggag aaagaagatg acaaggtgtt ccctggcggc      1020
agccacacct acgtgtggca ggtgctgaaa gaaaacggcc ccatggcctc cgacccctg       1080 tgcctgacct acagctacct gagccacgtg gacctggtga aggacctgaa cagcggcctg      1140
atcggcgctc tgctcgtctg ccggggaggc agcctggcca agagaaaac ccagaccctg       1200 cacaagttca tcctgctgtt cgccgtgttc gacgagggca agagctggca cagcgagaca      1260

```
aagaacagcc tgatgcagga ccgggacgcc gcctctgcca gagcctggcc caagatgcac    1320
accgtgaacg gctacgtgaa cagaagcctg cccggcctga ttggctgcca ccggaagagc    1380
gtgtactggc acgtgatcgg catgggcacc acacccgagg tgcacagcat ctttctggaa    1440
gggcacacct ttctggtccg gaaccaccgg caggccagcc tggaaatcag ccctatcacc    1500
ttcctgaccg cccagacact gctgatggac ctgggccagt cctgctgtt ttgccacatc    1560 agctctcacc agcacgacgg catggaagcc tacgtgaagg tggactcttg ccccgaggaa    1620
ccccagctgc ggatgaagaa caacgaggaa gccgaggact acgacgacga cctgaccgac    1680
agcgagatgg acgtggtgcg gttcgacgac gacaacagcc ccagcttcat ccagatcaga    1740
agcgtggcca agaagcaccc caagacctgg gtgcactata tcgccgccga ggaagaggac    1800
tgggactacg ccccccctggt gctgccccc gacgacagaa gctacaagag ccagtacctg    1860
aacaatggcc cccagcggat cggccggaag tacaagaaag tgcggttcat ggcctacacc    1920
gacgagacat tcaagacccg ggaggccatc cagcacgaga gcggcatcct gggccccctg    1980
ctgtacggcg aagtgggcga cacactgctg atcatcttca agaaccaggc tagccggccc    2040
tacaacatct accccacgg catcaccgac gtgcggcccc tgtacagcag gcggctgccc    2100
aagggcgtga agcacctgaa ggacttcccc atcctgcccg gcgagatctt caagtacaag    2160
tggaccgtga ccgtggagga cggccccacc aagagcgacc ccagatgcct gacccggtac    2220
tacagcagct tcgtgaacat ggaacgggac ctggcctccg gctgatcgg acctctgctg    2280 atctgctaca agaaagcgt ggaccagcgg ggcaaccaga tcatgagcga caagcggaac    2340
gtgatcctgt tcagcgtgtt cgatgagaac cggtcctggt atctgaccga aacatccag    2400 cggtttctgc ccaaccctgc cggcgtgcag ctggaagatc ccgagttcca ggccagcaac    2460
atcatgcact ccatcaatgg ctacgtgttc gactctctgc agctcccgt gtgtctgcac    2520 gaggtggcct actggtacat cctgagcatc ggcgcccaga ccgacttcct gagcgtgttc    2580
ttcagcggct acaccttcaa gcacaagatg gtgtacgagg acaccctgac cctgttccct    2640
ttcagcggcg agacagtgtt catgagcatg aaaaaccccg gcctgtggat tctgggctgc    2700
cacaacagcg acttccggaa ccggggcatg accgccctgc tgaaggtgtc cagctgcgac    2760
aagaacaccg gcgactacta cgaggacagc tacgaggata tcagcgccta cctgctgtcc    2820
aagaacaacg ccatcgaacc ccggagcttc agccagaacc ccccgtgct gacgcgtcac    2880 cagcgggaga tcacccggac aaccctgcag tccgaccagg aagagatcga ttacgacgac    2940
accatcagcg tggagatgaa gaaagaggat ttcgatatct acgacgagga cgagaaccag    3000
agccccagaa gcttccagaa gaaaacccgg cactacttca ttgccgccgt ggagaggctg    3060
tgggactacg gcatgagttc tagccccac gtgctgcgga accgggccca gagcggcagc    3120
gtgccccagt tcaagaaagt ggtgttccag gaattcacag acggcagctt cacccagcct    3180
ctgtatagag cgagctgaa cgagcacctg gggctgctgg ggcctacat cagggccgaa    3240 gtggaggaca acatcatggt gaccttccgg aatcaggcca gcagaccta ctccttctac    3300 agcagcctga tcagctacga agaggaccag cggcagggcg ccgaacccg gaagaacttc    3360 gtgaagccca acgaaaccaa gacctacttc tggaaagtgc agcaccacat ggccccacc    3420 aaggacgagt tcgactgcaa ggcctgggcc tacttcagcg acgtggatct ggaaaaggac    3480
gtgcactctg gactgattgg cccactcctg gtctgccaca ctaacaccct caaccccgcc    3540 cacgccgcc aggtgaccgt gcaggaattc gccctgttct tcaccatctt cgacgagaca    3600
aagtcctggt acttcaccga gaatatggaa cggaactgca gagccccctg caacatccag    3660
```

```
atggaagatc ctaccttcaa agagaactac cggttccacg ccatcaacgg ctacatcatg   3720
gacaccctgc ctggcctggt gatggcccag gaccagagaa tccggtggta tctgctgtcc   3780
atgggcagca acgagaatat ccacagcatc cacttcagcg ccacgtgtt caccgtgcgg   3840
aagaaagaag agtacaagat ggccctgtac aacctgtacc ccggcgtgtt cgagacagtg   3900
gagatgctgc ccagcaaggc cggcatctgg cgggtggagt gtctgatcgg cgagcacctg   3960
cacgctggca tgagcaccct gtttctggtg tacagcaaca agtgccagac cccactgggc   4020
atggcctctg ccacatccg ggacttccag atcaccgcct ccggccagta cggccagtgg   4080
gccccaagc tggccagact gcactacagc ggcagcatca cgcctggtc caccaaagag   4140
cccttcagct ggatcaaggt ggacctgctg gccctatga tcatccacgg cattaagacc   4200
cagggcgcca gcagaagtt cagcagcctg tacatcagcc agttcatcat catgtacagc   4260
ctggacggca agaagtggca gacctaccgg ggcaacagca ccggcaccct gatggtgttc   4320
ttcggcaatg tggacagcag cggcatcaag cacaacatct tcaacccccc catcattgcc   4380
cggtacatcc ggctgcaccc cacccactac agcattgagt ccacactgag aatggaactg   4440
atgggctgcg acctgaactc ctgcagcatg cctctgggca tggaaagcaa ggccatcagc   4500
gacgcccaga tcacagccag cagctacttc accaacatgt cgccacctg gtccccctcc   4560
aaggccaggc tgcacctgca gggcggtcc aacgcctggc ggcctcaggt caacaacccc   4620
aaagaatggc tgcaggtgga ctttcagaaa ccatgaagg tgaccggcgt gaccacccag   4680
ggcgtgaaaa gcctgctgac cagcatgtac gtgaaagagt ttctgatcag cagctctcag   4740
gatgccacc agtggaccct gttctttcag aacggcaagg tgaaagtgtt ccagggcaac   4800
caggactcct tcaccccgt ggtgaactcc ctggaccccc cctgctgac ccgctacctg   4860
agaatccacc cccagtcttg ggtgcaccag atcgccctca ggatggaagt cctgggatgt   4920
gaggcccagg atctgtactg atgaggatct aggctcgaca tgctttattt gtgaaatttg   4980
tgatgctatt gctttatttg taaccattat aagctgcaat aaacaagtta caacaacaa   5040
ttgcattcat tttatgtttc aggttcaggg ggaggtgtgg gaggttttt aaactcgaga   5100
tccacggccg caggaacccc tagtgatgga gttggccact ccctctctgc gcgctcgctc   5160
gctcactgag gccgggcgac caaaggtcgc ccgacgcccg ggctttgccc gggcggcctc   5220
agtgagcgag cgagcgcgca gctgcctgca ggggcgcctg atgcggtatt ttctccttac   5280
gcatctgtgc ggtatttcac accgcatacg tcaaagcaac catagtacgc gccctgtagc   5340
ggcgcattaa gcgcggcggg tgtggtggtt acgcgcagcg tgaccgctac acttgccagc   5400
gccctagcgc ccgctccttt cgctttcttc ccttccttc tcgccacgtt cgccggcttt   5460
ccccgtcaag ctctaaatcg ggggctccct ttagggttcc gatttagtgc tttacggcac   5520
ctcgacccca aaaaacttga tttgggtgat ggttcacgta gtgggccatc gccctgatag   5580
acggttttc gccctttgac gttggagtcc acgttcttta atagtggact cttgttccaa   5640
actggaacaa cactcaaccc tatctcgggc tattcttttg atttataagg gattttgccg   5700
atttcggcct attggttaaa aaatgagctg atttaacaaa aatttaacgc gaattttaac   5760
aaaatattaa cgtttacaat tttatggtgc actctcagta caatctgctc tgatgccgca   5820
tagttaagcc agccccgaca cccgccaaca cccgctgacg cgccctgacg gcttgtctg   5880
ctcccggcat ccgcttacag acaagctgtg accgtctccg ggagctgcat gtgtcagagg   5940
ttttcaccgt catcaccgaa acgcgcgaga cgaaagggcc tcgtgatacg cctatttta   6000
taggttaatg tcatgataat aatggtttct tagacgtcag gtggcacttt tcggggaaat   6060
```

```
gtgcgcggaa cccctatttg tttattttc taaatacatt caaatatgta tccgctcatg    6120
agacaataac cctgataaat gcttcaataa tattgaaaaa ggaagagtat gagtattcaa    6180
catttccgtg tcgcccttat tcccttttt gcggcatttt gccttcctgt ttttgctcac    6240
ccagaaacgc tggtgaaagt aaaagatgct gaagatcagt tgggtgcacg agtgggttac    6300
atcgaactgg atctcaacag cggtaagatc cttgagagtt ttcgccccga gaacgtttt    6360
ccaatgatga gcacttttaa agttctgcta tgtggcgcgg tattatcccg tattgacgcc    6420
gggcaagagc aactcggtcg ccgcatacac tattctcaga atgacttggt tgagtactca    6480
ccagtcacag aaaagcatct tacggatggc atgacagtaa gagaattatg cagtgctgcc    6540
ataaccatga gtgataacac tgcggccaac ttacttctga acgatcgg aggaccgaag    6600
gagctaaccg cttttttgca acatgggga tcatgtaa ctcgccttga tcgttgggaa    6660
ccggagctga atgaagccat accaaacgac gagcgtgaca ccacgatgcc tgtagcaatg    6720
gcaacaacgt tgcgcaaact attaactggc gaactactta ctctagcttc ccggcaacaa    6780
ttaatagact ggatggaggc ggataaagtt gcaggaccac ttctgcgctc ggcccttccg    6840
gctggctggt ttattgctga taaatctgga gccggtgagc gtgggtctcg cggtatcatt    6900
gcagcactgg ggccagatgg taagccctcc cgtatcgtag ttatctacac gacggggagt    6960
caggcaacta tggatgaacg aaatagacag atcgctgaga taggtgcctc actgattaag    7020
cattggtaac tgtcagacca agtttactca tatatacttt agattgattt aaaacttcat    7080
ttttaattta aaaggatcta ggtgaagatc ctttttgata atctcatgac caaaatccct    7140
taacgtgagt tttcgttcca ctgagcgtca ccccgtag aaaagatcaa aggatcttct    7200
tgagatcctt ttttctgcg cgtaatctgc tgcttgcaaa caaaaaaacc accgctacca    7260
gcggtggttt gtttgccgga tcaagagcta ccaactcttt ttccgaaggt aactggcttc    7320
agcagagcgc agataccaaa tactgtcctt ctagtgtagc cgtagttagg ccaccacttc    7380
aagaactctg tagcaccgcc tacatacctc gctctgctaa tcctgttacc agtggctgct    7440
gccagtggcg ataagtcgtg tcttaccggg ttggactcaa gacgatagtt accggataag    7500
gcgcagcggt cgggctgaac ggggggttcg tgcacacagc ccagcttgga gcgaacgacc    7560
tacaccgaac tgagatacct acagcgtgag ctatgagaaa gcgccacgct tcccgaaggg    7620
agaaaggcgg acaggtatcc ggtaagcggc agggtcggaa caggagagcg cacgagggag    7680
cttccagggg gaaacgcctg gtatctttat agtcctgtcg ggtttcgcca cctctgactt    7740
gagcgtcgat ttttgtgatg ctcgtcaggg gggcggagcc tatggaaaaa cgccagcaac    7800
gcggcctttt tacggttcct ggccttttgc tggccttttg ctcacatgt                7849
```

<210> SEQ ID NO 7
<211> LENGTH: 4377
<212> TYPE: DNA
<213> ORGANISM: Artificial
<220> FEATURE:
<223> OTHER INFORMATION: Codon-optimized B domain deleted human
      coagulation factor VIII (hFVIIIcopt)

<400> SEQUENCE: 7

```
atgcagatcg agctgtccac ctgctttttt ctgtgcctgc tgcggttctg cttcagcgcc      60
acccggcggt actacctggg cgccgtggag ctgtcctggg actacatgca gagcgacctg     120
ggcgagctgc ccgtgacgc ccggttcccc ccagagtgc caagagctt cccttcaac       180
accagcgtgg tgtacaagaa aaccctgttc gtggagttca ccgaccacct gttcaatatc     240
```

| | |
|---|---|
| gccaagccca ggccccctg gatgggcctg ctgggcccca ccatccaggc cgaggtgtac | 300 |
| gacaccgtgg tgatcaccct gaagaacatg gccagccacc ccgtgagcct gcacgccgtg | 360 |
| ggcgtgagct actggaaggc cagcgagggc gccgagtacg acgaccagac cagccagcgg | 420 |
| gagaaagaag atgacaaggt gttccctggc ggcagccaca cctacgtgtg gcaggtgctg | 480 |
| aaagaaaacg gccccatggc ctccgacccc ctgtgcctga cctacagcta cctgagccac | 540 |
| gtggacctgg tgaaggacct gaacagcggc ctgatcggcg ctctgctcgt ctgccgggag | 600 |
| ggcagcctgg ccaaagagaa acccagacc ctgcacaagt tcatcctgct gttcgccgtg | 660 |
| ttcgacgagg gcaagagctg gcacagcgag acaaagaaca gcctgatgca ggaccgggac | 720 |
| gccgcctctg ccagagcctg gcccaagatg cacaccgtga acggctacgt gaacagaagc | 780 |
| ctgcccggcc tgattggctg ccaccggaag agcgtgtact ggcacgtgat cggcatgggc | 840 |
| accacacccg aggtgcacag catctttctg aagggcaca cctttctggt ccggaaccac | 900 |
| cggcaggcca gcctggaaat cagccctatc accttcctga ccgcccagac actgctgatg | 960 |
| gacctgggcc agttcctgct gttttgccac atcagctctc accagcacga cggcatggaa | 1020 |
| gcctacgtga aggtggactc ttgccccgag aaccccagc tgcggatgaa gaacaacgag | 1080 |
| gaagccgagg actacgacga cgacctgacc gacagcgaga tggacgtggt gcggttcgac | 1140 |
| gacgacaaca gccccagctt catccagatc agaagcgtgg ccaagaagca ccccaagacc | 1200 |
| tgggtgcact atatcgccgc cgaggaagag gactgggact acgccccct ggtgctggcc | 1260 |
| cccgacgaca gaagctacaa gagccagtac ctgaacaatg gcccccagcg gatcggccgg | 1320 |
| aagtacaaga agtgcggtt catggcctac accgacgaga cattcaagac ccgggaggcc | 1380 |
| atccagcacg agagcggcat cctgggcccc ctgctgtacg gcgaagtggg cgacacactg | 1440 |
| ctgatcatct tcaagaacca ggctagccgg ccctacaaca tctaccccca cggcatcacc | 1500 |
| gacgtgcggc ccctgtacag caggcggctg cccaagggcg tgaagcacct gaaggacttc | 1560 |
| cccatcctgc ccggcgagat cttcaagtac aagtggaccg tgaccgtgga ggacggcccc | 1620 |
| accaagagcg accccagatg cctgacccgg tactacagca gcttcgtgaa catggaacgg | 1680 |
| gacctggcct ccgggctgat cggacctctg ctgatctgct acaaagaaag cgtggaccag | 1740 |
| cggggcaacc agatcatgag cgacaagcgg aacgtgatcc tgttcagcgt gttcgatgag | 1800 |
| aaccggtcct ggtatctgac cgagaacatc cagcggtttc tgcccaaccc tgccggcgtg | 1860 |
| cagctggaag atcccgagtt ccaggccagc aacatcatgc actccatcaa tggctacgtg | 1920 |
| ttcgactctc tgcagctctc cgtgtgtctg cacgaggtgg cctactggta tatcctgagc | 1980 |
| atcggcgccc agaccgactt cctgagcgtg ttcttcagcg gctacacctt caagcacaag | 2040 |
| atggtgtacg aggacaccct gaccctgttc cctttcagcg gcgagacagt gttcatgagc | 2100 |
| atggaaaacc ccggcctgtg gattctgggc tgccacaaca gcgacttccg gaaccggggc | 2160 |
| atgaccgccc tgctgaaggt gtccagctgc gacaagaaca ccggcgacta ctacgaggac | 2220 |
| agctacgagg atatcagcgc ctacctgctg tccaagaaca cgccatcga accccggagc | 2280 |
| ttcagccaga accccccgt gctgacgcgt caccagcggg agatcacccg gacaaccctg | 2340 |
| cagtccgacc aggaagagat cgattacgac gacaccatca gcgtggagat gaagaaagag | 2400 |
| gatttcgata tctacgacga ggacgagaac cagagcccca aagcttcca agaaaaacc | 2460 |
| cggcactact tcattgccgc cgtggagagg ctgtgggact acggcatgag ttctagcccc | 2520 |
| cacgtgctgc ggaaccgggc ccagagcggc agcgtgcccc agttcaagaa agtggtgttc | 2580 |
| caggaattca cagacggcag cttcacccag cctctgtata gaggcgagct gaacgagcac | 2640 |

```
ctggggctgc tggggcccta catcagggcc gaagtggagg acaacatcat ggtgaccttc    2700
cggaatcagg ccagcagacc ctactccttc tacagcagcc tgatcagcta cgaagaggac    2760
cagcggcagg gcgccgaacc ccggaagaac ttcgtgaagc ccaacgaaac caagacctac    2820
ttctggaaag tgcagcacca catggccccc accaaggacg agttcgactg caaggcctgg    2880
gcctacttca gcgacgtgga tctggaaaag gacgtgcact ctggactgat tggcccactc    2940
ctggtctgcc acactaacac cctcaacccc gcccacggcc gccaggtgac cgtgcaggaa    3000
ttcgccctgt tcttcaccat cttcgacgag acaaagtcct ggtacttcac cgagaatatg    3060
gaacggaact gcagagcccc ctgcaacatc cagatggaag atcctacctt caaagagaac    3120
taccggttcc acgccatcaa cggctacatc atggacaccc tgcctggcct ggtgatggcc    3180
caggaccaga gaatccggtg gtatctgctg tccatgggca gcaacgagaa tatccacagc    3240
atccacttca gcggccacgt gttcaccgtg cggaagaaag aagagtacaa gatggccctg    3300
tacaacctgt accccggcgt gttcgagaca gtggagatgc tgcccagcaa ggccggcatc    3360
tggcgggtgg agtgtctgat cggcgagcac ctgcacgctg gcatgagcac cctgtttctg    3420
gtgtacagca acaagtgcca gaccccactg ggcatggcct ctggccacat ccgggacttc    3480
cagatcaccg cctccggcca gtacggccag tgggcccca agctggccag actgcactac    3540
agcggcagca tcaacgcctg gtccaccaaa gagcccttca gctggatcaa ggtggacctg    3600
ctggccccta tgatcatcca cggcattaag acccagggcg ccaggcagaa gttcagcagc    3660
ctgtacatca gccagttcat catcatgtac agcctggacg gcaagaagtg gcagacctac    3720
cggggcaaca gcaccggcac cctgatggtg ttcttcggca atgtggacag cagcggcatc    3780
aagcacaaca tcttcaaccc ccccatcatt gcccggtaca tccggctgca ccccacccac    3840
tacagcatta atccacact gagaatggaa ctgatgggct cgacctgaa ctcctgcagc    3900 atgcctctgg gcatggaaag caaggccatc agcgacgccc agatcacagc cagcagctac    3960
ttcaccaaca tgttcgccac ctggtccccc tccaaggcca ggctgcacct gcagggccgg    4020
tccaacgcct ggcggcctca ggtcaacaac cccaaagaat ggctgcaggt ggactttcag    4080
aaaaccatga aggtgaccgg cgtgaccacc cagggcgtga aaagcctgct gaccagcatg    4140
tacgtgaaag agtttctgat cagcagctct caggatggcc accagtggac cctgttcttt    4200
cagaacggca aggtgaaagt gttccagggc aaccaggact ccttcacccc cgtggtgaac    4260
tccctggacc ccccctgct gacccgctac ctgagaatcc accccagtc ttgggtgcac    4320 cagatcgccc tcaggatgga agtcctggga tgtgaggccc aggatctgta ctgatga      4377
```

<210> SEQ ID NO 8
<211> LENGTH: 72
<212> TYPE: DNA
<213> ORGANISM: Artificial
<220> FEATURE:
<223> OTHER INFORMATION: Serpin enhancer (SerpEnh)

<400> SEQUENCE: 8

```
gggggaggct gctggtgaat attaaccaag gtcaccccag ttatcggagg agcaaacagg    60
ggctaagtcc ac                                                        72
```

<210> SEQ ID NO 9
<211> LENGTH: 202
<212> TYPE: DNA
<213> ORGANISM: Artificial
<220> FEATURE:
<223> OTHER INFORMATION: Minimal transthyretin promoter (TTRm)

<400> SEQUENCE: 9

| gtctgtctgc acatttcgta gagcgagtgt tccgatactc taatctccct aggcaaggtt | 60 |
| catatttgtg taggttactt attctccttt tgttgactaa gtcaataatc agaatcagca | 120 |
| ggtttggagt cagcttggca gggatcagca gcctgggttg aaggaggggg gtataaaagc | 180 |
| cccttcacca ggagaagccg tc | 202 |

<210> SEQ ID NO 10
<211> LENGTH: 92
<212> TYPE: DNA
<213> ORGANISM: Artificial
<220> FEATURE:
<223> OTHER INFORMATION: Minute virus mouse (MVM) intron
<220> FEATURE:
<221> NAME/KEY: misc_feature
<222> LOCATION: (38)..(38)
<223> OTHER INFORMATION: n is a, c, g, or t

<400> SEQUENCE: 10

| aagaggtaag ggtttaaggg atggttggtt ggtggggnat taatgtttaa ttacctggag | 60 |
| cacctgcctg aaatcacttt ttttcaggtt gg | 92 |

<210> SEQ ID NO 11
<211> LENGTH: 134
<212> TYPE: DNA
<213> ORGANISM: Artificial
<220> FEATURE:
<223> OTHER INFORMATION: Simian virus 40 (SV40) polyadenylation signal (pA)

<400> SEQUENCE: 11

| atgctttatt tgtgaaattt gtgatgctat tgctttattt gtaaccatta taagctgcaa | 60 |
| taaacaagtt aacaacaaca attgcattca ttttatgttt caggttcagg ggaggtgtg | 120 |
| ggaggttttt taaa | 134 |

<210> SEQ ID NO 12
<211> LENGTH: 7653
<212> TYPE: DNA
<213> ORGANISM: Artificial
<220> FEATURE:
<223> OTHER INFORMATION: pcDNA3_mouseCO_hyPiggyBac_Transposase_MT plasmid

<400> SEQUENCE: 12

| gacggatcgg gagatctccc gatcccctat ggtcgactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg cgtggagcta gttattaata gtaatcaatt | 240 |
| acggggtcat tagttcatag cccatatatg gagttccgcg ttacataact tacggtaaat | 300 |
| ggcccgcctg gctgaccgcc caacgacccc cgcccattga cgtcaataat gacgtatgtt | 360 |
| cccatagtaa cgtcaatagg gactttccat tgacgtcaat gggtggagta tttacggtaa | 420 |
| actgcccact tggcagtaca tcaagtgtat catatgccaa gtacgccccc tattgacgtc | 480 |
| aatgacggta aatggcccgc ctggcattat gcccagtaca tgaccttatg gactttcct | 540 |
| acttggcagt acatctacgt attagtcatc gctattacca tggtgatgcg gttttggcag | 600 |
| tacatcaatg ggcgtggata gcggtttgac tcacggggat ttccaagtct ccaccccatt | 660 |
| gacgtcaatg ggagtttgtt ttggcaccaa aatcaacggg actttccaaa atgtcgtaac | 720 |

```
aactccgccc cattgacgca aatgggcggt aggcgtgtac ggtgggaggt ctatataagc    780
agagctcgtt tagtgaaccg tcagatcgcc tggagacgcc atccacgctg ttttgacctc    840
catagaagac accgggaccg atccagcctc cgcggattcg aatcccggcc gggaacggtg    900
cattggaacg cggattcccc gtgccaagag tgacgtaagt accgcctata gagtctatag    960
gcccacaaaa aatgctttct tcttttaata actttttttg tttatcttat ttctaatact   1020
ttccctaatc tctttctttc agggcaataa tgatacaatg tatcatgcct ctttgcacca   1080
ttctaaagaa taacagtgat aatttctggg ttaaggcaat agcaatattt ctgcatataa   1140
atatttctgc atataaattg taactgatgt aagaggtttc atattgctaa tagcagctac   1200
aatccagcta ccattctgct tttatttat ggttgggata aggctggatt attctgagtc    1260
caagctaggc cctttttgcta atcatgttca tacctcttat cttcctccca cagctcctgg   1320
gcaacgtgct ggtctgtgtg ctggcccatc actttggcaa agaattggga ttcgaacatc   1380
gatgccgcca ccatgggcag cagcctggac gacgagcaca tcctgagcgc cctgctgcag   1440
agcgacgacg agctggtcgg cgaggacagc gacagcgagt gagcgaccca cgtgagcgag   1500
gacgacgtgc agtccgacac cgaggaggcc ttcatcgacg aggtgcacga ggtgcagcct   1560
accagcagcg gctccgagat cctggacgag cagaacgtga tcgagcagcc cggcagctcc   1620
ctggccagca caggatcct gaccctgccc cagaggacca tcaggggcaa gaacaagcac    1680
tgctggtcca cctccaagcc caccaggcgg agcagggtgt ccgccctgaa catcgtgaga   1740
agccagaggg gccccaccag gatgtgcagg aacatctacg acccctgct gtgcttcaag    1800 ctgttcttca ccgacgagat catcagcgag atcgtgaagt ggaccaacgc cgagatcagc   1860
ctgaagaggc gggagagcat gaccagcgcc accttcaggg acaccaacga ggacgagatc   1920
tacgccttct tcggcatcct ggtgatgacc gccgtgagga aggacaacca catgagcacc   1980
gacgacctgt tcgacagatc cctgagcatg gtgtacgtga gcgtgatgag cagggacaga   2040
ttcgacttcc tgatcagatg cctgaggatg gacgacaaga gcatcaggcc cacccctgcgg   2100 gagaacgacg tgttcacccc cgtgagaaag atctgggacc tgttcatcca ccagtgcatc   2160
cagaactaca cccctggcgc ccacctgacc atcgacgagc agctgctggg cttcaggggc   2220
aggtgcccct tcagggtgta tatccccaac aagcccagca agtacggcat caagatcctg   2280
atgatgtgcg acagcggcac caagtacatg atcaacggca tgccctacct gggcaggggc   2340
acccagacca acggcgtgcc cctgggcgag tactacgtga aggagctgtc caagcccgtc   2400
cacggcagct gcagaaacat cacctgcgac aactggttca ccagcatccc cctggccaag   2460
aacctgctgc aggagcccta caagctgacc atcgtgggca ccgtgagaag caacaagaga   2520
gagatccccg aggtcctgaa gaacagcagg tccaggcccg tgggcaccag catgttctgc   2580
ttcgacggcc ccctgaccct ggtgtcctac aagcccaagc ccgccaagat ggtgtacctg   2640
ctgtccagct gcgacgagga cgccagcatc aacgagagca ccggcaagcc ccagatggtg   2700
atgtactaca accagaccaa gggcggcgtg gacaccctgg accagatgtg cagcgtgatg   2760
acctgcagca gaaagaccaa caggtggccc atggccctgc tgtacggcat gatcaacatc   2820
gcctgcatca cagcttcat catctacagc cacaacgtga gcagcaaggg cgagaaggtg    2880
cagagccgga aaaagttcat gcggaacctg tacatgggcc tgacctccag cttcatgagg   2940
aagaggctgg aggcccccac cctgaagaga tacctgaggg acaacatcag caacatcctg   3000
cccaaggagg tgcccggcac cagcgacgac agcaccgagg agcccgtgat gaagaagagg   3060
acctactgca cctactgtcc cagcaagatc agaagaaagg ccagcgccag ctgcaagaag   3120
```

-continued

```
tgtaagaagg tcatctgccg ggagcacaac atcgacatgt gccagagctg tttctgactc   3180
gagcatgcat ctagagggcc ctattctata gtgtcaccta aatgctagag ctcgctgatc   3240
agcctcgact gtgccttcta gttgccagcc atctgttgtt tgcccctccc ccgtgccttc   3300
cttgaccctg gaaggtgcca ctcccactgt cctttcctaa taaaatgagg aaattgcatc   3360
gcattgtctg agtaggtgtc attctattct gggggtgggg gtggggcagg acagcaaggg   3420
ggaggattgg gaagacaata gcaggcatgc tggggatgcg gtgggctcta tggcttctga   3480
ggcggaaaga accagctggg gctctagggg gtatccccac gcgccctgta gcggcgcatt   3540
aagcgcggcg ggtgtggtgg ttacgcgcag cgtgaccgct acacttgcca gcgccctagc   3600
gcccgctcct ttcgctttct tcccttcctt tctcgccacg ttcgccggct ttccccgtca   3660
agctctaaat cggggcatcc ctttagggtt ccgatttagt gctttacggc acctcgaccc   3720
caaaaaactt gattagggtg atggttcacg tagtgggcca tcgccctgat agacggtttt   3780
tcgccctttg acgttggagt ccacgttctt aatagtgga ctcttgttcc aaactggaac   3840
aacactcaac cctatctcgg tctattcttt tgatttataa gggattttgg ggatttcggc   3900
ctattggtta aaaaatgagc tgatttaaca aaaatttaac gcgaattaat tctgtggaat   3960
gtgtgtcagt tagggtgtgg aaagtcccca ggctccccag gcaggcagaa gtatgcaaag   4020
catgcatctc aattagtcag caaccaggtg tggaaagtcc ccaggctccc cagcaggcag   4080
aagtatgcaa agcatgcatc tcaattagtc agcaaccata gtcccgcccc taactccgcc   4140
catcccgccc ctaactccgc ccagttccgc ccattctccg ccccatggct gactaatttt   4200
ttttatttat gcagaggccg aggccgcctc tgcctctgag ctattccaga agtagtgagg   4260 aggcttttt ggaggcctag gcttttgcaa aaagctcccg ggagcttgta tatccatttt   4320
cggatctgat caagagacag gatgaggatc gtttcgcatg attgaacaag atggattgca   4380
cgcaggttct ccggccgctt gggtggagag gctattcggc tatgactggg cacaacagac   4440
aatcggctgc tctgatgccg ccgtgttccg gctgtcagcg caggggcgcc cggttctttt   4500
tgtcaagacc gacctgtccg gtgccctgaa tgaactgcag gacgaggcag cgcggctatc   4560
gtggctggcc acgacgggcg ttccttgcgc agctgtgctc gacgttgtca ctgaagcggg   4620
aagggactgg ctgctattgg gcgaagtgcc ggggcaggat ctcctgtcat ctcaccttgc   4680
tcctgccgag aaagtatcca tcatggctga tgcaatgcgg cggctgcata cgcttgatcc   4740
ggctacctgc ccattcgacc accaagcgaa acatcgcatc gagcgagcac gtactcggat   4800
ggaagccggt cttgtcgatc aggatgatct ggacgaagag catcaggggc tcgcgccagc   4860
cgaactgttc gccaggctca aggcgcgcat gcccgacggc gaggatctcg tcgtgaccca   4920
tggcgatgcc tgcttgccga atatcatggt ggaaaatggc cgcttttctg gattcatcga   4980
ctgtggccgg ctgggtgtgg cggaccgcta tcaggacata gcgttggcta cccgtgatat   5040
tgctgaagag cttggcggcg aatgggctga ccgcttcctc gtgctttacg gtatcgccgc   5100
tcccgattcg cagcgcatcg ccttctatcg ccttcttgac gagttcttct gagcgggact   5160
ctggggttcg aaatgaccga ccaagcgacg cccaacctgc catcacgaga tttcgattcc   5220
accgccgcct tctatgaaag gttggcttc ggaatcgttt tccgggacgc cggctggatg   5280
atcctccagc gcggggatct catgctggag ttcttcgccc accccaactt gtttattgca   5340
gcttataatg gttacaaata aagcaatagc atcacaaatt tcacaaataa agcatttttt   5400
tcactgcatt ctagttgtgg tttgtccaaa ctcatcaatg tatcttatca tgtctgtata   5460
ccgtcgacct ctagctagag cttggcgtaa tcatggtcat agctgtttcc tgtgtgaaat   5520
```

```
tgttatccgc tcacaattcc acacaacata cgagccggaa gcataaagtg taaagcctgg    5580
ggtgcctaat gagtgagcta actcacatta attgcgttgc gctcactgcc cgcttttccag    5640 tcgggaaacc tgtcgtgcca gctgcattaa tgaatcggcc aacgcgcggg gagaggcggt    5700
ttgcgtattg ggcgctcttc cgcttcctcg ctcactgact cgctgcgctc ggtcgttcgg    5760
ctgcggcgag cggtatcagc tcactcaaag gcggtaatac ggttatccac agaatcaggg    5820
gataacgcag gaaagaacat gtgagcaaaa ggccagcaaa aggccaggaa ccgtaaaaag    5880
gccgcgttgc tggcgttttt ccataggctc cgcccccctg acgagcatca caaaaatcga    5940
cgctcaagtc agaggtggcg aaacccgaca ggactataaa gataccaggc gtttccccct    6000
ggaagctccc tcgtgcgctc tcctgttccg accctgccgc ttaccggata cctgtccgcc    6060
tttctccctt cgggaagcgt ggcgctttct caatgctcac gctgtaggta tctcagttcg    6120
gtgtaggtcg ttcgctccaa gctgggctgt gtgcacgaac cccccgttca gcccgaccgc    6180
tgcgccttat ccggtaacta tcgtcttgag tccaacccgg taagacacga cttatcgcca    6240
ctggcagcag ccactggtaa caggattagc agagcgaggt atgtaggcgg tgctacagag    6300
ttcttgaagt ggtggcctaa ctacggctac actagaagga cagtatttgg tatctgcgct    6360
ctgctgaagc cagttacctt cggaaaaaga gttggtagct cttgatccgg caaacaaacc    6420
accgctggta gcggtggttt ttttgtttgc aagcagcaga ttacgcgcag aaaaaaagga    6480
tctcaagaag atcctttgat cttttctacg ggtctgacg ctcagtggaa cgaaaactca    6540
cgttaaggga ttttggtcat gagattatca aaaaggatct cacctagat ccttttaaat    6600 taaaaatgaa gttttaaatc aatctaaagt atatatgagt aaacttggtc tgacagttac    6660
caatgcttaa tcagtgaggc acctatctca gcgatctgtc tatttcgttc atccatagtt    6720
gcctgactcc ccgtcgtgta gataactacg atacgggagg gcttaccatc tggccccagt    6780
gctgcaatga taccgcgaga cccacgctca ccggctccag atttatcagc aataaaccag    6840
ccagccggaa gggccgagcg cagaagtggt cctgcaactt tatccgcctc catccagtct    6900
attaattgtt gccgggaagc tagagtaagt agttcgccag ttaatagttt gcgcaacgtt    6960
gttgccattg ctacaggcat cgtggtgtca cgctcgtcgt ttggtatggc ttcattcagc    7020
tccggttccc aacgatcaag gcgagttaca tgatccccca tgttgtgcaa aaaagcggtt    7080
agctccttcg gtcctccgat cgttgtcaga agtaagttgg ccgcagtgtt atcactcatg    7140
gttatggcag cactgcataa ttctcttact gtcatgccat ccgtaagatg cttttctgtg    7200
actggtgagt actcaaccaa gtcattctga gaatagtgta tgcggcgacc gagttgctct    7260
tgcccggcgt caatacggga taataccgcg ccacatagca gaactttaaa agtgctcatc    7320
attggaaaac gttcttcggg gcgaaaactc tcaaggatct taccgctgtt gagatccagt    7380
tcgatgtaac ccactcgtgc acccaactga tcttcagcat cttttacttt caccagcgtt    7440
tctgggtgag caaaaacagg aaggcaaaat gccgcaaaaa agggaataag ggcgacacgg    7500
aaatgttgaa tactcatact cttcctttt caatattatt gaagcattta tcagggttat    7560
tgtctcatga gcggatacat atttgaatgt atttagaaaa ataaacaaat agggggttccg    7620 cgcacatttc cccgaaaagt gccacctgac gtc                                 7653

<210> SEQ ID NO 13
<211> LENGTH: 8514
<212> TYPE: DNA
<213> ORGANISM: Artificial
```

<220> FEATURE:
<223> OTHER INFORMATION: PB_Minimal_T_(T53C-C136T)_D4Z4_TTRminSerpMVM_
    hFVIIIcopt_SV40pA_D4 Z4 transposon
<220> FEATURE:
<221> NAME/KEY: misc_feature
<222> LOCATION: (1335)..(1335)
<223> OTHER INFORMATION: n is a, c, g, or t

<400> SEQUENCE: 13

```
ctaaattgta agcgttaata ttttgttaaa attcgcgtta aatttttgtt aaatcagctc      60
atttttaac caataggccg aaatcggcaa atcccttat aaatcaaaag aatagaccga        120
gataggttg agtgttgttc cagtttggaa caagagtcca ctattaaaga acgtggactc      180
caacgtcaaa gggcgaaaaa ccgtctatca gggcgatggc ccactacgtg aaccatcacc    240
ctaatcaagt tttttggggt cgaggtgccg taaagcacta atcggaacc ctaaagggag     300
cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg ccagtgagc gcgcttaacc ctagaaagat aatcatattg tgacgtacgt     660
taaagataat catgcgtaaa attgacgcat gtgttttatc ggtctgtata tcgaggttta    720
tttattaatt tgaatagata ttaagttta ttatatttac acttacatac taataataaa    780
ttcaacaaac aatttatta tgtttattta tttattaaaa aaaacaaaa actcaaaatt      840
tcttctataa agtaacaaaa cttttatcga taacttcgta taatgtatgc tatacgaagt   900
tatagagggg cggaagggac gttaggaggg aggcagggag gcaggaggc agggaggaac    960
ggagggaggc ggccgcggta ccggcgcgcc gggggaggct gctggtgaat attaaccaag   1020
gtcaccccag ttatcggagg agcaaacagg ggctaagtcc acacgcgtgg taccgtctgt   1080
ctgcacattt cgtagagcga gtgttccgat actctaatct ccctaggcaa ggttcatatt   1140
tgtgtaggtt acttattctc cttttgttga ctaagtcaat aatcagaatc agcaggtttg   1200
gagtcagctt ggcagggatc agcagcctgg gttggaagga gggggtataa aagcccttc    1260
accaggagaa gccgtcacac agatccacaa gctcctgaag aggtaagggt ttaagggatg   1320
gttggttggt ggggnattaa tgtttaatta cctggagcac ctgcctgaaa tcactttttt   1380
tcaggttggc tagtatgcag atcgagctgt ccacctgctt ttttctgtgc ctgctgcggt   1440
tctgcttcag cgccacccgg cggtactacc tgggcgccgt ggagctgtcc tgggactaca   1500
tgcagagcga cctgggcgag ctgccgtgg acgccggtt ccccccaga gtgcccaaga    1560
gcttcccctt caacaccagc gtggtgtaca agaaaccct gttcgtggag ttcaccgacc   1620
acctgttcaa tatcgccaag cccaggcccc cctggatggg cctgctgggc ccaccatcc   1680
aggccgaggt gtacgacacc gtggtgatca ccctgaagaa catggccagc cacccgtga   1740
gcctgcacgc cgtgggcgtg agctactgga aggccagcga gggcgccgag tacgacgacc   1800
agaccagcca gcgggagaaa gaagatgaca aggtgttccc tggcggcagc cacacctacg   1860
tgtggcaggt gctgaaagaa aacggccca tggcctccga ccccctgtgc ctgacctaca   1920
gctacctgag ccacgtggac ctggtgaagg acctgaacag cggcctgatc ggcgctctgc   1980
tcgtctgccg ggagggcagc ctggccaaag agaaaaccca gacctgcac aagttcatcc    2040
tgctgttcgc cgtgttcgac gagggcaaga gctggcacag cgagacaaag aacagcctga   2100
```

-continued

```
tgcaggaccg ggacgccgcc tctgccagag cctggcccaa gatgcacacc gtgaacggct    2160
acgtgaacag aagcctgccc ggcctgattg gctgccaccg gaagagcgtg tactggcacg    2220
tgatcggcat gggcaccaca cccgaggtgc acagcatctt tctggaaggg cacacctttc    2280
tggtccggaa ccaccggcag gccagcctgg aaatcagccc tatcaccttc ctgaccgccc    2340
agacactgct gatggacctg ggccagttcc tgctgttttg ccacatcagc tctcaccagc    2400
acgacggcat ggaagcctac gtgaaggtgg actcttgccc cgaggaaccc cagctgcgga    2460
tgaagaacaa cgaggaagcc gaggactacg acgacgacct gaccgacagc gagatggacg    2520
tggtgcggtt cgacgacgac aacagcccca gcttcatcca gatcagaagc gtggccaaga    2580
agcaccccaa gacctgggtg cactatatcg ccgccgagga agaggactgg gactacgccc    2640
ccctggtgct ggcccccgac acagaagct acaagagcca gtacctgaac aatggccccc    2700
agcggatcgg ccggaagtac aagaaagtgc ggttcatggc ctacaccgac gagacattca    2760
agacccggga ggccatccag cacgagagcg gcatcctggg ccccctgctg tacgccgaag    2820
tgggcgacac actgctgatc atcttcaaga accaggctag ccggccctac aacatctacc    2880
cccacggcat caccgacgtg cggcccctgt acagcaggcg gctgcccaag ggcgtgaagc    2940
acctgaagga cttcccatc ctgcccggcg agatcttcaa gtacaagtgg accgtgaccg    3000
tggaggacgg ccccaccaag agcgacccca tgcctgac ccggtactac agcagcttcg    3060
tgaacatgga acgggacctg gcctccgggc tgatcggacc tctgctgatc tgctacaaag    3120
aaagcgtgga ccagcggggc aaccagatca tgagcgacaa gcggaacgtg atcctgttca    3180
gcgtgttcga tgagaaccgg tcctggtatc tgaccgagaa catccagcgg tttctgccca    3240
accctgccgg cgtgcagctg gaagatcccg agttccaggc cagcaacatc atgcactcca    3300
tcaatggcta cgtgttcgac tctctgcagc tctccgtgtg tctgcacgag gtggcctact    3360
ggtacatcct gagcatcggc gcccagaccg acttcctgag cgtgttcttc agcggctaca    3420
ccttcaagca caagatggtg tacgaggaca ccctgacct gttccctttc agcggcgaga    3480
cagtgttcat gagcatggaa aaccccggcc tgtggattct gggctgccac aacagcgact    3540
tccggaaccg gggcatgacc gccctgctga aggtgtccag ctgcgacaag aacaccggcg    3600
actactacga ggacagctac gaggatatca gcgcctacct gctgtccaag aacaacgcca    3660
tcgaaccccg gagcttcagc cagaaccccc ccgtgctgac gcgtcaccag cgggagatca    3720
cccggacaac cctgcagtcc gaccaggaag agatcgatta cgacgacacc atcagcgtgg    3780
agatgaagaa agaggatttc gatatctacg acgaggacga aaccagagc cccagaagct    3840
tccagaagaa aacccggcac tacttcattg ccgccgtgga gaggctgtgg gactacggca    3900
tgagttctag ccccacgtg ctgcggaacc gggcccagag cggcagcgtg ccccagttca    3960
agaaagtggt gttccaggaa ttcacagacg gcagcttcac ccagcctctg tatagaggcg    4020
agctgaacga gcacctgggg ctgctggggc cctacatcag ggccgaagtg gaggacaaca    4080
tcatggtgac cttccggaat caggccagca gaccctactc cttctacagc agcctgatca    4140
gctacgaaga ggaccagcgg cagggcgccg aaccccggaa gaacttcgtg aagcccaacg    4200
aaaccaagac ctacttctgg aaagtgcagc accacatggc ccccaccaag gacgagttcg    4260
actgcaaggc ctgggcctac ttcagcgacg tggatctgga aaaggacgtg cactctggac    4320
tgattggccc actcctggtc tgccacacta cacccctcaa ccccgccac ggccgccagg    4380
tgaccgtgca ggaattcgcc ctgttcttca ccatcttcga cgagacaaag tcctggtact    4440
tcaccgagaa tatggaacgg aactgcagag cccctgcaa catccagatg aagatccta    4500
```

```
ccttcaaaga gaactaccgg ttccacgcca tcaacggcta catcatggac accctgcctg    4560
gcctggtgat ggcccaggac cagagaatcc ggtggtatct gctgtccatg ggcagcaacg    4620
agaatatcca cagcatccac ttcagcggcc acgtgttcac cgtgcggaag aaagaagagt    4680
acaagatggc cctgtacaac ctgtaccccg gcgtgttcga cagtggag atgctgccca     4740
gcaaggccgg catctggcgg gtggagtgtc tgatcggcga gcacctgcac gctggcatga    4800
gcaccctgtt tctggtgtac agcaacaagt gccagacccc actgggcatg gcctctggcc    4860
acatccggga cttccagatc accgcctccg gccagtacgg ccagtgggcc cccaagctgg    4920
ccagactgca ctacagcggc agcatcaacg cctggtccac caaagagccc ttcagctgga    4980
tcaaggtgga cctgctggcc cctatgatca tccacggcat taagacccag ggcgccaggc    5040
agaagttcag cagcctgtac atcagccagt tcatcatcat gtacagcctg acggcaaga    5100
agtggcagac ctaccggggc aacagcaccg gcaccctgat ggtgttcttc ggcaatgtgg    5160
acagcagcgg catcaagcac aacatcttca accccccat cattgcccgg tacatccggc    5220
tgcaccccac ccactacagc attagatcca cactgagaat ggaactgatg ggctgcgacc    5280
tgaactcctg cagcatgcct ctgggcatgg aaagcaaggc catcagcgac gcccagatca    5340
cagccagcag ctacttcacc aacatgttcg ccacctggtc cccctccaag gccaggctgc    5400
acctgcaggg ccggtccaac gcctggcggc tcaggtcaa caaccccaaa gaatggctgc    5460
aggtggactt tcagaaaacc atgaaggtga ccggcgtgac cacccaggc gtgaaaagcc    5520
tgctgaccag catgtacgtg aaagagtttc tgatcagcag ctctcaggat ggccaccagt    5580
ggacccctgtt ctttcagaac ggcaaggtga agtgttcca gggcaaccag gactccttca    5640
cccccgtggt gaactccctg accccccccc tgctgacccg ctacctgaga atccacccc    5700
agtcttgggt gcaccagatc gccctcagga tggaagtcct gggatgtgag gcccaggatc    5760
tgtactgatg aggatctagg ctcgacatgc tttatttgtg aaatttgtga tgctattgct    5820
ttatttgtaa ccattataag ctgcaataaa caagttaaca acaacaattg cattcatttt    5880
atgtttcagg ttcaggggga ggtgtgggag gttttttaaa ctcgagaccg gtagaggggc    5940
ggaagggacg ttaggaggga ggcagggagg cagggaggca gggaggaacg gagggagata    6000
acttcgtata atgtatgcta tacgaagtta tgatatctat aacaagaaaa tatatatata    6060
ataagttatc acgtaagtag aacacgaaat aacaatataa ttatcgtatg agttaaatct    6120
taaaagtcac gtaaaagata atcatgcgtc attttgactc acgcggttgt tatagttcaa    6180
aatcagtgac acttaccgca ttgacaagca cgcctcacgg gagctccaag cggcgactga    6240
gatgtcctaa atgcacagcg acggattcgc gctatttaga aagagagagc aatatttcaa    6300
gaatgcatgc gtcaattta cgcagactat ctttctaggg ttaagcgcgc ttggcgtaat    6360
catggtcata gctgtttcct gtgtgaaatt gttatccgct cacaattcca cacaacatac    6420
gagccggaag cataaagtgt aaagcctggg gtgcctaatg agtgagctaa ctcacattaa    6480
ttgcgttgcg ctcactgccc gctttccagt cgggaaacct gtcgtgccag ctgcattaat    6540
gaatcggcca acgcgcgggg agaggcggtt tgcgtattgg gcgctcttcc gcttcctcgc    6600
tcactgactc gctgcgctcg tcgttcggc tgcggcgagc ggtatcagct cactcaaagg    6660
cggtaatacg gttatccaca gaatcagggg ataacgcagg aaagaacatg tgagcaaaag    6720
gccagcaaaa ggccaggaac cgtaaaaagg ccgcgttgct ggcgtttttc cataggctcc    6780
gcccccctga cgagcatcac aaaaatcgac gctcaagtca gaggtggcga aacccgacag    6840
gactataaag ataccaggcg tttccccctg gaagctccct cgtgcgctct cctgttccga    6900
```

```
ccctgccgct taccggatac ctgtccgcct ttctcccttc gggaagcgtg gcgctttctc    6960
atagctcacg ctgtaggtat ctcagttcgg tgtaggtcgt tcgctccaag ctgggctgtg    7020
tgcacgaacc ccccgttcag cccgaccgct gcgccttatc cggtaactat cgtcttgagt    7080
ccaacccggt aagacacgac ttatcgccac tggcagcagc cactggtaac aggattagca    7140
gagcgaggta tgtaggcggt gctacagagt tcttgaagtg gtggcctaac tacggctaca    7200
ctagaaggac agtatttggt atctgcgctc tgctgaagcc agttaccttc ggaaaaagag    7260
ttggtagctc ttgatccggc aaacaaacca ccgctggtag cggtggtttt tttgtttgca    7320
agcagcagat tacgcgcaga aaaaaggat ctcaagaaga tcctttgatc ttttctacgg    7380
ggtctgacgc tcagtggaac gaaaactcac gttaagggat tttggtcatg agattatcaa    7440
aaaggatctt cacctagatc cttttaaatt aaaaatgaag ttttaaatca atctaaagta    7500
tatatgagta aacttggtct gacagttacc aatgcttaat cagtgaggca cctatctcag    7560
cgatctgtct atttcgttca tccatagttg cctgactccc cgtcgtgtag ataactacga    7620
tacgggaggg cttaccatct ggccccagtg ctgcaatgat accgcgagac ccacgctcac    7680
cggctccaga tttatcagca ataaaccagc cagccggaag ggccgagcgc agaagtggtc    7740
ctgcaacttt atccgcctcc atccagtcta ttaattgttg ccgggaagct agagtaagta    7800
gttcgccagt taatagtttg cgcaacgttg ttgccattgc tacaggcatc gtggtgtcac    7860
gctcgtcgtt tggtatggct tcattcagct ccggttccca acgatcaagg cgagttacat    7920 gatccccat gttgtgcaaa aaagcggtta gctccttcgg tcctccgatc gttgtcagaa    7980
gtaagttggc cgcagtgtta tcactcatgg ttatggcagc actgcataat tctcttactg    8040
tcatgccatc cgtaagatgc ttttctgtga ctggtgagta ctcaaccaag tcattctgag    8100
aatagtgtat gcggcgaccg agttgctctt gcccggcgtc aatacgggat aataccgcgc    8160
cacatagcag aactttaaaa gtgctcatca ttggaaaacg ttcttcgggg cgaaaactct    8220
caaggatctt accgctgttg agatccagtt cgatgtaacc cactcgtgca cccaactgat    8280
cttcagcatc ttttactttc accagcgttt ctgggtgagc aaaaacagga aggcaaaatg    8340
ccgcaaaaaa gggaataagg gcgacacgga aatgttgaat actcatactc ttcctttttc    8400
aatattattg aagcatttat cagggttatt gtctcatgag cggatacata tttgaatgta    8460
tttagaaaaa taaacaaata ggggttccgc gcacatttcc ccgaaaagtg ccac          8514
```

<210> SEQ ID NO 14
<211> LENGTH: 5097
<212> TYPE: DNA
<213> ORGANISM: Artificial
<220> FEATURE:
<223> OTHER INFORMATION: PB_micro_T_No_ins_TTRminSerpMVM_FIXco_bghpA
transposon

<400> SEQUENCE: 14

```
ctaaattgta agcgttaata ttttgttaaa attcgcgtta aattttttgtt aaatcagctc     60 attttttaac caataggccg aaatcggcaa aatcccttat aaatcaaaag aatagaccga    120
gatagggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt tttttggggt cgaggtgccg taaagcacta aatcggaacc ctaaagggag    300
cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
```

```
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcttaacc ctagaaagat aatcatattg tgacgtacgt    660
taaagataat catgcgtaaa attgacgcat gataacttcg tataatgtat gctatacgaa    720
gttatgcggc cgcggtaccg gcgcgccggg ggaggctgct ggtgaatatt aaccaaggtc    780
accccagtta tcggaggagc aaacaggggc taagtccaca cgcgtggtac cgtctgtctg    840
cacatttcgt agagcgagtg ttccgatact ctaatctccc taggcaaggt tcatatttgt    900
gtaggttact tattctcctt ttgttgacta agtcaataat cagaatcagc aggtttggag    960
tcagcttggc agggatcagc agcctgggtt ggaaggaggg ggtataaaag ccccttcacc   1020
aggagaagcc gtcacacaga tccacaagct cctgaagagg taagggttta agggatggtt   1080
ggttggtggg gtattaatgt ttaattacct ggagcacctg cctgaaatca cttttttca    1140 ggttgggcta gcccaccatg cagcgcgtga acatgatcat ggccgagagc cccggcctga   1200
tcaccatctg cctgctgggc tacctgctga gcgccgagtg caccgtgttc ctggaccacg   1260
agaacgccaa caagatcctg aaccgcccca agcgctacaa cagcggcaag ctggaggagt   1320
tcgtgcaggg caacctggag cgcgagtgca tggaggagaa gtgcagcttc gaggaggccc   1380
gcgaggtgtt cgagaacacc gagcgcacca ccgagttctg gaagcagtac gtggacggcg   1440
accagtgcga gagcaacccc tgcctgaacg gcggcagctg caaggacgac atcaacagct   1500
acgagtgctg gtgccccttc ggcttcgagg gcaagaactg cgagctggac gtgacctgca   1560
acatcaagaa cggccgctgc gagcagttct gcaagaacag cgccgacaac aaggtggtgt   1620
gcagctgcac cgagggctac cgcctggccg agaaccagaa gagctgcgag cccgccgtgc   1680
ccttcccctg cggccgcgtg agcgtgagcc agaccagcaa gctgacccgc ccgaggccg    1740 tgttccccga cgtggactac gtgaacagca ccgaggccga gaccatcctg gacaacatca   1800
cccagagcac ccagagcttc aacgacttca cccgcgtggt gggcggcgag gacgccaagc   1860
ccggccagtt cccctggcag gtggtgctga acggcaaggt ggacgccttc tgcggcggca   1920
gcatcgtgaa cgagaagtgg atcgtgaccg ccgcccactg cgtggagacc ggcgtgaaga   1980
tcaccgtggt ggccggcgag cacaacatcg aggagaccga gcacaccgag cagaagcgca   2040
acgtgatccg catcatcccc caccacaact acaacgccgc catcaacaag tacaaccacg   2100
acatcgccct gctggagctg gacgagcccc tggtgctgaa cagctacgtg acccccatct   2160
gcatcgccga caaggagtac accaacatct tcctgaagtt cggcagcggc tacgtgagcg   2220
gctggggccg cgtgttccac aagggccgca gcgccctggt gctgcagtac ctgcgcgtgc   2280
ccctggtgga ccgcgccacc tgcctgcgca gcaccaagtt caccatctac aacaacatgt   2340
tctgcgccgg cttccacgag ggcggccgcg acagctgcca gggcgacagc ggcggccccc   2400
acgtgaccga ggtggagggc accagcttcc tgaccggcat catcagctgg ggcgaggagt   2460
gcgccatgaa gggcaagtac ggcatctaca ccaaggtgag ccgctacgtg aactggatca   2520
aggagaagac caagctgacc taatgaaaga tggatttcca aggttaattc attggaattg   2580
aaaattaaca gccccccccc ccccccccct gcagatctag agctcgctga tcagcctcga   2640
ctgtgccttc tagttgccag ccatctgttg tttgcccctc cccgtgcct tccttgaccc    2700 tggaaggtgc cactcccact gtcctttcct aataaaatga ggaaattgca tcgcattgtc   2760
```

```
tgagtaggtg tcattctatt ctgggggtg gggtggggca ggacagcaag ggggaggatt      2820
gggaagacaa tagcaggcat gctggggacc ggtataactt cgtataatgt atgctatacg      2880
aagttatgca tgcgtcaatt ttacgcagac tatctttcta gggttaagcg cgcttggcgt      2940
aatcatggtc atagctgttt cctgtgtgaa attgttatcc gctcacaatt ccacacaaca      3000
tacgagccgg aagcataaag tgtaaagcct ggggtgccta atgagtgagc taactcacat      3060
taattgcgtt gcgctcactg cccgctttcc agtcgggaaa cctgtcgtgc cagctgcatt      3120
aatgaatcgg ccaacgcgcg gggagaggcg gtttgcgtat gggcgctct tccgcttcct      3180 cgctcactga ctcgctgcgc tcggtcgttc ggctgcggcg agcggtatca gctcactcaa      3240
aggcggtaat acggttatcc acagaatcag gggataacgc aggaaagaac atgtgagcaa      3300
aaggccagca aaaggccagg aaccgtaaaa aggccgcgtt gctggcgttt ttccataggc      3360 tccgccccc tgacgagcat cacaaaaatc gacgctcaag tcagaggtgg cgaaacccga      3420
caggactata aagataccag gcgtttcccc ctggaagctc cctcgtgcgc tctcctgttc      3480
cgaccctgcc gcttaccgga tacctgtccg cctttctccc ttcgggaagc gtggcgcttt      3540
ctcatagctc acgctgtagg tatctcagtt cggtgtaggt cgttcgctcc aagctgggct      3600
gtgtgcacga accccccgtt cagcccgacc gctgcgcctt atccggtaac tatcgtcttg      3660
agtccaaccc ggtaagacac gacttatcgc cactggcagc agccactggt aacaggatta      3720
gcagagcgag gtatgtaggc ggtgctacag agttcttgaa gtggtggcct aactacggct      3780
acactagaag gacagtattt ggtatctgcg ctctgctgaa gccagttacc ttcggaaaaa      3840
gagttggtag ctcttgatcc ggcaaacaaa ccaccgctgg tagcggtggt ttttttgttt      3900
gcaagcagca gattacgcgc agaaaaaaag gatctcaaga agatcctttg atcttttcta      3960
cggggtctga cgctcagtgg aacgaaaact cacgttaagg gattttggtc atgagattat      4020
caaaaaggat cttcacctag atccttttaa attaaaaatg aagttttaaa tcaatctaaa      4080
gtatatatga gtaaacttgg tctgacagtt accaatgctt aatcagtgag gcacctatct      4140
cagcgatctg tctatttcgt tcatccatag ttgcctgact ccccgtcgtg tagataacta      4200
cgatacggga gggcttacca tctggcccca gtgctgcaat gataccgcga gacccacgct      4260
caccggctcc agatttatca gcaataaacc agccagccgg aagggccgag cgcagaagtg      4320
gtcctgcaac tttatccgcc tccatccagt ctattaattg ttgccgggaa gctagagtaa      4380
gtagttcgcc agttaatagt ttgcgcaacg ttgttgccat tgctacaggc atcgtggtgt      4440
cacgctcgtc gtttggtatg gcttcattca gctccggttc ccaacgatca aggcgagtta      4500
catgatcccc catgttgtgc aaaaaagcgg ttagctcctt cggtcctccg atcgttgtca      4560
gaagtaagtt ggccgcagtg ttatcactca tggttatggc agcactgcat aattctctta      4620
ctgtcatgcc atccgtaaga tgcttttctg tgactggtga gtactcaacc aagtcattct      4680
gagaatagtg tatgcggcga ccgagttgct cttgcccggc gtcaatacgg gataataccg      4740
cgccacatag cagaacttta aaagtgctca tcattggaaa acgttcttcg ggcgaaaac      4800 tctcaaggat cttaccgctg ttgagatcca gttcgatgta acccactcgt gcacccaact      4860
gatcttcagc atcttttact ttcaccagcg tttctgggtg agcaaaaaca ggaaggcaaa      4920
atgccgcaaa aaagggaata agggcgacac ggaaatgttg aatactcata ctcttccttt      4980
ttcaatatta ttgaagcatt tatcagggtt attgtctcat gagcggatac atatttgaat      5040
gtatttagaa aaataaacaa ataggggttc cgcgcacatt tccccgaaaa gtgccac       5097
```

<210> SEQ ID NO 15
<211> LENGTH: 5097
<212> TYPE: DNA
<213> ORGANISM: Artificial
<220> FEATURE:
<223> OTHER INFORMATION: PB_micro_T_No_ins_TTRminSerpMVM_FIXco_Padua_bghpA transposon

<400> SEQUENCE: 15

```
ctaaattgta agcgttaata ttttgttaaa attcgcgtta aattttgtt aaatcagctc       60
atttttaac caataggccg aaatcggcaa atcccttat aaatcaaaag aatagaccga      120
gatagggttg agtgttgttc cagtttggaa caagagtcca ctattaaaga acgtggactc      180
caacgtcaaa gggcgaaaaa ccgtctatca gggcgatggc ccactacgtg aaccatcacc      240
ctaatcaagt tttttggggt cgaggtgccg taaagcacta atcggaacc ctaaagggag       300
cccccgattt agagcttgac ggggaaagcc ggcgaacgtg gcgagaaagg aagggaagaa      360
agcgaaagga gcgggcgcta gggcgctggc aagtgtagcg gtcacgctgc gcgtaaccac      420
cacacccgcc gcgcttaatg cgccgctaca gggcgcgtcc cattcgccat tcaggctgcg      480
caactgttgg aagggcgat cggtgcgggc ctcttcgcta ttacgccagc tggcgaaagg      540
gggatgtgct gcaaggcgat taagttgggt aacgccaggt ttttcccagt cacgacgttg      600
taaaacgacg gccagtgagc gcgcttaacc ctagaaagat aatcatattg tgacgtacgt      660
taaagataat catgcgtaaa attgacgcat gataacttcg tataatgtat gctatacgaa      720
gttatgcggc cgcggtaccg gcgcgccggg ggaggctgct ggtgaatatt aaccaaggtc      780
accccagtta tcggaggagc aaacaggggc taagtccaca cgcgtggtac cgtctgtctg      840
cacatttcgt agagcgagtg ttccgatact ctaatctccc taggcaaggt tcatatttgt      900
gtaggttact tattctcctt ttgttgacta agtcaataat cagaatcagc aggtttggag      960
tcagcttggc agggatcagc agcctgggtt ggaaggaggg ggtataaaag cccttcacc      1020
aggagaagcc gtcacacaga tccacaagct cctgaagagg taagggttta agggatggtt     1080
ggttggtggg gtattaatgt ttaattacct ggagcacctg cctgaaatca cttttttca     1140
ggttgggcta gccaccatg cagcgcgtga acatgatcat ggccgagagc cccggcctga     1200
tcaccatctg cctgctgggc tacctgctga gcgccgagtg caccgtgttc ctggaccacg     1260
agaacgccaa caagatcctg aaccgcccca agcgctacaa cagcggcaag ctggaggagt     1320
tcgtgcaggg caacctggag cgcgagtgca tggaggagaa gtgcagcttc gaggaggccc     1380
gcgaggtgtt cgagaacacc gagcgcacca ccgagttctg gaagcagtac gtggacggcg     1440
accagtgcga gagcaacccc tgcctgaacg gcggcagctg caaggacgac atcaacagct     1500
acgagtgctg gtgccccttc ggcttcgagg gcaagaactg cgagctggac gtgacctgca     1560
acatcaagaa cggccgctgc gagcagttct gcaagaacag cgccgacaac aaggtggtgt     1620
gcagctgcac cgagggctac cgcctggccg agaaccagaa gagctgcgag cccgccgtgc     1680
ccttcccctg cggccgcgtg agcgtgagcc agaccagcaa gctgacccgc gccgaggccg     1740
tgttccccga cgtggactac gtgaacagca ccgaggccga ccatcctg gacaacatca     1800
cccagagcac ccagagcttc aacgacttca cccgcgtggt gggcggcgag gacgccaagc     1860
ccggccagtt ccccctggcag gtggtgctga acggcaaggt ggacgccttc tgcggcggca     1920
gcatcgtgaa cgagaagtgg atcgtgaccg ccgcccactg cgtggagacc ggcgtgaaga     1980
tcaccgtggt ggccggcgag cacaacatcg aggagaccga gcacaccgag cagaagcgca     2040
acgtgatccg catcatcccc caccacaact acaacgccgc catcaacaag tacaaccacg     2100
```

```
acatcgccct gctggagctg gacgagcccc tggtgctgaa cagctacgtg accccccatct    2160 gcatcgccga caaggagtac accaacatct tcctgaagtt cggcagcggc tacgtgagcg    2220
gctggggccg cgtgttccac aagggccgca gcgccctggt gctgcagtac ctgcgcgtgc    2280
ccctggtgga ccgcgccacc tgcctgctga gcaccaagtt caccatctac aacaacatgt    2340
tctgcgccgg cttccacgag ggcggccgcg acagctgcca gggcgacagc ggcggccccc    2400
acgtgaccga ggtggagggc accagcttcc tgaccggcat catcagctgg ggcgaggagt    2460
gcgccatgaa gggcaagtac ggcatctaca ccaaggtgag ccgctacgtg aactggatca    2520
aggagaagac caagctgacc taatgaaaga tggatttcca aggttaattc attggaattg    2580
aaaattaaca gcccccccccc ccccccccct gcagatctag agctcgctga tcagcctcga    2640
ctgtgccttc tagttgccag ccatctgttg tttgcccctc cccgtgcct tccttgaccc     2700 tggaaggtgc cactcccact gtcctttcct aataaaatga ggaaattgca tcgcattgtc    2760
tgagtaggtg tcattctatt ctgggggtg gggtggggca ggacagcaag ggggaggatt     2820
gggaagacaa tagcaggcat gctggggacc ggtataactt cgtataatgt atgctatacg    2880
aagttatgca tgcgtcaatt ttacgcagac tatcttttcta gggttaagcg cgcttggcgt    2940
aatcatggtc atagctgttt cctgtgtgaa attgttatcc gctcacaatt ccacacaaca    3000
tacgagccgg aagcataaag tgtaaagcct ggggtgccta atgagtgagc taactcacat    3060
taattgcgtt gcgctcactg cccgctttcc agtcgggaaa cctgtcgtgc cagctgcatt    3120
aatgaatcgg ccaacgcgcg gggagaggcg gtttgcgtat tgggcgctct ccgcttcct    3180 cgctcactga ctcgctgcgc tcggtcgttc ggctgcggcg agcggtatca gctcactcaa    3240
aggcggtaat acggttatcc acagaatcag gggataacgc aggaaagaac atgtgagcaa    3300
aaggccagca aaaggccagg aaccgtaaaa aggccgcgtt gctggcgttt ttccataggc    3360 tccgccccc tgacgagcat cacaaaaatc gacgctcaag tcagaggtgg cgaaacccga     3420
caggactata aagataccag gcgtttcccc ctggaagctc cctcgtgcgc tctcctgttc    3480
cgaccctgcc gcttaccgga tacctgtccg cctttctccc ttcgggaagc gtggcgcttt    3540
ctcatagctc acgctgtagg tatctcagtt cggtgtaggt cgttcgctcc aagctgggct    3600
gtgtgcacga accccccgtt cagcccgacc gctgcgcctt atccggtaac tatcgtcttg    3660
agtccaaccc ggtaagacac gacttatcgc cactggcagc agccactggt aacaggatta    3720
gcagagcgag gtatgtaggc ggtgctacag agttcttgaa gtggtggcct aactacggct    3780
acactagaag gacagtattt ggtatctgcg ctctgctgaa gccagttacc ttcggaaaaa    3840
gagttggtag ctcttgatcc ggcaaacaaa ccaccgctgg tagcggtggt ttttttgttt    3900
gcaagcagca gattacgcgc agaaaaaaag gatctcaaga agatcctttg atcttttcta    3960
cggggtctga cgctcagtgg aacgaaaact cacgttaagg gattttggtc atgagattat    4020
caaaaaggat cttcacctag atccttttaa attaaaaatg aagttttaaa tcaatctaaa    4080
gtatatatga gtaaacttgg tctgacagtt accaatgctt aatcagtgag gcacctatct    4140
cagcgatctg tctatttcgt tcatccatag ttgcctgact ccccgtcgtg tagataacta    4200
cgatacggga gggcttacca tctggcccca gtgctgcaat gataccgcga gacccacgct    4260
caccggctcc agatttatca gcaataaacc agccagccgg aagggccgag cgcagaagtg    4320
gtcctgcaac tttatccgcc tccatccagt ctattaattg ttgccgggaa gctagagtaa    4380
gtagttcgcc agttaatagt ttgcgcaacg ttgttgccat tgctacaggc atcgtggtgt    4440
cacgctcgtc gtttggtatg gcttcattca gctccggttc ccaacgatca aggcgagtta    4500
```

| | |
|---|---|
| catgatcccc catgttgtgc aaaaaagcgg ttagctcctt cggtcctccg atcgttgtca | 4560 |
| gaagtaagtt ggccgcagtg ttatcactca tggttatggc agcactgcat aattctctta | 4620 |
| ctgtcatgcc atccgtaaga tgcttttctg tgactggtga gtactcaacc aagtcattct | 4680 |
| gagaatagtg tatgcggcga ccgagttgct cttgcccggc gtcaatacgg gataataccg | 4740 |
| cgccacatag cagaacttta aaagtgctca tcattggaaa acgttcttcg ggcgaaaac | 4800 |
| tctcaaggat cttaccgctg ttgagatcca gttcgatgta acccactcgt gcacccaact | 4860 |
| gatcttcagc atcttttact ttcaccagcg tttctgggtg agcaaaaaca ggaaggcaaa | 4920 |
| atgccgcaaa aaagggaata agggcgacac ggaaatgttg aatactcata ctcttccttt | 4980 |
| ttcaatatta ttgaagcatt tatcagggtt attgtctcat gagcggatac atatttgaat | 5040 |
| gtatttagaa aaataaacaa ataggggttc cgcgcacatt tccccgaaaa gtgccac | 5097 |

<210> SEQ ID NO 16
<211> LENGTH: 14
<212> TYPE: PRT
<213> ORGANISM: Artificial
<220> FEATURE:
<223> OTHER INFORMATION: linker

<400> SEQUENCE: 16

Ser Phe Ser Gln Asn Pro Pro Val Leu Thr Arg His Gln Arg
1               5                   10

<210> SEQ ID NO 17
<211> LENGTH: 6891
<212> TYPE: DNA
<213> ORGANISM: Artificial
<220> FEATURE:
<223> OTHER INFORMATION: pCDNA3 _CMVBGI _SBMAX_bghpA plasmid

<400> SEQUENCE: 17

| | |
|---|---|
| gacggatcgg gagatctccc gatccctat ggtcgactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg cgtggagcta gttattaata gtaatcaatt | 240 |
| acggggtcat tagttcatag cccatatatg gagttccgcg ttacataact tacggtaaat | 300 |
| ggcccgcctg gctgaccgcc caacgacccc cgcccattga cgtcaataat gacgtatgtt | 360 |
| cccatagtaa cgtcaatagg gactttccat tgacgtcaat gggtggagta tttacggtaa | 420 |
| actgcccact tggcagtaca tcaagtgtat catatgccaa gtacgccccc tattgacgtc | 480 |
| aatgacggta aatggcccgc ctggcattat gcccagtaca tgaccttatg gactttcct | 540 |
| acttggcagt acatctacgt attagtcatc gctattacca tggtgatgcg gttttggcag | 600 |
| tacatcaatg ggcgtggata gcggtttgac tcacggggat ttccaagtct ccaccccatt | 660 |
| gacgtcaatg ggagtttgtt ttggcaccaa aatcaacggg actttccaaa atgtcgtaac | 720 |
| aactccgccc cattgacgca aatgggcggt aggcgtgtac ggtgggaggt ctatataagc | 780 |
| agagctcgtt tagtgaaccg tcagatcgcc tggagacgcc atccacgctg ttttgacctc | 840 |
| catagaagac accgggaccg atccagcctc cgcggattcg aatcccggcc gggaacggtg | 900 |
| cattggaacg cggattcccc gtgccaagag tgacgtaagt accgcctata gagtctatag | 960 |
| gcccacaaaa aatgctttct tcttttaata tactttttg tttatcttat ttctaatact | 1020 |
| ttccctaatc tctttctttc agggcaataa tgatacaatg tatcatgcct ctttgcacca | 1080 |

```
ttctaaagaa taacagtgat aatttctggg ttaaggcaat agcaatattt ctgcatataa    1140
atatttctgc atataaattg taactgatgt aagaggtttc atattgctaa tagcagctac    1200
aatccagcta ccattctgct tttatttat ggttgggata aggctggatt attctgagtc    1260
caagctaggc cctttgcta atcatgttca tacctcttat cttcctccca cagctcctgg    1320
gcaacgtgct ggtctgtgtg ctggcccatc actttggcaa agaattggga ttcgaacatc    1380
gatgccgcca ccatgggaaa atcaaaagaa atcagccaag acctcagaaa agaattgta    1440
gacctccaca agtctggttc atccttggga gcaatttccc gacgcctggc ggtaccacgt    1500
tcatctgtac aaacaatagt acgcaagtat aaacaccatg ggaccacgca gccgtcatac    1560
cgctcaggaa ggagacgcgt tctgtctcct agagatgaac gtactttggt gcgaaaagtg    1620
caaatcaatc ccagaacaac agcaaaggac cttgtgaaga tgctggagga acaggtaca    1680
aaagtatcta tatccacagt aaaacgagtc ctatatcgac ataacctgaa aggccactca    1740
gcaaggaaga agccactgct ccaaaaccga cataagaaag ccagactacg gtttgcaact    1800
gcacatgggg acaaagatct aacttttgg agaaatgtcc tctggtctga tgaaacaaaa    1860
atagaactgt ttggccataa tgaccatcgt tatgtttgga ggaagaaggg ggaggcttgc    1920
aagccgaaga acaccatccc aaccgtgaag cacggggtg gcagcatcat gttgtggggg    1980
tgctttgctg caggagggac tggtaaactt gtccgaatag aaggcatcat ggacgcggtg    2040
cagtatgtgg atatattgaa gcaacatctc aagacatcag tcaggaagtt aaagcttggt    2100
cgcaaatggg tcttccaaca cgacaatgac cccaagcata cttccaaagt tgtggcaaaa    2160
tggcttaagg acaacaaagt caaggtattg gactggccat cacaaagccc tgacctcaat    2220
cctatagaaa atttgtgggc agaactgaaa aagcgtgtgc gagcaaggag gcctacaaac    2280
ctgactcagt taccagct ctgtcaggag gaatgggcca aaattcaccc aaattattgt    2340
gggaagcttg tggaaggcta cccgaaacgt ttgacccaag ttaaacaatt taaaggcaat    2400
gctaccaaat actagctcga gcatgcatct agagggccct attctatagt gtcacctaaa    2460
tgctagagct cgctgatcag cctcgactgt gccttctagt tgccagccat ctgttgtttg    2520
ccccctcccc gtgccttcct tgaccctgga aggtgccact cccactgtcc tttcctaata    2580
aaatgaggaa attgcatcgc attgtctgag taggtgtcat tctattctgg ggggtggggt    2640
ggggcaggac agcaagggg aggattggga agacaatagc aggcatgctg gggatgcggt    2700
gggctctatg gcttctgagg cggaaagaac cagctggggc tctagggggt atccccacgc    2760
gccctgtagc ggcgcattaa gcgcggcggg tgtggtggtt acgcgcagcg tgaccgctac    2820
acttgccagc gccctagcgc ccgctccttt cgctttcttc ccttcctttc tcgccacgtt    2880
cgccggcttt cccgtcaag ctctaaatcg gggcatccct ttagggttcc gatttagtgc    2940
tttacggcac ctcgacccca aaaaacttga ttagggtgat ggttcacgta gtgggccatc    3000
gccctgatag acggtttttc gcccttttgac gttggagtcc acgttcttta atagtggact    3060
cttgttccaa actggaacaa cactcaaccc tatctcggtc tattcttttg atttataagg    3120
gattttgggg atttcggcct attggttaaa aaatgagctg atttaacaaa aatttaacgc    3180
gaattaattc tgtggaatgt gtgtcagtta gggtgtggaa agtccccagg ctccccagc    3240
aggcagaagt atgcaaagca tgcatctcaa ttagtcagca accaggtgtg gaaagtcccc    3300
aggctcccca gcaggcagaa gtatgcaaag catgcatctc aattagtcag caaccatagt    3360
cccgccccta actccgccca tcccgcccct aactccgccc agttccgccc attctccgcc    3420
ccatggctga ctaatttttt ttatttatgc agaggccgag gccgcctctg cctctgagct    3480
```

```
attccagaag tagtgaggag gctttttttgg aggcctaggc ttttgcaaaa agctcccggg    3540
agcttgtata tccattttcg gatctgatca agagacagga tgaggatcgt ttcgcatgat    3600
tgaacaagat ggattgcacg caggttctcc ggccgcttgg gtggagaggc tattcggcta    3660
tgactgggca caacagacaa tcggctgctc tgatgccgcc gtgttccggc tgtcagcgca    3720
ggggcgcccg gttcttttg tcaagaccga cctgtccggt gccctgaatg aactgcagga    3780
cgaggcagcg cggctatcgt ggctggccac gacgggcgtt ccttgcgcag ctgtgctcga    3840
cgttgtcact gaagcgggaa gggactggct gctattgggc gaagtgccgg ggcaggatct    3900
cctgtcatct caccttgctc ctgccgagaa agtatccatc atggctgatg caatgcggcg    3960
gctgcatacg cttgatccgg ctacctgccc attcgaccac caagcgaaac atcgcatcga    4020
gcgagcacgt actcggatgg aagccggtct tgtcgatcag gatgatctgg acgaagagca    4080 tcagggctc gcgccagccg aactgttcgc caggctcaag gcgcgcatgc ccgacggcga    4140
ggatctcgtc gtgacccatg gcgatgcctg cttgccgaat atcatggtgg aaaatggccg    4200
cttttctgga ttcatcgact gtggccggct gggtgtggcg gaccgctatc aggacatagc    4260
gttggctacc cgtgatattg ctgaagagct tggcggcgaa tgggctgacc gcttcctcgt    4320
gctttacggt atcgccgctc ccgattcgca gcgcatcgcc ttctatcgcc ttcttgacga    4380
gttcttctga gcgggactct ggggttcgaa atgaccgacc aagcgacgcc caacctgcca    4440
tcacgagatt tcgattccac cgccgccttc tatgaaaggt tgggcttcgg aatcgttttc    4500
cgggacgccg gctggatgat cctccagcgc ggggatctca tgctggagtt cttcgcccac    4560
cccaacttgt ttattgcagc ttataatggt tacaaataaa gcaatagcat cacaaatttc    4620
acaaataaag catttttttc actgcattct agttgtggtt tgtccaaact catcaatgta    4680
tcttatcatg tctgtatacc gtcgacctct agctagagct tggcgtaatc atggtcatag    4740
ctgtttcctg tgtgaaattg ttatccgctc acaattccac acaacatacg agccggaagc    4800
ataaagtgta aagcctgggg tgcctaatga gtgagctaac tcacattaat tgcgttgcgc    4860
tcactgcccg ctttccagtc gggaaacctg tcgtgccagc tgcattaatg aatcggccaa    4920
cgcgcgggga gaggcggttt gcgtattggg cgctcttccg cttcctcgct cactgactcg    4980
ctgcgctcgg tcgttcggct gcggcgagcg gtatcagctc actcaaaggc ggtaatacgg    5040
ttatccacag aatcagggga taacgcagga aagaacatgt gagcaaaagg ccagcaaaag    5100
gccaggaacc gtaaaaaggc cgcgttgctg gcgtttttcc ataggctccg ccccctgac    5160 gagcatcaca aaaatcgacg ctcaagtcag aggtggcgaa acccgacagg actataaaga    5220
taccaggcgt ttccccctgg aagctccctc gtgcgctctc ctgttccgac cctgccgctt    5280
accggatacc tgtccgcctt tctcccttcg ggaagcgtgg cgctttctca atgctcacgc    5340
tgtaggtatc tcagttcggt gtaggtcgtt cgctccaagc tgggctgtgt gcacgaaccc    5400
cccgttcagc ccgaccgctg cgccttatcc ggtaactatc gtcttgagtc aacccggta    5460 agacacgact tatcgccact ggcagcagcc actggtaaca ggattagcag agcgaggtat    5520
gtaggcggtg ctacagagtt cttgaagtgg tggcctaact acggctacac tagaaggaca    5580
gtatttggta tctgcgctct gctgaagcca gttaccttcg gaaaaagagt tggtagctct    5640
tgatccggca aacaaaccac cgctggtagc ggtggttttt ttgtttgcaa gcagcagatt    5700
acgcgcagaa aaaaggatc tcaagaagat cctttgatct tttctacggg gtctgacgct    5760
cagtggaacg aaaactcacg ttaagggatt ttggtcatga gattatcaaa aaggatcttc    5820
acctagatcc ttttaaatta aaaatgaagt tttaaatcaa tctaaagtat atatgagtaa    5880
```

```
acttggtctg acagttacca atgcttaatc agtgaggcac ctatctcagc gatctgtcta    5940
tttcgttcat ccatagttgc ctgactcccc gtcgtgtaga taactacgat acgggagggc    6000
ttaccatctg gccccagtgc tgcaatgata ccgcgagacc cacgctcacc ggctccagat    6060
ttatcagcaa taaccagcc agccggaagg gccgagcgca gaagtggtcc tgcaacttta    6120
tccgcctcca tccagtctat taattgttgc cgggaagcta gagtaagtag ttcgccagtt    6180
aatagtttgc gcaacgttgt tgccattgct acaggcatcg tggtgtcacg ctcgtcgttt    6240
ggtatggctt cattcagctc cggttcccaa cgatcaaggc gagttacatg atcccccatg    6300
ttgtgcaaaa aagcggttag ctccttcggt cctccgatcg ttgtcagaag taagttggcc    6360
gcagtgttat cactcatggt tatggcagca ctgcataatt ctcttactgt catgccatcc    6420
gtaagatgct tttctgtgac tggtgagtac tcaaccaagt cattctgaga atagtgtatg    6480
cggcgaccga gttgctcttg cccggcgtca atacgggata ataccgcgcc acatagcaga    6540
actttaaaag tgctcatcat tggaaaacgt tcttcggggc gaaaactctc aaggatctta    6600
ccgctgttga gatccagttc gatgtaaccc actcgtgcac ccaactgatc ttcagcatct    6660
tttactttca ccagcgtttc tgggtgagca aaaacaggaa ggcaaaatgc cgcaaaaaag    6720
ggaataaggg cgacacggaa atgttgaata ctcatactct ccttttttca atattattga    6780
agcatttatc agggttattg tctcatgagc ggatacatat ttgaatgtat ttagaaaaat    6840
aaacaaatag ggttccgcg cacatttccc cgaaaagtgc cacctgacgt c              6891
```

<210> SEQ ID NO 18
<211> LENGTH: 19
<212> TYPE: DNA
<213> ORGANISM: Artificial
<220> FEATURE:
<223> OTHER INFORMATION: primer

<400> SEQUENCE: 18
gaaggtgaag gtcggagtc                                                    19

<210> SEQ ID NO 19
<211> LENGTH: 20
<212> TYPE: DNA
<213> ORGANISM: Artificial
<220> FEATURE:
<223> OTHER INFORMATION: primer

<400> SEQUENCE: 19
gaagatggtg atgggatttc                                                   20

<210> SEQ ID NO 20
<211> LENGTH: 25
<212> TYPE: DNA
<213> ORGANISM: Artificial
<220> FEATURE:
<223> OTHER INFORMATION: primer

<400> SEQUENCE: 20
tgatgctatt gctttatttg taacc                                             25

<210> SEQ ID NO 21
<211> LENGTH: 23
<212> TYPE: DNA
<213> ORGANISM: Artificial
<220> FEATURE:
<223> OTHER INFORMATION: primer

<400> SEQUENCE: 21
cctgaacctg aaacataaaa tga         23

<210> SEQ ID NO 22
<211> LENGTH: 34
<212> TYPE: DNA
<213> ORGANISM: Artificial
<220> FEATURE:
<223> OTHER INFORMATION: probe

<400> SEQUENCE: 22
agctgcaata aacaagttaa caacaacaat tgca         34

<210> SEQ ID NO 23
<211> LENGTH: 19
<212> TYPE: DNA
<213> ORGANISM: Artificial
<220> FEATURE:
<223> OTHER INFORMATION: Fragment codon-optimized human coagulation
      factor IX with Padua mutation

<400> SEQUENCE: 23
cctgcctgct gagcaccaa         19

<210> SEQ ID NO 24
<211> LENGTH: 19
<212> TYPE: DNA
<213> ORGANISM: Artificial
<220> FEATURE:
<223> OTHER INFORMATION: Fragment codon-optimized human coagulation
      factor IX

<400> SEQUENCE: 24
cctgcctgcg cagcaccaa         19

<210> SEQ ID NO 25
<211> LENGTH: 20
<212> TYPE: DNA
<213> ORGANISM: Artificial
<220> FEATURE:
<223> OTHER INFORMATION: primer

<400> SEQUENCE: 25 aacagggct aagtccacac         20

<210> SEQ ID NO 26
<211> LENGTH: 21
<212> TYPE: DNA
<213> ORGANISM: Artificial
<220> FEATURE:
<223> OTHER INFORMATION: primer

<400> SEQUENCE: 26
gagcgagtgt tccgatactc t         21

<210> SEQ ID NO 27
<211> LENGTH: 24
<212> TYPE: DNA
<213> ORGANISM: Artificial
<220> FEATURE:
<223> OTHER INFORMATION: primer

<400> SEQUENCE: 27
atcaagaagg tggtgaagca ggca         24

```
<210> SEQ ID NO 28
<211> LENGTH: 24
<212> TYPE: DNA
<213> ORGANISM: Artificial
<220> FEATURE:
<223> OTHER INFORMATION: primer

<400> SEQUENCE: 28
tggaagagtg ggagttgctg ttga                                          24

<210> SEQ ID NO 29
<211> LENGTH: 67
<212> TYPE: DNA
<213> ORGANISM: Artificial
<220> FEATURE:
<223> OTHER INFORMATION: IR micro

<400> SEQUENCE: 29
ttaaccctag aaagataatc atattgtgac gtacgttaaa gataatcatg cgtaaaattg    60
acgcatg                                                             67

<210> SEQ ID NO 30
<211> LENGTH: 40
<212> TYPE: DNA
<213> ORGANISM: Artificial
<220> FEATURE:
<223> OTHER INFORMATION: IR micro

<400> SEQUENCE: 30
gcatgcgtca attttacgca gactatcttt ctagggttaa                         40
```